US011542508B2

(12) United States Patent
Sorek et al.

(10) Patent No.: US 11,542,508 B2
(45) Date of Patent: Jan. 3, 2023

(54) ISOLATED POLYNUCLEOTIDES AND POLYPEPTIDES AND METHODS OF USING SAME FOR EXPRESSING AN EXPRESSION PRODUCT OF INTEREST

(71) Applicant: Yeda Research and Development Co. Ltd., Rehovot (IL)

(72) Inventors: Rotem Sorek, Rehovot (IL); Gil Amitai, Rehovot (IL); Erez Zohar, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 844 days.

(21) Appl. No.: 16/346,124

(22) PCT Filed: Nov. 28, 2017

(86) PCT No.: PCT/IL2017/051293
§ 371 (c)(1),
(2) Date: Apr. 30, 2019

(87) PCT Pub. No.: WO2018/096547
PCT Pub. Date: May 31, 2018

(65) Prior Publication Data

US 2019/0264213 A1 Aug. 29, 2019

Related U.S. Application Data

(60) Provisional application No. 62/426,669, filed on Nov. 28, 2016.

(51) Int. Cl.

| | |
|---|---|
| ***C12N 15/63*** | (2006.01) |
| ***C12N 15/75*** | (2006.01) |
| ***C12N 15/67*** | (2006.01) |
| ***C12N 15/90*** | (2006.01) |
| ***C07K 14/00*** | (2006.01) |
| ***C12N 7/00*** | (2006.01) |
| ***C07K 14/005*** | (2006.01) |

(52) U.S. Cl.
CPC .......... *C12N 15/635* (2013.01); *C07K 14/005* (2013.01); *C12N 7/00* (2013.01); *C12N 15/67* (2013.01); *C12N 15/75* (2013.01); *C12N 15/90* (2013.01); *C12N 2795/00022* (2013.01); *C12N 2795/00032* (2013.01); *C12N 2795/10343* (2013.01)

(58) Field of Classification Search
None
See application file for complete search history.

(56) References Cited

FOREIGN PATENT DOCUMENTS

| | | |
|---|---|---|
| WO | WO 2015/033343 | 3/2015 |
| WO | WO 2018/096547 | 5/2018 |
| WO | WO 2018/096547 A8 | 5/2018 |

OTHER PUBLICATIONS

International Preliminary Report on Patentability dated Jun. 6, 2019 From the International Bureau of WIPO Re. Application No. PCT/IL2017/051293. (10 Pages).
International Search Report and the Written Opinion dated Feb. 6, 2018 From the International Searching Authority Re. Application No. PCT/IL2017/051293. (20 Pages).
Blatch et al. "The Tetratricopeptide Repeat: A Structural Motif Mediating Protein-Protein Interactions", BioEssays, XP009002727, 21(11): 932-939, Nov. 1, 1999. Abstract, p. 933, 935-936, Figs.1-2, Table 1.
Do et al. "Structural Mechanisms of Peptide Recognition and Allosteric Modulation of Gene Regulation by the RRNPP Family of Quorum-Sensing Regulators", Journal of Molecular Biology, XP029630345, 428(14): 2793-2804, Jun. 7, 2016.
Erez et al. "Communication Between Viruses Guides Lysis-Lysogeny Decisions", Nature, XP055442596, 541(7638): 488-493, Jan. 26, 2017.
Grenha et al. "Structural Basis for the Activation Mechanism of the PlcR Virulence Regulator by the Quorum-Sensing Signal Peptide PapR", Proc. Natl. Acad. Sci. USA, PNAS, XP055445042, 110(3): 1047-1052, Jan. 15, 2013. Abstract, p. 1047, Right col., p. 1049-1051.
Kim et al. "ARS-Interacting Multi-Functional Protein 1 Induces Proliferation of Human Bone Marrow-Derived Mesenchymal Stem Cells by Accumulation of Beta-Catenin Via Fibroblast Growth Factor Receptor 2-Mediated Activation of Akt", Stem Cells and Development, XP055442125, 22(19): 2630-2640, Published Online May 14, 2013. Abstract.
Perego "Forty Years in the Making: Understanding the Molecular Mechanism of Peptide Regulation in Bacterial Development", PLOS Biology, XP055443054, 11(3): 31001516-1-e1001516-5, Mar. 19, 2013.
Perez-Pascual et al. "Bacterial Cell-Cell Communication in the Host Via RRNPP Peptide-Binding Regulators", Frontiers in Microbiology, XP055442623, 7(Art.706): 1-8, May 20, 2016.
Pottathil et al. "The Extracellular PHR Peptide-Rap Phosphatase Signaling Circuit of Bacillus Subtilis", Frontiers in Bioscience, XP002367985, 8: d32-d45, Jan. 1, 2003. Abstract, p. 1047-1048, Fig.5.
Ulrich et al. "One-Component Systems Dominate Signal Transduction in Prokaryotes", Trands in Microbiology, XP027616924, 13(2): 52-56, Available Online Dec. 22, 2004. Abstract, p. 52, Right col., p. 53-54.
Waters et al. "Quorum Sensing: Cell-to-Cell Communication in Bacteria", Annual Review of Cell and Developmental Biology, XP055393486, 21(1): 319-346, Published Online Jun. 28, 2005.
Communication Pursuant to Article 94(3) EPC Dated Jan. 12, 2021 From the European Patent Office Re. Application No. 17817906.5. (4 Pages).

*Primary Examiner* — Suzanne M Noakes

(57) ABSTRACT

Methods of expressing an expression product of interest are provided. Accordingly there is provided a method comprising introducing into a cell a polynucleotide comprising an AimR responsive element operatively linked to a nucleic acid sequence encoding the expression product of interest, and contacting said cell with an AimP peptide comprising an amino acid sequence of XXXXGG/A, wherein said AimP peptide is capable of binding said AimR polypeptide and dissociating said AimR polypeptide from said AimR responsive element. Also provided are articles of manufacture, isolated peptides, polynucleotides and nucleic acid constructs.

30 Claims, 13 Drawing Sheets
(13 of 13 Drawing Sheet(s) Filed in Color)

Specification includes a Sequence Listing.

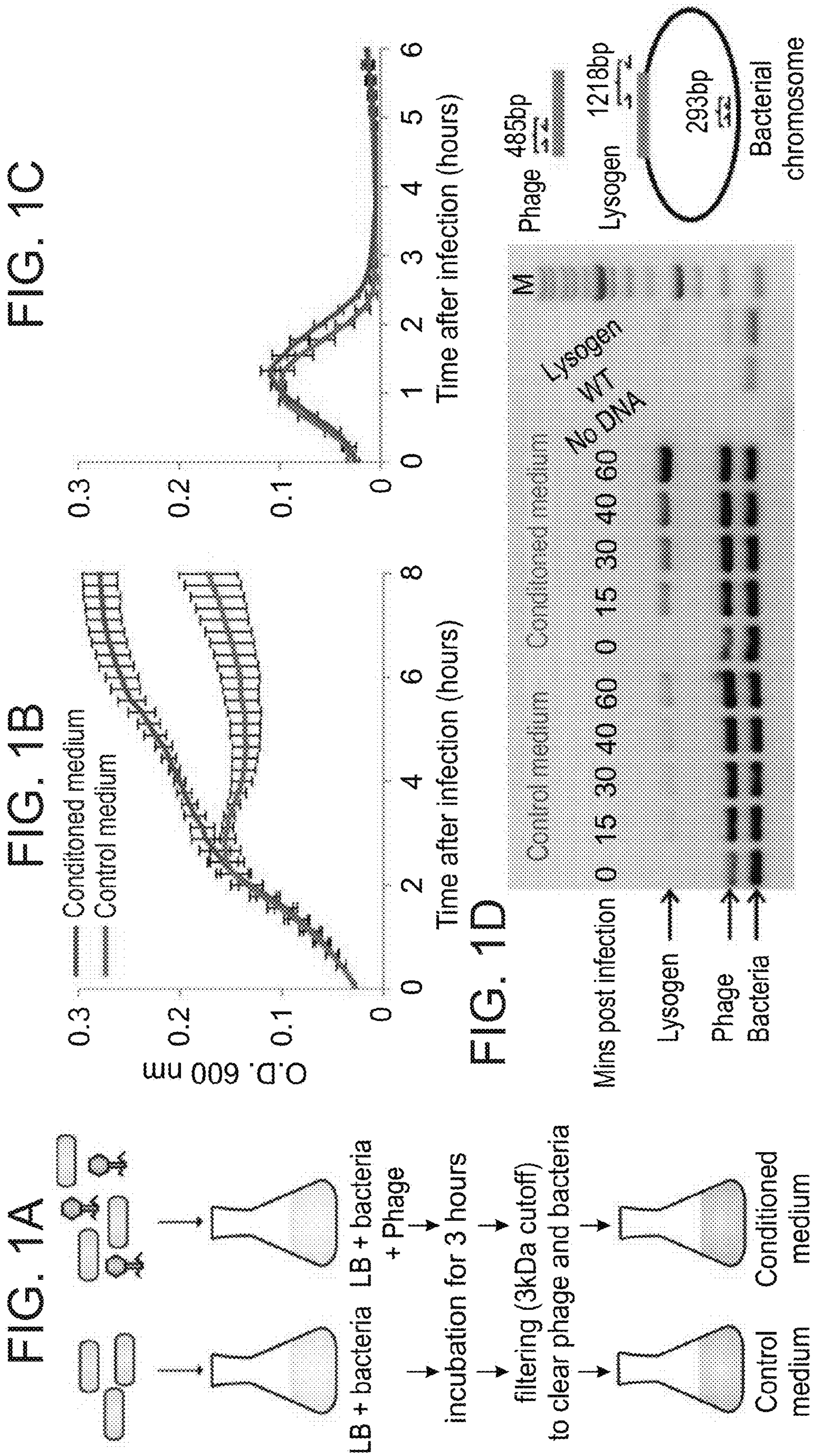
FIG. 1A
LB + bacteria
LB + bacteria + Phage
incubation for 3 hours
filtering (3kDa cutoff) to clear phage and bacteria
Control medium
Conditioned medium
FIG. 1B
Conditioned medium
Control medium
O.D. 600 nm
Time after infection (hours)
FIG. 1C
Time after infection (hours)
FIG. 1D
Mins post infection
Control medium
Conditioned medium
0 15 30 40 60 0 15 30 40 60
Lysogen
WT
No DNA
M
Lysogen
Phage
Bacteria
Phage 485bp
Lysogen 1218bp
293bp
Bacterial chromosome

FIG. 2B

| | Signal peptide | Pro - peptide | Mature peptide | |
|---|---|---|---|---|
| PhrA | MKSKWMSGLLLVAVGFSFTQVMVHA | GETANTEGKTFHIA | ARNQT | SEQ ID NO: 337,343,349 |
| PhrC | MKLKSKLFVICLAAAIFTAAGVASANA | EALDFHVT | ERGMT | SEQ ID NO: 338,344,350 |
| PhrF | MKLKSKLLLSCLALSTVGVATTIANA | PTHQIEVA | QRGMI | SEQ ID NO: 339,345,351 |
| PhrG | MKRFLIGAGVAAVILSGWFIA | DHQTHSQEMKVA | EKMIG | SEQ ID NO: 340,346,352 |
| Phr - pTA1060 | MKFKGLFSAVLIVSLLVGAGYSFV | HHDEVSVA | SRNAT | SEQ ID NO: 341,347,353 |
| AimP | MKKVFFGLVILTALAISFVAGQQSVSTASA | SDEVTVA | SAIRGA | SEQ ID NO: 342,348,269 |

FIG. 2C

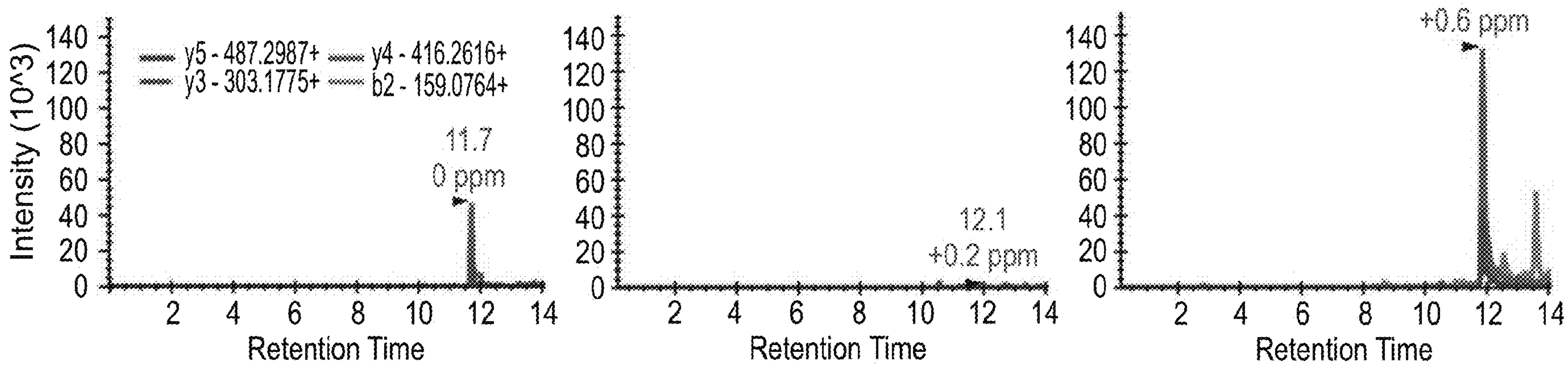

FIG. 4E
FIG. 4F
FIG. 4G
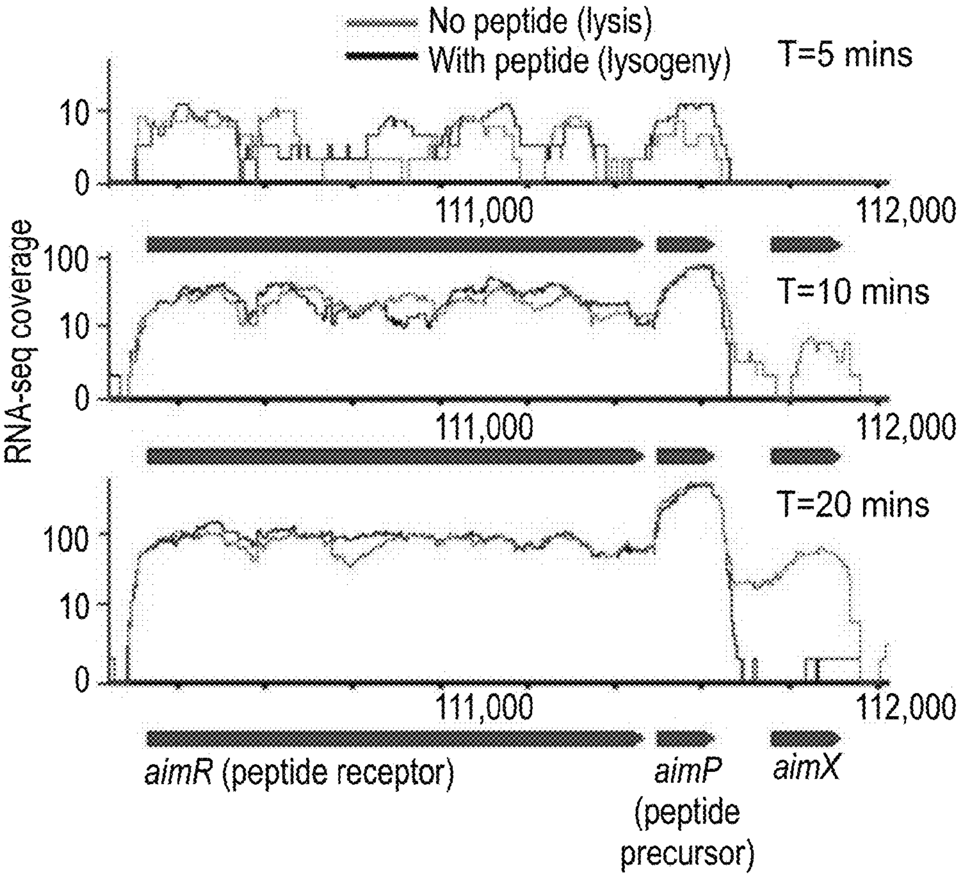
FIG. 4H
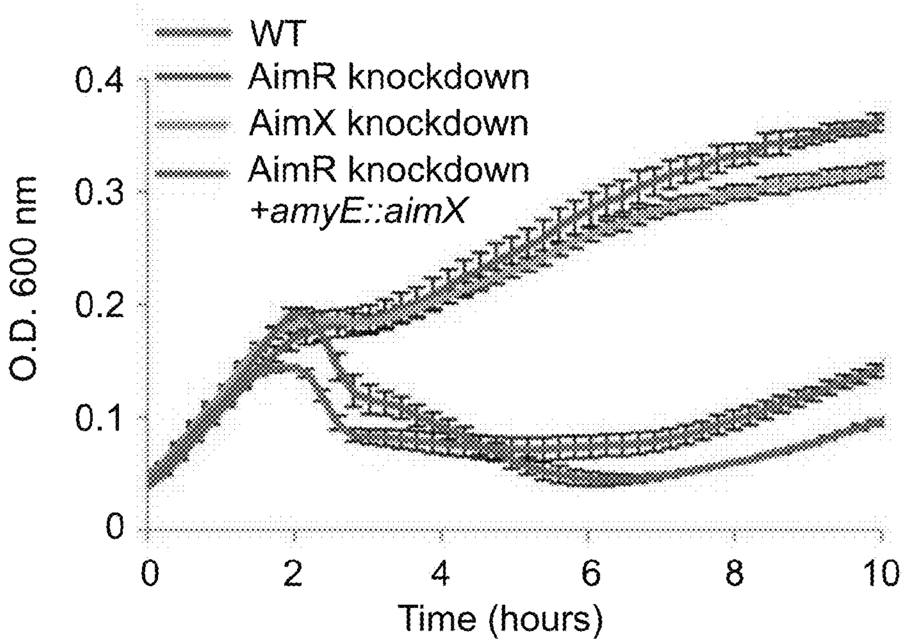

SEQUENCE LISTING

<160> NUMBER OF SEQ ID NOS: 378

<210> SEQ ID NO 1
<211> LENGTH: 1137
<212> TYPE: DNA
<213> ORGANISM: Bacteriophage phi-3T

<400> SEQUENCE: 1
atgattaaga atgaatgcga aaaggataat cagcttgcag ctcgacttgc aaaattggcc 60
ggttatgaaa aagtaaatgg tttttataag tttgtgaaca ccccagaaaa agaaatggaa 120
aacttgggtg gattactcaa gatcgtaaaa aacttgtttc ctgatagtga agagcaactt 180
ttaagtgaat acttcttaga attagaccct aataaaaaat gtgcaaggca atcagttgag 240
tactcagata taaaccaatg ggacacactt actgataaga ttatcattaa cttatgcaac 300
tcaaaaaatt ccacaagtca agagtgggga aaagtttaca gcttacatag aaaattaaac 360
aaaaacgaaa tcagtttaaa tgatgctatt agggaatcag ggaaatgtaa aataaaatcc 420
gcggaaatgc tcttcttttc aaatgcaatg ctgatgtatg cgtatttaaa cattggtgaa 480
tttggattaa tgaagagcac ttcaaaattg ttagaatttg atgatttacc cgaagggttc 540
attaaagagt cattcaaaag cagagtatct atgctcgaag cgaacataag cttaaatgaa 600
aatagcctac ttgaagcgag acagcattct aaccgcgcaa ttgaaaattc taacgtgaat 660
cgtatttgtt tttttgcata tttaacaatt ggcaacactt taatttttga ggattatgat 720
gaggccaaaa aggcgtacat taaaggtcaa aaatatgcta aaaatccagt gcaccaagaa 780
atgcttgatg gtgcgttgtg ctttttgtca aacatctgga aaaaagaaaa tcaatgggtg 840
aattataact ctgataacat taaatatttg caattaagag ctttttatta cataaatcaa 900
ggtaacattg aggaagccac ggaaatttta gatgaactgt catcaagaga tcaagatgag 960
aatgaattag gattctacta ttactacaaa ggattaatat ctcaggataa gacagactat 1020
tataaatcaa taagatattt caaaaaatca gatgataaat attttataca attgccatta 1080
cttcaactcg aacgaatggg ggctgatctt gaattattaa accttatctc tatttag 1137

<210> SEQ ID NO 2
<211> LENGTH: 1146
<212> TYPE: DNA
<213> ORGANISM: Bacillus amyloliquefaciens

<400> SEQUENCE: 2
atgaatctta agcagatgat taagaatgaa tgtgaaaaag acaaccagct cgcagcgaaa 60
ctctcaaaaa tagcagggta cgaaaaggtt aatggttttt acaaattcat caacacccca 120
gagaaagaaa tggacaactt aggcggttta attaatattg ttaaaagctt atttcctgat 180
aatgaagagc aacttctaag cgattatttt ttatcattgg atcccaataa aaaatgtgct 240
agacaatctg ttgaatatgc ggatttaaat cagtggaatg cattaactga taaaataatt 300
ttaaatttat gcaattcgaa aaatgcgaca agtaaagaat ggggtaagac ctataatata 360
catagaaagt taacagaaaa caagatatcc ttaactgaag caatcaggga aactggaaaa 420
tgcaaaacag cagaaatgat atttttctca aatgcaatgt taatgtatga atacctaaag 480
atcggtgaat ttggattaat gaaaagcaca gcaaaattgc tggattttca aggattatca 540
gacggttaca taaaaggttt atacacctcc agagtaagct tgttgaaagc taatataagc 600
ttcaatgaga acaatttaat tgaagcaaga aaatattgtt tatatgccac tgaaactacg 660
aacgtggata ggatttgttt ttttgcatat ttaacaatcg gaaactcttt catattcgaa 720
aattttgaag aggccaagcg atcatatatt aatggtgcta agtatgcaag caacacaatt 780
cataaagaga tgttagacgg agcattatgt tttcttgcaa gcttttggaa caaagagaat 840
ttatgggtga attatgaatc acagcacact aaatacttgc aattgagagc ataccatcat 900
atacgaaaag gcgaagttga taaagctaat gagattttaa atgagttatc aataagagaa 960
caagatgaga atgagatggg attttatttt tattatagag gtttaatatc tgtagataaa 1020
tctgattttt ataaatctat acgctgtttc aaaaaatcag atgacaaata ttcagttcaa 1080
ttgcccttga ttgaacttaa aaaaatgggc gcggacacag aactgttaag tcttatttca 1140
atttag 1146

<210> SEQ ID NO 3
<211> LENGTH: 1161
<212> TYPE: DNA
<213> ORGANISM: Bacillus subtilis

<400> SEQUENCE: 3
atggagttaa taaagatagc tatgaagaaa gacttggaaa atgacaactc tttaatgaat 60
aaatgggcaa cagtagctgg ccttaaaaac cccaatcctc tttatgactt cttaaaccat 120
gatgggaaaa cttttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggt 420
aaattaaata taaaaacacc tgaaatgaat tctttctcaa gacttttgct gctttatcat 480
tatttaagca ctggtaactt ttctccgatg gcccaactta taaaacaaat tgacctaagt 540
gagatttctg agaacatgta cattagaaat acatatcaaa caagagctca tgttctaatg 600
tctaatataa agctaaatga aaattcatta gaggagtgca gagagtactc taaaaaggca 660
ttggaaagta caaatatcct gagatttcag gttttcagct acttaactat tggcaactct 720
ctattatttt cgaattatga attggctcaa gaaaactttt taaaagggct aagcgtttct 780
gttcaaaatg aaaattacaa catgattttc caacaggctt tgtgcttctt aaataatgta 840
tggcgcaaag aaaataagtg gattaatttt gaatctgagt caattatgga tttgcaggag 900
caagctcatt gttttatcaa ctttaatgaa aattccaaag caaaagaagt tttggataaa 960
ctagatcttt tagttcacaa cgataatgag cttgcaatgc attattattt gaaaggaaga 1020
ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 4
<211> LENGTH: 1161
<212> TYPE: DNA
<213> ORGANISM: bacteriophage SP-beta

<400> SEQUENCE: 4
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180

-continued

```
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagcaatatg aaaagtaaag aatatggaaa agtgtataaa    360
atacatagag aactgtctaa cagtgttatt actgaatttg aggcagtgaa aagactcggc    420
aaattaaata taaaaacacc tgaaatgaat tctttctcaa gactcttgct gctttatcat    480
tatttaagca ctggtaactt ttctccgatg gcccaactta taaaacaaat tgacctaagt    540
gagatttctg agaacatgta cattagaaat acatatcaaa caagagttca tgttctaatg    600
tctaatataa agttaaatga aaattcatta gaggagtgca gagagtactc taaaaaggca    660
ttggaaagta caaatatcct gagatttcag gttttcagct acttaactat tggcaactct    720
ctattatttt cgaattatga attggctcaa gaaaactttt taaaagggct aagcatttct    780
gttcaaaatg aaaattacaa catgattttc cagcaggctt tgtgcttctt aaataatgta    840
tggcgcaaag aaaataagtg gattaatttt gaatctgatt caattatgga tttgcaggag    900
caagctcatt gttttatcaa ctttaatgaa aattccaaag caaaagaagt tttggataaa    960
ctagatcttt tagttcacaa cgataatgag cttgcaatgc attattattt gaaaggaaga   1020
ctcgaacaaa ataaagcatg tttctattct tcaatcgagt attttaaaaa gtctaatgac   1080
aaattcctta ttaggctgcc actgttagaa ctgcaaaaga tgggtgaaaa tcaaaaactt   1140
ttagaattac ttttacttta a                                             1161
```

<210> SEQ ID NO 5
<211> LENGTH: 1161
<212> TYPE: DNA
<213> ORGANISM: Bacillus subtilis

<400> SEQUENCE: 5

```
atggagttaa taaggatagc tatgaagaaa gacttggaaa atgacaactc tttaatgaat     60
aaatgggcaa cagtagctgg ccttaaaaac cccaatcctc tttatgactt cttaaaccat    120
gatgggaaaa catttaatga attttcttca atagtcaaca ttgttaagag tcagtatcca    180
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagcaatatg aaaagtaaag aatatggaaa agtgtataaa    360
atacatagag aactgtctaa cagtgttatt actgaatttg aggcagtgaa aagactcggc    420
aaattaaata taaaaacacc tgaaatgaat tctttctcaa gactcttgct gctttatcat    480
tatttaagca ctggtaactt ttctccgatg gcccaactta taaaacaaat tgacctaagt    540
gagatttctg agaacatgta cattagaaat acatatcaaa caagagttca tgttctaatg    600
tctaatataa agttaaatga aaattcatta gaggagtgca gagagtactc taaaaaggca    660
ttggaaagta caaatatcct gagatttcag gttttcagct acttaactat tggcaactct    720
ctattatttt cgaattatga attggctcaa gaaaactttt taaaagggct aagcatttct    780
gttcaaaatg aaaattacaa catgattttc cagcaggctt tgtgcttctt aaataatgta    840
tggcgcaaag aaaataagtg gattaatttt gaatctgatt caattatgga tttgcaggag    900
caagctcatt gttttatcaa ctttaatgaa aattccaaag caaaagaagt tttggataaa    960
ctagatcttt tagttcacaa cgataatgag cttgcaatgc attattattt gaaaggaaga   1020
ctcgaacaaa ataaagcatg tttctattct tcaatcgagt attttaaaaa gtctaatgac   1080
aaattcctta ttaggctgcc actgttagaa ctgcaaaaga tgggtgaaaa tcaaaaactt   1140
```

ttagaattac ttttacttta a 1161

<210> SEQ ID NO 6
<211> LENGTH: 1161
<212> TYPE: DNA
<213> ORGANISM: Bacillus subtilis

<400> SEQUENCE: 6
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgttttaacc tagatgttaa gacaaaggca 240
gctagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600
tctaatataa agttaaatga aaattcatta gaggagtgca gagagtactc taaaaaggca 660
ttggaaagta caaatatcct gagatttcag gttttcagct acttaactat tggcaactct 720
ctattatttt cgaattatga attggctcaa gaaaactttt taaaagggct aagcgtttct 780
gttcaaaatg aaaattacaa catgattttc cagcaggctt tgtgcttctt aaataatgta 840
tggcgcaaag aaaataagtg gattaatttt gaagctgatt caattatgga tttgcaggag 900
caagctcatt gttttatcaa ctttaatgaa aattccaaag caaaagaagt tttggataaa 960
ctagatcttt tagttcacaa cgataatgag cttgcaatgc attattattt gaaaggaaga 1020
ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 7
<211> LENGTH: 1161
<212> TYPE: DNA
<213> ORGANISM: Bacillus subtilis

<400> SEQUENCE: 7
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag agctgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaac acatatcaaa caagagttca tgttctaatg 600

```
tcgaatataa agctaaatga aaattcatta gaggagtgca gagagtactc taaaaaggca    660

ttggaaagta caaatatcct cagatttcag gttttcagct acttaactat tggcaactct    720

ctattatttt cgaattatga attggctcaa gaaaactttt taaaagggct aagcgtttct    780

gttcaaaatg aaaattacaa catgattttc cagcaggctt tgtgcttctt aaataatgta    840

tggcgcaaag aaaataagtg gattaatttt gaatctgagt caattatgga tttgcaggag    900

caagcccatt gttttatcaa ctttaatgaa aattccaaag caaaaaaagt tttggataaa    960

ctagatcttt tacgtcataa cgataatgag cttgcaatgc atcattattt gaaagggaga   1020

ctcgaacaaa ataaagcatg tttctattct tcaatcgagt attttaaaaa gtctaatgac   1080

aaattcctta ttaggctgcc gttgttagaa ctgcaaaaga tgggtgaaaa tcaaaaactt   1140

ttagaattac ttttacttta a                                              1161
```

<210> SEQ ID NO 8
<211> LENGTH: 1161
<212> TYPE: DNA
<213> ORGANISM: Bacillus subtilis

<400> SEQUENCE: 8

```
atggagttaa taaggatagc tatgaagaaa gacttggaaa atgacaactc tttaatgaat     60

aaatgggcaa cagtagctgg ccttaaaaac cccaatcctc tttatgactt cttaaaccat    120

gatgggaaaa catttaatga atttttcttca atagtcaaca ttgttaagag tcagtatcca    180

gaccgtgaat atgaattaat gaaagattac tgtttaaacc tagatgttaa gacaaaggca    240

gcaagaagtg cattggagta tgctgatgca aatatgtttt ttgaaataga agatgtttta    300

atagattcaa tgatttcttg cagcaatatg aaaagtaaag aatatggaaa agtgtataaa    360

atacatagag aactgtctaa cagtgttatt actgaatttg aggcagtgaa aagactcggc    420

aaattaaata taaaaacacc tgaaatgaat tctttctcaa gactcttgct gctttatcat    480

tatttaagca ctggtaactt ttctccgatg gcccaactta taaaacaaat tgacctaagt    540

gagatttctg agaacatgta cattagaaat acatatcaaa caagagttca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                              1161
```

<210> SEQ ID NO 9
<211> LENGTH: 1161
<212> TYPE: DNA
<213> ORGANISM: Bacillus subtilis

<400> SEQUENCE: 9

```
atggagttaa taaggatagc tatgaagaaa gacttggaaa atgacaactc tttaatgaat     60

aaatgggcaa cagtagctgg ccttaaaaac cccaatcctc tttatgactt cttaaaccat    120
```

-continued

```
gatgggaaaa catttaatga attttcttca atagtcaaca ttgttaagag tcagtatcca    180

gaccgtgaat atgaattaat gaaagattac tgtttaaacc tagatgttaa gacaaaggca    240

gcaagaagtg cattggagta tgctgatgca aatatgtttt ttgaaataga agatgtttta    300

atagattcaa tgatttcttg cagcaatatg aaaagtaaag aatatggaaa agtgtataaa    360

atacatagag aactgtctaa cagtgttatt actgaatttg aggcagtgaa aagactcggc    420

aaattaaata taaaaacacc tgaaatgaat tctttctcaa gactcttgct gctttatcat    480

tatttaagca ctggtaactt ttctccgatg gcccaactta taaaacaaat tgacctaagt    540

gagatttctg agaacatgta cattagaaat acatatcaaa caagagttca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                              1161
```

<210> SEQ ID NO 10
<211> LENGTH: 963
<212> TYPE: DNA
<213> ORGANISM: Bacillus amyloliquefaciens

<400> SEQUENCE: 10

```
atgatagcaa aagagagaga agctaagaaa ccagaagtag atgcaaaggt acgtcttgaa     60

atgtcagata ttaatgaaca gtatgaacaa actgacgcat taattgatca attaatcaac    120

agtagctgtt cgattgaacg tgaatgggca gcaatgtatc agatcaaacg taagcaagac    180

agaggcgaaa taaacgcaca tcaggcgctt aaagcaattg ggaagcttga tcccaagtct    240

caagaaatgc gtgtattcac ttacataatt ccgttgtatt actaccttag aatggctgaa    300

tactcaaatc ttgcagaaat gtcgacagtt gttgatcttg attttattga aaacaatgaa    360

cagattaaaa gctcctttta taaccgtctg atggctttgt tggcgcttc agcattcagt    420

cagaataaaa tgactcaagc tcgtttttat tgctcatacg gcattaatgt aacgaatatt    480

gataggcttg tcgcttatag ctatctaact ttgggtaaca cttatttgct tgatgattat    540

gaaaaagcaa aagaatatta cctggccggt ttaaaacata ctgagaataa ccccttggca    600

aaattacagc taactagaag cctttgtttc ttggaaaacc attggaatca agagaacttt    660

tggctaaacc ctgattcaaa tgaagttaca gatatccaag aaattgcaca ttatcacatc    720

aaaaaaaaca acttgcaaca ggctaaagaa atattggaga acttagagca gcaaccgaat    780

attcataatg actttggcat tcatttttat ctaaaaggac tagcttatga agataagaga    840

ttcttttatg agtctataaa acactttaag ctgtccggcg atctatacag cgtacgctta    900

cctttggata aattaaggga aatgggtgag gacgagcaga ttttggattt acttgccctt    960

taa                                                                  963
```

-continued

<210> SEQ ID NO 11
<211> LENGTH: 1161
<212> TYPE: DNA
<213> ORGANISM: Bacillus subtilis

<400> SEQUENCE: 11
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgttttaacc tagatgttaa gacaaaggca 240
gctagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600
tctaatataa agttaaatga aaattcatta gaggagtgca gagagtactc taaaaaggca 660
ttggaaagta caaatatcct gagatttcag gttttcagct acttaactat tggcaactct 720
ctattatttt cgaattatga attggctcaa gaaaactttt taaaagggct aagcgtttct 780
gttcaaaatg aaaattacaa catgattttc cagcaggctt tgtgcttctt aaataatgta 840
tggcgcaaag aaaataagtg gattaatttt gaagctgatt caattatgga tttgcaggag 900
caagctcatt gttttatcaa ctttaatgaa aattccaaag caaaagaagt tttggataaa 960
ctagatcttt tagttcacaa cgataatgag cttgcaatgc attattattt gaaaggaaga 1020
ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 12
<211> LENGTH: 1161
<212> TYPE: DNA
<213> ORGANISM: Bacillus murimartini

<400> SEQUENCE: 12
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600
tctaatataa agttaaatga aaattcatta gaggagtgca gagagtactc taaaaaggca 660
ttggaaagta caaatatcct gagatttcag gttttcagct acttaactat tggcaactct 720

```
ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                             1161
```

<210> SEQ ID NO 13
<211> LENGTH: 1161
<212> TYPE: DNA
<213> ORGANISM: Bacillus subtilis

<400> SEQUENCE: 13

```
atggagttaa taaggatagc tatgaagaaa gacttggaaa atgacaactc tttaatgaat     60

aaatgggcaa cagtagctgg ccttaaaaac cccaatcctc tttatgactt cttaaaccat    120

gatgggaaaa catttaatga attttcttca atagtcaaca ttgttaagag tcagtatcca    180

gaccgtgaat atgaattaat gaaagattac tgtttaaacc tagatgttaa gacaaaggca    240

gcaagaagtg cattggagta tgctgatgca aatatgtttt ttgaaataga agatgtttta    300

atagattcaa tgatttcttg cagcaatatg aaaagtaaag aatatggaaa agtgtataaa    360

atacatagag aactgtctaa cagtgttatt actgaatttg aggcagtgaa aagactcggc    420

aaattaaata taaaaacacc tgaaatgaat tctttctcaa gactcttgct gctttatcat    480

tatttaagca ctggtaactt ttctccgatg gcccaactta taaaacaaat tgacctaagt    540

gagatttctg agaacatgta cattagaaat acatatcaaa caagagttca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                             1161
```

<210> SEQ ID NO 14
<211> LENGTH: 1161
<212> TYPE: DNA
<213> ORGANISM: Bacillus subtilis

<400> SEQUENCE: 14

```
atggagttaa taaggatagc tatgaagaaa gacttggaaa atgacaactc tttaatgaat     60

aaatgggcaa cagtagctgg ccttaaaaac cccaatcctc tttatgactt cttaaaccat    120

gatgggaaaa catttaatga attttcttca atagtcaaca ttgttaagag tcagtatcca    180
```

```
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagcaatatg aaaagtaaag aatatggaaa agtgtataaa    360
atacatagag aactgtctaa cagtgttatt actgaatttg aggcagtgaa aagactcggc    420
aaattaaata taaaaacacc tgaaatgaat tctttctcaa gactcttgct gctttatcat    480
tatttaagca ctggtaactt ttctccgatg gcccaactta taaaacaaat tgacctaagt    540
gagatttctg agaacatgta cattagaaat acatatcaaa caagagttca tgttctaatg    600
tctaatataa agttaaatga aaattcatta gaggagtgca gagagtactc taaaaaggca    660
ttggaaagta caaatatcct gagatttcag gttttcagct acttaactat tggcaactct    720
ctattatttt cgaattatga attggctcaa gaaaactttt taaaagggct aagcatttct    780
gttcaaaatg aaaattacaa catgattttc cagcaggctt tgtgcttctt aaataatgta    840
tggcgcaaag aaaataagtg gattaatttt gaatctgatt caattatgga tttgcaggag    900
caagctcatt gttttatcaa ctttaatgaa aattccaaag caaaagaagt tttggataaa    960
ctagatcttt tagttcacaa cgataatgag cttgcaatgc attattattt gaaaggaaga   1020
ctcgaacaaa ataaagcatg tttctattct tcaatcgagt attttaaaaa gtctaatgac   1080
aaattcctta ttaggctgcc actgttagaa ctgcaaaaga tgggtgaaaa tcaaaaactt   1140
ttagaattac ttttacttta a                                              1161
```

<210> SEQ ID NO 15
<211> LENGTH: 1161
<212> TYPE: DNA
<213> ORGANISM: Bacillus subtilis

<400> SEQUENCE: 15

```
atggagttaa taaggatagc tatgaagaaa gacttggaaa atgacaactc tttaatgaat     60
aaatgggcaa cagtagctgg ccttaaaaac cccaatcctc tttatgactt cttaaaccat    120
gatgggaaaa catttaatga attttcttca atagtcaaca ttgttaagag tcagtatcca    180
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagcaatatg aaaagtaaag aatatggaaa agtgtataaa    360
atacatagag aactgtctaa cagtgttatt actgaatttg aggcagtgaa aagactcggc    420
aaattaaata taaaaacacc tgaaatgaat tctttctcaa gactcttgct gctttatcat    480
tatttaagca ctggtaactt ttctccgatg gcccaactta taaaacaaat tgacctaagt    540
gagatttctg agaacatgta cattagaaat acatatcaaa caagagttca tgttctaatg    600
tctaatataa agttaaatga aaattcatta gaggagtgca gagagtactc taaaaaggca    660
ttggaaagta caaatatcct gagatttcag gttttcagct acttaactat tggcaactct    720
ctattatttt cgaattatga attggctcaa gaaaactttt taaaagggct aagcatttct    780
gttcaaaatg aaaattacaa catgattttc cagcaggctt tgtgcttctt aaataatgta    840
tggcgcaaag aaaataagtg gattaatttt gaatctgatt caattatgga tttgcaggag    900
caagctcatt gttttatcaa ctttaatgaa aattccaaag caaaagaagt tttggataaa    960
ctagatcttt tagttcacaa cgataatgag cttgcaatgc attattattt gaaaggaaga   1020
ctcgaacaaa ataaagcatg tttctattct tcaatcgagt attttaaaaa gtctaatgac   1080
aaattcctta ttaggctgcc actgttagaa ctgcaaaaga tgggtgaaaa tcaaaaactt   1140
```

ttagaattac ttttacttta a 1161

<210> SEQ ID NO 16
<211> LENGTH: 1161
<212> TYPE: DNA
<213> ORGANISM: Bacillus subtilis

<400> SEQUENCE: 16
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600
tctaatataa agttaaatga aaattcatta gaggagtgca gagagtactc taaaaaggca 660
ttggaaagta caaatatcct gagatttcag gttttcagct acttaactat tggcaactct 720
ctattatttt cgaattatga attggctcaa gaaaactttt taaaagggct aagcatttct 780
gttcaaaatg aaaattacaa catgattttc cagcaggctt tgtgcttctt aaataatgta 840
tggcgcaaag aaaataagtg gattaatttt gaatctgatt caattatgga tttgcaggag 900
caagctcatt gttttatcaa ctttaatgaa aattccaaag caaaagaagt tttggataaa 960
ctagatcttt tagttcacaa cgataatgag cttgcaatgc attattattt gaaaggaaga 1020
ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 17
<211> LENGTH: 1140
<212> TYPE: DNA
<213> ORGANISM: Bacillus subtilis

<400> SEQUENCE: 17
atgaagaaag acttggaaaa tgacaactct ttaatgaata aatgggcaac agtagctggc 60
cttaaaaacc ccaatcctct ttatgacttc ttaaaccatg atgggaaaac atttaatgaa 120
ttttcttcaa tagtcaacat tgttaagagt cagtatccag accgtgaata tgaattaatg 180
aaagattact gtttaaacct agatgttaag acaaaggcag caagaagtgc attggagtat 240
gctgatgcaa atatgttttt tgaaatagaa gatgttttaa tagattcaat gatttcttgc 300
agcaatatga aaagtaaaga atatggaaaa gtgtataaaa tacatagaga actgtctaac 360
agtgttatta ctgaatttga ggcagtgaaa agactcggca aattaaatat aaaaacacct 420
gaaatgaatt ctttctcaag actcttgctg ctttatcatt atttaagcac tggtaacttt 480
tctccgatgg cccaacttat aaaacaaatt gacctaagtg agatttctga gaacatgtac 540
attagaaata catatcaaac aagagttcat gttctaatgt ctaatataaa gttaaatgaa 600

-continued aattcattag aggagtgcag agagtactct aaaaaggcat tggaaagtac aaatatcctg 660
agatttcagg ttttcagcta cttaactatt ggcaactctc tattattttc gaattatgaa 720
ttggctcaag aaaacttttt aaaagggcta agcatttctg ttcaaaatga aaattacaac 780
atgattttcc agcaggcttt gtgcttctta aataatgtat ggcgcaaaga aaataagtgg 840
attaattttg aatctgattc aattatggat ttgcaggagc aagctcattg ttttatcaac 900
tttaatgaaa attccaaagc aaaagaagtt ttggataaac tagatctttt agttcacaac 960
gataatgagc ttgcaatgca ttattatttg aaaggaagac tcgaacaaaa taaagcatgt 1020
ttctattctt caatcgagta ttttaaaaag tctaatgaca aattccttat taggctgcca 1080
ctgttagaac tgcaaaagat gggtgaaaat caaaaacttt tagaattact tttactttaa 1140

<210> SEQ ID NO 18
<211> LENGTH: 1161
<212> TYPE: DNA
<213> ORGANISM: Bacillus subtilis

<400> SEQUENCE: 18
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600
tctaatataa agttaaatga aaattcatta gaggagtgca gagagtactc taaaaaggca 660
ttggaaagta caaatatcct gagatttcag gttttcagct acttaactat tggcaactct 720
ctattatttt cgaattatga attggctcaa gaaaactttt taaaagggct aagcatttct 780
gttcaaaatg aaaattacaa catgattttc cagcaggctt tgtgcttctt aaataatgta 840
tggcgcaaag aaaataagtg gattaatttt gaatctgatt caattatgga tttgcaggag 900
caagctcatt gttttatcaa ctttaatgaa aattccaaag caaaagaagt tttggataaa 960
ctagatcttt tagttcacaa cgataatgag cttgcaatgc attattattt gaaaggaaga 1020
ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 19
<211> LENGTH: 1161
<212> TYPE: DNA
<213> ORGANISM: Bacillus subtilis

<400> SEQUENCE: 19
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180

-continued

```
gaccgtgaat atgaattaat gaaagattac tgttttaacc tagatgttaa gacaaaggca    240

gctagaagtg cattggagta tgctgatgca aatatgtttt ttgaaataga agatgtttta    300

atagattcaa tgatttcttg cagcaatatg aaaagtaaag aatatggaaa agtgtataaa    360

atacatagag aactgtctaa cagtgttatt actgaatttg aggcagtgaa aagactcggc    420

aaattaaata taaaaacacc tgaaatgaat tctttctcaa gactcttgct gctttatcat    480

tatttaagca ctggtaactt ttctccgatg gcccaactta taaaacaaat tgacctaagt    540

gagatttctg agaacatgta cattagaaat acatatcaaa caagagttca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcgtttct    780

gttcaaaatg aaaattacaa catgattttc cagcaggctt tgtgcttctt aaataatgta    840

tggcgcaaag aaaataagtg gattaatttt gaagctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                              1161
```

<210> SEQ ID NO 20
<211> LENGTH: 1161
<212> TYPE: DNA
<213> ORGANISM: Bacillus subtilis

<400> SEQUENCE: 20

```
atggagttaa taaggatagc tatgaagaaa gacttggaaa atgacaactc tttaatgaat     60

aaatgggcaa cagtagctgg ccttaaaaac cccaatcctc tttatgactt cttaaaccat    120

gatgggaaaa catttaatga attttcttca atagtcaaca ttgttaagag tcagtatcca    180

gaccgtgaat atgaattaat gaaagattac tgtttaaacc tagatgttaa gacaaaggca    240

gcaagaagtg cattggagta tgctgatgca aatatgtttt ttgaaataga agatgtttta    300

atagattcaa tgatttcttg cagcaatatg aaaagtaaag aatatggaaa agtgtataaa    360

atacatagag aactgtctaa cagtgttatt actgaatttg aggcagtgaa aagactcggc    420

aaattaaata taaaaacacc tgaaatgaat tctttctcaa gactcttgct gctttatcat    480

tatttaagca ctggtaactt ttctccgatg gcccaactta taaaacaaat tgacctaagt    540

gagatttctg agaacatgta cattagaaat acatatcaaa caagagttca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080
```

aaattcctta ttaggctgcc actgttagaa ctgcaaaaga tgggtgaaaa tcaaaaactt 1140
ttagaattac ttttacttta a 1161

<210> SEQ ID NO 21
<211> LENGTH: 1161
<212> TYPE: DNA
<213> ORGANISM: Bacillus subtilis

<400> SEQUENCE: 21
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600
tctaatataa agttaaatga aaattcatta gaggagtgca gagagtactc gaaaaaggca 660
ttggaaagta caaatatcct gagatttcag gttttcagct acttaactat tggcaactct 720
ctattatttt cgaattatga attggctcaa gaaaactttt taaaagggct aagcgtttct 780
gttcaaaatg aaaattacaa catgattttc cagcaggctt tgtgcttctt aaataatgta 840
tggcgcaaag aaaataagtg gattaatttt gaatctgatt caattatgga tttgcaggag 900
caagcccatt gttttatcaa ctttaatgaa aattccaaag caaaagaagt tttggataaa 960
ctagatcttt tagttcacaa cgataatgag cttgcaatgc attattattt gaaaggaaga 1020
ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 22
<211> LENGTH: 1161
<212> TYPE: DNA
<213> ORGANISM: Bacillus subtilis

<400> SEQUENCE: 22
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtaaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600

```
tctaatataa agttaaatga aaattcatta gaggagtgca gagagtactc gaaaaaggca    660

ttggaaagta caaatatcct gagatttcag gttttcagct acttaactat tggcaactct    720

ctattatttt cgaattatga attggctcaa gaaaactttt taaaagggct aagcgtttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagcccatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                              1161
```

```
<210> SEQ ID NO 23
<211> LENGTH: 1161
<212> TYPE: DNA
<213> ORGANISM: Bacillus subtilis

<400> SEQUENCE: 23

atggagttaa taaggatagc tatgaagaaa gacttggaaa atgacaactc tttaatgaat     60

aaatgggcaa cagtagctgg ccttaaaaac cccaatcctc tttatgactt cttaaaccat    120

gatgggaaaa catttaatga attttcttca atagtcaaca ttgttaagag tcagtatcca    180

gaccgtgaat atgaattaat gaaagattac tgtttaaacc tagatgttaa gacaaaggca    240

gcaagaagtg cattggagta tgctgatgca aatatgtttt ttgaaataga agatgtttta    300

atagattcaa tgatttcttg cagcaatatg aaaagtaaag aatatggaaa agtgtataaa    360

atacatagag aactgtctaa cagtgttatt actgaatttg aggcagtgaa aagactcggc    420

aaattaaata taaaaacacc tgaaatgaat tctttctcaa gactcttgct gctttatcat    480

tatttaagca ctggtaactt ttctccgatg gcccaactta taaaacaaat tgacctaagt    540

gagatttctg agaacatgta cattagaaat acatatcaaa caagagttca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                              1161
```

```
<210> SEQ ID NO 24
<211> LENGTH: 1161
<212> TYPE: DNA
<213> ORGANISM: Bacillus subtilis

<400> SEQUENCE: 24

atggagttaa taaagatagc tatgaagaaa gacttggaaa atgacaactc tttaatgaat     60
```

-continued

```
aaatgggcaa cagtagctgg ccttaaaaac cccaatcctc tttatgactt cttaaaccat    120
gatgggaaaa cttttaatga attttcttca atagtcaaca ttgttaagag tcagtatcca    180
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagcaatatg aaaagtaaag aatatggaaa agtgtataaa    360
atacatagag aactgtctaa cagtgttatt actgaatttg aggcagtgaa aagactcggt    420
aaattaaata taaaaacacc tgaaatgaat tctttctcaa gacttttgct gctttatcat    480
tatttaagca ctggtaactt ttctccgatg gcccaactta taaaacaaat tgacctaagt    540
gagatttctg agaacatgta cattagaaat acatatcaaa caagagttca tgttctaatg    600
tctaatataa agctaaatga aaattcatta gaggagtgca gagagtactc taaaaaggca    660
ttggaaagta caaatatcct gagatttcag gttttcagct acttaactat tggcaactct    720
ctattatttt cgaattatga attggctcaa gaaaactttt taaaagggct aagcgtttct    780
gttcaaaatg aaaattacaa catgattttc caacaggctt tgtgcttctt aaataatgta    840
tggcgcaaag aaaataagtg gattaatttt gaatctgagt caattatgga tttgcaggag    900
caagctcatt gttttatcaa ctttaatgaa aattccaaag caaaagaagt tttggataaa    960
ctagatcttt tagttcacaa cgataatgag cttgcaatgc attattattt gaaaggaaga   1020
ctcgaacaaa ataaagcatg tttctattct tcaatcgagt attttaaaaa gtctaatgac   1080
aaattcctta ttaggctgcc actgttagaa ctgcaaaaga tgggtgaaaa tcaaaaactt   1140
ttagaattac ttttacttta a                                              1161
```

<210> SEQ ID NO 25
<211> LENGTH: 1161
<212> TYPE: DNA
<213> ORGANISM: Bacillus subtilis

<400> SEQUENCE: 25

```
atggagttaa taaagatagc tatgaagaaa gacttggaaa atgacaactc tttaatgaat     60
aaatgggcaa cagtagctgg ccttaaaaac cccaatcctc tttatgactt cttaaaccat    120
gatgggaaaa cttttaatga attttcttca atagtcaaca ttgttaagag tcagtatcca    180
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagcaatatg aaaagtaaag aatatggaaa agtgtataaa    360
atacatagag aactgtctaa cagtgttatt actgaatttg aggcagtgaa aagactcggt    420
aaattaaata taaaaacacc tgaaatgaat tctttctcaa gacttttgct gctttatcat    480
tatttaagca ctggtaactt ttctccgatg gcccaactta taaaacaaat tgacctaagt    540
gagatttctg agaacatgta cattagaaat acatatcaaa caagagctca tgttctaatg    600
tctaatataa agctaaatga aaattcatta gaggagtgca gagagtactc taaaaaggca    660
ttggaaagta caaatatcct gagatttcag gttttcagct acttaactat tggcaactct    720
ctattatttt cgaattatga attggctcaa gaaaactttt taaaagggct aagcgtttct    780
gttcaaaatg aaaattacaa catgattttc caacaggctt tgtgcttctt aaataatgta    840
tggcgcaaag aaaataagtg gattaatttt gaatctgagt caattatgga tttgcaggag    900
caagctcatt gttttatcaa ctttaatgaa aattccaaag caaaagaagt tttggataaa    960
ctagatcttt tagttcacaa cgataatgag cttgcaatgc attattattt gaaaggaaga   1020
```

ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 26
<211> LENGTH: 1161
<212> TYPE: DNA
<213> ORGANISM: Bacillus subtilis

<400> SEQUENCE: 26
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600
tctaatataa agttaaatga aaattcatta gaggagtgca gagagtactc taaaaaggca 660
ttggaaagta caaatatcct gagatttcag gttttcagct acttaactat tggcaactct 720
ctattatttt cgaattatga attggctcaa gaaaactttt taaaagggct aagcatttct 780
gttcaaaatg aaaattacaa catgattttc cagcaggctt tgtgcttctt aaataatgta 840
tggcgcaaag aaaataagtg gattaatttt gaatctgatt caattatgga tttgcaggag 900
caagctcatt gttttatcaa ctttaatgaa aattccaaag caaaagaagt tttggataaa 960
ctagatcttt tagttcacaa cgataatgag cttgcaatgc attattattt gaaaggaaga 1020
ctcgaacaaa ataaagcatg tttctattct tcaatcgagt attttaaaaa gtctaatgac 1080
aaattcctta ttaggctgcc actgttagaa ctgcaaaaga tgggtgaaaa tcaaaaactt 1140
ttagaattac ttttacttta a 1161

<210> SEQ ID NO 27
<211> LENGTH: 1161
<212> TYPE: DNA
<213> ORGANISM: Bacillus subtilis

<400> SEQUENCE: 27
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480

-continued

```
tatttaagca ctggtaactt ttctccgatg gcccaactta taaaacaaat tgacctaagt    540

gagatttctg agaacatgta cattagaaat acatatcaaa caagagttca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                             1161
```

<210> SEQ ID NO 28
<211> LENGTH: 1161
<212> TYPE: DNA
<213> ORGANISM: Bacillus subtilis

<400> SEQUENCE: 28

```
atggagttaa taaggatagc tatgaagaaa gacttggaaa atgacaactc tttaatgaat     60

aaatgggcaa cagtagctgg ccttaaaaac cccaatcctc tttatgactt cttaaaccat    120

gatgggaaaa catttaatga attttcttca atagtcaaca ttgttaagag tcagtatcca    180

gaccgtgaat atgaattaat gaaagattac tgtttaaacc tagatgttaa gacaaaggca    240

gcaagaagtg cattggagta tgcggatgca aatatgtttt ttgaaataga agatgtttta    300

atagattcaa tgatttcttg cagcaatatg aaaagtaaag aatatggaaa agtgtataaa    360

atacatagag aactgtctaa cagtgttatt actgaatttg aggcagtgaa aagactcggc    420

aaattaaata taaaaacacc tgaaatgaat tctttctcaa gactcttgct gctttatcat    480

tatttaagca ctggtaactt ttctccgatg gcccaactta taaaacaaat tgacctaagt    540

gagatttctg agaacatgta cattagaaat acatatcaaa caagagtcca tgttctaatg    600

tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcgtttct    780

gttcaaaatg aaaattacaa catgattttc cagcaggctt tgtgcttctt aaataatgta    840

tggcgtaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                             1161
```

<210> SEQ ID NO 29
<211> LENGTH: 1161
<212> TYPE: DNA
<213> ORGANISM: Bacillus subtilis

<400> SEQUENCE: 29

```
atggagttaa taaggatagc tatgaagaaa gacttggaaa atgacaactc tttaatgaat     60
aaatgggcaa cagtagctgg ccttaaaaac cccaatcctc tttatgactt cttaaaccat    120
gatgggaaaa catttaatga atttcttca atagtcaaca ttgttaaaag tcagtatcca    180
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagtaatatg aaaagtaaag aatatggaaa agtgtataaa    360
atacatagag aactgtctaa ctgtgatatt actgaatttg aggcagtgaa aagactcggt    420
aaattaaata ttaaaacacc tgaaatgaat tctttctcaa gactcttgct gctttatcat    480
tatttaagca ctggtaactt ttctccgatg ccccaactta taaaacaaat tgaccttagt    540
gaaatttctg agaacatgta tattagaaat acatatcaaa caagagttta tgttctaatg    600
tctaatataa agctaaatga aaattcatta gaggagtgca gagattactc taaaatggca    660
ttggaaagta caaatatcca gagatttcag gttttcagct acttaacaat tggcaactct    720
ttattatttt cgaattatga attggctcaa gaaaactttt taaaagggct aagcgtttct    780
gttcaaaatg aaaattacaa catgattttc cagcaggctt tgtgcttctt aaataatgta    840
tggcgcaaag aaaataagtg gattaatttt gaatctgagt caattatgga tttgcaggag    900
caagcccatt gttttatcaa ctttaatgaa aattccaaag caaaaaaagt tttggataaa    960
ctagatcttt tacgtcataa cgataatgag cttgcaatgc atcattattt gaaaggaaga   1020
ctcgaacaaa ataaagcatg tttctattct tcaatcgagt attttaaaaa gtctaatgac   1080
aaattcctta ttaggctgcc actgttagaa ctgcaaaaga tgggtgaaaa tcaaaaactt   1140
ttagaattac ttttacttta a                                             1161
```

```
<210> SEQ ID NO 30
<211> LENGTH: 1140
<212> TYPE: DNA
<213> ORGANISM: Bacillus subtilis

<400> SEQUENCE: 30
```

```
atgaagaaag acttggaaaa tgacaactct ttaatgaata aatgggcaac agtagctggc     60
cttaaaaacc ccaatcctct ttatgacttc ttaaaccatg atgggaaaac atttaatgaa    120
ttttcttcaa tagtcaacat tgttaagagt cagtatccag accgtgaata tgaattaatg    180
aaagattact gtttaaacct agatgttaag acaaaggcag caagaagtgc attggagtat    240
gctgatgcaa atatgttttt tgaaatagaa gatgttttaa tagattcaat gatttcttgc    300
agcaatatga aaagtaaaga atatggaaaa gtgtataaaa tacatagaga actgtctaac    360
agtgttatta ctgaatttga ggcagtgaaa agactcggca aattaaatat aaaaacacct    420
gaaatgaatt ctttctcaag actcttgctg ctttatcatt atttaagcac tggtaacttt    480
tctccgatgg cccaacttat aaaacaaatt gacctaagtg agatttctga gaacatgtac    540
attagaaata catatcaaac aagagttcat gttctaatgt ctaatataaa gttaaatgaa    600
aattcattag aggagtgcag agagtactct aaaaaggcat tggaaagtac aaatatcctg    660
agatttcagg ttttcagcta cttaactatt ggcaactctc tattattttc gaattatgaa    720
ttggctcaag aaaacttttt aaaagggcta agcatttctg ttcaaaatga aaattacaac    780
atgattttcc agcaggcttt gtgcttctta aataatgtat ggcgcaaaga aaataagtgg    840
attaattttg aatctgattc aattatggat ttgcaggagc aagctcattg ttttatcaac    900
```

-continued

```
tttaatgaaa attccaaagc aaaagaagtt ttggataaac tagatctttt agttcacaac     960

gataatgagc ttgcaatgca ttattatttg aaaggaagac tcgaacaaaa taaagcatgt    1020

ttctattctt caatcgagta ttttaaaaag tctaatgaca aattccttat taggctgcca    1080

ctgttagaac tgcaaaagat gggtgaaaat caaaaacttt tagaattact tttactttaa    1140
```

<210> SEQ ID NO 31
<211> LENGTH: 1203
<212> TYPE: DNA
<213> ORGANISM: Bacillus sp.

<400> SEQUENCE: 31

```
atgatattat taatgtatat taaaagggga aacgtggtga aagaattgga gttgaaaagg      60

ttattaaaga acaaatgcga agaagagcga ggactcgaaa aagaactcgc tagagtagct     120

ggatattcta attcatctgg gtttcatcag tttattttta acgataaaaa agaaatggat     180

aacatccaag gcttaataga tgttgttcaa agggtctccc ctgataatga atttgaatta     240

atgagtgaat acatattgac tttagatcct aataagtctg cagcaagaca aggtttagaa     300

tatttaagtg taaatcagtt atacgatgct ttagatactc atatcgagaa cttaagagct     360

gctaataata caatcagtaa ggaatgggga aaggtatact cccttcaaag agagcttgat     420

aacggaaaga taagcattga agagtgtata aggattctag gagaaattaa tcccaaatca     480

cctgaaatga aggtcttttc aaggttgatt cctatgtatt ccatacttgc atcaaggcag     540

tttaccagac ttagagatat gagtgagaac gtagtcttag acatcattag gaaccagaat     600

tatgtttatt attcatttaa aagtagatat atgctgttgt tagctaactg tttttttgga     660

actaatgagc ttgaaaaagc acgggagtat gccaaatatg gaatagaaaa ctcaaatgta     720

aaaagaataa attttttctc gcttcttacc tatgggagtt ctttaatgat gactgattat     780

gtgaaatcta aaagtagttt tctaaaaggg ttagctgttg taaaagggga tacctttaat     840

gaacgatttg ctattaggaa cctttgtttt ttagagaact tatggaataa agaaaataaa     900

tatttaaatg tagactccaa ggaaattata gatagacaag agattgttca ttatcttatc     960

agaaaagggc atattggaca ggccaaaaaa atgctttctg aattagaggt tgtagagcaa    1020

gacgctaatg aattgggatt gcattattat tacaaaggac ttattgaaaa ttctaaagat    1080

tatttcttaa aatcagttaa gtattttaaa atgagtggtg ataaattctc ttgtagactg    1140

cctttaatag agttggagaa attgggtgta gacaaaggaa ttttagagat aatggtaatg    1200

taa                                                                  1203
```

<210> SEQ ID NO 32
<211> LENGTH: 1032
<212> TYPE: DNA
<213> ORGANISM: Bacillus amyloliquefaciens

<400> SEQUENCE: 32

```
ttgatcaaag agaaacaagc aagccttata aatgtacatc atggtgttga gcatttcatc      60

aaacagaacc gcaataataa ttctaagtac gagctgtttt ccacatacgc aaaggcttta     120

aagcccgatt cttattacat attagaagca ttagagtatg ctgatacaaa taattggcac     180

gacatatttg atttattaat tgaaagagca accaacaaag aatggacaga gctttataaa     240

ctgaaaaagc gatctcagtc attgtcaatt ggagagatgg aatttcaaat caaaaaaatc     300

aatccaaagt cagacgaaat gaaaatattc tctaagctta ttatggttta taaaacttgt     360

gatacaacta attttaaatt gatgaataag tatgctgaca gcattgatac agaagaaatg     420
```

```
gaagatggtt ttatcaaaag ttcatttaga tcaaggctcc tggttctctt ggcaaacact    480

ttcctgtttg aggggaatct ttacgcagca agatattatg caagtcttgc aatcatagag    540

tcaaatattg ataggttttc agcgttcgga tatcttcaca ttggtaactc atacatgctg    600

acagattaca aaacagctaa ggataacttt ttaagcggtt taaaatttgc taagccaggg    660

gacaaccatt ataagcaatt aatacggtca ttaagcttct tggaaaacta ttgggaaaat    720

gatcacaaat acaccgattt tcaaagtggt tgcacggagg atgtacatga acaagcgttc    780

tattggatta atagaaatga gcacgaaaag gctctgaact tattgaatgg gatagataga    840

agcaccttat caaatggact acttgcattt cattattttt atagaggttt aatttcttct    900

gacaagtctg acttttataa ctctataaaa tactttaaat tatctggaga taagttcttc    960

gtcgaatgtc ctttaagaga gttgaacaag cttggagagg atagaaaaat tgtagacatc   1020

tttgcgattt aa                                                       1032
```

<210> SEQ ID NO 33
<211> LENGTH: 1158
<212> TYPE: DNA
<213> ORGANISM: Bacillus pumilus

<400> SEQUENCE: 33

```
atgaatctta aaacatacat aaaaaataaa tgcgaagatg attcttcatt ggctatgaaa     60

ttagctaaaa tagctggcta ttcggataga actggccttt ataaattctt aaatagccct    120

aacaaagaga tggatgattt aaacaatctt attaatttag ttagggaagt tgatcaagaa    180

agagaaattg aaataattag cacctatatt acaacactcg accctaacaa atcagctgct    240

agacaagctg tagaatattt agatgctaat caacttggcg acgaaactga tgagctagtt    300

attaaattat gtaatgccag caacgcagtg agcaaagagt gggggaatgt atatcgcatc    360

catagattgc tcacaaaagg tgaaattgat ttaacttctg ctatcaaaga aactggaact    420

attaaaatca agagtgagga aatgtttgtt ttttcaagaa tgatgacatt atatgaatac    480

ctaaacattg gtgagtttgg tcttatgaaa agcacttcaa catatatcga tctatctaat    540

ttgaaaaagg gatacgttaa ggattccttt agctcaaggt atttgttgct tatggccaac    600

gtgtttttaa atgataacaa tttaaaacct cttagagact actgtaatca aattatatct    660

gaagaagtta aggtgaatcg atttcaagtg tttgctcacc tcacttgcgg gaattcttat    720

gtgtttgatg attatgataa agcaaaagca tattacatca acggtatgaa attcgcaaaa    780

aacagttttc ataaatataa acttagatct gcattagcat tcttagaaaa cacatgggga    840

ataaaagaaa acaaatacct ggaacaggaa cctaagaatg attctgattt tatagaactc    900

gcacatcatt taatgcttaa tgatcaaacc gaaaaaatga tggaggtgtt taataaatta    960

gattcatcta ctatgcatga caatgattta ggttttctct actacgttaa aggaattttc   1020

tataaagata aggcttgcta tttgaaatca gttaaacatt ttaagaaatc agatgacaag   1080

tattttatca agctacctct aattaagtta aaaacaatgg gcatagatag tgagatttta   1140

gatttattgg ctatctaa                                                 1158
```

<210> SEQ ID NO 34
<211> LENGTH: 1155
<212> TYPE: DNA
<213> ORGANISM: Bacillus amyloliquefaciens

<400> SEQUENCE: 34

-continued

```
atgaatctta agcagatgat taagaatgaa tgtgaaaaag acaaccagct cgcagcgaaa     60

ctctcaaaaa tagcagggta cgaaaaggtt aatggttttt acaaattcat caacacccca    120

gagaaagaaa tggacaactt aggcggttta attaatattg ttaagagctt gtttccggat    180

aatgaagagc agcttctaag tgactacttc ttatcattgg atcccaataa aaaaagcgca    240

agacagtctg tcgagtatgc agatttaaac caatggaatg cattgactga taagatcgta    300

agcaatcttt gcgaatcatc taattcaata agtcgtgaat ggggacaggt ttattcccta    360

catagaaaac tgaataataa taaaatttct ataaatgaag cgatccggga aactgggaaa    420

tatagaatta aatctcctga aatgtattca ttttcgaata ttatgattat gtacgaatac    480

ttgaaaattg gagaatttgg cttaatgaaa agtacagctc agtttctgga gattgacgaa    540

ctgtctaatg gatttataaa agattcgtac agtggtcgaa ttgaactgtt aaaggccaat    600

ataagcttaa atgattatga actagaagaa acccgaaaac attgtagcgc tgtaattgaa    660

gaatgcaata ataacagatt gattgtattt agttatttaa cacttgggaa tacatacatt    720

tttgaagatt atgctaaagc aaaactatgc tatgaaaaag gcttgaactt tgcaaaagac    780

aatagccatc atcattataa attacgactc gcactttgct ttttagataa tgtctgggcg    840

agagaaaaca aatgggtaga tttcgagtct caagaaatac cggatatgat tgaagctgct    900

ttttatttga ctaatatcaa agaaactaag aaagcagaag atgttattaa aaaaattgaa    960

gaacatgatg ttctggatga tgatttaggg tttctttatc acgttaaggg cttgctgtat   1020

aatgatatgt cccattttca cgagagtata aagaaattca aaaagtcagg cgataggctc   1080

tgtctaaatc tacctttgat tgaattgaaa aagcatggat actcagatga aatattaaat   1140

ttaattgcgc tatag                                                    1155
```

<210> SEQ ID NO 35
<211> LENGTH: 1155
<212> TYPE: DNA
<213> ORGANISM: Bacillus amyloliquefaciens

<400> SEQUENCE: 35

```
atgagtctta agcagatgat taagaatgaa tgtgaaaaag acaaccagct cgcagcgaaa     60

ctctcaaaaa tagcagggta cgaaaaggtt aatggttttt acaaattcat caacacccca    120

gagaaagaaa tggacaactt aggcggttta attaatattg ttaagagctt gtttccggat    180

aatgaagagc agcttctaag tgactacttc ttatcattgg atcccaataa aaaaagcgca    240

agacaatctg tcgagtatgc agatttaaac caatggaatg cattgactga taagatcgta    300

agcaatcttt gcgaatcatc taattcaata agtcgtgaat ggggacaggt ttattcccta    360

catagaaaac tgaataataa taaaatttct ataaatgaag cgatccggga aactgggaaa    420

tatagaatta aatctcctga aatgtattca ttttcgaata ttatgattat gtacgaatac    480

ttgaaaattg gagaatttgg cttaatgaaa agtacagctc agtttctgga gattgacgaa    540

ctgtctgatg gatttataaa agattcgtac agtggtcgaa ttgaactgtt aaaggccaat    600

ataagcttaa atgattatga actagaagaa acccgaaaac attgtagcgc tgtaattgaa    660

gaatgcaata ataacagatt gattgtattt agttatttaa cacttgggaa tacatacatt    720

tttgaagatt atgctaaagc aaaactatgc tatgaaaaag gcttgaactt tgcaaaagac    780

aatagccatc atcattataa attacgactc gcactttgct ttttagataa tgtctgggcg    840

agagaaaaca aatgggtaga tttcgagtct caagaaatac cggatatgat tgaagctgct    900

ttttatttga ctaatatcaa agaaactaag aaagcagaag atgttattaa aaaaattgaa    960
```

gaacatgatg ttctggatga tgatttaggg tttctttatc acgttaaggg cttgctgtat 1020
aatgatatgt cccattttca cgagagtata aagaaattca aaaagtcagg cgataggctc 1080
tgtctaaatc tacctttgat tgaattgaaa aagcgtggat actcagatga aatattaaat 1140
ttaattgcgc tatag 1155

<210> SEQ ID NO 36
<211> LENGTH: 1155
<212> TYPE: DNA
<213> ORGANISM: Bacillus amyloliquefaciens

<400> SEQUENCE: 36
atgaatctta agcagatgat taagaatgaa tgtgaaaaag acaaccagct cgcagcgaaa 60
ctctcaaaaa tagcagggta cgaaaaggtt aatggttttt acaaattcat caacacccca 120
gagaaagaaa tggacaactt aggcggttta attaatattg ttaagagctt gtttccggat 180
aatgaagagc agcttctaag tgactacttc ttatcattgg atcccaataa aaaaagcgca 240
agacagtctg tcgagtatgc agatttaaac caatggaatg cattgactga taagatcgta 300
agcaatcttt gcgaatcatc taattcaata agtcgtgaat ggggacaggt ttattcccta 360
catagaaaac tgaataataa taaaatttct ataaatgaag cgatccggga aactgggaaa 420
tatagaatta aatctcctga aatgtattca ttttcgaata ttatgattat gtacgaatac 480
ttgaaaattg gagaatttgg cttaatgaaa agtacagctc agtttctgga gattgacgaa 540
ctgtctgatg gatttataaa agattcgtac agtggtcgaa ttgaactgtt aaaggccaat 600
ataagcttaa atgattatga actagaagaa acccgaaaac attgtagcgc tgtaattgaa 660
gaatgcaata ataacagatt gattgtattt agttatttaa cacttgggaa tacatacatt 720
tttgaagatt atgctaaagc aaaactatgc tatgaaaaag gcttgaactt tgcaaaagac 780
aatagccatc atcattataa attacgactc gcactttgct ttttagataa tgtctgggcg 840
agagaaaaca aatgggtaga tttcgagtct caagaaatac cggatatgat tgaagctgct 900
ttttatttga ctaatatcaa agaaactaag aaagcagaag atgttattaa aaaaattgaa 960
gaacatgatg ttctggatga tgatttaggg tttctttatc acgttaaggg cttgctgtat 1020
aatgatatgt cccattttca cgagagtata aagaaattca aaaagtcagg cgataggctc 1080
tgtctaaatc tacctttgat tgaattgaaa aagcgtggat actcagatga aatattaaat 1140
ttaattgcgc tatag 1155

<210> SEQ ID NO 37
<211> LENGTH: 1155
<212> TYPE: DNA
<213> ORGANISM: Bacillus subtilis

<400> SEQUENCE: 37
atgaatctta agcagatgat taagaatgaa tgtgaaaaag acaaccagct cgcagcgaaa 60
ctctcaaaaa tagcagggta cgaaaaggtt aatggttttt acaaattcat caacacccca 120
gagaaagaaa tggacaactt aggcggttta attaatattg ttaaaagctt gtttcctgat 180
aaagaagagc agcttctaag tgattacttc ttatcattgg atcccaataa aaaaagcgca 240
agacagtctg tcgagtatgc agatttaaac caatggaatg ccttgactga taagatcgta 300
agcaatcttt gcgaatcatc taattcaata agtcgtgaat ggggacaggt ttattcccta 360
catagaaaac tgaataataa taaaatttct ataaatgaag cgatccggga aacggggaaa 420

```
tatagaatta aatctcctga aatgtattca ttttcgaata ttatgattat gtacgaatac    480

ttgaaaattg gagaatttgg cttaatgaaa agtacagctc agtttctgga gattgacgaa    540

ctgtctgatg gatttataaa agattcgtac agtggtcgaa ttgaactgtt aaaggccaat    600

ataagcttaa atgattatga actagaagaa acccgaaaac attgtagcgc tgtaattgaa    660

gaatgtaata ataacagatt gattgtattt agttatttaa cacttgggaa tacatacatt    720

tttgaagatt atgataaagc aaaactgtgc tatgaaaaag gcttgaactt tgcaaaagac    780

aataaccatc atcattataa attgcgactc gcactttgct ttttagataa tgtctgggcg    840

agagaaaaca aatgggtaga tttcgaatct caagaaatac cggatatgat tgaagctgct    900

ttttatttga ctaatatcaa agaaactaag aaagcagaag atgttattaa aaaaattgaa    960

gaacatgatg ttctggatga tgatttaggg tttctttatc acgttaaggg cttgctgtat   1020

aatgatatgt cccattttca cgagagtata aagaaattca aaaaatcagg cgataggctc   1080

tgtctaaatc tacctttgat tgaattgaaa aagcgtggat actcagatga aatattaaat   1140

ttaattgcgc tctag                                                    1155
```

<210> SEQ ID NO 38
<211> LENGTH: 1155
<212> TYPE: DNA
<213> ORGANISM: Paenibacillus polymyxa

<400> SEQUENCE: 38

```
atgaatctta agcagatgat taagaatgaa tgtgaaaaag acaaccagct cgcagcgaaa     60

ctctcaaaaa tagcagggta cgaaaaggtt aatggttttt acaaattcat caacacccca    120

gagaaagaaa tggacaactt aggcggttta attaatattg ttaaaagctt gtttcctgat    180

aaagaagagc agcttctaag tgattacttc ttatcattgg atcccaataa aaaaagcgca    240

agacagtctg tcgagtatgc agatttaaac caatggaatg ccttgactga taagatcgta    300

agcaatcttt gcgaatcatc taattcaata agtcgtgaat ggggacaggt ttattcccta    360

catagaaaac tgaataataa taaaatttct ataaatgaag cgatccggga aacggggaaa    420

tatagaatta aatctcctga aatgtattca ttttcgaata ttatgattat gtacgaatac    480

ttgaaaattg gagaatttgg cttaatgaaa agtacagctc agtttctgga gattgacgaa    540

ctgtctgatg gatttataaa agattcgtac agtggtcgaa ttgaactgtt aaaggccaat    600

ataagcttaa atgattatga actagaagaa acccgaaaac attgtagcgc tgtaattgaa    660

gaatgtaata ataacagatt gattgtattt agttatttaa cacttgggaa tacatacatt    720

tttgaagatt atgataaagc aaaactgtgc tatgaaaaag gcttgaactt tgcaaaagac    780

aataaccatc atcattataa attgcgactc gcactttgct ttttagataa tgtctgggcg    840

agagaaaaca aatgggtaga tttcgaatct caagaaatac cggatatgat tgaagctgct    900

ttttatttga ctaatatcaa agaaactaag aaagcagaag atgttattaa aaaaattgaa    960

gaacatgatg ttctggatga tgatttaggg tttctttatc acgttaaggg cttgctgtat   1020

aatgatatgt cccattttca cgagagtata aagaaattca aaaaatcagg cgataggctc   1080

tgtctaaatc tacctttgat tgaattgaaa aagcgtggat actcagatga aatattaaat   1140

ttaattgcgc tctag                                                    1155
```

<210> SEQ ID NO 39
<211> LENGTH: 894
<212> TYPE: DNA
<213> ORGANISM: Bacillus atrophaeus

<400> SEQUENCE: 39
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aaatgattcc catgtacgat 480
tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 40
<211> LENGTH: 894
<212> TYPE: DNA
<213> ORGANISM: Bacillus atrophaeus

<400> SEQUENCE: 40
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aaatgattcc catgtacgat 480
tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 41
<211> LENGTH: 894
<212> TYPE: DNA
<213> ORGANISM: Bacillus atrophaeus

<400> SEQUENCE: 41

-continued

```
atggaactta taagaaaagc tatgaggaaa gacttagaaa atgataaaac actcatgagt     60

aaatgggcta cggtagctgg acttaaaaat ccaaatcctc tttacgattt tctaaatcat    120

gatggaaaga cttttagtga gttttccacg ttggtgaata ttgtgaagag tcagtaccct    180

gatcgagaat atgaacttat ggaagattat tgtctgatcc ttgaccccaa gactaaagct    240

gcaagaagtg ccctgaaata cgcagatgcc aacagtttta atgatctaac tgataagctg    300

gttgataaaa tgagtatttc ctcaaatttg aaaagcaaag agtacggaaa aatttacggg    360

atacatagga agctatcaaa aggagaaata gatgttcttg aagcaacaaa aaatattggg    420

aaacagagaa ttaaaactga tgaaatgaat atcttttcaa aaatgattcc catgtacgat    480

tatttaagta aaggaaattt ctctccgatg aagcctttgc ttaagcaaat taaccttaat    540

gagattaaag aaaataagta tctaaaaaag tcgtttgaaa ctcgtataca cgttctttta    600

tctaatatgt acttaaatga aaataaactc gaattgtgca gagaatatgc aaaaaaagcg    660

attcaatcaa ctagcactaa acgatttttg gtttttagtt atttaacaat agggacgtct    720

tacatttttt tagactacaa tttaagtcgg cagaattatt tatctggcta cgagatttct    780

aaaggtaaca atgtatttga agaattcttt aaaaggaatt tgagtttttt aaataactat    840

tggaataaag aaaattcatg gatcaactat gactcagaca gacgcagtga ctga          894
```

<210> SEQ ID NO 42
<211> LENGTH: 894
<212> TYPE: DNA
<213> ORGANISM: Bacillus atrophaeus

<400> SEQUENCE: 42

```
atggaactta taagaaaagc tatgaggaaa gacttagaaa atgataaaac actcatgagt     60

aaatgggcta cggtagctgg acttaaaaat ccaaatcctc tttacgattt tctaaatcat    120

gatggaaaga cttttagtga gttttccacg ttggtgaata ttgtgaagag tcagtaccct    180

gatcgagaat atgaacttat ggaagattat tgtctgatcc ttgaccccaa gactaaagct    240

gcaagaagtg ccctgaaata cgcagatgcc aacagtttta atgatctaac tgataagctg    300

gttgataaaa tgagtatttc ctcaaatttg aaaagcaaag agtacggaaa aatttacggg    360

atacatagga agctatcaaa aggagaaata gatgttcttg aagcaacaaa aaatattggg    420

aaacagagaa ttaaaactga tgaaatgaat atcttttcaa aaatgattcc catgtacgat    480

tatttaagta aaggaaattt ctctccgatg aagcctttgc ttaagcaaat taaccttaat    540

gagattaaag aaaataagta tctaaaaaag tcgtttgaaa ctcgtataca cgttctttta    600

tctaatatgt acttaaatga aaataaactc gaattgtgca gagaatatgc aaaaaaagcg    660

attcaatcaa ctagcactaa acgatttttg gtttttagtt atttaacaat agggacgtct    720

tacatttttt tagactacaa tttaagtcgg cagaattatt tatctggcta cgagatttct    780

aaaggtaaca atgtatttga agaattcttt aaaaggaatt tgagtttttt aaataactat    840

tggaataaag aaaattcatg gatcaactat gactcagaca gacgcagtga ctga          894
```

<210> SEQ ID NO 43
<211> LENGTH: 894
<212> TYPE: DNA
<213> ORGANISM: Bacillus atrophaeus

<400> SEQUENCE: 43

```
atggaactta taagaaaagc tatgaggaaa gacttagaaa atgataaaac actcatgagt     60

aaatgggcta cggtagctgg acttaaaaat ccaaatcctc tttacgattt tctaaatcat    120
```

```
gatggaaaga cttttagtga gttttccacg ttggtgaata ttgtgaagag tcagtaccct    180

gatcgagaat atgaacttat ggaagattat tgtctgatcc ttgaccccaa gactaaagct    240

gcaagaagtg ccctgaaata cgcagatgcc aacagtttta atgatctaac tgataagctg    300

gttgataaaa tgagtatttc ctcaaatttg aaaagcaaag agtacggaaa aatttacggg    360

atacatagga agctatcaaa aggagaaata gatgttcttg aagcaacaaa aaatattggg    420

aaacagagaa ttaaaactga tgaaatgaat atcttttcaa aaatgattcc catgtacgat    480

tatttaagta aaggaaattt ctctccgatg aagcctttgc ttaagcaaat taaccttaat    540

gagattaaag aaaataagta tctaaaaaag tcgtttgaaa ctcgtataca cgttctttta    600

tctaatatgt acttaaatga aaataaactc gaattgtgca gagaatatgc aaaaaaagcg    660

attcaatcaa ctagcactaa acgatttttg gtttttagtt atttaacaat agggacgtct    720

tacatttttt tagactacaa tttaagtcgg cagaattatt tatctggcta cgagatttct    780

aaaggtaaca atgtatttga agaattcttt aaaaggaatt tgagtttttt aaataactat    840

tggaataaag aaaattcatg gatcaactat gactcagaca gacgcagtga ctga          894
```

```
<210> SEQ ID NO 44
<211> LENGTH: 894
<212> TYPE: DNA
<213> ORGANISM: Bacillus atrophaeus

<400> SEQUENCE: 44

atggaactta taagaaaagc tatgaggaaa gacttagaaa atgataaaac actcatgagt     60

aaatgggcta cggtagctgg acttaaaaat ccaaatcctc tttacgattt tctaaatcat    120

gatggaaaga cttttagtga gttttccacg ttggtgaata ttgtgaagag tcagtaccct    180

gatcgagaat atgaacttat ggaagattat tgtctgatcc ttgaccccaa gactaaagct    240

gcaagaagtg ccctgaaata cgcagatgcc aacagtttta atgatctaac tgataagctg    300

gttgataaaa tgagtatttc ctcaaatttg aaaagcaaag agtacggaaa aatttacggg    360

atacatagga agctatcaaa aggagaaata gatgttcttg aagcaacaaa aaatattggg    420

aaacagagaa ttaaaactga tgaaatgaat atcttttcaa aaatgattcc catgtacgat    480

tatttaagta aaggaaattt ctctccgatg aagcctttgc ttaagcaaat taaccttaat    540

gagattaaag aaaataagta tctaaaaaag tcgtttgaaa ctcgtataca cgttctttta    600

tctaatatgt acttaaatga aaataaactc gaattgtgca gagaatatgc aaaaaaagcg    660

attcaatcaa ctagcactaa acgatttttg gtttttagtt atttaacaat agggacgtct    720

tacatttttt tagactacaa tttaagtcgg cagaattatt tatctggcta cgagatttct    780

aaaggtaaca atgtatttga agaattcttt aaaaggaatt tgagtttttt aaataactat    840

tggaataaag aaaattcatg gatcaactat gactcagaca gacgcagtga ctga          894
```

```
<210> SEQ ID NO 45
<211> LENGTH: 894
<212> TYPE: DNA
<213> ORGANISM: Bacillus atrophaeus

<400> SEQUENCE: 45

atggaactta taagaaaagc tatgaggaaa gacttagaaa atgataaaac actcatgagt     60

aaatgggcta cggtagctgg acttaaaaat ccaaatcctc tttacgattt tctaaatcat    120

gatggaaaga cttttagtga gttttccacg ttggtgaata ttgtgaagag tcagtaccct    180
```

gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aatgattcc catgtacgat 480 tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 46
<211> LENGTH: 894
<212> TYPE: DNA
<213> ORGANISM: Bacillus atrophaeus

<400> SEQUENCE: 46
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aatgattcc catgtacgat 480 tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 47
<211> LENGTH: 1149
<212> TYPE: DNA
<213> ORGANISM: Bacillus amyloliquefaciens

<400> SEQUENCE: 47
atgaatctaa agcagatgat taagaatgaa tgtgaaaaag acaaccagct cgcagcgaaa 60
ctctcaaaaa tagcagggta cgaaaaggtt aacggctttt acaaattcat caacacccca 120
gagaaagaaa tggacaactt aggcggttta attaatattg ttaaaagctt gtttcctgat 180
aatgaggagc agcttctaag tgattacttc ttatcactgg atcccaacaa aaaatgtgcc 240
agacaatctg ttgaatactc agatattaat caatgggata cgttaacaga caagatagtg 300

-continued

```
tcgaggctat ctagttcaaa aaacctagca agtcaagaat ggggcaatac atacagtata    360
catagaagat tgagcgaaag taagataagt ttaactgatg caataagagc aaccggaaag    420
tgcaaaacag atgaaatgtt gtttttctca aatgctatgc tgatgtatga gtatttgaag    480
gtaggcgagt ttggattgat gaaaagcaca ttgtcacttc tcaatttcaa cgacttaccc    540
gaaggctttg tgaaagattg ctatatgaat agaatttcat tattaaatgc aaatatttat    600
ttgaatgata atgaaattga aaaatctagg tattattcag aacaagttat tcaaaattca    660
aatataaatc gcctaaaagt atttgggcat ttaacatatg ggaacacatt aatttttgaa    720
agctactcta aagccaaaga gcagtatctt aaaggattgg aatttgcgcg tgataatgaa    780
catcataaat ataagctgcg attagctctt tgctttttaa gtaacgtatg gaacaaggat    840
aataaatggc ttgacttcga cactgataat atccctgata agattgaggt agcatattac    900
tatactaata ataaggaatt taataaagca gagaaagtaa taaatgagct tgaaaatatg    960
aaattatacg aatatgattc tgggattcta gattacatta aggggattct ataccaaaat   1020
aagaattatt tttatgaaag cactgcaaag ttgaaaaaat ctggtgataa attatttatc   1080
aatcttccat tagcggagct aaggaaaatg ggctgtgacg aaaaattact tgaattaatc   1140
atggtctaa                                                           1149
```

<210> SEQ ID NO 48
<211> LENGTH: 963
<212> TYPE: DNA
<213> ORGANISM: Bacillus amyloliquefaciens

<400> SEQUENCE: 48

```
atgttagtaa aagagagaga agttaagaag ccggaagtag atgcaaaggt acgtcttgaa     60
atgtcagata ttaatgaaca gtatgaactg actgacacat taattgatca attaattaat    120
agtacctgtt caattgaacg tgaatgggcc gcaatgtatc agatcaaacg taagcaagac    180
agaggcgaaa taaacgcaca tcaggcgctt aaagcaattg ggaagcttga tcccaagtct    240
caagaaatgc gtgtattcac ttacataatc ccgttgtatt actaccttag aatggctgaa    300
tactcaaatc ttgcagaaat gtcgatgatt gtagatcttg attttattga aaacaatgaa    360
cagattaaaa gctcgtttta ttaccgtctg atggctttgt tgggcgcttc agcattcagt    420
cagaataaaa tgactcaagc ccgtttttat tgctcatacg gcattaatgt aacgaatatt    480
gataggcttg tcgcttatag ctatctaact ttgggaaata cttatttgct tgatgattat    540
gaaaaagcaa aagaatatta cctgaccggt ttaaaacata ctgagaataa ccccttggca    600
aaattacagc taactagaag cctttgtttc ttggaaaacc attggaatca agagaacttt    660
tggttaaacc ctgattcaaa tgaagtaaca gatatccaag aaattgcaca ttatcacatc    720
aagaaaaaca acttgcaaca ggctaaagaa atattggaga acttagagca gcaaccgaat    780
attcataatg actttggcat tcatttttat ctaaaaggac tagcttatga agataagaga    840
ttcttttatg agtctataaa acactttaag ctgtccggcg atctatacag cgtacgctta    900
cctttggata aattaaggga aatgggtgag gacgagcaga ttttggattt acttgccctt    960
taa                                                                  963
```

<210> SEQ ID NO 49
<211> LENGTH: 963
<212> TYPE: DNA
<213> ORGANISM: Bacillus subtilis -continued

<400> SEQUENCE: 49

```
atgttagtaa aagagagaga agttaagaag ccggaagtag atgcaaaggt acgtcttgaa     60
atgtcagata ttaatgaaca gtatgaactg actgacacat taattgatca attaattaat    120
agtacctgtt caattgaacg tgaatgggcc gcaatgtatc agatcaaacg taagcaagac    180
agaggcgaaa taaacgcaca tcaggcgctt aaagcaattg ggaagcttga tcccaagtct    240
caagaaatgc gtgtattcac ttacataatc ccgttgtatt actaccttag aatggctgaa    300
tactcaaatc ttgcagaaat gtcgatgatt gtagatcttg attttattga aaacaatgaa    360
cagattaaaa gctcgtttta ttaccgtctg atggctttgt tgggcgcttc agcattcagt    420
cagaataaaa tgactcaagc ccgtttttat tgctcatacg gcattaatgt aacgaatatt    480
gataggcttg tcgcttatag ctatctaact ttgggaaata cttatttgct tgatgattat    540
gaaaaagcaa aagaatatta cctgaccggt ttaaaacata ctgagaataa ccccttggca    600
aaattacagc taactagaag cctttgtttc ttggaaaacc attggaatca agagaacttt    660
tggttaaacc ctgattcaaa tgaagtaaca gatatccaag aaattgcaca ttatcacatc    720
aagaaaaaca acttgcaaca ggctaaagaa atattggaga acttagagca gcaaccgaat    780
attcataatg actttggcat tcatttttat ctaaaaggac tagcttatga agataagaga    840
ttcttttatg agtctataaa acactttaag ctgtccggcg atctatacag cgtacgctta    900
cctttggata aattaaggga aatgggtgag gacgagcaga ttttggattt acttgccctt    960
taa                                                                  963
```

<210> SEQ ID NO 50
<211> LENGTH: 963
<212> TYPE: DNA
<213> ORGANISM: Bacillus amyloliquefaciens

<400> SEQUENCE: 50

```
atgttagtaa aagagagaga agttaagaag ccggaagtag atgcaaaggt acgtcttgaa     60
atgtcagata ttaatgaaca gtatgaactg actgacacat taattgatca attaattaat    120
agtacctgtt caattgaacg tgaatgggcc gcaatgtatc agatcaaacg taagcaagac    180
agaggcgaaa taaacgcaca tcaggcgctt aaagcaattg ggaagcttga tcccaagtct    240
caagaaatgc gtgtattcac ttacataatc ccgttgtatt actaccttag aatggctgaa    300
tactcaaatc ttgcagaaat gtcgatgatt gtagatcttg attttattga aaacaatgaa    360
cagattaaaa gctcgtttta ttaccgtctg atggctttgt tgggcgcttc agcattcagt    420
cagaataaaa tgactcaagc ccgtttttat tgctcatacg gcattaatgt aacgaatatt    480
gataggcttg tcgcttatag ctatctaact ttgggaaata cttatttgct tgatgattat    540
gaaaaagcaa aagaatatta cctgaccggt ttaaaacata ctgagaataa ccccttggca    600
aaattacagc taactagaag cctttgtttc ttggaaaacc attggaatca agagaacttt    660
tggttaaacc ctgattcaaa tgaagtaaca gatatccaag aaattgcaca ttatcacatc    720
aagaaaaaca acttgcaaca ggctaaagaa atattggaga acttagagca gcaaccgaat    780
attcataatg actttggcat tcatttttat ctaaaaggac tagcttatga agataagaga    840
ttcttttatg agtctataaa acactttaag ctgtccggcg atctatacag cgtacgctta    900
cctttggata aattaaggga aatgggtgag gacgagcaga ttttggattt acttgccctt    960
taa                                                                  963
```

-continued

<210> SEQ ID NO 51
<211> LENGTH: 963
<212> TYPE: DNA
<213> ORGANISM: Bacillus amyloliquefaciens

<400> SEQUENCE: 51

```
atgttagtaa aagagagaga agttaagaag ccggaagtag atgcaaaggt acgtcttgaa      60
atgtcagata ttaatgaaca gtatgaactg actgacacat taattgatca attaattaat     120
agtacctgtt caattgaacg tgaatgggcc gcaatgtatc agatcaaacg taagcaagac     180
agaggcgaaa taaacgcaca tcaggcgctt aaagcaattg ggaagcttga tcccaagtct     240
caagaaatgc gtgtattcac ttacataatc ccgttgtatt actaccttag aatggctgaa     300
tactcaaatc ttgcagaaat gtcgatgatt gtagatcttg attttattga aaacaatgaa     360
cagattaaaa gctcgtttta ttaccgtctg atggctttgt tgggcgcttc agcattcagt     420
cagaataaaa tgactcaagc ccgtttttat tgctcatacg gcattaatgt aacgaatatt     480
gataggcttg tcgcttatag ctatctaact ttgggaaata cttatttgct tgatgattat     540
gaaaaagcaa aagaatatta cctgaccggt ttaaaacata ctgagaataa ccccttggca     600
aaattacagc taactagaag cctttgtttc ttggaaaacc attggaatca agagaacttt     660
tggttaaacc ctgattcaaa tgaagtaaca gatatccaag aaattgcaca ttatcacatc     720
aagaaaaaca acttgcaaca ggctaaagaa atattggaga acttagagca gcaaccgaat     780
attcataatg actttggcat tcatttttat ctaaaaggac tagcttatga agataagaga     840
ttcttttatg agtctataaa acactttaag ctgtccggcg atctatacag cgtacgctta     900
cctttggata aattaaggga aatgggtgag gacgagcaga ttttggattt acttgccctt     960
taa                                                                   963
```

<210> SEQ ID NO 52
<211> LENGTH: 963
<212> TYPE: DNA
<213> ORGANISM: Bacillus amyloliquefaciens

<400> SEQUENCE: 52

```
atgatagcaa aagagagaga agttaagaag ccggaagtag atgcaaaggt acgtcttgaa      60
atgtcagata ttaatgaaca gtatgaacaa actgacgcat taattgatca attaatcaac     120
agtagctgtt cgattgaacg tgaatgggca gcaatgtatc agatcaaacg taagcaagac     180
agaggcgaaa taaacgcaca tcaggcgctt aaagcaattg gaaagcttga tcctaagtct     240
caagaaatgc gtgtattcac ttacataatc ccgttgtatt actaccttag aatggctgaa     300
tactcaaacc ttgcagaaat gtcgatgatt gtagatcttg attttattga aaataatgaa     360
cagattaaaa gctcgtttta ttaccgtctg atggctttgt tgggcgcttc agcattcagt     420
cagaataaaa tgactcaagc ccgtttttat tgctcatacg gcattaatgt gacgaatatt     480
gatagacttg tcgcttatag ctatctaact atgggtaaca cttatttgct tgatgattat     540
gaaaaagcaa aagaatatta cctggccggt ttaaagcata ctgagaataa tcccttggcg     600
aaattacagc taactagaag cctttgtttc ttggaaaacc attggaatca agagaacttt     660
tggttagacc ctgattcaaa tgaagttaca gatatccaag aaattgcaca ctatcacatc     720
aagaaaaaca acttgcaaca ggctaaagaa atattggaga acttagagca gcaaccgaat     780
attcataatg actttggtat tcatttttat ctaaagggac tagcttatga agataagaga     840
ttcttttatg agtctataaa acactttaag ctgtctggtg atctatacag cgtacgcttg     900
```

cctttggatc aattaaggga aatgggggag gacgagcaga ttttagattt acttgccctt 960
taa 963

<210> SEQ ID NO 53
<211> LENGTH: 963
<212> TYPE: DNA
<213> ORGANISM: Bacillus methylotrophicus

<400> SEQUENCE: 53
atgatagcaa aagagagaga agctaagaaa ccagaagtag atgcaaaggt acgtcttgaa 60
atgtcagata ttaatgaaca gtatgaacaa actgacgcat taattgatca attaatcaac 120
agtagctgtt cgattgaacg tgaatgggca gcaatgtatc agatcaaacg taagcaagac 180
agaggcgaaa taaacgcaca tcaggcgctt aaagcaattg ggaagcttga tcccaagtct 240
caagaaatgc gtgtattcac ttacataatt ccgttgtatt actaccttag aatggctgaa 300
tactcaaatc ttgcagaaat gtcgacagtt gttgatcttg attttattga aaacaatgaa 360
cagattaaaa gctcctttta taaccgtctg atggctttgt tgggcgcttc agcattcagt 420
cagaataaaa tgactcaagc tcgtttttat tgctcatacg gcattaatgt aacgaatatt 480
gataggcttg tcgcttatag ctatctaact ttgggtaaca cttatttgct tgatgattat 540
gaaaaagcaa aagaatatta cctggccggt ttaaaacata ctgagaataa ccccttggca 600
aaattacagc taactagaag cctttgtttc ttggaaaacc attggaatca agagaacttt 660
tggctaaacc ctgattcaaa tgaagttaca gatatccaag aaattgcaca ttatcacatc 720
aaaaaaaaca acttgcaaca ggctaaagaa atattggaga acttagagca gcaaccgaat 780
attcataatg actttggcat tcatttttat ctaaaaggac tagcttatga agataagaga 840
ttcttttatg agtctataaa acactttaag ctgtccggcg atctatacag cgtacgctta 900
cctttggata aattaaggga aatgggtgag gacgagcaga ttttggattt acttgccctt 960
taa 963

<210> SEQ ID NO 54
<211> LENGTH: 963
<212> TYPE: DNA
<213> ORGANISM: Bacillus amyloliquefaciens

<400> SEQUENCE: 54
atgatagcaa aagagagaga agctaagaaa ccaaaagtag atgcaaaggt acgtcttgaa 60
atgtcagata ttaatgaaca gtatgaacaa actgacgtat taattgatca attaatcaac 120
agtaactgtt cgattgaacg tgaatgggca gtaatgtatc agatcaaacg taagcaagac 180
agaggcgaaa taaacgcaca tcaggcgctt aaagcaattg ggaagcttga tcccaagtct 240
caagaaatgc gtgtattcac ttacataatc ccgttgtatt actaccttag aatggctgaa 300
tactcaaatc ttgcagaaat gtcgacagtt gttgatcttg attttattga aaacaatgaa 360
cagattaaaa gctcctttta taaccgtctg atggctttgt tgggcgcttc agcattcagt 420
cagaataaaa tgactcaagc tcgtttttat tgctcatacg gcattaatgt aacgaatatt 480
gatagacttg tcgcttatag ctatctaact ttgggaaata cttatttgct tgatgattat 540
gaaaaagcaa aggaatatta cctggccggt ttaaaacata ctgagaataa ccctttggca 600
aaattacagt taactagaag cctttgtttc ttggaaaacc attggaatca agagaacttt 660
tggttaaatc ctgattcaaa tgaaattaca gacatgcaag aaatcgcaca ttatcacatc 720
aaaagaaaca acttacaaca ggcaaaagaa atattggaga acttagagca gcaaccgaat 780
attcataatg actttggcat tcatttttat ctaaaaggac tagcttatga agataagaga 840
ttcttttatg agtctataaa acattttaag ctgtccggtg atttattcag tgttcgctta 900
cctttagata aattaaggga aatgggtgag gacgagcaga ttttagattt acttgccctt 960
taa 963

<210> SEQ ID NO 55
<211> LENGTH: 963
<212> TYPE: DNA
<213> ORGANISM: Bacillus amyloliquefaciens

<400> SEQUENCE: 55
atgatagcaa aagagagaga agctaagaaa ccaaaagtag atgcaaaggt acgtcttgaa 60
atgtcagata ttaatgaaca gtatgaacaa actgacgtat taattgatca attaatcaac 120
agtaactgtt cgattgaacg tgaatgggca gtaatgtatc agatcaaacg taagcaagac 180
agaggcgaaa taaacgcaca tcaggcgctt aaagcaattg ggaagcttga tcccaagtct 240
caagaaatgc gtgtattcac ttacataatc ccgttgtatt actaccttag aatggctgaa 300
tactcaaatc ttgcagaaat gtcgacagtt gttgatcttg attttattga aaacaatgaa 360
cagattaaaa gctcctttta taaccgtctg atggctttgt tgggcgcttc agcattcagt 420
cagaataaaa tgactcaagc tcgtttttat tgctcatacg gcattaatgt aacgaatatt 480
gatagacttg tcgcttatag ctatctaact ttgggaaata cttatttgct tgatgattat 540
gaaaaagcaa aggaatatta cctggccggt ttaaaacata ctgagaataa ccctttggca 600
aaattacagt taactagaag cctttgtttc ttggaaaacc attggaatca agagaacttt 660
tggttaaatc ctgattcaaa tgaaattaca gacatgcaag aaatcgcaca ttatcacatc 720
aaaagaaaca acttacaaca ggcaaaagaa atattggaga acttagagca gcaaccgaat 780
attcataatg actttggcat tcatttttat ctaaaaggac tagcttatga agataagaga 840
ttcttttatg agtctataaa acattttaag ctgtccggtg atttattcag tgttcgctta 900
cctttagata aattaaggga aatgggtgag gacgagcaga ttttagattt acttgccctt 960
taa 963

<210> SEQ ID NO 56
<211> LENGTH: 963
<212> TYPE: DNA
<213> ORGANISM: Bacillus amyloliquefaciens

<400> SEQUENCE: 56
atgatagcaa aagagagaga agctaagaaa ccaaaagtag atgcaaaggt acgtcttgaa 60
atgtcagata ttaatgaaca gtatgaactg actgacacat taattaatca attaatcaat 120
agtacctgtt cgattgaacg tgaatgggca gcaatgtatc agattaaacg taagcaagac 180
agaggcgaaa taaacgcaca tcaggcgctt aaagcaattg ggaagcttga tcccaagtct 240
caagaaatgc gtgtattcac ttacataatt ccgttgtatt actaccttag aatggctgaa 300
tactcaaacc ttgcggaaat gtcgacagtt gttgatcttg attttattga aaacaatgaa 360
cagattaaaa gctcctttta taaccgtctg atggctttgt tgggcgcttc ggcattcagt 420
cagaataata tgactcaagc tcgtttttat tgctcatacg gcattaatgt aacgaatatt 480
gataggcttg tcgcttatag ctatctaact ttgggaaata cttatttgct tgatgattat 540
gaaaaagcaa aagaaaatta cctggccggt ttaaaacata ctgagaataa ccccttggca 600

-continued

```
aaattacagt taactagaag cctttgcttc ttagaaaacc attggaatca agagaacttt    660
tggttaaacc ctgattcaaa tgaagttaca gatatccaag aaattgcaca ctatcacatc    720
aagaaaaaca acttgcaaca ggctaaagaa atattggaga acttagagca gcaaccgaat    780
attcataatg actttggcat tcacttttat ctaaagggac tagcttatga agataagaga    840
ttcttttatg agtctataaa acactttaag ctgtccggcg atctatacag cgtgcgattg    900
cctttagata aattaaggga aatgggtgag gacgagcaga ttttagattt acttgcactc    960
taa                                                                   963
```

<210> SEQ ID NO 57
<211> LENGTH: 1164
<212> TYPE: DNA
<213> ORGANISM: Bacillus sp.

<400> SEQUENCE: 57

```
ttgagcaaat taaaagcatt catcaaaagt aagtgtgaag acgattcttc aatggctatg     60
aaattggcaa agatagcagg gtatacagac agaagtggtt tttaccgatt tctaaatgac    120
ggtagaaaag aaacaactga tattcaaagt atcataaata ttgtcaaaga aatcgatcca    180
gcaaatgaaa gagttgttat gggagaatac ataatgacgc ttgatccaaa taagtctgca    240
gcaagacagg ctcttgaata tttagatgta aataaatatt acattgaacg taatgcatta    300
ctggataaaa tgaagtatgc tcacaacgga aagtctcaag aatggtataa aatctattca    360
attcatagcg aggttcaaga cggtaattta acgtatcttg aagcgatgaa taaagtggga    420
tcggtcaaca cgaagacacc tgaaatgaat gtgtttaaaa atattttgct tttatatcca    480
ctgtgttcaa aaggtgagtt cggattgatg agtgaaattg ctgacttaat cgatgtggat    540
tcacttcata taaccggtta cgttaatgat tcctatagat gtaggctgtt gattatgagt    600
gccagtgcag cagtaagtca gaacaagctt aaaagagcac gattcaatgc aggaatggct    660
ttatcagaaa ctaagattga tagattcgct gttttcgcct gtctacatct tggtaactca    720
tatatctata caagttatga gaaagcaaaa gaaaacttct tcaaagggtt aggatacgca    780
aatgctaatt cagaatacaa aagggaaatc aaaagaagtt tagcgatgct tgaaaatgta    840
tggaacaaag aagaaaacga gtggttagat ttagattcaa gagatactac agatatgcaa    900
gaggtagctt tccatcatat tgttaacaag cgtaatgatc aagctagatc aattttaaat    960
cagcttgacg aaagggattc aagcaatcac gaattagctt acaatacctt tttaagaggg   1020
tttttgatga atgattttaa ttgttattgt caatcggtga aactttttaa ggacactgga   1080
gacaagtaca cgctccaact accoctaaga aatatcgaaa ggctgggtgc ggacaagagt   1140
ctagtggaac ttattgctca ctag                                          1164
```

<210> SEQ ID NO 58
<211> LENGTH: 963
<212> TYPE: DNA
<213> ORGANISM: Bacillus amyloliquefaciens

<400> SEQUENCE: 58

```
atgaaactat taaaagatga aaacagacaa agcacactca aaaaagtcag actcttggaa     60
caagcagact tgaatgaaaa ttatgaagaa atggactgta ttattgaaaa gttccgttac    120
tctatagatc caattctaaa tgaatttgga aatgtatatc aaatacatag acagcttcag    180
aaaggtgaaa taaacagaat tgaagcttca cgaaagtttg gaaagatgga cttgaaaacc    240
ccagagtgta aagtattttc acgtttaatg attctcccta tatgtttaca gactgcagaa    300
```

taccgtttga tgtacgaggt tggaaatgaa attgacctgg acattattga agaagaaagc 360
tacatcaaat catcgtatcg ttgcagactg ctaagtatgt tagctaatgc tgaattaggc 420
atcggtgatt taaagaaggc tcagctatat gctggtttaa caattaactg tgctatttcg 480
gacaatttct ttgcaagtgg ctatttaatt catggaaaca cccttttatt ttcagactat 540
gaagcagcta agcaaagctt tatgcatggt ttgaatttta cagaagaagg taaatttcat 600
tataaagagc ttagacgctc attatctttc ttggaaaatt actacggagt agaaaatgag 660
ttccttgatc atgattctga agaggttgga gaacagcaag gagtggtctt ctcgctaatc 720
aaacaaggca aaaagagtga agcacttagg atccttgaaa gcctggagaa tagagagcag 780
aacaaaaata tcttagcctt tcacttcttt tataaggggc tttgtacaga cagtaaggag 840
tatttcttta agtctgtgag atattttaaa gaatcagatg atacattctg cattaagttg 900
cctttggatg agcttgaaag attaggagag aataaggctc ttcttgaatt aatcacagtt 960
taa 963

<210> SEQ ID NO 59
<211> LENGTH: 963
<212> TYPE: DNA
<213> ORGANISM: Bacillus amyloliquefaciens

<400> SEQUENCE: 59
atgaaactat taaaagatga aaacagacaa agcacactca aaaaagtcag actcttggaa 60
caagcagact tgaatgaaaa ttatgaagaa atggactgta ttattgaaaa gttccgttac 120
tctatagatc caattctaaa tgaatttgga aatgtatatc aaatacatag acagcttcag 180
aaaggtgaaa taaacagaat tgaagcttca cgaaagtttg gaaagatgga cttgaaaacc 240
ccagagtgta aagtattttc acgtttaatg attctcccta tatgtttaca gactgcagaa 300
taccgtttga tgtacgaggt tggaaatgaa attgacctgg acattattga agaagaaagc 360
tacatcaaat catcgtatcg ttgcagactg ctaagtatgt tagctaatgc tgaattaggc 420
atcggtgatt taaagaaggc tcagctatat gctggtttaa caattaactg tgctatttcg 480
gacaatttct ttgcaagtgg ctatttaatt catggaaaca cccttttatt ttcagactat 540
gaagcagcta agcaaagctt tatgcatggt ttgaatttta cagaagaagg taaatttcat 600
tataaagagc ttagacgctc attatctttc ttggaaaatt actacggagt agaaaatgag 660
ttccttgatc atgattctga agaggttgga gaacagcaag gagtggtctt ctcgctaatc 720
aaacaaggca aaaagagtga agcacttagg atccttgaaa gcctggagaa tagagagcag 780
aacaaaaata tcttagcctt tcacttcttt tataaggggc tttgtacaga cagtaaggag 840
tatttcttta agtctgtgag atattttaaa gaatcagatg atacattctg cattaagttg 900
cctttggatg agcttgaaag attaggagag aataaggctc ttcttgaatt aatcacagtt 960
taa 963

<210> SEQ ID NO 60
<211> LENGTH: 1173
<212> TYPE: DNA
<213> ORGANISM: Bacillus subtilis

<400> SEQUENCE: 60
atgggtgtaa atgtccaact aagaaagaag cttaaaaacg gtattgaaaa taaaagatta 60
acagttcaac aactaaatga atatttagag ttgaaaaatt gcaatccgat ttatgatttt 120

```
cttaatgata aaaaggatac ttttcatgac ttcggtgctc taattagatt ggttaaaggg    180
atattccctg aagaagagta cgagcttatg tcagattaca tacttcattt agatccgaat    240
aagcattctc aagttttgcg ctgcggtatg gagtatgcag atgtcaacca attggacgag    300
ctcgctgatg aggtagcata tagacttctt aactcatcaa ataaccatag taaagaatgg    360
gggagcattt acacgcttca cagaaagcta tctaaaggtg aaatggagat acatgacgct    420
attcgtcaaa ctggaagaat tagaatccac acccctgaaa tgctcgtctt ttctaatgcg    480
atgttgatgt atgcatacct aaatatcgga gatttccatt tgttaaaaag tacgtttgat    540
ttgcttgata tagacgagtt acctgaaggc tatgtaaaag agtcttatta cggaagaacg    600
gctttactac atgccaatgt tagtctgaat gaaaacaacc tccttagtgc caggcactat    660
tcaagctacg ttctcgaaaa agcaaacaat aaccgtttta tggtttttgg acatttaaca    720
tctgggaaca cctatgtctt tgaagattac gataaggcta aagatcatta tttaaaaggt    780
ttgcagtatg ccaatactaa tccatttcat tattacaagc ttcgtttagc cctgtgcttt    840
ttgaataatg tttggaaaaa ggaaaatgag tgggttgatt ttgaatccaa tgagataaca    900
gacagaattg aagtggctta ctattacgta aatcaaaatg aagaacaaaa agcaattaag    960
gtttttcaag aacttgatag tagaaagatt ccgaaagatg atttgggatt tctattctat   1020
gttaaagggt tactatatca agaaaagtct tacttttatg agagtattga gtatttcaaa   1080
aagtcaggag ataaaatgtt tgtcaattta cctttaatgg aactgaaaaa gcaaggtgaa   1140
aatgaacgcc ttctccaatt attaaccatc taa                                1173
```

<210> SEQ ID NO 61
<211> LENGTH: 1161
<212> TYPE: DNA
<213> ORGANISM: Bacillus subtilis

<400> SEQUENCE: 61

```
atggagttaa taaggatagc tatgaagaaa gacttggaaa atgacaactc tttaatgaat     60
aaatgggcaa cagtagctgg ccttaaaaac tccaatcctc tttatgactt cttaaaccat    120
gatgggaaaa cttttaatga attttcttca atagtcaaca ttgttaaaag tcagtatcca    180
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagtaatttg aaaagtaaag aatatggaaa agtgtataaa    360
atacatagag aactgtctaa ctgtgatatt actgaatttg aggcagtgaa aagactcggt    420
aaattaaata ttaaaacacc tgaaatgaat tctttctcaa gactcttgct gctttatcat    480
tatttaagca ctggtaactt ttctccgatg gcccaactta taaaacaaat tgacctaagt    540
gagatttctg agaacatgta cattagaaac acatatcaaa caagagttca tgttctaatg    600
tcgaatataa agctaaatga aaattcatta gaggagtgca gagagtactc taaaaaggca    660
ttggaaagta caaatatcct cagatttcag gttttcagct acttaactat tggcaactct    720
ctattatttt cgaattatga attggctcaa gaaaactttt taaaagggct aagcgtttct    780
gttcaaaatg aaaattacaa catgattttc cagcaggctt tgtgcttctt aaataatgta    840
tggcgcaaag aaaataagtg gattaatttt gaatctgagt caattatgga tttgcaggag    900
caagcccatt gttttatcaa ctttaatgaa aattccaaag caaaaaaagt tttggataaa    960
ctagatcttt tacgtcataa cgataatgag cttgcaatgc atcattattt gaaagggaga   1020
ctcgaacaaa ataaagcatg tttctattct tcaatcgagt attttaaaaa gtctaatgac   1080
```

aaattcctta ttaggctgcc gttgttagaa ctgcaaaaga tgggtgaaaa tcaaaaactt 1140
ttagaattac ttttacttta a 1161

<210> SEQ ID NO 62
<211> LENGTH: 1140
<212> TYPE: DNA
<213> ORGANISM: Bacillus methylotrophicus

<400> SEQUENCE: 62
atgaatctta agcagatgat taagaatgaa tgtgaaaaag acaaccagct cgcagcgaaa 60
ctctcaaaaa tagcagggta cgaaaaggtt aacggctttt acaaattcat caacacccca 120
gagaaagaaa tggacaactt aggcggttta attaatattg ttaaaagctt gtttccagat 180
aatgaggagc agcttctaag tgattacttc ttatcactgg atcccaacaa aaaatgtgct 240
agacaatctg ttgaatactc agatattaat caatgggata cgttaacaga caagattatt 300
ttaaatttaa gcaactcaaa aaacaccaca agtcaagaat ggggcaacat ctacagcata 360
cacagaaagc tttataaaaa cgaaatctca ataccagaag caataagaga gtgcgggaga 420
tgcaaagccc cagaaatgtc atttttctca gatgcaatgc tgatgtataa atacttgaat 480
attggtgagt ttggattgat gaaaagcacc ttaacacttt tagattttaa aagcttgcca 540
gaaggattta taaaagattc gtacaaaagt agagtgtcaa tgttacaagc gaatataagc 600
ttaaatgaaa acaatttaat cgaagcgagg aaacattcaa atattgcaat aatgcagtcc 660
aatgtgaacc gaatatgttt ttttgcgcat ctgacaatag gaaacactct aattttcgaa 720
aactatgaag aagctatgct ggcgtataat gaggcaaaga agtatgttct taatgatacc 780
cataaagaaa tgctaaatgg tgctctttgc ttcctagcta acgtatggga caaggggaat 840
ccatgggtta actatgaatc agatgatatt aaatatcagc agcttagagc tttttattac 900
ataaaaaata ataatctcga caaggctaac gaattattgg aaagcttatc aactagggat 960
caagatgaaa atgaattagg attttatttt tattataaag gtttgatttc aaaacaaaaa 1020
tctgattttt ataaatcaat aacatatttc aaaaaatcag atgataaata ttttatccaa 1080
ttgacaataa tggaactcga aaaattaggc tgtgatccgg agctgctaaa tttaatttag 1140

<210> SEQ ID NO 63
<211> LENGTH: 1140
<212> TYPE: DNA
<213> ORGANISM: Bacillus methylotrophicus

<400> SEQUENCE: 63
atgaatctta agcagatgat taagaatgaa tgtgaaaaag acaaccagct cgcagcgaaa 60
ctctcaaaaa tagcagggta cgaaaaggtt aacggctttt acaaattcat caacacccca 120
gagaaagaaa tggacaactt aggcggttta attaatattg ttaaaagctt gtttccagat 180
aatgaggagc agcttctaag tgattacttc ttatcactgg atcccaacaa aaaatgtgct 240
agacaatctg ttgaatactc agatattaat caatgggata cgttaacaga caagattatt 300
ttaaatttaa gcaactcaaa aaacaccaca agtcaagaat ggggcaacat ctacagcata 360
cacagaaagc tttataaaaa cgaaatctca ataccagaag caataagaga gtgcgggaga 420
tgcaaagccc cagaaatgtc atttttctca gatgcaatgc tgatgtataa atacttgaat 480
attggtgagt ttggattgat gaaaagcacc ttaacacttt tagattttaa aagcttgcca 540
gaaggattta taaaagattc gtacaaaagt agagtgtcaa tgttacaagc gaatataagc 600

-continued ttaaatgaaa acaatttaat cgaagcgagg aaacattcaa atattgcaat aatgcagtcc 660
aatgtgaacc gaatatgttt ttttgcgcat ctgacaatag gaaacactct aattttcgaa 720
aactatgaag aagctatgct ggcgtataat gaggcaaaga agtatgttct taatgatacc 780
cataaagaaa tgctaaatgg tgctctttgc ttcctagcta acgtatggga caaggggaat 840
ccatgggtta actatgaatc agatgatatt aaatatcagc agcttagagc tttttattac 900
ataaaaaata ataatctcga caaggctaac gaattattgg aaagcttatc aactagggat 960
caagatgaaa atgaattagg attttatttt tattataaag gtttgatttc aaaacaaaaa 1020
tctgattttt ataaatcaat aacatatttc aaaaaatcag atgataaata ttttatccaa 1080
ttgacaataa tggaactcga aaaattaggc tgtgatccgg agctgctaaa tttaatttag 1140

<210> SEQ ID NO 64
<211> LENGTH: 963
<212> TYPE: DNA
<213> ORGANISM: Bacillus amyloliquefaciens

<400> SEQUENCE: 64
atgatagcaa aagagagaga agctaagaaa ccagaagtag atgcaaaggt acgtcttgaa 60
atgtcagata ttaatgaaca gtatgaacaa actgacgcat taattgatca attaatcaac 120
agtagctgtt cgattgaacg tgaatgggca gcaatgtatc agatcaaacg taagcaagac 180
agaggcgaaa taaacgcaca tcaggcgctt aaagcaattg ggaagcttga tcccaagtct 240
caagaaatgc gtgtattcac ttacataatc ccgttgtatt actaccttag aatggctgaa 300
tactcaaatc ttgcagaaat gtcgacaatt gttgatcttg attttattga aaacaatgaa 360
cagattaaaa gctcctttta taaccgtctg atggctttgt tgggcgcttc ggcattcagt 420
cagaataaaa tgactcaagc tcgtttttat tgctcatacg gcattaatgt aacgaatatt 480
gatagacttg tcgcttatag ctatctaact atgggtaaca cttatttgct tgatgattat 540
gaaaaagcaa aagaatatta cctagccggt ttaaaacata ctgagaataa ccccttggca 600
aaattacagc taactagaag cctttgtttt ttggaaaacc attgggatca agagaacttt 660
tggttaaacc ctgattcaaa tgaagttaca gatatccaag aaattgcaca ttatcacatc 720
aagaaaaaca acttgcaaca ggctaaagaa atattggaga acttagagca gcaaccaaat 780
attcataatg actttggcat tcatttttat ctaaaaggaa tagcttatga agataagaga 840
ttcttttatg agtctataaa acactttaag ctgtccggcg atctatacag cgtacgattg 900
cctttagata aattaaggga aatgggtgag gacgagcaga ttttagattt acttgccctt 960
taa 963

<210> SEQ ID NO 65
<211> LENGTH: 1140
<212> TYPE: DNA
<213> ORGANISM: Bacillus amyloliquefaciens

<400> SEQUENCE: 65
atgaatctta agcagatgat taagaatgaa tgtgaaaaag acaaccagct cgcagcgaaa 60
ctctcaaaaa tagcagggta cgaaaaggtt aatggttttt acaaattcat caacacccca 120
gagaaagaaa tggacaactt aggcggttta attaatattg ttaaaagctt gtttcctgat 180
aatgaggagc agcttctaag tgattacttc ttatcactgg atcccaacaa aaaatgcgct 240
agacaatctg ttgaatactc cgatatcaat caatgggatt cattaacaga caagattatt 300
ttaaatttat gccactcaaa aaacacaaca agtcaagaat ggggtaacat ctacaacata 360

```
catagaaagc tatataaaaa cgaaatctca ataccagaag caataagaga atgtgggaga    420
tgtaaagctc cagaaatgtc attttttca gatgcaatgc tgatgtataa atacttgaat    480
attggtgagt tcggattgat gaaaagcacc ttaacacttt tagattttaa aagcttacca    540
gaaggattta taaaagattc gtacaaaagt agagtgtcaa tgttaaaagc gaatataagc    600
ttaaacgaaa acaatttaat cgaagcaagg aaacattcaa atattgcaat aatgcagtcc    660
aatgtgaacc gaatatgttt ctttgcacat ctgacaatag gtaataccct aattttcgaa    720
aattatgaag aagctatgct ggcgtatgtt gaggcaaaga agtatgttct gaatgatact    780
catgaagaaa tgctaaatgg cgctctttgc ttcttagcta atgtatggaa caaggaaaat    840
ctatgggtta actatgaatc aaatgaaatc aaatatcaac agctaagggc tttttattac    900
ataaaaagta ataatctcga caaggctaac gaattattag aaagcttatc aaaaagagat    960
caagatgaaa atgaattagg attttatttt tattataaag gtttaatatc gaggcaaaaa   1020
tctgattttt ttaaatcaat aacatatttt aaagaatcag atgataaata ttttatccaa   1080
ttggcaataa tagaactcga aaaattaggc tgtgacccgg agctgctaaa tttaatttag   1140
```

<210> SEQ ID NO 66
<211> LENGTH: 1140
<212> TYPE: DNA
<213> ORGANISM: Bacillus amyloliquefaciens

<400> SEQUENCE: 66

```
atgaatctta agcagatgat taagaatgaa tgtgaaaaag acagccagct cgcagcgaaa     60
ctctcaaaaa tagcagggta cgaaaaggtt aatggttttt acaaattcat caacacccca    120
gagaaagaaa tggacaactt aggcggttta attaatattg ttaaaagctt gtttcctgat    180
aatgaggagc agcttctaag tgattacttc ttatcactgg atcccaacaa aaaatgcgct    240
agacaatctg ttgaatactc cgatatcaat caatgggatt cattaacaga caagattatt    300
ttaaatttat gccactcaaa aaacacaaca agtcaagaat ggggcaacat ctacaacata    360
catagaaagc tatataaaaa cgaaatctca ataccagaag caataagaga atgtgggaga    420
tgtaaagctc cagaaatgtc attttttca gatgcaatgc tgatgtataa atacttgaat    480
attggtgagt tcggattgat gaaaagcacc ttaacacttt tagattttaa aagcttacca    540
gaaggattta taaaagattc gtacaaaagt agagtgtcaa tgttaaaagc gaatataagc    600
ttaaacgaaa acaatttaat cgaagcaagg aaacattcaa atattgcaat aatgcagtcc    660
aatgtgaacc gaatatgttt ctttgcacat ctgacaatag gtaataccct aattttcgaa    720
aattatgaag aagctatgct ggcgtatgtt gaggcaaaga agtatgttct gaatgatact    780
catgaagaaa tgctaaatgg cgctctttgc ttcttagcta atgtatggat caaggaaaat    840
ctatgggtta actatgaatc aaatgaaatc aaatatcaac agctaagggc tttttattac    900
ataaaaagta ataatctcga caaggctaac gaattattag aaaacttatc aaaaagagat    960
caagatgaaa atgaattagg attttatttt tattataaag gtttaatatc gaggcaaaaa   1020
tctgattttt ttaaatcaat aacatatttt aaagaatcag atgataaata ttttatccaa   1080
ttggcaataa tagaactcga aaaattaggc tgtgacccgg agctgctaaa tttaatttag   1140
```

<210> SEQ ID NO 67
<211> LENGTH: 1140
<212> TYPE: DNA
<213> ORGANISM: Bacillus amyloliquefaciens

<400> SEQUENCE: 67
atgaatctta agcagatgat taagaatgaa tgtgaaaaag acaaccagct cgcagcgaaa 60
ctctcaaaaa tagcagggta cgaaaaggtt aatggttttt acaaattcat caacacccca 120
gagaaagaaa tggacaactt aggcggttta attaatattg ttaaaagctt gtttcctgat 180
aatgaggagc agcttctaag tgattacttc ttatcactgg atcccaacaa aaaatgcgct 240
agacaatctg ttgaatactc cgatatcaat caatgggatt cattaacaga caagattatt 300
ttaaatttat gccactcaaa aaacacaaca agtcaagaat ggggtaacat ctacaacata 360
catagaaagc tatataaaaa cgaaatctca ataccagaag caataagaga atgtgggaga 420
tgtaaagctc cagaaatgtc atttttttca gatgcaatgc tgatgtataa atacttgaat 480
attggtgagt tcggattgat gaaaagcacc ttaacacttt tagattttaa aagcttacca 540
gaaggattta taaaagattc gtacaaaagt agagtgtcaa tgttaaaagc gaatataagc 600
ttaaacgaaa acaatttaat cgaagcaagg aaacattcaa atattgcaat aatgcagtcc 660
aatgtgaacc gaatatgttt ctttgcacat ctgacaatag gtaataccct aattttcgaa 720
aattatgaag aagctatgct ggcgtatgtt gaggcaaaga agtatgttct gaatgatact 780
catgaagaaa tgctaaatgg cgctctttgc ttcttagcta atgtatggaa caaggaaaat 840
ctatgggtta actatgaatc aaatgaaatc aaatatcaac agctaagggc tttttattac 900
ataaaaagta ataatctcga caaggctaac gaattattag aaagcttatc aaaaagagat 960
caagatgaaa atgaattagg attttatttt tattataaag gtttaatatc gaggcaaaaa 1020
tctgattttt ttaaatcaat aacatatttt aaagaatcag atgataaata ttttatccaa 1080
ttggcaataa tagaactcga aaaattaggc tgtgacccgg agctgctaaa tttaatttag 1140

<210> SEQ ID NO 68
<211> LENGTH: 966
<212> TYPE: DNA
<213> ORGANISM: Bacillus amyloliquefaciens

<400> SEQUENCE: 68
atgaacttat tggacagagg tttagaaaaa gaaagtttga acgaagatat cagatttttg 60
gaactagcag atttgaatga aaactttgac gaaatggaac ttctaattga aaagctacgt 120
ttttcgaaga atacagaggc aaaacagtat agtgaagttt acagcataca tagaaaacta 180
gccaaaggcg aattaactgt taatgaagca tccaaaatga ttggacgtat ggatatcaac 240
atacctgaac taaaagtctt ttctgaacta atgctccttc ctgagtatct gaacctatca 300
gaatataagg ttatgaatgg aattgccaac aagattgatt tagacactat tgaaaatgaa 360
aacttcttta agtcgtcata ccgttgcaga ctgctgatta tgtcagctaa tgcttattta 420
ggcttaggcg atctgaaaaa agcgcaattc tacgcaggat taaccattga acatgctact 480
gatagccgct ttcttgctta tggttatctt attcatggta atactttatt gttttcagat 540
tataaagagg ctaaaaagag cttcttaaaa ggcttagagc actctgaaaa gggaaaatcc 600
cattataaag agcttagaag atcgttatcc ttcctcgaaa attactatgg tgaaaaaaat 660
gaataccttg attataactc attagaagtt ggggagcagc agggcgtggc ttattcattt 720
ataaatgaag ggaagattgt tgaagcactt caaattctcg atagaattga aaatgaaaag 780
cagaataaca acttacttgg ctttcacttc ttttataaag ggttggcgac taaaagtaaa 840
gattatttct tcaagtctgt taaacacttt aaattatcgg atgataagta ttgtgtaaaa 900
ctccctttgg acgaactgga gaaattgggt gagaataaag cccttttaga attaatcact 960
ttgtga 966

<210> SEQ ID NO 69
<211> LENGTH: 1140
<212> TYPE: DNA
<213> ORGANISM: Bacillus amyloliquefaciens

<400> SEQUENCE: 69
atgaatctta agcagatgat taagaatgaa tgtgaaaaag acagccagct cgcagcgaaa 60
ctctcaaaaa tagcagggta cgaaaaggtt aatggttttt acaaattcat caacacccca 120
gagaaagaaa tggacaactt aggcggttta attaatattg ttaaaagctt gtttcctgat 180
aatgaggagc agcttctaag tgattacttc ttatcactgg atcccaacaa aaaatgcgct 240
agacaatctg ttgaatactc cgatatcaat caatgggatt cattaacaga caagattatt 300
ttaaatttat gccactcaaa aaacacaaca agtcaagaat ggggcaacat ctacaacata 360
catagaaagc tatataaaaa cgaaatctca ataccagaag caataagaga atgtgggaga 420
tgtaaagctc cagaaatgtc atttttttca gatgcaatgc tgatgtataa atacttgaat 480
attggtgagt tcggattgat gaaaagcacc ttaacacttt tagattttaa aagcttacca 540
gaaggattta taaaagattc gtacaaaagt agagtgtcaa tgttaaaagc gaatataagc 600
ttaaacgaaa acaatttaat cgaagcaagg aaacattcaa atattgcaat aatgcagtcc 660
aatgtgaacc gaatatgttt ctttgcacat ctgacaatag gtaataccct aattttcgaa 720
aattatgaag aagctatgct ggcgtatgtt gaggcaaaga agtatgttct gaatgatact 780
catgaagaaa tgctaaatgg cgctctttgc ttcttagcta atgtatggat caaggaaaat 840
ctatgggtta actatgaatc aaatgaaatc aaatatcaac agctaagggc tttttattac 900
ataaaaagta ataatctcga caaggctaac gaattattag aaaacttatc aaaaagagat 960
caagatgaaa atgaattagg attttatttt tattataaag gtttaatatc gaggcaaaaa 1020
tctgattttt ttaaatcaat aacatatttt aaagaatcag atgataaata ttttatccaa 1080
ttggcaataa tagaactcga aaaattaggc tgtgacccgg agctgctaaa tttaatttag 1140

<210> SEQ ID NO 70
<211> LENGTH: 1167
<212> TYPE: DNA
<213> ORGANISM: Bacillus licheniformis

<400> SEQUENCE: 70
gtgaaagaat tggagttgaa aaatttttta aagaataaat gtgaagaaga acgcggactc 60
gaaaaggagc ttgcacgaat agcaggatac tctaactcgt caggctttca tcatttcatt 120
tacaatgaaa agaaagaaat ggataatatt caaggtatca ttgaagtgat tcagaagatt 180
tccccggaat atgagtttga tttaatgagt gaatacatat tgacattaga cataaataaa 240
tctgcagcaa ggcaaggctt agaatacctt agtgtaaatc agctatatga cactctagat 300
aaacatatta agaaaatggt gtctgcaaag aattcagtta gtaaagaatg gggaaaagtc 360
tatgcagccc aaagagagct agacaaaggc aacattggta ttgaagagtg cattaggctg 420
ttggctgaag tacaccccaa atcatctgaa atgaaggttt actctaggat tatccccatg 480
tatgccatac tacctttaaa gcaatttggt agattaaaag atatgagtga tattgtcttg 540
attgacacaa tcagtagtca aaattatgtt tatcattcgt ttaagagtcg ctatatgcta 600
ttactggcaa actgcttctt tggaaacaat gagattgaga aagcacaaga atacgcaaga 660
catgggatag agaattcaaa tgtgaagagg atcatttttt tctcatacct cacgtatgga 720
agttctttaa tgttagatga ttacgagaaa tcaaaaagca gttttttgaa aggtttagaa 780
gttggcaaag gaaacaaaat ttatgagcaa catgcgatta gaaatctttg tttcctagaa 840
aatctatggg ggaaagagaa tcaatatttg aatatacaat ctaatgaaat aatggacagg 900
caagaagttg ttcattatct tataagaaaa ggttctaagc aacaggctaa aaagatgctt 960
gaccagctag atctcgtaga gcaagatgat aacgatttgg gtttacatta ttatttaaag 1020
ggacttttgg aaaactctcg cgattatttc ttggaatcag tcaaatattt caaattaagt 1080
ggtgataagt tttcctgcac ccttccaata attgaactcg aaaagttagg tgttgataag 1140
caaattctag agatgatatc aatttga 1167

<210> SEQ ID NO 71
<211> LENGTH: 1158
<212> TYPE: DNA
<213> ORGANISM: Bacillus sp.

<400> SEQUENCE: 71
atgaatctta aaacatacat aaaaaataaa tgtgaagatg attcttcttt ggctatgaaa 60
ctagctaaga tagcgggcta ttcggataga actggccttt acaaattttt aaatagctct 120
aacaaagaga tggatgactt gagcaatctt ataaatttag ttagagaagt tgatcaagaa 180
agagaaattg aaataattag cacctatatc acaacactcg accctaacaa gtcagctgct 240
agacaagctg tagaatattt agatgctaat caacttgggg aagaaacaga tgaacttgtt 300
gataaattat gcaacgccag caacgcatta agcaaagagt gggggaatgt atatcgcata 360
catagaatgc tcacaaaagg tgaaattgat ttaacttctg ctatcaaaga aactggtact 420
ataaaaatca agagtgaaga aatgtttgtg tttgcaagga tgatgacatt gtatgaatac 480
ctaaactcag gtgagtttgg tctaatgaag agtacatcag catatattga tctttctaat 540
ttaaaaaagg gttatgttaa agactctttt agttcaaggt atttgctgct tatggccaac 600
gtgtttttaa atgacaacaa tttaaagcct ctcagagact actgtgatca aattataact 660
gaagatgtta aggtgaatcg atttcaagtg tttgctcatc ttacctgcgg taattcttat 720
gtgtttgatg attataagaa agcaaaaaca tattatatca acggtttgaa attcgcaaaa 780
aatagcttcc ataaatataa acttacatca gctttggcat tcttagaaaa catttgggga 840
gtaaaagaaa ataaatacct cgaacaggaa ccgaaaaatg attctgattt tatagaactt 900
gcacatcact ttatgcttaa tgatcaggca gataaaatga tggatgtgtt taataaatta 960
gactcaacta ctatgcatga taatgattta gggttccttt actatgttaa aggtatattc 1020
tataaagaca aagggtgctt cttgaaatca gttaaacatt tcaagaaatc agatgataaa 1080
tattttgtta aactgccttt aattaaatta aagaatatgg gcgtagaaaa tgaaatttta 1140
gaacttttag ctatttga 1158

<210> SEQ ID NO 72
<211> LENGTH: 1167
<212> TYPE: DNA
<213> ORGANISM: Bacillus sonorensis

<400> SEQUENCE: 72
gtgaaagaat tggagttgaa aagtttatta aagaacaaat gtgaagaaga acgaggactc 60
gaaaaagaac tcgctaaaat agctggatat tctaattcat ctgggtttca tcagtttatt 120
tttaatgata aaaaagaaat ggataacatc cagggcttaa taaatgttgt tcaaagagta 180

-continued

```
tcccctgata atgaatttga attaatgagt gaatacatac taactttaga tcctaataag    240
tctgcagcaa gacaaggttt agaatattta agtgtaaatc agttatacga tactttagat    300
actcatatcg agaacttaag agctgctaaa aatacaatca gtaaggaatg gggaaaggta    360
tactctctcc aaagggaact cgactgcgga aagataagca tcgaagagtg tataaggatt    420
ctaggagaaa ttaatcctaa atcacctgaa atgaaggttt attcaaggtt aattcctatg    480
tacgccgcat tatcattaaa tcaattcact aggttgatgg ccatgagtga agatgtaatt    540
ttaaatagaa ttacaacaca aaattatgtt tattattcgt acaaaagcag gtatatgctt    600
ttgttggcaa actgttgttt tggtagtaat gatttgaaaa aagctaggga gtatgccaag    660
tacggcataa acaattcgaa cgttaaaaga atcatttttt tctcctacct tacatatgga    720
accactttaa tgtttagcga ttactcttct gctaaggaaa tctttttaaa gggtatggaa    780
attgcaaaag gaaatgattt ttatgaacag caaataaaga gaagcctttg ttttctagaa    840
aacgtgtgga ataaagaaaa ccaatatttg aacatagagt ccaatgaaat tatggataag    900
caagaagtta ttcactatct tattagaaaa ggaaacattg atgaggctaa aagaatgcta    960
gagcaaattg aaaaattaca tcatgatgat tatgaattgg gaatgcattt ttatttaaaa   1020
gggttaattg ataactctca aagtcatttt ttgagatcaa tcaagcactt taagattagt   1080
ggagataaat tttcgactac tttgcccatt atagaattag aaaaattagg tttagacaag   1140
gctatcttag atgttttaac actatag                                       1167
```

<210> SEQ ID NO 73
<211> LENGTH: 1170
<212> TYPE: DNA
<213> ORGANISM: Bacillus licheniformis

<400> SEQUENCE: 73

```
gtggtgaaag aattggagtt gaaaaatttt ttaaagaata aatgtgaaga agaacgcgga     60
ctcgaaaagg agcttgcacg aatagcagga tactctaact cgtcaggctt tcatcatttc    120
atttacaatg aaaagaaaga aatggataat attcaaggta tcattgacgt gattcagaag    180
atttccccgg aatatgagtt tgatttaatg agtgaataca tatttacatt agacataaat    240
aaatctgcag caaggcaagg cttagaatat cttagtgtaa atcagctata tgacactcta    300
gataaacata ttaagaaaat ggtgtctgca aagaattcag ttagtaaaga atggggaaaa    360
gtctatgcag cccaaagaga gctagacaaa ggcaacattg gtattgaaga gtgcattagg    420
ctgttggctg aaatccaacc caaatcatct gaaatgaagg tttactctag gattatcccc    480
atgtatgcca tactaccttt aaagcaattt ggtagattaa aagatatgag tgatagtgtc    540
ttgattgaca caatcagtaa tcaaaattat gtttatcatt cgtttaagag tcgctatatg    600
ctattactgg caaactgctt ctttggaaac aatgagattg agaaagcaca agaatacgca    660
agacatggga tagagaattc aaatgtgaag aggatcattt ttttctcata cctcacgtat    720
ggaagttctt taatgttaga tgattacgag aaatcaaaaa gcagtttttt gaaaggttta    780
gaagttggca aaggaaacaa aatttatgag caacatgcga ttagaaatct ttgtttccta    840
gaaaatctat gggggaaaga gaatcaatat ttgaatatac aatctaatga aataatagat    900
aggcaagaag ttgttcatta tcttataaga aaaggttcta agcaacaggc caaaaaaatg    960
cttgaccagt tagatctcat ggagcacgat gataacgatc tgggattaca ttattattta   1020
aagggacttt tggaaagctc tcgcgaatat tttttagaat cagtcaaata ttttaaatta   1080
```

-continued agtggtgata agttttcctg caccottcca ataattgaac tcgaaaagtt aggtgttgaa 1140
aaacaaattt tagagataat atcaatttga 1170

<210> SEQ ID NO 74
<211> LENGTH: 1170
<212> TYPE: DNA
<213> ORGANISM: Bacillus licheniformis

<400> SEQUENCE: 74
gtggtgaaag aattggagtt gaaaaatttt ttaaagaata aatgtgaaga agaacgcgga 60
ctcgaaaagg agcttgcacg aatagcagga tactctaact cgtcaggctt tcatcatttc 120
atttacaatg aaaagaaaga aatggataat attcaaggta tcattgacgt gattcagaag 180
atttccccgg aatatgagtt tgatttaatg agtgaataca tatttacatt agacataaat 240
aaatctgcag caaggcaagg cttagaatat cttagtgtaa atcagctata tgacactcta 300
gataaacata ttaagaaaat ggtgtctgca aagaattcag ttagtaaaga atggggaaaa 360
gtctatgcag cccaaagaga gctagacaaa ggcaacattg gtattgaaga gtgcattagg 420
ctgttggctg aaatccaacc caaatcatct gaaatgaagg tttactctag gattatcccc 480
atgtatgcca tactaccttt aaagcaattt ggtagattaa aagatatgag tgatagtgtc 540
ttgattgaca caatcagtaa tcaaaattat gtttatcatt cgtttaagag tcgctatatg 600
ctattactgg caaactgctt ctttggaaac aatgagattg agaaagcaca agaatacgca 660
agacatggga tagagaattc aaatgtgaag aggatcattt ttttctcata cctcacgtat 720
ggaagttctt taatgttaga tgattacgag aaatcaaaaa gcagtttttt gaaaggttta 780
gaagttggca aaggaaacaa aatttatgag caacatgcga ttagaaatct ttgtttccta 840
gaaaatctat gggggaaaga gaatcaatat ttgaatatac aatctaatga aataatagat 900
aggcaagaag ttgttcatta tcttataaga aaaggttcta agcaacaggc caaaaaaatg 960
cttgaccagt tagatctcat ggagcacgat gataacgatc tgggattaca ttattattta 1020
aagggacttt tggaaagctc tcgcgaatat tttttagaat cagtcaaata ttttaaatta 1080
agtggtgata agttttcctg caccottcca ataattgaac tcgaaaagtt aggtgttgaa 1140
aaacaaattt tagagataat atcaatttga 1170

<210> SEQ ID NO 75
<211> LENGTH: 1170
<212> TYPE: DNA
<213> ORGANISM: Bacillus sp.

<400> SEQUENCE: 75
gtggtgaaag aattggagtt gaaaaatttt ttaaagaata aatgtgaaga agaacgcgga 60
ctcgaaaagg agcttgcacg aatagcagga tactctaact cgtcaggctt tcatcatttc 120
atttacaatg aaaagaaaga aatggataat attcaaggta tcattgacgt gattcagaag 180
atttccccgg aatatgagtt tgatttaatg agtgaataca tattgacatt agacataaat 240
aaatctgcag caaggcaagg cttagaatac cttagtgtaa atcagctata tgacactcta 300
gataaacata ttaagaaaat ggtgtctgca aagaattcag ttagtaaaga atggggaaaa 360
gtctatgcag cccaaagaga gctagacaaa ggcaacattg gtattgaaga gtgcattagg 420
ctgttggctg aaatacaccc caaatcatct gaaatgaagg tttactctag gattatcccc 480
atgtatgcca tactaccttt aaagcaattt ggtagattaa aagatatgag tgatattgtc 540
ttgattgaca caatcagtaa tcaaaattat gtttatcatt cgtttaagag tcgctatatg 600
ctattactgg caaactgctt ctttggaaac aatgagattg agaaagcaca agaatacgca 660
agacatggga tagagaattc aaatgtgaag aggatcattt ttttctcata cctcacgtat 720
ggaagttctt taatgttaga tgattacgag aaatcaaaaa gcagtttttt gaaaggttta 780
gaagttggca aaggaaacaa aatttatgag caacatgcga ttagaaatct ttgtttccta 840
gaaaatctat gggggaaaga gaatcaatat ttgaatatac aatctaatga aataatggac 900
aggcaagaag ttgttcatta tcttataaga aaaggttcta agcaacaggc caaaaaaatg 960
cttgaccagt tagatctcat ggagcacgat gataacgatc tgggattgca ttattattta 1020
aaaggacttt tggaaagctc tcgcgaatat tttttagaat cagtcaaata ttttaaatta 1080
agtggtgata agttttcctg cacccttcca ataattgaac tcgaaaagtt aggtgttgaa 1140
aaacaaattt tagagataat atcaatttga 1170

<210> SEQ ID NO 76
<211> LENGTH: 1056
<212> TYPE: DNA
<213> ORGANISM: Bacillus licheniformis

<400> SEQUENCE: 76
gtggtgaaag aattggagtt gaaaaatttt ttaaagaata aatgtgaaga agaacgcgga 60
ctcgaaaagg agcttgcacg aatagcagga tactctaact cgtcaggctt tcatcatttc 120
atttacaatg aaaagaaaga aatggataat attcaaggta tcattgacgt gattcagaag 180
atttccccgg aatatgagtt tgatttaatg agtgaataca tattgacatt agacataaat 240
aaatctgcag caaggcaagg cttagaatac cttagtgtaa atcagctata tgacactcta 300
gataaacata ttaagaaaat ggtgtctgca aagaattcag ttagtaaaga atggggaaaa 360
gtctatgcag cccaaagaga gctagacaaa ggcaacattg gtattgaaga gtgcattagg 420
ctgttggctg aaatacaccc caaatcatct gaaatgaagg tttactctag gattatcccc 480
atgtatgcca tactaccttt aaagcaattt ggtagattaa aagatatgag tgatagtgtc 540
ttgattgaca caatcagtaa tcaaaattat gtttatcatt cgtttaagag tcgctatatg 600
ctattactgg caaactgctt ctttggaaac aatgagattg agaaagcaca agaatacgca 660
agacatggga tagagaattc aaatgtgaag aggatcattt ttttctcata cctcacgtat 720
ggaagttctt taatgttaga tgattacgag aaatcaaaaa gcagtttttt gaaaggttta 780
gaagttggca aaggaaacaa aatttatgag caacatgcga ttagaaatct ttgtttccta 840
gaaaatctat gggggaaaga gaatcaatat ttgaatatac aatctaatga aataatggac 900
aggcaagaag ttgttcatta tcttataaga aaaggttcta agcaacaggc caaaaaaatg 960
cttgaccagt tagatttcat ggagcacgat gataacgatc tgggattaca ttattattta 1020
aagggacttt tggaaagctc tcgcgaatat ttttag 1056

<210> SEQ ID NO 77
<211> LENGTH: 1170
<212> TYPE: DNA
<213> ORGANISM: Bacillus sp.

<400> SEQUENCE: 77
gtggtgaaag aattggagtt gaaaaatttt ttaaagaata aatgtgaaga agaacgcgga 60
ctcgaaaagg agcttgcacg aatagcagga tactctaact cgtcaggctt tcatcatttc 120
atttacaatg aaaagaaaga aatggataat attcaaggta tcattgacgt gattcagaag 180

```
atttccccgg aatatgagtt tgatttaatg agtgaataca tattgacatt agacataaat    240
aaatctgcag caaggcaagg cttagaatac cttagtgtaa atcagctcta tggcactcta    300
gataagcata ttaagaaaat gatgtccgca aagaattcag ttagcaaaga atggggaaaa    360
gtctatgcag cgcaaaggga gttagacaaa ggcaacattg gtattgaaga gtgcattagg    420
ctgttggctg aaatacaccc caaatcatct gaaatgaagg tttactctag gattatcccc    480
atgtatgcca tactaccttt aaagcaattt ggtagattaa aagatatgag tgatattgtc    540
ttgattgaca caatcagtaa tcagaattat gtttatcatt cgtttaagag tcgctatatg    600
ctattactgg caaattgctt ctttggaaac aatgagattg agaaagcaca agaatacgca    660
agacatggga tagagaattc aaatgtgaag aggatcattt ttttctcata tctcacgcat    720
ggaagttctt taatgttaga tgattacgag aaatcaaaaa gcagcttttt gaaagggtta    780
gaagttggca aaggaaacaa aatttatgag caacatgcga ttagaaatct ttgtttttta    840
gaaaatctat gggggaaaga gaataaatat ttgaatatac aatctaatga aataatggac    900
aggcaagaag ttgttcatta tcttataaga aaaggttcta agcaacaggc caaaaaaatg    960
cttgaccagt tagatctcat ggagcacgat gataacgatc tgggattaca ttattattta   1020
aagggacttt tggaaagctc tcgcgaatat tttttagaat cagtcaaata ttttaaatta   1080
agtggtgata agttttcctg caccccttcca ataattgaac tcgaaaagtt aggtgttgaa   1140
aaacaaattt tagagataat atcaatttga                                    1170
```

<210> SEQ ID NO 78
<211> LENGTH: 1158
<212> TYPE: DNA
<213> ORGANISM: Bacillus licheniformis

<400> SEQUENCE: 78

```
ttggagttga aaaggttcat aaaaaataaa tgcgaagagg aacgtggact cgaaaaagag     60
cttgcacgaa tagctggata ttctaactcg tcaggcttcc atcatttcat ttacaacgaa    120
aagaaagaaa tggataatat tcaaggcatc attgacgtga ttcagaaggt ttccccggaa    180
tatgagtttg atttaatgag tgaatacata ttgacattag atataaataa atctgcagca    240
agacaaggtt tagaatacct tagtgtaaac cagctctatg acaccctaga taaacatatt    300
aagaaaatgg tgtccgcgaa gaattcagtt agcaaagaat ggggaaaggt ctatgcagcc    360
caaagggagt tagacaaagg cagcattggt attgaagagt gcattagact tttatctgaa    420
atacacccca agtcgtcaga aatgagggtt tattctagga ttatacccat gtatgccata    480
cttcctttaa agcaattcgg cagattaaaa gatatgagcg atattgtttt gattgacaca    540
atcagtaatc agaattatgt ttatcattcg tttaagagtc gttacatgct attattggcg    600
aattgctttt ttgggaacaa tgagattgag aaagcacaaa aatacgcaag gcacgggata    660
gagaattcaa atgtaaagag gattattttt ttctcatatc ttacgtatgg aagctcttta    720
atgttagatg attatgagaa atcaaaaagc agctttttaa aagggttaga agttggaaaa    780
ggaaacaaaa tttatgagca acatgcaatt agaaatcttt gctttctaga aaatttatgg    840
gggaaagaga atcaatattt aaatatagaa tctaatgaaa tagtggacaa gcaagaagtt    900
gttcattatc ttataagaaa aggttctaag caacaggcta aaaaaatgct tgaccagcta    960
gatctcgtag agcatgatga taacgatttg ggattacatt attatttaaa gggacttttg   1020
gaaaactctc gcgaatattt cttagaatca gtcaaatatt ttaaattaag tggtgataag   1080
ttttcctgca cccttccaat aattgaactc gaaaagttag gtgttgataa acaaattcta   1140
```

gagataatat caatttga 1158

<210> SEQ ID NO 79
<211> LENGTH: 1158
<212> TYPE: DNA
<213> ORGANISM: Bacillus licheniformis

<400> SEQUENCE: 79
ttggagttga aaaatttatt aaaaaataaa tgtgaagaag aacgcggact cgaaaaggag 60
cttgcacgaa tagctggata ttctaactct tcaggcttcc accatttcat ttacaacgaa 120
aagaaagaaa tggataatat tcaaggcatc attgacgtga ttcagaaggt ttccccggaa 180
tatgagtttg atttaatgag tgaatacata ttgacattag atataaataa atctgcagca 240
agacaaggct tagaatacct tagtgtaaac cagctctatg acaccctaga taaacatatt 300
aagaaaatgg tgtccgcgaa aaattcagtt agcaaagaat ggggaaaggt ctatgcagct 360
caaagggaat tagacaaagg caacatttgc attgaagagt gcattagatt gttagctgaa 420
atacacccca aatcatctga aatgaaggtt tactctagaa ttatcccaat gtatgccata 480
cttcctttaa agcaattcgg cagattaaaa gatatgagcg atattgtttt gattgacaca 540
atcagtaatc ataattatgt ttatcattcg tttaagagtc gttatatgct gttattggca 600
aattgctttt ttgggaacaa tgagactgag aaagcgcaaa aatatgcaag gcacgggata 660
gagaattcaa atgtaaaaag gatcattttt ttctcatatc tcacgtatgg aagctcttta 720
atgctggatg attacgagaa atcaaaaagc agctttttaa aaggattaga agttggaaaa 780
ggaaacaaaa tttatgagca acatgcaatt aggaatcttt gttttctaga aaatctatgg 840
gggaaagaga atcaatattt aaatatagaa tctaatgaaa tagtggacaa gcaagaagtt 900
gttcattatc ttataaaaaa aggttctaag caacaggcta aaaagatgct tgaccagcta 960
gatctcgtag agcaagatga taacgatttg ggtttacatt attatttaaa gggacttttg 1020
gaaaactctc gcgattattt cttggaatca gtcaaatatt tcaaattaag tggtgataag 1080
ttttcctgca cccttccaat aattgaactc gaaaagttag gagttgataa gcaaattcta 1140
gaggtgatat caatttga 1158

<210> SEQ ID NO 80
<211> LENGTH: 894
<212> TYPE: DNA
<213> ORGANISM: Bacillus subtilis

<400> SEQUENCE: 80
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aaatgattcc catgtacgat 480
tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 81
<211> LENGTH: 894
<212> TYPE: DNA
<213> ORGANISM: Bacillus atrophaeus

<400> SEQUENCE: 81
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aaatgattcc catgtacgat 480
tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 82
<211> LENGTH: 963
<212> TYPE: DNA
<213> ORGANISM: Bacillus subtilis

<400> SEQUENCE: 82
atgtcaacta acactaaaga agtagaatca aatgtatcag aagaaataaa acttttggaa 60
ctagcagatt tagatgaaaa ttatgaagaa atggatctca taatcgaacg gttacgtttt 120
tcatcagatt cagtgttaaa tgagttcggt aacgtatacc aaatacatag acagctgcaa 180
aaaggtcaaa taaatagaat agaagcttca aggaagttag ggaaaatgga tttaaaaact 240
ccagagtgta aagtgttctc acgcttaatg attcttccta tctgcttaca aacggcagag 300
tataagctaa tgtatgaggt tggtaatgaa atcgacttag atattattga agaagaaagt 360
ttccttaaaa agtcttatcg tagccgattg ttgagcatgt tggctaatgc agaattgggg 420
atagggaatt taaagaaagc ccaattctat gctagtttga cagttgacag cgctattaca 480
gacaatttct atgctagtgg gtacttaatt catgggaaca ctcttttatt ctcagattac 540
aatgaagcca agcttagttt cttgcaaggg ttggaataca ctgaagaagg aaaattccat 600
tatagagagc ttagacggtc gctttctttc ctagaaaatt atcatggcga ggaaaacatt 660
taccttgatc ataattctaa tgaagttggt gaacgtcaag gagtagccta tgccttaatc 720
aaagaaggca aaaagagcga agcgcttaaa atccttgaag aattagagaa tcgtgaacag 780
aataagaaca ttcttgcttt tcattactac tataagggac tctgcacaga tagcaaagat 840
tacttcttta aatctgtcag atactttaaa gaatctgatg acacgtattg tgtcaagtta 900
ccattggatg aactcgaaag gctcggagag aacaaaactt tattagattt aataacaatt 960
taa 963

<210> SEQ ID NO 83
<211> LENGTH: 1161
<212> TYPE: DNA
<213> ORGANISM: Bacillus amyloliquefaciens

<400> SEQUENCE: 83
atggagctta taagaatagc tatgcggaaa gatttagaaa atgataaatc actcatgagt 60
aaatgggctg cggtagctgg tcttaaaaac ccaaaccctc tttacgattt cctaaaccat 120
gatggtaaga cttttagtga atttaactcg atagttaaca ttgtgaagac ccactaccct 180
gaccaagaat atgaactcat ggaaaattac tgtctattgc ttgacccaaa tactaaggct 240
gcaagaagcg cactggaata tgcagacgct aacagtttta atactctaac tgataagctg 300
gtagaaaaaa tgagcatcgc ctctaatttg aaaagtaaag agtacggaaa aatttacgag 360
atacatagga agctatcaag aggagagata gatgttctag aagcatcaaa aaatattgga 420
aagtacagaa tcaaaactga tgaaatgaat atttttcaa aaatgattcc catgtacgac 480
tatttaagta aagggaactt ctctccgatg aagtctttac tgaagcaaat agaccttaat 540
gatattaaag aaaataatta tttgaaaaag tcgtttgaga ctagaattta cgttctttta 600
tctaatattt atttaaatga aaatgaactt gaattgtcta gaaagtatgc agaaaaagcg 660
attaaatcaa ctgataccaa acgtttttttg gtttttagtt atttaacaat aggtacgtcc 720 tatattttt ccgactatgc cttaagcaag cagaattatt tatctggcta tgaaattgca 780
aaagggaaca gtgtttttga agaattcttc aagagaaatt tgagcttttt aaataacttt 840
tggaataaag aaaatccatg gatcaactac gattcaaatg cagtgactga tgtccaagaa 900
gttatttttg aacttataaa ccaaaaaaaa ttggagagag ctttaacttt gttaaagagt 960
ctggaaagaa aaaagcaaaa cgaaaatgat cttgggtttc attattactt agagggtctt 1020
ataaccaatg ataaagaagc attttataaa tcagttgaat attttaaact ttcgcaagac 1080
aagcttttta ttaaaatgcc tcttattaaa ttggagagct taggtgagaa tccaaggcta 1140
ctaaaaatta tttctatgta a 1161

<210> SEQ ID NO 84
<211> LENGTH: 1161
<212> TYPE: DNA
<213> ORGANISM: Bacillus subtilis

<400> SEQUENCE: 84
atggagctta taagaatagc tatgcggaaa gatttagaaa atgataaatc actcatgagt 60
aaatgggctg cggtagctgg tcttaaaaac ccaaaccctc tttacgattt cctaaaccat 120
gatggtaaga cttttagtga atttaactcg atagttaaca ttgtgaagac ccactaccct 180
gaccaagaat atgaactcat ggaaaattac tgtctattgc ttgacccaaa tactaaggct 240
gcaagaagcg cactggaata tgcagacgct aacagtttta atactctaac tgataagctg 300
gtagaaaaaa tgagcatcgc ctctaatttg aaaagtaaag agtacggaaa aatttacgag 360

```
atacatagga agctatcaag aggagagata gatgttctag aagcatcaaa aaatattgga    420

aagtacagaa tcaaaactga tgaaatgaat attttttcaa aaatgattcc catgtacgac    480

tatttaagta aagggaactt ctctccgatg aagtctttac tgaagcaaat agaccttaat    540

gatattaaag aaaataatta tttgaaaaag tcgtttgaga ctagaattta cgttctttta    600

tctaatattt atttaaatga aaatgaactt gaattgtcta gaaagtatgc agaaaaagcg    660

attaaatcaa ctgataccaa acgttttttg gtttttagtt atttaacaat aggtacgtcc    720

tatattttttt ccgactatgc cttaagcaag cagaattatt tatctggcta tgaaattgca    780

aaagggaaca gtgtttttga agaattcttc aagagaaatt tgagcttttt aaataacttt    840

tggaataaag aaaatccatg gatcaactac gattcaaatg cagtgactga tgtccaagaa    900

gttatttttg aacttataaa ccaaaaaaaa ttggagagag ctttaacttt gttaaagagt    960

ctggaaagaa aaaagcaaaa cgaaaatgat cttgggtttc attattactt agagggtctt   1020

ataaccaatg ataaagaagc attttataaa tcagttgaat attttaaact ttcgcaagac   1080

aagcttttta ttaaaatgcc tcttattaaa ttggagagct taggtgagaa tccaaggcta   1140

ctaaaaatta tttctatgta a                                              1161
```

<210> SEQ ID NO 85
<211> LENGTH: 717
<212> TYPE: DNA
<213> ORGANISM: Bacillus subtilis

<400> SEQUENCE: 85

```
atgagggtat ttacatacat aattccattg tattactacc ttgaagtggc agaatactct     60

aatcttgcag aaatgtcgac tattgtagat cttgatttaa tcgagaacaa tgatgatatt    120

aaaagctact tttataaccg tctgatggct ctgctaggtg cttcagcgtt cagtcaaaat    180

aaaatgactc aagcacgctt ttactgctcc tacggcatta atttaaagaa tattgataga    240

ttggttgcat acagctgtct gacaatgggg aacacgtaca tccttgatga ttatgaacga    300

gcgaaagaat atttcttaaa aggtttgaat catactgata ataaccattt ggcagaatta    360

caattaacta gaagtctttg cttcttggag aatcactggc gaaaagagaa cttttggcta    420

aatcctgatt cggaagaaac cacagacatc caagaaattg cacattatca catcaagaga    480

aacaatctag attatgctaa agaaatttta gattacctag aagaaatacc aagcatcgat    540

aatgactatg gcatccattt ctatctaaaa ggactcgctt ataaggacaa gagatacttt    600

tataaatcga ttaaacattt caagctgtcc ggtgatttat tctgtgttcg cttacctta     660

gatcaattaa gggaaatggg tgaggatgcg cagattttgg atttgcttgc cctctaa       717
```

<210> SEQ ID NO 86
<211> LENGTH: 963
<212> TYPE: DNA
<213> ORGANISM: Bacillus subtilis

<400> SEQUENCE: 86

```
ttgacagtta aagagagaga agttgaaaaa acgaatgtag atgtaaaagt acaacttgaa     60

atgtcagata tcaatgaaca gtgtgaacaa actgacacat tgattgaaca attaagcaat    120

agcagctgtc caattgaacg tgaatgggct gcgatgtatc agatcaaacg tagacaagac    180

aaaggcgaat taaacgcaca tcaggcactt aaagcaattg gaaagctcga tcccaagaca    240

caggaaatga gggtatttac atacataatt ccattgtatt actaccttga agtggcagga    300

tactctaatc ttgcagaaat gtcgactatt gtagatcttg atttaatcga gaacaatgat    360
```

gatattaaaa gctactttta taaccgtttg atggctctgc taggtgcttc agcgttcagt 420
caaaataaaa tgactcaagc acgcttttac tgctcctacg gcattaattt aaagaatatt 480
gatagattgg ttgcatgcag ctgtctgaca atggggaaca cgtacatcct tgatgattat 540
gaacgagcga aagaatattt cttaaaaggt ttgaatcata ctgataataa ccatttggca 600
gaattacaat taactagaag tctttgcttc ttggagaatc actggcgaaa agagaacttt 660
tggctaaatc ctgattcgga agaaaccaca gacatccaag aaattgcaca ttatcacatc 720
aagagaaaca atctagatta tgctaaagaa attttagatt acctagaaga aataccaagc 780
atcgataatg attatggcat ccatttctat ctaaaaggac tcgcttataa ggacaagaga 840
tatttttata aatcgattaa acatttcaag ctgtccggtg atttattctg tgttcgctta 900
cctttagatc aattaaggga aatgggtgag gatgcgcaga ttttggattt gcttgccctc 960
taa 963

<210> SEQ ID NO 87
<211> LENGTH: 1161
<212> TYPE: DNA
<213> ORGANISM: Bacillus aerophilus

<400> SEQUENCE: 87
ttgagcaaat tgaaagcatt catcaaaagc aagtgtgaag acgattcttc aatggctatg 60
aaactagcta agatagcggg ctatacagac agaagtggtt tttaccgatt tctaaatgac 120
cgcagaaaag aaacaactga tattcaaagc atcatagata ttgttaaaga aattgatcca 180
ggcaaagaaa tggaaatgat gagtgaatac ataccaacgc tcgatccagg aaagcaatgc 240
tcaagacaag cgttagaata cttttctgtt aacgctgaaa ttgaaaagct tgatactcac 300
atcgagaata tccttaacaa cacagctaac attaaaagtc tagagtgggc taagacttac 360
aaagcacaaa gggatgctga aaaaggtctt gtaaattctg aagatttggt caggttacta 420
gggagtttca aattaaaaac agacgagatg aaagtttaca gtcgaatcat tccgatgtat 480
ttcgcattat ggaataacca atttaacaga cttgattcgt tgtcagaaga cgttgtgatt 540
gaaagtttag aagagtcata tgttaagcaa tcgttccaca gccgattgat gttactctta 600
gctaactgtt cactaaggca gaataagctg gaaagagtgc tccattattc aagctatgga 660
atactcaact ccaacgtaaa aagaattaca gcctactcgt atttagcaca aggtaactct 720
caaatgttta cagactacga ttcaagtaaa aaatgttttc tctttgcatt agaacattca 780
actgagaaca gagagagatc aatccaagct ctaagaagtt tgtgcttcct tgaaaattta 840
tggggaaaag aaaacaaatg gttacatcat gactcagagg aaattagtga ccgacaagag 900
gttgcccaca gctacattcg caaaggtgaa atgtcaatcg ctaaatcgat tctagaagca 960
ctagaagccg aggaacatga tgacaaccag ttaggtatgc atatgtatct aaaagggctt 1020
gcgtatggct cagacggcta tttctataag tctattaagc attttaaatt aagtggtgat 1080
aagttctctg ctaacttgcc attgcttgaa cttgaaaagt taggtacaga taaacttatt 1140
ctcgaagtat tggcagttta a 1161

<210> SEQ ID NO 88
<211> LENGTH: 1161
<212> TYPE: DNA
<213> ORGANISM: Bacillus sp.

<400> SEQUENCE: 88

-continued

```
ttgagcaaat taaaagcatt catcaaaagc aagtgtgaag acgattcttc gcttgcagca      60

aaattggcat ctattgcagg ttactctcaa acatcaggat tgtacaaatt tcttaatatc     120

agtggaaaag aaacgagtga cttgcagatg atcattgata tgataaaaga aattgatcca     180

gatagagaga ttgatttgat gtgtgactac atattcacgc ttgatccagg taaacaatgt     240

gcaagacagg ctttggaata cttgtctgtt aacgctcaaa gtgaaaagct tgatgattat     300

atcgaatttg ttttaagtaa cactgggaat ggtaaaacca tagagtgggc aaagacgtac     360

aagttgcaaa gggatgcaga aaaaggtcta gtgaattttg aaaatttaat cagatcacta     420

gggaacttaa aactaaagac tgaagaaatg caggtctaca gtatgatcat cccgatgtat     480

ccagcattat ggaacaacta tttcaataga cttgaatcat tatctgaaaa tgtttttatt     540

gataatctgg aagattcgta tgttaaacaa tcattccaca gtaggttgtt gttacttcta     600

gccaactgtg cttttaacca aaatcagctt ggtaaggttc aacactacac cgactattgc     660

atccttaatt caaatgttag aagaatcaca gcatattctt acttaactca aggcaactct     720

ttaatgctta ctgattactc aacaagcaag cgttgctttc tctcagcttt agaacactca     780

actgaaaata gagagagatc aattcaagca ttaagaagct tgtgcttcct tgaaaactta     840

tggagtaaag aaaataaatg gttacagtat gactcagatg aaatcactga tagacaagaa     900

gtggctcacg cttacatccg caagggagaa ctagagctcg ctaaatcgat tttagatagc     960

ctagaagccg aggaacacga tgacaaccag ttaggtatgc atatgtacct caaaggtctg    1020

ttgcatcgct cagaggacta tttctataag tctattagac acttcaaatt aagtggggac    1080

aaattctctg ttggctttcc attgcttgaa cttgaaaagt taggcgcaga taaactcatt    1140

ctagaagtat tggcaattta a                                              1161
```

<210> SEQ ID NO 89
<211> LENGTH: 1179
<212> TYPE: DNA
<213> ORGANISM: Bacillus amyloliquefaciens

<400> SEQUENCE: 89

```
atgagccagt atacgaagtt tgcccaagaa ttaaaatact tacttgataa tgaaaaaatc      60

acaatgaacg gtattcttga ttcaactaat ctcaaaacta gaagtagact gtatgagatg     120

gttaatggaa aacgtgaaac gcttaaagat tttgagaaca tattaaacat tgccaaatat     180

gcatttcctg atacttttga agaacagcta gaagattaca tctgttcact agctgagagt     240

gatccaagca gaatgattgt tgttgaagcg atggagtggg cagatgccag tcaaagggac     300

gaattaactg atttcgtcgt tgataaatta aagaactgta acaatattaa atgtaaagag     360

tacggtaatg tctattatct tcataggcaa ttaactaagg gtgaaataac cgcacatgaa     420

gcacttgttg ctagtgggaa gcttggtcta aaacagatgg agacagttgt tttttctaga     480

cttatggtgc tttacaaata tttagagtta agacaatttg atacactgtc tgatatggcg     540

agagatatac atagcgaaat tgttgaaaat gagagtttta ttagtagatc atattcttca     600

cgtatacaaa ctttattggc aaatatgtct ttaacacaag gtgacttggt taatacaaga     660

aaacacgctg aattagctgt ctatgagtct aataatccta gattcttagc ctttggttat     720

ctgcacttag gaaactctta tttgtttgaa agctttgaga aatcaaaaga aaagttgcta     780

atgggtatgg agcatgcgga acgttatcct gagaggtaca aacaattaag aagaagcatg     840

gttttcctgg ataactattg gaacaaggga caggcgtatc taaatcatga ttcggacgag     900

atagaagaca ttcagggtat tatctataat catattcaaa atggtcgtaa ggaagttgca     960
```

ttggatatgc tactaaaact tgaggatcga aaccaaaatg acaaccttaa aggatatcat 1020
tattacttta aaggcttgat tgatgagaat atttccaatt tttatttatc tgttaagcat 1080
ttcaagctgt ctggagacaa gttttgtgta acacttcctt tagttgaatt gcaaaagcgt 1140
ggtgagaata ctcaattgct tgatttattg actatttaa 1179

<210> SEQ ID NO 90
<211> LENGTH: 1179
<212> TYPE: DNA
<213> ORGANISM: Bacillus amyloliquefaciens

<400> SEQUENCE: 90
atgagccagt atacgaagtt tgcccaagaa ttaaaatact tacttgataa tgaaaaaatc 60
acaatgaacg gtattcttga ttcaactaat ctcaaaacta gaagtagact gtatgagatg 120
gttaatggaa aacgtgaaac gcttaaagat tttgagaaca tattaaacat tgccaaatat 180
gcatttcctg atacttttga agaacagcta gaagattaca tctgttcact agctgagagt 240
gatccaagca gaatgattgt tgttgaagcg atggagtggg cagatgccag tcaaagggac 300
gaattaactg atttcgtcgt tgataaatta aagaactgta acaatattaa atgtaaagag 360
tacggtaatg tctattatct tcataggcaa ttaactaagg gtgaaataac cgcacatgaa 420
gcacttgttg ctagtgggaa gcttggtcta aaacagatgg agacagttgt tttttctaga 480
cttatggtgc tttacaaata tttagagtta agacaatttg atacactgtc tgatatggcg 540
agagatatac atagcgaaat tgttgaaaat gagagtttta ttagtagatc atattcttca 600
cgtatacaaa ctttattggc aaatatgtct ttaacacaag gtgacttggt taatacaaga 660
aaacacgctg aattagctgt ctatgagtct aataatccta gattcttagc ctttggttat 720
ctgcacttag gaaactctta tttgtttgaa agctttgaga aatcaaaaga aaagttgcta 780
atgggtatgg agcatgcgga acgttatcct gagaggtaca aacaattaag aagaagcatg 840
gttttcctgg ataactattg gaacaaggga caggcgtatc taaatcatga ttcggacgag 900
atagaagaca ttcagggtat tatctataat catattcaaa atggtcgtaa ggaagttgca 960
ttggatatgc tactaaaact tgaggatcga aaccaaaatg acaaccttaa aggatatcat 1020
tattacttta aaggcttgat tgatgagaat atttccaatt tttatttatc tgttaagcat 1080
ttcaagctgt ctggagacaa gttttgtgta acacttcctt tagttgaatt gcaaaagcgt 1140
ggtgagaata ctcaattgct tgatttattg actatttaa 1179

<210> SEQ ID NO 91
<211> LENGTH: 1155
<212> TYPE: DNA
<213> ORGANISM: Bacillus subtilis

<400> SEQUENCE: 91
ttgaaattaa agcagatgat taagaacgaa tgtgaaaaag ataatcagct tgcagctcga 60
cttgctaaat tggctggtta tgaaaaagta aatggttttt ataagtttgt gaacacccca 120
gaaaaagaaa tggaaaactt gggtggtcta attaagattg ttaagagctt attttcagaa 180
aaagaagaac agcttttgag cgaatacttt ttacagctag accctaataa aaagtgtgca 240
aggcagtcgg ttgaatactc agatataaat caatgggatt cacttacaga caaaatcatt 300
ttaaatttat gtaattctaa aaatgcaact agccaagaat ggggcaatat ctacagcata 360
cataggaaat tgaacaaaag tgaactaggt ttaaatgatg caattagaga aactggtaaa 420
tgtaagataa agacccctga aatgcttttc ttttcaaatg caatgcttat gtatgaatat 480
ctaaacattg gtgaatttgg attaatgaag agcactgcaa aactgcttga tttggatgag 540
ttgccaaatg gctttataaa agactcgtat gcgtcaagag ttgctttatt aaaggcaaat 600
atttacctga atgataatga tcttgagaaa tctaggtatt attctgaaga ggtaataaca 660
aacactgata tcgaacgttt aaaggtcttt gggtatttga cttatggtaa tacattaata 720
tttgaaagct atgataaggc aaaagaaagc tatgaattag gtcgtacttt tgctaagacg 780
aatacacatc atgactacaa gcttcgttta gcattgtgtt ttttaaataa tgtgtggaat 840
aaggaaaatc aatgggttga tttcaactct aatctagtag ctgatcaaat tgaggtagca 900
tattattata caaacaaaaa gcaatacgat aaagcaattt cagttataag cagccttgaa 960
aaaagggatt tatatcttta tgatgcggga attttagatt atataaaggg gttgatttat 1020
caagaaaagt cttattttta tgaaagtaca gcaaaattga aaaagtcagg ggacaaaatg 1080
tttattaacc ttcccttagg aaagctcaga aaaatgggat gcgatgagaa tctgcttgag 1140
ttaatcctta tttaa 1155

<210> SEQ ID NO 92
<211> LENGTH: 1041
<212> TYPE: DNA
<213> ORGANISM: Bacillus cellulosilyticus

<400> SEQUENCE: 92
gtgaatatca tggtacaaaa ggatacatca tttaataatc ctgataatat atttagaaca 60
tctgataatt tggatgagta cataaaagga cttgacccta atagttattt agctagagtg 120
gctttagaat ataccgtcag taatagtaaa atagaattgc atgaagaact aatagattgt 180
ctactacact ccggaaatca agaaagtaag gaatgggctg aagtatacaa aattgacaac 240
ttagtttcta agcaagaatt aagtctacct gattcaataa cacaactaac atatatacta 300
tgttcttcta aggaaatgtc tgttttacaa aaaatatttc agttatataa ctactacgat 360
ctaaaagcat ttcaaatgat agaaattgtc agtgaactaa taaataaaga attaaaagaa 420
attcctgatg gatacatgaa ggactccctt caatcacgtt tggatcttgc gatgcaaagt 480
gtatatacac atttaaatga acttgagaaa gctagaattt atggtgaaaa cctcaaagat 540
attgctctaa caccagtaat gaaagcaata gcatataaaa atctaggaat gacttatctt 600
tatgaagatt acgataaact ctgtacatat tttgaaatgt cattaaaaat atttaaagaa 660
atggataact cagatcgatt atataatgtc caatctaagt ataactttgc ccaaactttt 720
tggagttatc cagataaaac agtgtggcta aggaaagaaa ctattgatga actgcaaatt 780
tatgcatatt cacttattaa gagtggtaat aaagaagagg ctcataaaat attagatagt 840
accaaaaact ctttatcaaa tgactttcaa tttggttacc attactattt tctaggatta 900
cttaatgata atgaaaagaa ttactatgaa tctgttaaat acttcagcaa gtctggggat 960 agattttta gacagttacc gcttattgct ctaaaagaaa aaggtgtgga cacttcgctg 1020
ctatcagctt taagtgtata a 1041

<210> SEQ ID NO 93
<211> LENGTH: 1161
<212> TYPE: DNA
<213> ORGANISM: Bacillus subtilis

<400> SEQUENCE: 93
atggagttaa taaggatagc tatgaagaaa gacttggaaa atgacaactc tttaatgaat 60

```
aaatgggcaa cagtagctgg ccttaaaaac cccaatcctc tttatgactt cttaaaccat    120
gatgggaaaa catttaatga attttcttca atagtcaaca ttgttaagag tcagtatcca    180
gaccgtgaat atgaattaat gaaagattac tgtttaaacc tagatgttaa gacaaaggca    240
gcaagaagtg cattggagta tgctgatgca aatatgtttt ttgaaataga agatgtttta    300
atagattcaa tgatttcttg cagcaatatg aaaagtaaag aatatggaaa agtgtataaa    360
atacatagag aactgtctaa cagtgttatt actgaatttg aggcagtgaa aagactcggc    420
aaattaaata taaaaacacc tgaaatgaat tctttctcaa gactcttgct gctttatcat    480
tatttaagca ctggtaactt ttctccgatg gcccaactta taaaacaaat tgacctaagt    540
gagatttctg agaacatgta cattagaaat acatatcaaa caagagttca tgttctaatg    600
tctaatataa agttaaatga aaattcatta gaggagtgca gagagtactc taaaaaggca    660
ttggaaagta caaatatcct gagatttcag gttttcagct acttaactat tggcaactct    720
ctattatttt cgaattatga attggctcaa gaaaactttt taaaagggct aagcatttct    780
gttcaaaatg aaaattacaa catgattttc cagcaggctt tgtgcttctt aaataatgta    840
tggcgcaaag aaaataagtg gattaatttt gaatctgatt caattatgga tttgcaggag    900
caagctcatt gttttatcaa ctttaatgaa aattccaaag caaaagaagt tttggataaa    960
ctagatcttt tagttcacaa cgataatgag cttgcaatgc attattattt gaaaggaaga   1020
ctcgaacaaa ataaagcatg tttctattct tcaatcgagt attttaaaaa gtctaatgac   1080
aaattcctta ttaggctgcc actgttagaa ctgcaaaaga tgggtgaaaa tcaaaaactt   1140
ttagaattac ttttacttta a                                              1161
```

<210> SEQ ID NO 94
<211> LENGTH: 1140
<212> TYPE: DNA
<213> ORGANISM: Bacillus amyloliquefaciens

<400> SEQUENCE: 94

```
atgaatctta agcagatgat taagaatgaa tgtgaaaaag acaaccagct cgcagcgaaa     60
ctctcaaaaa tagcagggta cgaaaaggtt aatggttttt acaaattcat caacacccca    120
gagaaagaaa tggacaactt aggcggttta attaatattg ttaaaagctt gtttcctgat    180
aatgaagagc agcttctaag tgattacttc ttatcactgg atcccaataa aaaaagcgca    240
agacagtctg ttgaatactc agatattaat caatgggata cgttaacaga caagattatt    300
ttaaatttaa gcaactcaaa aaacaccaca agtcaagaat ggggcaacat ctacagcata    360
catagaaagc tttataaaaa cgaaatctca ataccagaag caataagaga gtgcggaaga    420
tgcaaagccc cagaaatgtc atttttctca gatgcaatgc tgatgtataa atacttgaat    480
attggtgagt ttggattgat gaaaagcacc ttaacacttt tagattttag cagcttgcca    540
gaaggattta taaaagattc gtacaaaagt agagtgtcaa tgttacaagc gaatataagc    600
ttaaatgaaa acaatttaat cgaagcgagg aaacattcaa atattgcaat aatgcagtcc    660
aatgtgaacc gaatatgttt ttttgcgcat ctgactatag gaaataccct aattttcgaa    720
aactatgaag aagctatgct ggcgtatatt gaggcaaaga agtatgttct taatgatacc    780
cataaagaaa tgctaaacgg cgctctttgc ttcctagcta acgtatggaa caaggaaaat    840
ccatgggtta actatgaatc agatgatatc aaatatcagc agcttagggc tttttattac    900
ataaaaaata ataatctcga caaggctaac gaattattgg aaagcttatc aaatagggat    960
```

caagatgaaa atgaattagg attttatttt tattataaag gtttgatatc aaaacaaaaa 1020
tctgattttt ataaatcaat aacatatttc aaaaaatcag atgataaata ttttatccaa 1080
ttgactataa tagaactcga aaaattaggc tgtgatccgg agctactaaa tttaatttag 1140

<210> SEQ ID NO 95
<211> LENGTH: 1161
<212> TYPE: DNA
<213> ORGANISM: Bacillus subtilis

<400> SEQUENCE: 95
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag agctgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaac acatatcaaa caagagttca tgttctaatg 600
tcgaatataa agctaaatga aaattcatta gaggagtgca gagagtactc taaaaaggca 660
ttggaaagta caaatatcct cagatttcag gttttcagct acttaactat tggcaactct 720
ctattatttt cgaattatga attggctcaa gaaaactttt taaaagggct aagcgtttct 780
gttcaaaatg aaaattacaa catgattttc cagcaggctt tgtgcttctt aaataatgta 840
tggcgcaaag aaaataagtg gattaatttt gaatctgagt caattatgga tttgcaggag 900
caagcccatt gttttatcaa ctttaatgaa aattccaaag caaaaaaagt tttggataaa 960
ctagatcttt tacgtcataa cgataatgag cttgcaatgc atcattattt gaaagggaga 1020
ctcgaacaaa ataaagcatg tttctattct tcaatcgagt attttaaaaa gtctaatgac 1080
aaattcctta ttaggctgcc gttgttagaa ctgcaaaaga tgggtgaaaa tcaaaaactt 1140
ttagaattac ttttacttta a 1161

<210> SEQ ID NO 96
<211> LENGTH: 1161
<212> TYPE: DNA
<213> ORGANISM: Bacillus amyloliquefaciens

<400> SEQUENCE: 96
atggagctta taagaatagc tatgcggaaa gatttagaaa atgataaatc actcatgagt 60
aaatgggctg cggtagctgg tcttaaaaac ccaaaccctc tttacgattt cctaaaccat 120
gatggtaaga cttttagtga atttaactcg atagttaaca ttgtgaagac ccactaccct 180
gaccaagaat atgaactcat ggaaaattac tgtctattgc ttgacccaaa tactaaggct 240
gcaagaagcg cactggaata tgcagacgct aacagtttta atactctaac tgataagctg 300
gtagaaaaaa tgagcatcgc ctctaatttg aaaagtaaag agtacggaaa aatttacgag 360
atacatagga agctatcaag aggagagata gatgttctag aagcatcaaa aaatattgga 420
aagtacagaa tcaaaactga tgaaatgaat attttttcaa aaatgattcc catgtacgac 480
tatttaagta aagggaactt ctctccgatg aagtctttac tgaagcaaat agaccttaat 540

```
gatattaaag aaaataatta tttgaaaaag tcgtttgaga ctagaattta cgttctttta    600

tctaatattt atttaaatga aaatgaactt gaattgtcta gaaagtatgc agaaaaagcg    660

attaaatcaa ctgataccaa acgtttttg gtttttagtt atttaacaat aggtacgtcc    720

tatatttttt ccgactatgc cttaagcaag cagaattatt tatctggcta tgaaattgca    780

aaagggaaca gtgtttttga agaattcttc aagagaaatt tgagcttttt aaataacttt    840

tggaataaag aaaatccatg gatcaactac gattcaaatg cagtgactga tgtccaagaa    900

gttatttttg aacttataaa ccaaaaaaaa ttggagagag ctttaacttt gttaaagagt    960

ctggaaagaa aaaagcaaaa cgaaaatgat cttgggtttc attattactt agagggtctt   1020

ataaccaatg ataaagaagc attttataaa tcagttgaat attttaaact ttcgcaagac   1080

aagcttttta ttaaaatgcc tcttattaaa ttggagagct taggtgagaa tccaaggcta   1140

ctaaaaatta tttctatgta a                                             1161
```

<210> SEQ ID NO 97
<211> LENGTH: 963
<212> TYPE: DNA
<213> ORGANISM: Bacillus amyloliquefaciens

<400> SEQUENCE: 97

```
atgatagcaa aagagagaga agctaagaaa ccaaaagtag atgcaaaggt acgtcttgaa     60

atgtcagata ttaatgaaca gtatgaactg actgacacat taattgatca attaattaat    120

agtacctgtt cgattgaacg tgaatgggca gcaatgtatc agatcaaacg taagcaagac    180

agaggcgaaa taaacgcaca tcaggcgctt aaagcaattg gaaagcttga tcccaagtct    240

caagaaatgc gtgtattcac ttacataatc ccgttgtatt actaccttag aatggctgaa    300

tactcaaatc ttgcagaaat gtcgatgatt gtagatcttg attttattga aaacaatgaa    360

cagattaaaa gctcgtttta ttaccgtctg atggctttgt tgggcgcttc agcattcagt    420

cagaataaaa tgactcaagc ccgtttttat tgctcatacg gcattaatgt aacgaatatt    480

gatagacttg tcgcttatag ctatctaact atgggtaaca cttatttgct tgatgattat    540

gaaaaagcaa aagaatatta cctggccggt ttaaaacata ctgagaataa cccctttggca   600

aaattacagc taactagaag cctttgtttc ttggaaaacc attggaatca agagaacttt    660

tggctaaacc ctgattcaaa tgaagttaca gatatccaag aaattgcaca ttatcacatc    720

aaaaaaaaca acttgcaaca ggctaaagaa atattggaga acttagagca gcaaccgaat    780

attcataatg actttggcat tcatttttat ctaaaaggac tagcttatga agataagaga    840

ttcttttatg agtctataaa acactttaag ctgtccggcg atctatacag cgtacgctta    900

cctttggata aattaaggga aatgggtgag gacgagcaga ttttggattt acttgccctt    960

taa                                                                  963
```

<210> SEQ ID NO 98
<211> LENGTH: 963
<212> TYPE: DNA
<213> ORGANISM: Bacillus amyloliquefaciens

<400> SEQUENCE: 98

```
atgttaacga aagagagaga agttgaaaaa aaggtaaatg acttaaaagt gcagcttgaa     60

atgtcagaca ttaatgaaga gtatgaaacg actgataaat taatagacca attaaataat    120

agcaaatgtc caattgaacg tgaatgggct accttgtatc agattaaacg taagcaagac    180
```

agaggcgaaa taaacgcaca tgaagcactc aaagcaattg gtcagtttga ccccaaaact 240
cctgagatga gagtgtttac ttacataatc ccgttgtatt actaccttag aatggctgaa 300
tactcaaacc ttgcggaaat gtctacaatt gttgatgttg attcgattga acaaaaccaa 360
gtaattagag attcttatta taaccgttta caggcattac ttgcagcgtc agctttcagc 420
cagcataaat taacaagagc acgattccat tgtacatacg gtatcaattg cactaatact 480
gacagactta ttgcttatag ctaccttaca atgggtaaca catatatcct tagtaattat 540
gaaaaagcaa aggagaactt cataaagggt ttagaaaaat caatgaagaa cccagaaaga 600
aaaactcaac taactagaag tctcgccttc cttgagaact attgggggaa ggaaaataaa 660
tggattaaca ggcaatcaaa agagcaagac gatctttatg gacaagtttt tgagttgatt 720
gtaaaaaagg agaatgatca agctatcgca ttattagacg aattgtttga gtcaggtctg 780
agcgataatc aactaggatt ccattattat tatttaggat tgattcacga caaagaagac 840
tatttcttaa aatcagttga acacttcaaa aaatccggag aaaaacattt tcttgagtgc 900
cctataactg agcttcgtcg acttggaaca gatagtagac ttctagattt acttgtcctt 960
taa 963

<210> SEQ ID NO 99
<211> LENGTH: 1155
<212> TYPE: DNA
<213> ORGANISM: Bacillus amyloliquefaciens

<400> SEQUENCE: 99
atgaatctta agcagatgat taagaatgaa tgtgaaaaag acaaccagct cgcagcgaaa 60
ctctcaaaaa tagcagggta cgaaaaggtt aatggttttt acaaattcat caacacccca 120
gagaaagaaa tggacaactt aggcggttta attaatattg ttaagagctt gtttccggat 180
aatgaagagc agcttctaag tgactacttc ttatcattgg atcccaataa aaaaagcgca 240
agacagtctg tcgagtatgc agatttaaac caatggaatg cattgactga taagatcgta 300
agcaatcttt gcgaatcatc taattcaata agtcgtgaat ggggacaggt ttattccctc 360
catagaaaac tgaataataa taaaatttct ataaatgaag caatccggga aactgggaaa 420
tatagaatta aatctcctga aatgtattca ttttcgaata ttatgattat gtacgaatac 480
ttgaaaattg gagaatttgg cttaatgaaa agtacagctc agtttctgga gattgacgaa 540
ctgtctgatg gatttataaa agattcgtac agtggtcgaa ttgaactgtt aaaggccaat 600
ataagcttaa atgattatga actagaagaa acccgaaaac attgtagcgc tgtaattgaa 660
gaatgcaata ataacaggtt gattgtattt agttatttaa cacttgggaa tacatacatt 720
tttgaagatt atgctaaagc aaaactatgc tatgaaaaag gcttgaactt tgcaaaagac 780
aatagccatc atcattataa attacgactc gcactttgct ttttagataa tgtctgggcg 840
agagaaaaca aatgggtaga tttcgagtct caagaaatac cggatatgat tgaagctgct 900
ttttatttga ctaatactaa agaaactaag aaagcagaag atgttattaa aaaaattgaa 960
gaacatgatg ttctggatga tgatttaggg tttctttatc acgttaaggg cttgctgtat 1020
aatgatatgt cccattttca cgagagtata aagaaattca aaaagtcagg cgataggctc 1080
tgtctaaatc tacctttgat tgaattgaaa aagcgtggat actcagatga aatattaaat 1140
ttaattgcgc tatag 1155

<210> SEQ ID NO 100
<211> LENGTH: 1140

<212> TYPE: DNA
<213> ORGANISM: Bacillus subtilis

<400> SEQUENCE: 100
atgaagaaag acttggaaaa tgacaactct ttaatgaata aatgggcaac agtagctggc 60
cttaaaaacc ccaatcctct ttatgacttc ttaaaccatg atgggaaaac atttaatgaa 120
ttttcttcaa tagtcaacat tgttaagagt cagtatccag accgtgaata tgaattaatg 180
aaagattact gtttaaacct agatgttaag acaaaggcag caagaagtgc attggagtat 240
gctgatgcaa atatgttttt tgaaatagaa gatgttttaa tagattcaat gatttcttgc 300
agcaatatga aaagtaaaga atatggaaaa gtgtataaaa tacatagaga actgtctaac 360
agtgttatta ctgaatttga ggcagtgaaa agactcggca aattaaatat aaaaacacct 420
gaaatgaatt ctttctcaag actcttgctg ctttatcatt atttaagcac tggtaacttt 480
tctccgatgg cccaacttat aaaacaaatt gacctaagtg agatttctga gaacatgtac 540
attagaaata catatcaaac aagagttcat gttctaatgt ctaatataaa gttaaatgaa 600
aattcattag aggagtgcag agagtactct aaaaaggcat tggaaagtac aaatatcctg 660
agatttcagg ttttcagcta cttaactatt ggcaactctc tattattttc gaattatgaa 720
ttggctcaag aaaacttttt aaaagggcta agcatttctg ttcaaaatga aaattacaac 780
atgattttcc agcaggcttt gtgcttctta aataatgtat ggcgcaaaga aaataagtgg 840
attaattttg aatctgattc aattatggat ttgcaggagc aagctcattg ttttatcaac 900
tttaatgaaa attccaaagc aaaagaagtt ttggataaac tagatctttt agttcacaac 960
gataatgagc ttgcaatgca ttattatttg aaaggaagac tcgaacaaaa taaagcatgt 1020
ttctattctt caatcgagta ttttaaaaag tctaatgaca aattccttat taggctgcca 1080
ctgttagaac tgcaaaagat gggtgaaaat caaaaacttt tagaattact tttactttaa 1140

<210> SEQ ID NO 101
<211> LENGTH: 963
<212> TYPE: DNA
<213> ORGANISM: Bacillus amyloliquefaciens

<400> SEQUENCE: 101
atgatagcaa aagagagaga agctaagaaa ccaaaagtag atgcaaaggt acgtcttgaa 60
atgtcagata ttaatgaaca gtatgaactg actgacacat taattgatca attaattaat 120
agtacctgtt cgattgaacg tgaatgggca gcaatgtatc agatcaaacg taagcaagac 180
agaggcgaaa taaacgcaca tcaggcgctt aaagcaattg gaaagcttga tcccaagtct 240
caagaaatgc gtgtattcac ttacataatc ccgttgtatt actaccttag aatggctgaa 300
tactcaaatc ttgcagaaat gtcgatgatt gtagatcttg attttattga aaacaatgaa 360
cagattaaaa gctcgtttta ttaccgtctg atggctttgt tgggcgcttc agcattcagt 420
cagaataaaa tgactcaagc ccgtttttat tgctcatacg gcattaatgt aacgaatatt 480
gatagacttg tcgcttatag ctatctaact atgggtaaca cttatttgct tgatgattat 540
gaaaaagcaa aagaatatta cctggccggt ttaaaacata ctgagaataa ccccttggca 600
aaattacagc taactagaag cctttgtttc ttggaaaacc attggaatca agagaacttt 660
tggctaaacc ctgattcaaa tgaagttaca gatatccaag aaattgcaca ttatcacatc 720
aaaaaaaaca acttgcaaca ggctaaagaa atattggaga acttagagca gcaaccgaat 780
attcataatg actttggcat tcatttttat ctaaaaggac tagcttatga agataagaga 840
ttcttttatg agtctataaa acactttaag ctgtccggcg atctatacag cgtacgctta 900
cctttggata aattaaggga aatgggtgag gacgagcaga ttttggattt acttgccctt 960
taa 963

<210> SEQ ID NO 102
<211> LENGTH: 963
<212> TYPE: DNA
<213> ORGANISM: Bacillus amyloliquefaciens

<400> SEQUENCE: 102
atgttaacga aagagagaga agttgaaaaa aaggtaaatg acttaaaagt gcagcttgaa 60
atgtcagaca ttaatgaaga gtatgaaacg actgataaat taatagacca attaaataat 120
agcaaatgtc caattgaacg tgaatgggct accttgtatc agattaaacg taagcaagac 180
agaggcgaaa taaacgcaca tgaagcactc aaagcaattg gtcagtttga ccccaaaact 240
cctgagatga gagtgtttac ttacataatc ccgttgtatt actaccttag aatggctgaa 300
tactcaaacc ttgcggaaat gtctacaatt gttgatgttg attcgattga acaaaaccaa 360
gtaattagag attcttatta taaccgttta caggcattac ttgcagcgtc agctttcagc 420
cagcataaat taacaagagc acgattccat tgtacatacg gtatcaattg cactaatact 480
gacagactta ttgcttatag ctaccttaca atgggtaaca catatatcct tagtaattat 540
gaaaaagcaa aggagaactt cataaagggt ttagaaaaat caatgaagaa cccagaaaga 600
aaaactcaac taactagaag tctcgccttc cttgagaact attgggggaa ggaaaataaa 660
tggattaaca ggcaatcaaa agagcaagac gatctttatg gacaagtttt tgagttgatt 720
gtaaaaaagg agaatgatca agctatcgca ttattagacg aattgtttga gtcaggtctg 780
agcgataatc aactaggatt ccattattat tatttaggat tgattcacga caaagaagac 840
tatttcttaa aatcagttga acacttcaaa aaatccggag aaaaacattt tcttgagtgc 900
cctataactg agcttcgtcg acttggaaca gatagtagac ttctagattt acttgtcctt 960
taa 963

<210> SEQ ID NO 103
<211> LENGTH: 1155
<212> TYPE: DNA
<213> ORGANISM: Bacillus amyloliquefaciens

<400> SEQUENCE: 103
atgaatctta agcagatgat taagaatgaa tgtgaaaaag acaaccagct cgcagcgaaa 60
ctctcaaaaa tagcagggta cgaaaaggtt aatggttttt acaaattcat caacacccca 120
gagaaagaaa tggacaactt aggcggttta attaatattg ttaagagctt gtttccggat 180
aatgaagagc agcttctaag tgactacttc ttatcattgg atcccaataa aaaaagcgca 240
agacagtctg tcgagtatgc agatttaaac caatggaatg cattgactga taagatcgta 300
agcaatcttt gcgaatcatc taattcaata agtcgtgaat ggggacaggt ttattccctc 360
catagaaaac tgaataataa taaaatttct ataaatgaag caatccggga aactgggaaa 420
tatagaatta aatctcctga aatgtattca ttttcgaata ttatgattat gtacgaatac 480
ttgaaaattg gagaatttgg cttaatgaaa agtacagctc agtttctgga gattgacgaa 540
ctgtctgatg gatttataaa agattcgtac agtggtcgaa ttgaactgtt aaaggccaat 600
ataagcttaa atgattatga actagaagaa acccgaaaac attgtagcgc tgtaattgaa 660
gaatgcaata ataacaggtt gattgtattt agttatttaa cacttgggaa tacatacatt 720
tttgaagatt atgctaaagc aaaactatgc tatgaaaaag gcttgaactt tgcaaaagac 780
aatagccatc atcattataa attacgactc gcactttgct ttttagataa tgtctgggcg 840
agagaaaaca aatgggtaga tttcgagtct caagaaatac cggatatgat tgaagctgct 900
ttttatttga ctaatactaa agaaactaag aaagcagaag atgttattaa aaaaattgaa 960
gaacatgatg ttctggatga tgatttaggg tttctttatc acgttaaggg cttgctgtat 1020
aatgatatgt cccattttca cgagagtata aagaaattca aaaagtcagg cgataggctc 1080
tgtctaaatc tacctttgat tgaattgaaa aagcgtggat actcagatga aatattaaat 1140
ttaattgcgc tatag 1155

<210> SEQ ID NO 104
<211> LENGTH: 1011
<212> TYPE: DNA
<213> ORGANISM: Bacillus vallismortis

<400> SEQUENCE: 104
atggatttaa taaggatagc tatgaagaaa gacttggaaa atgacaactc tttaatgaat 60
aaatgggcaa cagtagctgg ccttaaaaac ccaaatcctc tttatgactt cttaaaccat 120
aatgggaaaa cttttaatga attttcttca atagtcaaca ttgttaagag tcagtatcca 180
gaccgtgaat atgaattaat gaaagattac tgtttaaacc tagatgttaa gacaaaagca 240
gcaagaagtg ctttggagta cgccgatgca aatatgtttt ttgaaataga ggatgcttta 300
atagaatcaa tgatttcttg tagcaatatg aaaagtaaag aatatggaaa agtgtataaa 360
atacatagag aactgtctaa ctttgatatt actgaatttg aggcagtgaa aaggctcggt 420
aaattaaata ttaaaacacc tgaaatgaat tctttctcaa gactcttgct gctttatcat 480
tatttaagca ctggtaactt ttctccgatg gcccaactta taaaacaaat tgaccttagt 540
gagatttctg agaacatgta cattagaaat acatatcaaa caagagttca tgttctaatg 600
tctaatataa agctaaatga aaattcatta gaggagtgca gagagtactc tagaatggca 660
ttggaaagta caaatatcct gagatttcag gttttcagct acttaacaat tggcaactct 720
ctattatttt cgaattatga attggctcaa gaaaactttt taaaagggct aagcgtttct 780
gttcaaaatg aaaattacaa catgattttc cagcaggctt tgtgcttctt aaataatgta 840
tggcgcaaag aaaataagtg gattaatttt gaatctgagt caattatgga tttgcaggag 900
caagctcatt gttttatcaa ctttaatgaa aattccaaag caaaaaagtt ttggataaat 960
tatatctttt acgtcataac gataatgagc ttgcaatgca tcattatttg a 1011

<210> SEQ ID NO 105
<211> LENGTH: 894
<212> TYPE: DNA
<213> ORGANISM: Bacillus atrophaeus

<400> SEQUENCE: 105
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360

-continued

```
atacatagga agctatcaaa aggagaaata gatgttcttg aagcaacaaa aaatattggg    420

aaacagagaa ttaaaactga tgaaatgaat atcttttcaa aaatgattcc catgtacgat    480

tatttaagta aaggaaattt ctctccgatg aagcctttgc ttaagcaaat taaccttaat    540

gagattaaag aaaataagta tctaaaaaag tcgtttgaaa ctcgtataca cgttctttta    600

tctaatatgt acttaaatga aaataaactc gaattgtgca gagaatatgc aaaaaaagcg    660

attcaatcaa ctagcactaa acgatttttg gtttttagtt atttaacaat agggacgtct    720

tacatttttt tagactacaa tttaagtcgg cagaattatt tatctggcta cgagatttct    780

aaaggtaaca atgtatttga agaattcttt aaaaggaatt tgagtttttt aaataactat    840

tggaataaag aaaattcatg gatcaactat gactcagaca gacgcagtga ctga          894
```

```
<210> SEQ ID NO 106
<211> LENGTH: 894
<212> TYPE: DNA
<213> ORGANISM: Bacillus atrophaeus

<400> SEQUENCE: 106

atggaactta taagaaaagc tatgaggaaa gacttagaaa atgataaaac actcatgagt     60

aaatgggcta cggtagctgg acttaaaaat ccaaatcctc tttacgattt tctaaatcat    120

gatggaaaga cttttagtga gttttccacg ttggtgaata ttgtgaagag tcagtaccct    180

gatcgagaat atgaacttat ggaagattat tgtctgatcc ttgaccccaa gactaaagct    240

gcaagaagtg ccctgaaata cgcagatgcc aacagtttta atgatctaac tgataagctg    300

gttgataaaa tgagtatttc ctcaaatttg aaaagcaaag agtacggaaa aatttacggg    360

atacatagga agctatcaaa aggagaaata gatgttcttg aagcaacaaa aaatattggg    420

aaacagagaa ttaaaactga tgaaatgaat atcttttcaa aaatgattcc catgtacgat    480

tatttaagta aaggaaattt ctctccgatg aagcctttgc ttaagcaaat taaccttaat    540

gagattaaag aaaataagta tctaaaaaag tcgtttgaaa ctcgtataca cgttctttta    600

tctaatatgt acttaaatga aaataaactc gaattgtgca gagaatatgc aaaaaaagcg    660

attcaatcaa ctagcactaa acgatttttg gtttttagtt atttaacaat agggacgtct    720

tacatttttt tagactacaa tttaagtcgg cagaattatt tatctggcta cgagatttct    780

aaaggtaaca atgtatttga agaattcttt aaaaggaatt tgagtttttt aaataactat    840

tggaataaag aaaattcatg gatcaactat gactcagaca gacgcagtga ctga          894
```

```
<210> SEQ ID NO 107
<211> LENGTH: 894
<212> TYPE: DNA
<213> ORGANISM: Bacillus atrophaeus

<400> SEQUENCE: 107

atggaactta taagaaaagc tatgaggaaa gacttagaaa atgataaaac actcatgagt     60

aaatgggcta cggtagctgg acttaaaaat ccaaatcctc tttacgattt tctaaatcat    120

gatggaaaga cttttagtga gttttccacg ttggtgaata ttgtgaagag tcagtaccct    180

gatcgagaat atgaacttat ggaagattat tgtctgatcc ttgaccccaa gactaaagct    240

gcaagaagtg ccctgaaata cgcagatgcc aacagtttta atgatctaac tgataagctg    300

gttgataaaa tgagtatttc ctcaaatttg aaaagcaaag agtacggaaa aatttacggg    360

atacatagga agctatcaaa aggagaaata gatgttcttg aagcaacaaa aaatattggg    420

aaacagagaa ttaaaactga tgaaatgaat atcttttcaa aaatgattcc catgtacgat    480
```

tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 108
<211> LENGTH: 894
<212> TYPE: DNA
<213> ORGANISM: Bacillus atrophaeus

<400> SEQUENCE: 108
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aaatgattcc catgtacgat 480
tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 109
<211> LENGTH: 894
<212> TYPE: DNA
<213> ORGANISM: Bacillus atrophaeus

<400> SEQUENCE: 109
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aaatgattcc catgtacgat 480
tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 110
<211> LENGTH: 1161
<212> TYPE: DNA
<213> ORGANISM: Bacillus subtilis

<400> SEQUENCE: 110
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa cttttaatga attttcttca atagtcaaca ttgttaagag tcagtatcca 180
gaccgtgaat atgaattaat gaaagattac tgtttaaacc tagatgtaaa gacaaaggca 240
gcaagaagtg cattggagta tgctgatgca aatatgtttt ttgaaataga ggatgcttta 300
atagattcaa tgatttcttg cagcaatatg aaaagtaaag aatatggaaa agtgtataaa 360
atacatagag aactgtcaaa aggggaaata gatgtttttg aagcctctgc aaacattgga 420
aaacaaagaa ttaaaactgc agagatgaac atattctcaa aaatgctcct tatgtatgat 480
tgtttaaata aaggaaactt cgctccgatg atgcttttat ttcagcaaat agaccttagt 540
gaaataaaag aaaatcgata tttaaaaaac tcttttgaaa ctcgcataaa tgtgctctta 600
tcaaatattt atttgaatga aaataatctt gaattgtgta gggagtatgc acaaaaagca 660
atatcatcta ctgacactca aagatttttg gtatttagtt atttaaccat tggaacttca 720
tacatttttt cagactttaa tttaagcaag cagaattatt taattggatt gaagtttgct 780
aaagggaatc cagggtttga ggagtttttc aaaagaaatt taagtttttt aaacaatttt 840
tggaacaagg aaaatgaatg gatcaattat gactcagatg cagtgacaga catgcaagag 900
gttatattcg aattaattaa tcataaagaa ctaagcaaag cacttcaatt gttaaacaaa 960
ctagaggaaa gagaccaaaa tgagaacgaa ttggggttcc attattattt aaaaggactt 1020
ataacgaacg agaaagaagc attttttaaa tctgtcgagt atttcaaagc atcgcaggac 1080
aagctctcta ttaaaatgcc tcttattcag ttagaaaaaa tgggcgaaaa tccaagatta 1140
ctaaagatta ttactatgta a 1161

<210> SEQ ID NO 111
<211> LENGTH: 717
<212> TYPE: DNA
<213> ORGANISM: Bacillus subtilis

<400> SEQUENCE: 111
gaaatgctcg tcttttctaa tgcgatgttg atgtatgcat acctaaatat cggagacttc 60
catttgttaa agagtacatt cgatttgctt gatatagacg agttacctga aggctatgtc 120
aaagagtctt attacggaag agcagcttta ttacatgcca atgttagtct gaatgaaaat 180
gatatcctta gtgccagaca ttattcaagc tacgttcttg aaaaagcaaa caatgaccgt 240
tttatggttt ttggacattt aacatctggg aacacctatg tctttgaaga ttacgataag 300
gctaaagatc attatttaaa aggtttgcgg tatgccaata ctaatccatt tcattattac 360
aagcttcggt tagctttatg ctttttgaat aatgtttgga aaaaggaaaa taaatgggtt 420
gattttgaat ccaatgagat aacagacaga attgaagtgg cttactatta cgtaaatcaa 480
aatgaagaac aaaaagcaat taaggttttt caagaacttg atagtagaaa gattccgaaa 540
gatgatttag ggtttctatt ctatgttaaa gggttactac atcaagaaaa gtcttacttt 600
tatgagagta ttgagttttt caaaaagtca ggagataaaa tgtttgtcaa tttaccttta 660
atggaactga aaaaacaagg tgaaaatgaa cgtcttctcc aattattaac tatctaa 717

<210> SEQ ID NO 112
<211> LENGTH: 894
<212> TYPE: DNA
<213> ORGANISM: Bacillus atrophaeus

<400> SEQUENCE: 112
atggaactta taagaaaagc tatgaggaaa gacttagaaa atgataaaac actcatgagt 60
aaatgggcta cggtagctgg acttaaaaat ccaaatcctc tttacgattt tctaaatcat 120
gatggaaaga cttttagtga gttttccacg ttggtgaata ttgtgaagag tcagtaccct 180
gatcgagaat atgaacttat ggaagattat tgtctgatcc ttgaccccaa gactaaagct 240
gcaagaagtg ccctgaaata cgcagatgcc aacagtttta atgatctaac tgataagctg 300
gttgataaaa tgagtatttc ctcaaatttg aaaagcaaag agtacggaaa aatttacggg 360
atacatagga agctatcaaa aggagaaata gatgttcttg aagcaacaaa aaatattggg 420
aaacagagaa ttaaaactga tgaaatgaat atcttttcaa aaatgattcc catgtacgat 480
tatttaagta aaggaaattt ctctccgatg aagcctttgc ttaagcaaat taaccttaat 540
gagattaaag aaaataagta tctaaaaaag tcgtttgaaa ctcgtataca cgttctttta 600
tctaatatgt acttaaatga aaataaactc gaattgtgca gagaatatgc aaaaaaagcg 660
attcaatcaa ctagcactaa acgatttttg gtttttagtt atttaacaat agggacgtct 720
tacatttttt tagactacaa tttaagtcgg cagaattatt tatctggcta cgagatttct 780
aaaggtaaca atgtatttga agaattcttt aaaaggaatt tgagtttttt aaataactat 840
tggaataaag aaaattcatg gatcaactat gactcagaca gacgcagtga ctga 894

<210> SEQ ID NO 113
<211> LENGTH: 1161
<212> TYPE: DNA
<213> ORGANISM: Bacillus sp.

<400> SEQUENCE: 113
atggagttaa taaggatagc tatgaagaaa gacttggaaa atgacaactc tttaatgaat 60
aaatgggcaa cagtagctgg ccttaaaaac cccaatcctc tttatgactt cttaaaccat 120
gatgggaaaa catttaatga attttcttca atagtcaaca ttgttaagag tcagtatcca 180
gaccgtgaat atgaattaat gaaagattac tgtttaaacc tagatgttaa gacaaaggca 240
gcaagaagtg cattggagta tgctgatgca aatatgtttt ttgaaataga agatgtttta 300
atagattcaa tgatttcttg cagcaatatg aaaagtaaag aatatggaaa agtgtataaa 360
atacatagag aactgtctaa cagtgttatt actgaatttg aggcagtgaa aagactcggc 420
aaattaaata taaaaacacc tgaaatgaat tctttctcaa gactcttgct gctttatcat 480
tatttaagca ctggtaactt ttctccgatg gcccaactta taaaacaaat tgacctaagt 540
gagatttctg agaacatgta cattagaaat acatatcaaa caagagttca tgttctaatg 600

```
tctaatataa agttaaatga aaattcatta gaggagtgca gagagtactc taaaaaggca    660

ttggaaagta caaatatcct gagatttcag gttttcagct acttaactat tggcaactct    720

ctattatttt cgaattatga attggctcaa gaaaactttt taaaagggct aagcatttct    780

gttcaaaatg aaaattacaa catgattttc cagcaggctt tgtgcttctt aaataatgta    840

tggcgcaaag aaaataagtg gattaatttt gaatctgatt caattatgga tttgcaggag    900

caagctcatt gttttatcaa ctttaatgaa aattccaaag caaaagaagt tttggataaa    960

ctagatcttt tagttcacaa cgataatgag cttgcaatgc attattattt gaaaggaaga   1020

ctcgaacaaa ataaagcatg tttctattct tcaatcgagt attttaaaaa gtctaatgac   1080

aaattcctta ttaggctgcc actgttagaa ctgcaaaaga tgggtgaaaa tcaaaaactt   1140

ttagaattac ttttacttta a                                              1161
```

```
<210> SEQ ID NO 114
<211> LENGTH: 378
<212> TYPE: PRT
<213> ORGANISM: Bacteriophage phi-3T

<400> SEQUENCE: 114

Met Ile Lys Asn Glu Cys Glu Lys Asp Asn Gln Leu Ala Ala Arg Leu
1               5                   10                  15

Ala Lys Leu Ala Gly Tyr Glu Lys Val Asn Gly Phe Tyr Lys Phe Val
            20                  25                  30

Asn Thr Pro Glu Lys Glu Met Glu Asn Leu Gly Gly Leu Leu Lys Ile
        35                  40                  45

Val Lys Asn Leu Phe Pro Asp Ser Glu Glu Gln Leu Leu Ser Glu Tyr
    50                  55                  60

Phe Leu Glu Leu Asp Pro Asn Lys Lys Cys Ala Arg Gln Ser Val Glu
65                  70                  75                  80

Tyr Ser Asp Ile Asn Gln Trp Asp Thr Leu Thr Asp Lys Ile Ile Ile
                85                  90                  95

Asn Leu Cys Asn Ser Lys Asn Ser Thr Ser Gln Glu Trp Gly Lys Val
            100                 105                 110

Tyr Ser Leu His Arg Lys Leu Asn Lys Asn Glu Ile Ser Leu Asn Asp
        115                 120                 125

Ala Ile Arg Glu Ser Gly Lys Cys Lys Ile Lys Ser Ala Glu Met Leu
    130                 135                 140

Phe Phe Ser Asn Ala Met Leu Met Tyr Ala Tyr Leu Asn Ile Gly Glu
145                 150                 155                 160

Phe Gly Leu Met Lys Ser Thr Ser Lys Leu Leu Glu Phe Asp Asp Leu
                165                 170                 175

Pro Glu Gly Phe Ile Lys Glu Ser Phe Lys Ser Arg Val Ser Met Leu
            180                 185                 190

Glu Ala Asn Ile Ser Leu Asn Glu Asn Ser Leu Leu Glu Ala Arg Gln
        195                 200                 205

His Ser Asn Arg Ala Ile Glu Asn Ser Asn Val Asn Arg Ile Cys Phe
    210                 215                 220

Phe Ala Tyr Leu Thr Ile Gly Asn Thr Leu Ile Phe Glu Asp Tyr Asp
225                 230                 235                 240

Glu Ala Lys Lys Ala Tyr Ile Lys Gly Gln Lys Tyr Ala Lys Asn Pro
                245                 250                 255

Val His Gln Glu Met Leu Asp Gly Ala Leu Cys Phe Leu Ser Asn Ile
            260                 265                 270
```

-continued

Trp Lys Lys Glu Asn Gln Trp Val Asn Tyr Asn Ser Asp Asn Ile Lys
        275                 280                 285

Tyr Leu Gln Leu Arg Ala Phe Tyr Tyr Ile Asn Gln Gly Asn Ile Glu
    290                 295                 300

Glu Ala Thr Glu Ile Leu Asp Glu Leu Ser Ser Arg Asp Gln Asp Glu
305                 310                 315                 320

Asn Glu Leu Gly Phe Tyr Tyr Tyr Tyr Lys Gly Leu Ile Ser Gln Asp
                325                 330                 335

Lys Thr Asp Tyr Tyr Lys Ser Ile Arg Tyr Phe Lys Lys Ser Asp Asp
            340                 345                 350

Lys Tyr Phe Ile Gln Leu Pro Leu Leu Gln Leu Glu Arg Met Gly Ala
        355                 360                 365

Asp Leu Glu Leu Leu Asn Leu Ile Ser Ile
    370                 375

<210> SEQ ID NO 115
<211> LENGTH: 381
<212> TYPE: PRT
<213> ORGANISM: Bacillus amyloliquefaciens

<400> SEQUENCE: 115

Met Asn Leu Lys Gln Met Ile Lys Asn Glu Cys Glu Lys Asp Asn Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Cys Ala
65                  70                  75                  80

Arg Gln Ser Val Glu Tyr Ala Asp Leu Asn Gln Trp Asn Ala Leu Thr
                85                  90                  95

Asp Lys Ile Ile Leu Asn Leu Cys Asn Ser Lys Asn Ala Thr Ser Lys
            100                 105                 110

Glu Trp Gly Lys Thr Tyr Asn Ile His Arg Lys Leu Thr Glu Asn Lys
        115                 120                 125

Ile Ser Leu Thr Glu Ala Ile Arg Glu Thr Gly Lys Cys Lys Thr Ala
    130                 135                 140

Glu Met Ile Phe Phe Ser Asn Ala Met Leu Met Tyr Glu Tyr Leu Lys
145                 150                 155                 160

Ile Gly Glu Phe Gly Leu Met Lys Ser Thr Ala Lys Leu Leu Asp Phe
                165                 170                 175

Gln Gly Leu Ser Asp Gly Tyr Ile Lys Gly Leu Tyr Thr Ser Arg Val
            180                 185                 190

Ser Leu Leu Lys Ala Asn Ile Ser Phe Asn Glu Asn Asn Leu Ile Glu
        195                 200                 205

Ala Arg Lys Tyr Cys Leu Tyr Ala Thr Glu Thr Thr Asn Val Asp Arg
    210                 215                 220

Ile Cys Phe Phe Ala Tyr Leu Thr Ile Gly Asn Ser Phe Ile Phe Glu
225                 230                 235                 240

Asn Phe Glu Glu Ala Lys Arg Ser Tyr Ile Asn Gly Ala Lys Tyr Ala
                245                 250                 255

Ser Asn Thr Ile His Lys Glu Met Leu Asp Gly Ala Leu Cys Phe Leu
            260                 265                 270

Ala Ser Phe Trp Asn Lys Glu Asn Leu Trp Val Asn Tyr Glu Ser Gln
275 280 285

His Thr Lys Tyr Leu Gln Leu Arg Ala Tyr His His Ile Arg Lys Gly
290 295 300

Glu Val Asp Lys Ala Asn Glu Ile Leu Asn Glu Leu Ser Ile Arg Glu
305 310 315 320

Gln Asp Glu Asn Glu Met Gly Phe Tyr Phe Tyr Tyr Arg Gly Leu Ile
325 330 335

Ser Val Asp Lys Ser Asp Phe Tyr Lys Ser Ile Arg Cys Phe Lys Lys
340 345 350

Ser Asp Asp Lys Tyr Ser Val Gln Leu Pro Leu Ile Glu Leu Lys Lys
355 360 365

Met Gly Ala Asp Thr Glu Leu Leu Ser Leu Ile Ser Ile
370 375 380

<210> SEQ ID NO 116
<211> LENGTH: 386
<212> TYPE: PRT
<213> ORGANISM: Bacillus subtilis

<400> SEQUENCE: 116

Met Glu Leu Ile Lys Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

Val Ile Thr Glu Phe Glu Ala Val Lys Arg Leu Gly Lys Leu Asn Ile
130 135 140

Lys Thr Pro Glu Met Asn Ser Phe Ser Arg Leu Leu Leu Leu Tyr His
145 150 155 160

Tyr Leu Ser Thr Gly Asn Phe Ser Pro Met Ala Gln Leu Ile Lys Gln
165 170 175

Ile Asp Leu Ser Glu Ile Ser Glu Asn Met Tyr Ile Arg Asn Thr Tyr
180 185 190

Gln Thr Arg Ala His Val Leu Met Ser Asn Ile Lys Leu Asn Glu Asn
195 200 205

Ser Leu Glu Glu Cys Arg Glu Tyr Ser Lys Lys Ala Leu Glu Ser Thr
210 215 220

Asn Ile Leu Arg Phe Gln Val Phe Ser Tyr Leu Thr Ile Gly Asn Ser
225 230 235 240

Leu Leu Phe Ser Asn Tyr Glu Leu Ala Gln Glu Asn Phe Leu Lys Gly
245 250 255

Leu Ser Val Ser Val Gln Asn Glu Asn Tyr Asn Met Ile Phe Gln Gln

```
            260                 265                 270

Ala Leu Cys Phe Leu Asn Asn Val Trp Arg Lys Glu Asn Lys Trp Ile
        275                 280                 285

Asn Phe Glu Ser Glu Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 117
<211> LENGTH: 386
<212> TYPE: PRT
<213> ORGANISM: bacteriophage SP-beta

<400> SEQUENCE: 117

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240
```

Leu Leu Phe Ser Asn Tyr Glu Leu Ala Gln Glu Asn Phe Leu Lys Gly
245 250 255

Leu Ser Ile Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

Asn Phe Glu Ser Asp Ser Ile Met Asp Leu Gln Glu Gln Ala His Cys
290 295 300

Phe Ile Asn Phe Asn Glu Asn Ser Lys Ala Lys Glu Val Leu Asp Lys
305 310 315 320

Leu Asp Leu Leu Val His Asn Asp Asn Glu Leu Ala Met His Tyr Tyr
325 330 335

Leu Lys Gly Arg Leu Glu Gln Asn Lys Ala Cys Phe Tyr Ser Ser Ile
340 345 350

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 118
<211> LENGTH: 386
<212> TYPE: PRT
<213> ORGANISM: Bacillus subtilis

<400> SEQUENCE: 118

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

Val Ile Thr Glu Phe Glu Ala Val Lys Arg Leu Gly Lys Leu Asn Ile
130 135 140

Lys Thr Pro Glu Met Asn Ser Phe Ser Arg Leu Leu Leu Leu Tyr His
145 150 155 160

Tyr Leu Ser Thr Gly Asn Phe Ser Pro Met Ala Gln Leu Ile Lys Gln
165 170 175

Ile Asp Leu Ser Glu Ile Ser Glu Asn Met Tyr Ile Arg Asn Thr Tyr
180 185 190

Gln Thr Arg Val His Val Leu Met Ser Asn Ile Lys Leu Asn Glu Asn
195 200 205

Ser Leu Glu Glu Cys Arg Glu Tyr Ser Lys Lys Ala Leu Glu Ser Thr
210 215 220

```
Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 119
<211> LENGTH: 386
<212> TYPE: PRT
<213> ORGANISM: Bacillus subtilis

<400> SEQUENCE: 119

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Phe Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
```

```
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ala Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 120
<211> LENGTH: 386
<212> TYPE: PRT
<213> ORGANISM: Bacillus subtilis

<400> SEQUENCE: 120

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175
```

```
Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Glu Ser Ile Met Asp Leu Gln Glu Gln Ala His Cys
    290                 295                 300

Phe Ile Asn Phe Asn Glu Asn Ser Lys Ala Lys Lys Val Leu Asp Lys
305                 310                 315                 320

Leu Asp Leu Leu Arg His Asn Asp Asn Glu Leu Ala Met His His Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385
```

<210> SEQ ID NO 121
<211> LENGTH: 386
<212> TYPE: PRT
<213> ORGANISM: Bacillus subtilis

<400> SEQUENCE: 121

```
Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160
```

Tyr Leu Ser Thr Gly Asn Phe Ser Pro Met Ala Gln Leu Ile Lys Gln
165 170 175

Ile Asp Leu Ser Glu Ile Ser Glu Asn Met Tyr Ile Arg Asn Thr Tyr
180 185 190

Gln Thr Arg Val His Val Leu Met Ser Asn Ile Lys Leu Asn Glu Asn
195 200 205

Ser Leu Glu Glu Cys Arg Glu Tyr Ser Lys Lys Ala Leu Glu Ser Thr
210 215 220

Asn Ile Leu Arg Phe Gln Val Phe Ser Tyr Leu Thr Ile Gly Asn Ser
225 230 235 240

Leu Leu Phe Ser Asn Tyr Glu Leu Ala Gln Glu Asn Phe Leu Lys Gly
245 250 255

Leu Ser Ile Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

Asn Phe Glu Ser Asp Ser Ile Met Asp Leu Gln Glu Gln Ala His Cys
290 295 300

Phe Ile Asn Phe Asn Glu Asn Ser Lys Ala Lys Glu Val Leu Asp Lys
305 310 315 320

Leu Asp Leu Leu Val His Asn Asp Asn Glu Leu Ala Met His Tyr Tyr
325 330 335

Leu Lys Gly Arg Leu Glu Gln Asn Lys Ala Cys Phe Tyr Ser Ser Ile
340 345 350

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 122
<211> LENGTH: 386
<212> TYPE: PRT
<213> ORGANISM: Bacillus subtilis

<400> SEQUENCE: 122

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

Val Ile Thr Glu Phe Glu Ala Val Lys Arg Leu Gly Lys Leu Asn Ile

```
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 123
<211> LENGTH: 320
<212> TYPE: PRT
<213> ORGANISM: Bacillus amyloliquefaciens

<400> SEQUENCE: 123

Met Ile Ala Lys Glu Arg Glu Ala Lys Lys Pro Glu Val Asp Ala Lys
1               5                   10                  15

Val Arg Leu Glu Met Ser Asp Ile Asn Glu Gln Tyr Glu Gln Thr Asp
            20                  25                  30

Ala Leu Ile Asp Gln Leu Ile Asn Ser Ser Cys Ser Ile Glu Arg Glu
        35                  40                  45

Trp Ala Ala Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Thr Val Val Asp
            100                 105                 110
```

```
Leu Asp Phe Ile Glu Asn Asn Glu Gln Ile Lys Ser Ser Phe Tyr Asn
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Leu Gly Asn Thr Tyr Leu
                165                 170                 175

Leu Asp Asp Tyr Glu Lys Ala Lys Glu Tyr Tyr Leu Ala Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asn Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320


<210> SEQ ID NO 124
<211> LENGTH: 386
<212> TYPE: PRT
<213> ORGANISM: Bacillus subtilis

<400> SEQUENCE: 124

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Phe Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175
```

Ile Asp Leu Ser Glu Ile Ser Glu Asn Met Tyr Ile Arg Asn Thr Tyr
180 185 190

Gln Thr Arg Val His Val Leu Met Ser Asn Ile Lys Leu Asn Glu Asn
195 200 205

Ser Leu Glu Glu Cys Arg Glu Tyr Ser Lys Lys Ala Leu Glu Ser Thr
210 215 220

Asn Ile Leu Arg Phe Gln Val Phe Ser Tyr Leu Thr Ile Gly Asn Ser
225 230 235 240

Leu Leu Phe Ser Asn Tyr Glu Leu Ala Gln Glu Asn Phe Leu Lys Gly
245 250 255

Leu Ser Val Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

Asn Phe Glu Ala Asp Ser Ile Met Asp Leu Gln Glu Gln Ala His Cys
290 295 300

Phe Ile Asn Phe Asn Glu Asn Ser Lys Ala Lys Glu Val Leu Asp Lys
305 310 315 320

Leu Asp Leu Leu Val His Asn Asp Asn Glu Leu Ala Met His Tyr Tyr
325 330 335

Leu Lys Gly Arg Leu Glu Gln Asn Lys Ala Cys Phe Tyr Ser Ser Ile
340 345 350

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 125
<211> LENGTH: 386
<212> TYPE: PRT
<213> ORGANISM: Bacillus murimartini

<400> SEQUENCE: 125

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

Val Ile Thr Glu Phe Glu Ala Val Lys Arg Leu Gly Lys Leu Asn Ile
130 135 140

Lys Thr Pro Glu Met Asn Ser Phe Ser Arg Leu Leu Leu Leu Tyr His 145 150 155 160

Tyr Leu Ser Thr Gly Asn Phe Ser Pro Met Ala Gln Leu Ile Lys Gln
165 170 175

Ile Asp Leu Ser Glu Ile Ser Glu Asn Met Tyr Ile Arg Asn Thr Tyr
180 185 190

Gln Thr Arg Val His Val Leu Met Ser Asn Ile Lys Leu Asn Glu Asn
195 200 205

Ser Leu Glu Glu Cys Arg Glu Tyr Ser Lys Lys Ala Leu Glu Ser Thr
210 215 220

Asn Ile Leu Arg Phe Gln Val Phe Ser Tyr Leu Thr Ile Gly Asn Ser
225 230 235 240

Leu Leu Phe Ser Asn Tyr Glu Leu Ala Gln Glu Asn Phe Leu Lys Gly
245 250 255

Leu Ser Ile Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

Asn Phe Glu Ser Asp Ser Ile Met Asp Leu Gln Glu Gln Ala His Cys
290 295 300

Phe Ile Asn Phe Asn Glu Asn Ser Lys Ala Lys Glu Val Leu Asp Lys
305 310 315 320

Leu Asp Leu Leu Val His Asn Asp Asn Glu Leu Ala Met His Tyr Tyr
325 330 335

Leu Lys Gly Arg Leu Glu Gln Asn Lys Ala Cys Phe Tyr Ser Ser Ile
340 345 350

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 126
<211> LENGTH: 386
<212> TYPE: PRT
<213> ORGANISM: Bacillus subtilis

<400> SEQUENCE: 126

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

```
Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 127
<211> LENGTH: 386
<212> TYPE: PRT
<213> ORGANISM: Bacillus subtilis

<400> SEQUENCE: 127

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110
```

-continued

```
Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 128
<211> LENGTH: 386
<212> TYPE: PRT
<213> ORGANISM: Bacillus subtilis

<400> SEQUENCE: 128

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
```

```
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 129
<211> LENGTH: 386
<212> TYPE: PRT
<213> ORGANISM: Bacillus subtilis

<400> SEQUENCE: 129

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60
```

-continued

```
Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 130
<211> LENGTH: 379
<212> TYPE: PRT
<213> ORGANISM: Bacillus subtilis

<400> SEQUENCE: 130

Met Lys Lys Asp Leu Glu Asn Asp Asn Ser Leu Met Asn Lys Trp Ala
1               5                   10                  15

Thr Val Ala Gly Leu Lys Asn Pro Asn Pro Leu Tyr Asp Phe Leu Asn
            20                  25                  30

His Asp Gly Lys Thr Phe Asn Glu Phe Ser Ser Ile Val Asn Ile Val
        35                  40                  45
```

Lys Ser Gln Tyr Pro Asp Arg Glu Tyr Glu Leu Met Lys Asp Tyr Cys
50 55 60

Leu Asn Leu Asp Val Lys Thr Lys Ala Ala Arg Ser Ala Leu Glu Tyr
65 70 75 80

Ala Asp Ala Asn Met Phe Phe Glu Ile Glu Asp Val Leu Ile Asp Ser
85 90 95

Met Ile Ser Cys Ser Asn Met Lys Ser Lys Glu Tyr Gly Lys Val Tyr
100 105 110

Lys Ile His Arg Glu Leu Ser Asn Ser Val Ile Thr Glu Phe Glu Ala
115 120 125

Val Lys Arg Leu Gly Lys Leu Asn Ile Lys Thr Pro Glu Met Asn Ser
130 135 140

Phe Ser Arg Leu Leu Leu Leu Tyr His Tyr Leu Ser Thr Gly Asn Phe
145 150 155 160

Ser Pro Met Ala Gln Leu Ile Lys Gln Ile Asp Leu Ser Glu Ile Ser
165 170 175

Glu Asn Met Tyr Ile Arg Asn Thr Tyr Gln Thr Arg Val His Val Leu
180 185 190

Met Ser Asn Ile Lys Leu Asn Glu Asn Ser Leu Glu Glu Cys Arg Glu
195 200 205

Tyr Ser Lys Lys Ala Leu Glu Ser Thr Asn Ile Leu Arg Phe Gln Val
210 215 220

Phe Ser Tyr Leu Thr Ile Gly Asn Ser Leu Leu Phe Ser Asn Tyr Glu
225 230 235 240

Leu Ala Gln Glu Asn Phe Leu Lys Gly Leu Ser Ile Ser Val Gln Asn
245 250 255

Glu Asn Tyr Asn Met Ile Phe Gln Gln Ala Leu Cys Phe Leu Asn Asn
260 265 270

Val Trp Arg Lys Glu Asn Lys Trp Ile Asn Phe Glu Ser Asp Ser Ile
275 280 285

Met Asp Leu Gln Glu Gln Ala His Cys Phe Ile Asn Phe Asn Glu Asn
290 295 300

Ser Lys Ala Lys Glu Val Leu Asp Lys Leu Asp Leu Leu Val His Asn
305 310 315 320

Asp Asn Glu Leu Ala Met His Tyr Tyr Leu Lys Gly Arg Leu Glu Gln
325 330 335

Asn Lys Ala Cys Phe Tyr Ser Ser Ile Glu Tyr Phe Lys Lys Ser Asn
340 345 350

Asp Lys Phe Leu Ile Arg Leu Pro Leu Leu Glu Leu Gln Lys Met Gly
355 360 365

Glu Asn Gln Lys Leu Leu Glu Leu Leu Leu Leu
370 375

<210> SEQ ID NO 131
<211> LENGTH: 386
<212> TYPE: PRT
<213> ORGANISM: Bacillus subtilis

<400> SEQUENCE: 131

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe

```
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 132
<211> LENGTH: 386
<212> TYPE: PRT
<213> ORGANISM: Bacillus subtilis

<400> SEQUENCE: 132

Met Glu Leu Ile Arg Ile Ala Met Lys Lys Asp Leu Glu Asn Asp Asn
1               5                   10                  15
```

```
Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Phe Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ala Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385
```

<210> SEQ ID NO 133
<211> LENGTH: 386
<212> TYPE: PRT
<213> ORGANISM: Bacillus subtilis

<400> SEQUENCE: 133

```
Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385
```

<210> SEQ ID NO 134
<211> LENGTH: 386

```
<212> TYPE: PRT
<213> ORGANISM: Bacillus subtilis

<400> SEQUENCE: 134

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385
```

<210> SEQ ID NO 135
<211> LENGTH: 386
<212> TYPE: PRT
<213> ORGANISM: Bacillus subtilis

<400> SEQUENCE: 135

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu

```
    370                 375                 380

Leu Leu
385


<210> SEQ ID NO 136
<211> LENGTH: 386
<212> TYPE: PRT
<213> ORGANISM: Bacillus subtilis

<400> SEQUENCE: 136

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350
```

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 137
<211> LENGTH: 386
<212> TYPE: PRT
<213> ORGANISM: Bacillus subtilis

<400> SEQUENCE: 137

Met Glu Leu Ile Lys Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

Val Ile Thr Glu Phe Glu Ala Val Lys Arg Leu Gly Lys Leu Asn Ile
130 135 140

Lys Thr Pro Glu Met Asn Ser Phe Ser Arg Leu Leu Leu Leu Tyr His
145 150 155 160

Tyr Leu Ser Thr Gly Asn Phe Ser Pro Met Ala Gln Leu Ile Lys Gln
165 170 175

Ile Asp Leu Ser Glu Ile Ser Glu Asn Met Tyr Ile Arg Asn Thr Tyr
180 185 190

Gln Thr Arg Val His Val Leu Met Ser Asn Ile Lys Leu Asn Glu Asn
195 200 205

Ser Leu Glu Glu Cys Arg Glu Tyr Ser Lys Lys Ala Leu Glu Ser Thr
210 215 220

Asn Ile Leu Arg Phe Gln Val Phe Ser Tyr Leu Thr Ile Gly Asn Ser
225 230 235 240

Leu Leu Phe Ser Asn Tyr Glu Leu Ala Gln Glu Asn Phe Leu Lys Gly
245 250 255

Leu Ser Val Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

Asn Phe Glu Ser Glu Ser Ile Met Asp Leu Gln Glu Gln Ala His Cys
290 295 300

Phe Ile Asn Phe Asn Glu Asn Ser Lys Ala Lys Glu Val Leu Asp Lys
305 310 315 320

Leu Asp Leu Leu Val His Asn Asp Asn Glu Leu Ala Met His Tyr Tyr
325 330 335

```
Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 138
<211> LENGTH: 386
<212> TYPE: PRT
<213> ORGANISM: Bacillus subtilis

<400> SEQUENCE: 138

Met Glu Leu Ile Lys Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Ala His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Glu Ser Ile Met Asp Leu Gln Glu Gln Ala His Cys
    290                 295                 300

Phe Ile Asn Phe Asn Glu Asn Ser Lys Ala Lys Glu Val Leu Asp Lys
```

305 310 315 320

Leu Asp Leu Leu Val His Asn Asp Asn Glu Leu Ala Met His Tyr Tyr
325 330 335

Leu Lys Gly Arg Leu Glu Gln Asn Lys Ala Cys Phe Tyr Ser Ser Ile
340 345 350

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 139
<211> LENGTH: 386
<212> TYPE: PRT
<213> ORGANISM: Bacillus subtilis

<400> SEQUENCE: 139

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

Val Ile Thr Glu Phe Glu Ala Val Lys Arg Leu Gly Lys Leu Asn Ile
130 135 140

Lys Thr Pro Glu Met Asn Ser Phe Ser Arg Leu Leu Leu Leu Tyr His
145 150 155 160

Tyr Leu Ser Thr Gly Asn Phe Ser Pro Met Ala Gln Leu Ile Lys Gln
165 170 175

Ile Asp Leu Ser Glu Ile Ser Glu Asn Met Tyr Ile Arg Asn Thr Tyr
180 185 190

Gln Thr Arg Val His Val Leu Met Ser Asn Ile Lys Leu Asn Glu Asn
195 200 205

Ser Leu Glu Glu Cys Arg Glu Tyr Ser Lys Lys Ala Leu Glu Ser Thr
210 215 220

Asn Ile Leu Arg Phe Gln Val Phe Ser Tyr Leu Thr Ile Gly Asn Ser
225 230 235 240

Leu Leu Phe Ser Asn Tyr Glu Leu Ala Gln Glu Asn Phe Leu Lys Gly
245 250 255

Leu Ser Ile Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

```
Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 140
<211> LENGTH: 386
<212> TYPE: PRT
<213> ORGANISM: Bacillus subtilis

<400> SEQUENCE: 140

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270
```

```
Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 141
<211> LENGTH: 386
<212> TYPE: PRT
<213> ORGANISM: Bacillus subtilis

<400> SEQUENCE: 141

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
```

245 250 255

Leu Ser Val Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

Asn Phe Glu Ser Asp Ser Ile Met Asp Leu Gln Glu Gln Ala His Cys
290 295 300

Phe Ile Asn Phe Asn Glu Asn Ser Lys Ala Lys Glu Val Leu Asp Lys
305 310 315 320

Leu Asp Leu Leu Val His Asn Asp Asn Glu Leu Ala Met His Tyr Tyr
325 330 335

Leu Lys Gly Arg Leu Glu Gln Asn Lys Ala Cys Phe Tyr Ser Ser Ile
340 345 350

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 142
<211> LENGTH: 386
<212> TYPE: PRT
<213> ORGANISM: Bacillus subtilis

<400> SEQUENCE: 142

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Cys
115 120 125

Asp Ile Thr Glu Phe Glu Ala Val Lys Arg Leu Gly Lys Leu Asn Ile
130 135 140

Lys Thr Pro Glu Met Asn Ser Phe Ser Arg Leu Leu Leu Leu Tyr His
145 150 155 160

Tyr Leu Ser Thr Gly Asn Phe Ser Pro Met Pro Gln Leu Ile Lys Gln
165 170 175

Ile Asp Leu Ser Glu Ile Ser Glu Asn Met Tyr Ile Arg Asn Thr Tyr
180 185 190

Gln Thr Arg Val Tyr Val Leu Met Ser Asn Ile Lys Leu Asn Glu Asn
195 200 205

Ser Leu Glu Glu Cys Arg Asp Tyr Ser Lys Met Ala Leu Glu Ser Thr
210 215 220

-continued

Asn Ile Gln Arg Phe Gln Val Phe Ser Tyr Leu Thr Ile Gly Asn Ser
225 230 235 240

Leu Leu Phe Ser Asn Tyr Glu Leu Ala Gln Glu Asn Phe Leu Lys Gly
245 250 255

Leu Ser Val Ser Val Gln Asn Glu Asn Tyr Asn Met Ile Phe Gln Gln
260 265 270

Ala Leu Cys Phe Leu Asn Asn Val Trp Arg Lys Glu Asn Lys Trp Ile
275 280 285

Asn Phe Glu Ser Glu Ser Ile Met Asp Leu Gln Glu Gln Ala His Cys
290 295 300

Phe Ile Asn Phe Asn Glu Asn Ser Lys Ala Lys Lys Val Leu Asp Lys
305 310 315 320

Leu Asp Leu Leu Arg His Asn Asp Asn Glu Leu Ala Met His His Tyr
325 330 335

Leu Lys Gly Arg Leu Glu Gln Asn Lys Ala Cys Phe Tyr Ser Ser Ile
340 345 350

Glu Tyr Phe Lys Lys Ser Asn Asp Lys Phe Leu Ile Arg Leu Pro Leu
355 360 365

Leu Glu Leu Gln Lys Met Gly Glu Asn Gln Lys Leu Leu Glu Leu Leu
370 375 380

Leu Leu
385

<210> SEQ ID NO 143
<211> LENGTH: 379
<212> TYPE: PRT
<213> ORGANISM: Bacillus subtilis

<400> SEQUENCE: 143

Met Lys Lys Asp Leu Glu Asn Asp Asn Ser Leu Met Asn Lys Trp Ala
1 5 10 15

Thr Val Ala Gly Leu Lys Asn Pro Asn Pro Leu Tyr Asp Phe Leu Asn
20 25 30

His Asp Gly Lys Thr Phe Asn Glu Phe Ser Ser Ile Val Asn Ile Val
35 40 45

Lys Ser Gln Tyr Pro Asp Arg Glu Tyr Glu Leu Met Lys Asp Tyr Cys
50 55 60

Leu Asn Leu Asp Val Lys Thr Lys Ala Ala Arg Ser Ala Leu Glu Tyr
65 70 75 80

Ala Asp Ala Asn Met Phe Phe Glu Ile Glu Asp Val Leu Ile Asp Ser
85 90 95

Met Ile Ser Cys Ser Asn Met Lys Ser Lys Glu Tyr Gly Lys Val Tyr
100 105 110

Lys Ile His Arg Glu Leu Ser Asn Ser Val Ile Thr Glu Phe Glu Ala
115 120 125

Val Lys Arg Leu Gly Lys Leu Asn Ile Lys Thr Pro Glu Met Asn Ser
130 135 140

Phe Ser Arg Leu Leu Leu Leu Tyr His Tyr Leu Ser Thr Gly Asn Phe
145 150 155 160

Ser Pro Met Ala Gln Leu Ile Lys Gln Ile Asp Leu Ser Glu Ile Ser
165 170 175

Glu Asn Met Tyr Ile Arg Asn Thr Tyr Gln Thr Arg Val His Val Leu
180 185 190

Met Ser Asn Ile Lys Leu Asn Glu Asn Ser Leu Glu Glu Cys Arg Glu
195 200 205

```
Tyr Ser Lys Lys Ala Leu Glu Ser Thr Asn Ile Leu Arg Phe Gln Val
    210                 215                 220

Phe Ser Tyr Leu Thr Ile Gly Asn Ser Leu Leu Phe Ser Asn Tyr Glu
225                 230                 235                 240

Leu Ala Gln Glu Asn Phe Leu Lys Gly Leu Ser Ile Ser Val Gln Asn
                245                 250                 255

Glu Asn Tyr Asn Met Ile Phe Gln Gln Ala Leu Cys Phe Leu Asn Asn
            260                 265                 270

Val Trp Arg Lys Glu Asn Lys Trp Ile Asn Phe Glu Ser Asp Ser Ile
        275                 280                 285

Met Asp Leu Gln Glu Gln Ala His Cys Phe Ile Asn Phe Asn Glu Asn
    290                 295                 300

Ser Lys Ala Lys Glu Val Leu Asp Lys Leu Asp Leu Leu Val His Asn
305                 310                 315                 320

Asp Asn Glu Leu Ala Met His Tyr Tyr Leu Lys Gly Arg Leu Glu Gln
                325                 330                 335

Asn Lys Ala Cys Phe Tyr Ser Ser Ile Glu Tyr Phe Lys Lys Ser Asn
            340                 345                 350

Asp Lys Phe Leu Ile Arg Leu Pro Leu Leu Glu Leu Gln Lys Met Gly
        355                 360                 365

Glu Asn Gln Lys Leu Leu Glu Leu Leu Leu Leu
    370                 375
```

<210> SEQ ID NO 144
<211> LENGTH: 400
<212> TYPE: PRT
<213> ORGANISM: Bacillus sp.

<400> SEQUENCE: 144

```
Met Ile Leu Leu Met Tyr Ile Lys Arg Gly Asn Val Val Lys Glu Leu
1               5                   10                  15

Glu Leu Lys Arg Leu Leu Lys Asn Lys Cys Glu Glu Glu Arg Gly Leu
            20                  25                  30

Glu Lys Glu Leu Ala Arg Val Ala Gly Tyr Ser Asn Ser Ser Gly Phe
        35                  40                  45

His Gln Phe Ile Phe Asn Asp Lys Lys Glu Met Asp Asn Ile Gln Gly
    50                  55                  60

Leu Ile Asp Val Val Gln Arg Val Ser Pro Asp Asn Glu Phe Glu Leu
65                  70                  75                  80

Met Ser Glu Tyr Ile Leu Thr Leu Asp Pro Asn Lys Ser Ala Ala Arg
                85                  90                  95

Gln Gly Leu Glu Tyr Leu Ser Val Asn Gln Leu Tyr Asp Ala Leu Asp
            100                 105                 110

Thr His Ile Glu Asn Leu Arg Ala Ala Asn Asn Thr Ile Ser Lys Glu
        115                 120                 125

Trp Gly Lys Val Tyr Ser Leu Gln Arg Glu Leu Asp Asn Gly Lys Ile
    130                 135                 140

Ser Ile Glu Glu Cys Ile Arg Ile Leu Gly Glu Ile Asn Pro Lys Ser
145                 150                 155                 160

Pro Glu Met Lys Val Phe Ser Arg Leu Ile Pro Met Tyr Ser Ile Leu
                165                 170                 175

Ala Ser Arg Gln Phe Thr Arg Leu Arg Asp Met Ser Glu Asn Val Val
            180                 185                 190

Leu Asp Ile Ile Arg Asn Gln Asn Tyr Val Tyr Tyr Ser Phe Lys Ser
```

-continued

```
        195                 200                 205

Arg Tyr Met Leu Leu Leu Ala Asn Cys Phe Phe Gly Thr Asn Glu Leu
    210                 215                 220

Glu Lys Ala Arg Glu Tyr Ala Lys Tyr Gly Ile Glu Asn Ser Asn Val
225                 230                 235                 240

Lys Arg Ile Asn Phe Phe Ser Leu Leu Thr Tyr Gly Ser Ser Leu Met
                245                 250                 255

Met Thr Asp Tyr Val Lys Ser Lys Ser Ser Phe Leu Lys Gly Leu Ala
            260                 265                 270

Val Val Lys Gly Asp Thr Phe Asn Glu Arg Phe Ala Ile Arg Asn Leu
        275                 280                 285

Cys Phe Leu Glu Asn Leu Trp Asn Lys Glu Asn Lys Tyr Leu Asn Val
    290                 295                 300

Asp Ser Lys Glu Ile Ile Asp Arg Gln Glu Ile Val His Tyr Leu Ile
305                 310                 315                 320

Arg Lys Gly His Ile Gly Gln Ala Lys Lys Met Leu Ser Glu Leu Glu
                325                 330                 335

Val Val Glu Gln Asp Ala Asn Glu Leu Gly Leu His Tyr Tyr Tyr Lys
            340                 345                 350

Gly Leu Ile Glu Asn Ser Lys Asp Tyr Phe Leu Lys Ser Val Lys Tyr
        355                 360                 365

Phe Lys Met Ser Gly Asp Lys Phe Ser Cys Arg Leu Pro Leu Ile Glu
    370                 375                 380

Leu Glu Lys Leu Gly Val Asp Lys Gly Ile Leu Glu Ile Met Val Met
385                 390                 395                 400


<210> SEQ ID NO 145
<211> LENGTH: 343
<212> TYPE: PRT
<213> ORGANISM: Bacillus amyloliquefaciens

<400> SEQUENCE: 145

Leu Ile Lys Glu Lys Gln Ala Ser Leu Ile Asn Val His His Gly Val
1               5                   10                  15

Glu His Phe Ile Lys Gln Asn Arg Asn Asn Asn Ser Lys Tyr Glu Leu
            20                  25                  30

Phe Ser Thr Tyr Ala Lys Ala Leu Lys Pro Asp Ser Tyr Tyr Ile Leu
        35                  40                  45

Glu Ala Leu Glu Tyr Ala Asp Thr Asn Asn Trp His Asp Ile Phe Asp
    50                  55                  60

Leu Leu Ile Glu Arg Ala Thr Asn Lys Glu Trp Thr Glu Leu Tyr Lys
65                  70                  75                  80

Leu Lys Lys Arg Ser Gln Ser Leu Ser Ile Gly Glu Met Glu Phe Gln
                85                  90                  95

Ile Lys Lys Ile Asn Pro Lys Ser Asp Glu Met Lys Ile Phe Ser Lys
            100                 105                 110

Leu Ile Met Val Tyr Lys Thr Cys Asp Thr Thr Asn Phe Lys Leu Met
        115                 120                 125

Asn Lys Tyr Ala Asp Ser Ile Asp Thr Glu Glu Met Glu Asp Gly Phe
    130                 135                 140

Ile Lys Ser Ser Phe Arg Ser Arg Leu Leu Val Leu Leu Ala Asn Thr
145                 150                 155                 160

Phe Leu Phe Glu Gly Asn Leu Tyr Ala Ala Arg Tyr Tyr Ala Ser Leu
                165                 170                 175
```

-continued

```
Ala Ile Ile Glu Ser Asn Ile Asp Arg Phe Ser Ala Phe Gly Tyr Leu
            180                 185                 190

His Ile Gly Asn Ser Tyr Met Leu Thr Asp Tyr Lys Thr Ala Lys Asp
        195                 200                 205

Asn Phe Leu Ser Gly Leu Lys Phe Ala Lys Pro Gly Asp Asn His Tyr
    210                 215                 220

Lys Gln Leu Ile Arg Ser Leu Ser Phe Leu Glu Asn Tyr Trp Glu Asn
225                 230                 235                 240

Asp His Lys Tyr Thr Asp Phe Gln Ser Gly Cys Thr Glu Asp Val His
                245                 250                 255

Glu Gln Ala Phe Tyr Trp Ile Asn Arg Asn Glu His Glu Lys Ala Leu
            260                 265                 270

Asn Leu Leu Asn Gly Ile Asp Arg Ser Thr Leu Ser Asn Gly Leu Leu
        275                 280                 285

Ala Phe His Tyr Phe Tyr Arg Gly Leu Ile Ser Ser Asp Lys Ser Asp
    290                 295                 300

Phe Tyr Asn Ser Ile Lys Tyr Phe Lys Leu Ser Gly Asp Lys Phe Phe
305                 310                 315                 320

Val Glu Cys Pro Leu Arg Glu Leu Asn Lys Leu Gly Glu Asp Arg Lys
                325                 330                 335

Ile Val Asp Ile Phe Ala Ile
            340


<210> SEQ ID NO 146
<211> LENGTH: 385
<212> TYPE: PRT
<213> ORGANISM: Bacillus pumilus

<400> SEQUENCE: 146

Met Asn Leu Lys Thr Tyr Ile Lys Asn Lys Cys Glu Asp Asp Ser Ser
1               5                   10                  15

Leu Ala Met Lys Leu Ala Lys Ile Ala Gly Tyr Ser Asp Arg Thr Gly
            20                  25                  30

Leu Tyr Lys Phe Leu Asn Ser Pro Asn Lys Glu Met Asp Asp Leu Asn
        35                  40                  45

Asn Leu Ile Asn Leu Val Arg Glu Val Asp Gln Glu Arg Glu Ile Glu
    50                  55                  60

Ile Ile Ser Thr Tyr Ile Thr Thr Leu Asp Pro Asn Lys Ser Ala Ala
65                  70                  75                  80

Arg Gln Ala Val Glu Tyr Leu Asp Ala Asn Gln Leu Gly Asp Glu Thr
                85                  90                  95

Asp Glu Leu Val Ile Lys Leu Cys Asn Ala Ser Asn Ala Val Ser Lys
            100                 105                 110

Glu Trp Gly Asn Val Tyr Arg Ile His Arg Leu Leu Thr Lys Gly Glu
        115                 120                 125

Ile Asp Leu Thr Ser Ala Ile Lys Glu Thr Gly Thr Ile Lys Ile Lys
    130                 135                 140

Ser Glu Glu Met Phe Val Phe Ser Arg Met Met Thr Leu Tyr Glu Tyr
145                 150                 155                 160

Leu Asn Ile Gly Glu Phe Gly Leu Met Lys Ser Thr Ser Thr Tyr Ile
                165                 170                 175

Asp Leu Ser Asn Leu Lys Lys Gly Tyr Val Lys Asp Ser Phe Ser Ser
            180                 185                 190

Arg Tyr Leu Leu Leu Met Ala Asn Val Phe Leu Asn Asp Asn Asn Leu
        195                 200                 205
```

```
Lys Pro Leu Arg Asp Tyr Cys Asn Gln Ile Ile Ser Glu Glu Val Lys
    210                 215                 220

Val Asn Arg Phe Gln Val Phe Ala His Leu Thr Cys Gly Asn Ser Tyr
225                 230                 235                 240

Val Phe Asp Asp Tyr Asp Lys Ala Lys Ala Tyr Tyr Ile Asn Gly Met
                245                 250                 255

Lys Phe Ala Lys Asn Ser Phe His Lys Tyr Lys Leu Arg Ser Ala Leu
            260                 265                 270

Ala Phe Leu Glu Asn Thr Trp Gly Ile Lys Glu Asn Lys Tyr Leu Glu
        275                 280                 285

Gln Glu Pro Lys Asn Asp Ser Asp Phe Ile Glu Leu Ala His His Leu
    290                 295                 300

Met Leu Asn Asp Gln Thr Glu Lys Met Met Glu Val Phe Asn Lys Leu
305                 310                 315                 320

Asp Ser Ser Thr Met His Asp Asn Asp Leu Gly Phe Leu Tyr Tyr Val
                325                 330                 335

Lys Gly Ile Phe Tyr Lys Asp Lys Ala Cys Tyr Leu Lys Ser Val Lys
            340                 345                 350

His Phe Lys Lys Ser Asp Asp Lys Tyr Phe Ile Lys Leu Pro Leu Ile
        355                 360                 365

Lys Leu Lys Thr Met Gly Ile Asp Ser Glu Ile Leu Asp Leu Leu Ala
    370                 375                 380

Ile
385


<210> SEQ ID NO 147
<211> LENGTH: 384
<212> TYPE: PRT
<213> ORGANISM: Bacillus amyloliquefaciens

<400> SEQUENCE: 147

Met Asn Leu Lys Gln Met Ile Lys Asn Glu Cys Glu Lys Asp Asn Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Ser Ala
65                  70                  75                  80

Arg Gln Ser Val Glu Tyr Ala Asp Leu Asn Gln Trp Asn Ala Leu Thr
                85                  90                  95

Asp Lys Ile Val Ser Asn Leu Cys Glu Ser Ser Asn Ser Ile Ser Arg
            100                 105                 110

Glu Trp Gly Gln Val Tyr Ser Leu His Arg Lys Leu Asn Asn Asn Lys
        115                 120                 125

Ile Ser Ile Asn Glu Ala Ile Arg Glu Thr Gly Lys Tyr Arg Ile Lys
    130                 135                 140

Ser Pro Glu Met Tyr Ser Phe Ser Asn Ile Met Ile Met Tyr Glu Tyr
145                 150                 155                 160

Leu Lys Ile Gly Glu Phe Gly Leu Met Lys Ser Thr Ala Gln Phe Leu
                165                 170                 175

Glu Ile Asp Glu Leu Ser Asn Gly Phe Ile Lys Asp Ser Tyr Ser Gly
```

180 185 190

Arg Ile Glu Leu Leu Lys Ala Asn Ile Ser Leu Asn Asp Tyr Glu Leu
195 200 205

Glu Glu Thr Arg Lys His Cys Ser Ala Val Ile Glu Glu Cys Asn Asn
210 215 220

Asn Arg Leu Ile Val Phe Ser Tyr Leu Thr Leu Gly Asn Thr Tyr Ile
225 230 235 240

Phe Glu Asp Tyr Ala Lys Ala Lys Leu Cys Tyr Glu Lys Gly Leu Asn
245 250 255

Phe Ala Lys Asp Asn Ser His His His Tyr Lys Leu Arg Leu Ala Leu
260 265 270

Cys Phe Leu Asp Asn Val Trp Ala Arg Glu Asn Lys Trp Val Asp Phe
275 280 285

Glu Ser Gln Glu Ile Pro Asp Met Ile Glu Ala Ala Phe Tyr Leu Thr
290 295 300

Asn Ile Lys Glu Thr Lys Lys Ala Glu Asp Val Ile Lys Lys Ile Glu
305 310 315 320

Glu His Asp Val Leu Asp Asp Asp Leu Gly Phe Leu Tyr His Val Lys
325 330 335

Gly Leu Leu Tyr Asn Asp Met Ser His Phe His Glu Ser Ile Lys Lys
340 345 350

Phe Lys Lys Ser Gly Asp Arg Leu Cys Leu Asn Leu Pro Leu Ile Glu
355 360 365

Leu Lys Lys His Gly Tyr Ser Asp Glu Ile Leu Asn Leu Ile Ala Leu
370 375 380

<210> SEQ ID NO 148
<211> LENGTH: 384
<212> TYPE: PRT
<213> ORGANISM: Bacillus amyloliquefaciens

<400> SEQUENCE: 148

Met Ser Leu Lys Gln Met Ile Lys Asn Glu Cys Glu Lys Asp Asn Gln
1 5 10 15

Leu Ala Ala Lys Leu Ser Lys Ile Ala Gly Tyr Glu Lys Val Asn Gly
20 25 30

Phe Tyr Lys Phe Ile Asn Thr Pro Glu Lys Glu Met Asp Asn Leu Gly
35 40 45

Gly Leu Ile Asn Ile Val Lys Ser Leu Phe Pro Asp Asn Glu Glu Gln
50 55 60

Leu Leu Ser Asp Tyr Phe Leu Ser Leu Asp Pro Asn Lys Lys Ser Ala
65 70 75 80

Arg Gln Ser Val Glu Tyr Ala Asp Leu Asn Gln Trp Asn Ala Leu Thr
85 90 95

Asp Lys Ile Val Ser Asn Leu Cys Glu Ser Ser Asn Ser Ile Ser Arg
100 105 110

Glu Trp Gly Gln Val Tyr Ser Leu His Arg Lys Leu Asn Asn Asn Lys
115 120 125

Ile Ser Ile Asn Glu Ala Ile Arg Glu Thr Gly Lys Tyr Arg Ile Lys
130 135 140

Ser Pro Glu Met Tyr Ser Phe Ser Asn Ile Met Ile Met Tyr Glu Tyr
145 150 155 160

Leu Lys Ile Gly Glu Phe Gly Leu Met Lys Ser Thr Ala Gln Phe Leu
165 170 175

```
Glu Ile Asp Glu Leu Ser Asp Gly Phe Ile Lys Asp Ser Tyr Ser Gly
            180                 185                 190

Arg Ile Glu Leu Leu Lys Ala Asn Ile Ser Leu Asn Asp Tyr Glu Leu
        195                 200                 205

Glu Glu Thr Arg Lys His Cys Ser Ala Val Ile Glu Glu Cys Asn Asn
    210                 215                 220

Asn Arg Leu Ile Val Phe Ser Tyr Leu Thr Leu Gly Asn Thr Tyr Ile
225                 230                 235                 240

Phe Glu Asp Tyr Ala Lys Ala Lys Leu Cys Tyr Glu Lys Gly Leu Asn
                245                 250                 255

Phe Ala Lys Asp Asn Ser His His His Tyr Lys Leu Arg Leu Ala Leu
            260                 265                 270

Cys Phe Leu Asp Asn Val Trp Ala Arg Glu Asn Lys Trp Val Asp Phe
        275                 280                 285

Glu Ser Gln Glu Ile Pro Asp Met Ile Glu Ala Ala Phe Tyr Leu Thr
    290                 295                 300

Asn Ile Lys Glu Thr Lys Lys Ala Glu Asp Val Ile Lys Lys Ile Glu
305                 310                 315                 320

Glu His Asp Val Leu Asp Asp Asp Leu Gly Phe Leu Tyr His Val Lys
                325                 330                 335

Gly Leu Leu Tyr Asn Asp Met Ser His Phe His Glu Ser Ile Lys Lys
            340                 345                 350

Phe Lys Lys Ser Gly Asp Arg Leu Cys Leu Asn Leu Pro Leu Ile Glu
        355                 360                 365

Leu Lys Lys Arg Gly Tyr Ser Asp Glu Ile Leu Asn Leu Ile Ala Leu
    370                 375                 380


<210> SEQ ID NO 149
<211> LENGTH: 384
<212> TYPE: PRT
<213> ORGANISM: Bacillus amyloliquefaciens

<400> SEQUENCE: 149

Met Asn Leu Lys Gln Met Ile Lys Asn Glu Cys Glu Lys Asp Asn Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Ser Ala
65                  70                  75                  80

Arg Gln Ser Val Glu Tyr Ala Asp Leu Asn Gln Trp Asn Ala Leu Thr
                85                  90                  95

Asp Lys Ile Val Ser Asn Leu Cys Glu Ser Ser Asn Ser Ile Ser Arg
            100                 105                 110

Glu Trp Gly Gln Val Tyr Ser Leu His Arg Lys Leu Asn Asn Asn Lys
        115                 120                 125

Ile Ser Ile Asn Glu Ala Ile Arg Glu Thr Gly Lys Tyr Arg Ile Lys
    130                 135                 140

Ser Pro Glu Met Tyr Ser Phe Ser Asn Ile Met Ile Met Tyr Glu Tyr
145                 150                 155                 160

Leu Lys Ile Gly Glu Phe Gly Leu Met Lys Ser Thr Ala Gln Phe Leu
                165                 170                 175
```

Glu Ile Asp Glu Leu Ser Asp Gly Phe Ile Lys Asp Ser Tyr Ser Gly
180 185 190

Arg Ile Glu Leu Leu Lys Ala Asn Ile Ser Leu Asn Asp Tyr Glu Leu
195 200 205

Glu Glu Thr Arg Lys His Cys Ser Ala Val Ile Glu Glu Cys Asn Asn
210 215 220

Asn Arg Leu Ile Val Phe Ser Tyr Leu Thr Leu Gly Asn Thr Tyr Ile
225 230 235 240

Phe Glu Asp Tyr Ala Lys Ala Lys Leu Cys Tyr Glu Lys Gly Leu Asn
245 250 255

Phe Ala Lys Asp Asn Ser His His His Tyr Lys Leu Arg Leu Ala Leu
260 265 270

Cys Phe Leu Asp Asn Val Trp Ala Arg Glu Asn Lys Trp Val Asp Phe
275 280 285

Glu Ser Gln Glu Ile Pro Asp Met Ile Glu Ala Ala Phe Tyr Leu Thr
290 295 300

Asn Ile Lys Glu Thr Lys Lys Ala Glu Asp Val Ile Lys Lys Ile Glu
305 310 315 320

Glu His Asp Val Leu Asp Asp Asp Leu Gly Phe Leu Tyr His Val Lys
325 330 335

Gly Leu Leu Tyr Asn Asp Met Ser His Phe His Glu Ser Ile Lys Lys
340 345 350

Phe Lys Lys Ser Gly Asp Arg Leu Cys Leu Asn Leu Pro Leu Ile Glu
355 360 365

Leu Lys Lys Arg Gly Tyr Ser Asp Glu Ile Leu Asn Leu Ile Ala Leu
370 375 380

<210> SEQ ID NO 150
<211> LENGTH: 384
<212> TYPE: PRT
<213> ORGANISM: Bacillus subtilis

<400> SEQUENCE: 150

Met Asn Leu Lys Gln Met Ile Lys Asn Glu Cys Glu Lys Asp Asn Gln
1 5 10 15

Leu Ala Ala Lys Leu Ser Lys Ile Ala Gly Tyr Glu Lys Val Asn Gly
20 25 30

Phe Tyr Lys Phe Ile Asn Thr Pro Glu Lys Glu Met Asp Asn Leu Gly
35 40 45

Gly Leu Ile Asn Ile Val Lys Ser Leu Phe Pro Asp Lys Glu Glu Gln
50 55 60

Leu Leu Ser Asp Tyr Phe Leu Ser Leu Asp Pro Asn Lys Lys Ser Ala
65 70 75 80

Arg Gln Ser Val Glu Tyr Ala Asp Leu Asn Gln Trp Asn Ala Leu Thr
85 90 95

Asp Lys Ile Val Ser Asn Leu Cys Glu Ser Ser Asn Ser Ile Ser Arg
100 105 110

Glu Trp Gly Gln Val Tyr Ser Leu His Arg Lys Leu Asn Asn Asn Lys
115 120 125

Ile Ser Ile Asn Glu Ala Ile Arg Glu Thr Gly Lys Tyr Arg Ile Lys
130 135 140

Ser Pro Glu Met Tyr Ser Phe Ser Asn Ile Met Ile Met Tyr Glu Tyr
145 150 155 160

Leu Lys Ile Gly Glu Phe Gly Leu Met Lys Ser Thr Ala Gln Phe Leu

-continued

```
                165                 170                 175

Glu Ile Asp Glu Leu Ser Asp Gly Phe Ile Lys Asp Ser Tyr Ser Gly
            180                 185                 190

Arg Ile Glu Leu Leu Lys Ala Asn Ile Ser Leu Asn Asp Tyr Glu Leu
        195                 200                 205

Glu Glu Thr Arg Lys His Cys Ser Ala Val Ile Glu Glu Cys Asn Asn
    210                 215                 220

Asn Arg Leu Ile Val Phe Ser Tyr Leu Thr Leu Gly Asn Thr Tyr Ile
225                 230                 235                 240

Phe Glu Asp Tyr Asp Lys Ala Lys Leu Cys Tyr Glu Lys Gly Leu Asn
                245                 250                 255

Phe Ala Lys Asp Asn Asn His His His Tyr Lys Leu Arg Leu Ala Leu
            260                 265                 270

Cys Phe Leu Asp Asn Val Trp Ala Arg Glu Asn Lys Trp Val Asp Phe
        275                 280                 285

Glu Ser Gln Glu Ile Pro Asp Met Ile Glu Ala Ala Phe Tyr Leu Thr
    290                 295                 300

Asn Ile Lys Glu Thr Lys Lys Ala Glu Asp Val Ile Lys Lys Ile Glu
305                 310                 315                 320

Glu His Asp Val Leu Asp Asp Asp Leu Gly Phe Leu Tyr His Val Lys
                325                 330                 335

Gly Leu Leu Tyr Asn Asp Met Ser His Phe His Glu Ser Ile Lys Lys
            340                 345                 350

Phe Lys Lys Ser Gly Asp Arg Leu Cys Leu Asn Leu Pro Leu Ile Glu
        355                 360                 365

Leu Lys Lys Arg Gly Tyr Ser Asp Glu Ile Leu Asn Leu Ile Ala Leu
    370                 375                 380


<210> SEQ ID NO 151
<211> LENGTH: 384
<212> TYPE: PRT
<213> ORGANISM: Paenibacillus polymyxa

<400> SEQUENCE: 151

Met Asn Leu Lys Gln Met Ile Lys Asn Glu Cys Glu Lys Asp Asn Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Lys Glu Glu Gln
    50                  55                  60

Leu Leu Ser Asp Tyr Phe Leu Ser Leu Asp Pro Asn Lys Lys Ser Ala
65                  70                  75                  80

Arg Gln Ser Val Glu Tyr Ala Asp Leu Asn Gln Trp Asn Ala Leu Thr
                85                  90                  95

Asp Lys Ile Val Ser Asn Leu Cys Glu Ser Ser Asn Ser Ile Ser Arg
            100                 105                 110

Glu Trp Gly Gln Val Tyr Ser Leu His Arg Lys Leu Asn Asn Asn Lys
        115                 120                 125

Ile Ser Ile Asn Glu Ala Ile Arg Glu Thr Gly Lys Tyr Arg Ile Lys
    130                 135                 140

Ser Pro Glu Met Tyr Ser Phe Ser Asn Ile Met Ile Met Tyr Glu Tyr
145                 150                 155                 160
```

```
Leu Lys Ile Gly Glu Phe Gly Leu Met Lys Ser Thr Ala Gln Phe Leu
                165                 170                 175

Glu Ile Asp Glu Leu Ser Asp Gly Phe Ile Lys Asp Ser Tyr Ser Gly
            180                 185                 190

Arg Ile Glu Leu Leu Lys Ala Asn Ile Ser Leu Asn Asp Tyr Glu Leu
        195                 200                 205

Glu Glu Thr Arg Lys His Cys Ser Ala Val Ile Glu Glu Cys Asn Asn
    210                 215                 220

Asn Arg Leu Ile Val Phe Ser Tyr Leu Thr Leu Gly Asn Thr Tyr Ile
225                 230                 235                 240

Phe Glu Asp Tyr Asp Lys Ala Lys Leu Cys Tyr Glu Lys Gly Leu Asn
                245                 250                 255

Phe Ala Lys Asp Asn Asn His His His Tyr Lys Leu Arg Leu Ala Leu
            260                 265                 270

Cys Phe Leu Asp Asn Val Trp Ala Arg Glu Asn Lys Trp Val Asp Phe
        275                 280                 285

Glu Ser Gln Glu Ile Pro Asp Met Ile Glu Ala Ala Phe Tyr Leu Thr
    290                 295                 300

Asn Ile Lys Glu Thr Lys Lys Ala Glu Asp Val Ile Lys Lys Ile Glu
305                 310                 315                 320

Glu His Asp Val Leu Asp Asp Asp Leu Gly Phe Leu Tyr His Val Lys
                325                 330                 335

Gly Leu Leu Tyr Asn Asp Met Ser His Phe His Glu Ser Ile Lys Lys
            340                 345                 350

Phe Lys Lys Ser Gly Asp Arg Leu Cys Leu Asn Leu Pro Leu Ile Glu
        355                 360                 365

Leu Lys Lys Arg Gly Tyr Ser Asp Glu Ile Leu Asn Leu Ile Ala Leu
    370                 375                 380


<210> SEQ ID NO 152
<211> LENGTH: 297
<212> TYPE: PRT
<213> ORGANISM: Bacillus atrophaeus

<400> SEQUENCE: 152

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160
```

Tyr Leu Ser Lys Gly Asn Phe Ser Pro Met Lys Pro Leu Leu Lys Gln
165 170 175

Ile Asn Leu Asn Glu Ile Lys Glu Asn Lys Tyr Leu Lys Lys Ser Phe
180 185 190

Glu Thr Arg Ile His Val Leu Leu Ser Asn Met Tyr Leu Asn Glu Asn
195 200 205

Lys Leu Glu Leu Cys Arg Glu Tyr Ala Lys Lys Ala Ile Gln Ser Thr
210 215 220

Ser Thr Lys Arg Phe Leu Val Phe Ser Tyr Leu Thr Ile Gly Thr Ser
225 230 235 240

Tyr Ile Phe Leu Asp Tyr Asn Leu Ser Arg Gln Asn Tyr Leu Ser Gly
245 250 255

Tyr Glu Ile Ser Lys Gly Asn Asn Val Phe Glu Glu Phe Phe Lys Arg
260 265 270

Asn Leu Ser Phe Leu Asn Asn Tyr Trp Asn Lys Glu Asn Ser Trp Ile
275 280 285

Asn Tyr Asp Ser Asp Arg Arg Ser Asp
290 295

<210> SEQ ID NO 153
<211> LENGTH: 297
<212> TYPE: PRT
<213> ORGANISM: Bacillus atrophaeus

<400> SEQUENCE: 153

Met Glu Leu Ile Arg Lys Ala Met Arg Lys Asp Leu Glu Asn Asp Lys
1 5 10 15

Thr Leu Met Ser Lys Trp Ala Thr Val Ala Gly Leu Lys Asn Pro Asn
20 25 30

Pro Leu Tyr Asp Phe Leu Asn His Asp Gly Lys Thr Phe Ser Glu Phe
35 40 45

Ser Thr Leu Val Asn Ile Val Lys Ser Gln Tyr Pro Asp Arg Glu Tyr
50 55 60

Glu Leu Met Glu Asp Tyr Cys Leu Ile Leu Asp Pro Lys Thr Lys Ala
65 70 75 80

Ala Arg Ser Ala Leu Lys Tyr Ala Asp Ala Asn Ser Phe Asn Asp Leu
85 90 95

Thr Asp Lys Leu Val Asp Lys Met Ser Ile Ser Ser Asn Leu Lys Ser
100 105 110

Lys Glu Tyr Gly Lys Ile Tyr Gly Ile His Arg Lys Leu Ser Lys Gly
115 120 125

Glu Ile Asp Val Leu Glu Ala Thr Lys Asn Ile Gly Lys Gln Arg Ile
130 135 140

Lys Thr Asp Glu Met Asn Ile Phe Ser Lys Met Ile Pro Met Tyr Asp
145 150 155 160

Tyr Leu Ser Lys Gly Asn Phe Ser Pro Met Lys Pro Leu Leu Lys Gln
165 170 175

Ile Asn Leu Asn Glu Ile Lys Glu Asn Lys Tyr Leu Lys Lys Ser Phe
180 185 190

Glu Thr Arg Ile His Val Leu Leu Ser Asn Met Tyr Leu Asn Glu Asn
195 200 205

Lys Leu Glu Leu Cys Arg Glu Tyr Ala Lys Lys Ala Ile Gln Ser Thr
210 215 220

Ser Thr Lys Arg Phe Leu Val Phe Ser Tyr Leu Thr Ile Gly Thr Ser 225 230 235 240

Tyr Ile Phe Leu Asp Tyr Asn Leu Ser Arg Gln Asn Tyr Leu Ser Gly
245 250 255

Tyr Glu Ile Ser Lys Gly Asn Asn Val Phe Glu Glu Phe Phe Lys Arg
260 265 270

Asn Leu Ser Phe Leu Asn Asn Tyr Trp Asn Lys Glu Asn Ser Trp Ile
275 280 285

Asn Tyr Asp Ser Asp Arg Arg Ser Asp
290 295

<210> SEQ ID NO 154
<211> LENGTH: 297
<212> TYPE: PRT
<213> ORGANISM: Bacillus atrophaeus

<400> SEQUENCE: 154

Met Glu Leu Ile Arg Lys Ala Met Arg Lys Asp Leu Glu Asn Asp Lys
1 5 10 15

Thr Leu Met Ser Lys Trp Ala Thr Val Ala Gly Leu Lys Asn Pro Asn
20 25 30

Pro Leu Tyr Asp Phe Leu Asn His Asp Gly Lys Thr Phe Ser Glu Phe
35 40 45

Ser Thr Leu Val Asn Ile Val Lys Ser Gln Tyr Pro Asp Arg Glu Tyr
50 55 60

Glu Leu Met Glu Asp Tyr Cys Leu Ile Leu Asp Pro Lys Thr Lys Ala
65 70 75 80

Ala Arg Ser Ala Leu Lys Tyr Ala Asp Ala Asn Ser Phe Asn Asp Leu
85 90 95

Thr Asp Lys Leu Val Asp Lys Met Ser Ile Ser Ser Asn Leu Lys Ser
100 105 110

Lys Glu Tyr Gly Lys Ile Tyr Gly Ile His Arg Lys Leu Ser Lys Gly
115 120 125

Glu Ile Asp Val Leu Glu Ala Thr Lys Asn Ile Gly Lys Gln Arg Ile
130 135 140

Lys Thr Asp Glu Met Asn Ile Phe Ser Lys Met Ile Pro Met Tyr Asp
145 150 155 160

Tyr Leu Ser Lys Gly Asn Phe Ser Pro Met Lys Pro Leu Leu Lys Gln
165 170 175

Ile Asn Leu Asn Glu Ile Lys Glu Asn Lys Tyr Leu Lys Lys Ser Phe
180 185 190

Glu Thr Arg Ile His Val Leu Leu Ser Asn Met Tyr Leu Asn Glu Asn
195 200 205

Lys Leu Glu Leu Cys Arg Glu Tyr Ala Lys Lys Ala Ile Gln Ser Thr
210 215 220

Ser Thr Lys Arg Phe Leu Val Phe Ser Tyr Leu Thr Ile Gly Thr Ser
225 230 235 240

Tyr Ile Phe Leu Asp Tyr Asn Leu Ser Arg Gln Asn Tyr Leu Ser Gly
245 250 255

Tyr Glu Ile Ser Lys Gly Asn Asn Val Phe Glu Glu Phe Phe Lys Arg
260 265 270

Asn Leu Ser Phe Leu Asn Asn Tyr Trp Asn Lys Glu Asn Ser Trp Ile
275 280 285

Asn Tyr Asp Ser Asp Arg Arg Ser Asp
290 295

<210> SEQ ID NO 155
<211> LENGTH: 297
<212> TYPE: PRT
<213> ORGANISM: Bacillus atrophaeus

<400> SEQUENCE: 155

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295

<210> SEQ ID NO 156
<211> LENGTH: 297
<212> TYPE: PRT
<213> ORGANISM: Bacillus atrophaeus

<400> SEQUENCE: 156

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

-continued

```
Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295
```

<210> SEQ ID NO 157
<211> LENGTH: 297
<212> TYPE: PRT
<213> ORGANISM: Bacillus atrophaeus

<400> SEQUENCE: 157

```
Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110
```

```
Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295
```

<210> SEQ ID NO 158
<211> LENGTH: 297
<212> TYPE: PRT
<213> ORGANISM: Bacillus atrophaeus

<400> SEQUENCE: 158

```
Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
```

```
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295


<210> SEQ ID NO 159
<211> LENGTH: 297
<212> TYPE: PRT
<213> ORGANISM: Bacillus atrophaeus

<400> SEQUENCE: 159

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255
```

Tyr Glu Ile Ser Lys Gly Asn Asn Val Phe Glu Glu Phe Phe Lys Arg
260 265 270

Asn Leu Ser Phe Leu Asn Asn Tyr Trp Asn Lys Glu Asn Ser Trp Ile
275 280 285

Asn Tyr Asp Ser Asp Arg Arg Ser Asp
290 295

<210> SEQ ID NO 160
<211> LENGTH: 382
<212> TYPE: PRT
<213> ORGANISM: Bacillus amyloliquefaciens

<400> SEQUENCE: 160

Met Asn Leu Lys Gln Met Ile Lys Asn Glu Cys Glu Lys Asp Asn Gln
1 5 10 15

Leu Ala Ala Lys Leu Ser Lys Ile Ala Gly Tyr Glu Lys Val Asn Gly
20 25 30

Phe Tyr Lys Phe Ile Asn Thr Pro Glu Lys Glu Met Asp Asn Leu Gly
35 40 45

Gly Leu Ile Asn Ile Val Lys Ser Leu Phe Pro Asp Asn Glu Glu Gln
50 55 60

Leu Leu Ser Asp Tyr Phe Leu Ser Leu Asp Pro Asn Lys Lys Cys Ala
65 70 75 80

Arg Gln Ser Val Glu Tyr Ser Asp Ile Asn Gln Trp Asp Thr Leu Thr
85 90 95

Asp Lys Ile Val Ser Arg Leu Ser Ser Ser Lys Asn Leu Ala Ser Gln
100 105 110

Glu Trp Gly Asn Thr Tyr Ser Ile His Arg Arg Leu Ser Glu Ser Lys
115 120 125

Ile Ser Leu Thr Asp Ala Ile Arg Ala Thr Gly Lys Cys Lys Thr Asp
130 135 140

Glu Met Leu Phe Phe Ser Asn Ala Met Leu Met Tyr Glu Tyr Leu Lys
145 150 155 160

Val Gly Glu Phe Gly Leu Met Lys Ser Thr Leu Ser Leu Leu Asn Phe
165 170 175

Asn Asp Leu Pro Glu Gly Phe Val Lys Asp Cys Tyr Met Asn Arg Ile
180 185 190

Ser Leu Leu Asn Ala Asn Ile Tyr Leu Asn Asp Asn Glu Ile Glu Lys
195 200 205

Ser Arg Tyr Tyr Ser Glu Gln Val Ile Gln Asn Ser Asn Ile Asn Arg
210 215 220

Leu Lys Val Phe Gly His Leu Thr Tyr Gly Asn Thr Leu Ile Phe Glu
225 230 235 240

Ser Tyr Ser Lys Ala Lys Glu Gln Tyr Leu Lys Gly Leu Glu Phe Ala
245 250 255

Arg Asp Asn Glu His His Lys Tyr Lys Leu Arg Leu Ala Leu Cys Phe
260 265 270

Leu Ser Asn Val Trp Asn Lys Asp Asn Lys Trp Leu Asp Phe Asp Thr
275 280 285

Asp Asn Ile Pro Asp Lys Ile Glu Val Ala Tyr Tyr Tyr Thr Asn Asn
290 295 300

Lys Glu Phe Asn Lys Ala Glu Lys Val Ile Asn Glu Leu Glu Asn Met
305 310 315 320

Lys Leu Tyr Glu Tyr Asp Ser Gly Ile Leu Asp Tyr Ile Lys Gly Ile
325 330 335

```
Leu Tyr Gln Asn Lys Asn Tyr Phe Tyr Glu Ser Thr Ala Lys Leu Lys
            340                 345                 350

Lys Ser Gly Asp Lys Leu Phe Ile Asn Leu Pro Leu Ala Glu Leu Arg
        355                 360                 365

Lys Met Gly Cys Asp Glu Lys Leu Leu Glu Leu Ile Met Val
    370                 375                 380


<210> SEQ ID NO 161
<211> LENGTH: 320
<212> TYPE: PRT
<213> ORGANISM: Bacillus amyloliquefaciens

<400> SEQUENCE: 161

Met Leu Val Lys Glu Arg Glu Val Lys Lys Pro Glu Val Asp Ala Lys
1               5                   10                  15

Val Arg Leu Glu Met Ser Asp Ile Asn Glu Gln Tyr Glu Leu Thr Asp
            20                  25                  30

Thr Leu Ile Asp Gln Leu Ile Asn Ser Thr Cys Ser Ile Glu Arg Glu
        35                  40                  45

Trp Ala Ala Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Met Ile Val Asp
            100                 105                 110

Leu Asp Phe Ile Glu Asn Asn Glu Gln Ile Lys Ser Ser Phe Tyr Tyr
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Leu Gly Asn Thr Tyr Leu
                165                 170                 175

Leu Asp Asp Tyr Glu Lys Ala Lys Glu Tyr Tyr Leu Thr Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asn Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320
```

<210> SEQ ID NO 162
<211> LENGTH: 320
<212> TYPE: PRT
<213> ORGANISM: Bacillus subtilis

<400> SEQUENCE: 162

Met Leu Val Lys Glu Arg Glu Val Lys Lys Pro Glu Val Asp Ala Lys
1 5 10 15

Val Arg Leu Glu Met Ser Asp Ile Asn Glu Gln Tyr Glu Leu Thr Asp
20 25 30

Thr Leu Ile Asp Gln Leu Ile Asn Ser Thr Cys Ser Ile Glu Arg Glu
35 40 45

Trp Ala Ala Met Tyr Gln Ile Lys Arg Lys Gln Asp Arg Gly Glu Ile
50 55 60

Asn Ala His Gln Ala Leu Lys Ala Ile Gly Lys Leu Asp Pro Lys Ser
65 70 75 80

Gln Glu Met Arg Val Phe Thr Tyr Ile Ile Pro Leu Tyr Tyr Tyr Leu
85 90 95

Arg Met Ala Glu Tyr Ser Asn Leu Ala Glu Met Ser Met Ile Val Asp
100 105 110

Leu Asp Phe Ile Glu Asn Asn Glu Gln Ile Lys Ser Ser Phe Tyr Tyr
115 120 125

Arg Leu Met Ala Leu Leu Gly Ala Ser Ala Phe Ser Gln Asn Lys Met
130 135 140

Thr Gln Ala Arg Phe Tyr Cys Ser Tyr Gly Ile Asn Val Thr Asn Ile
145 150 155 160

Asp Arg Leu Val Ala Tyr Ser Tyr Leu Thr Leu Gly Asn Thr Tyr Leu
165 170 175

Leu Asp Asp Tyr Glu Lys Ala Lys Glu Tyr Tyr Leu Thr Gly Leu Lys
180 185 190

His Thr Glu Asn Asn Pro Leu Ala Lys Leu Gln Leu Thr Arg Ser Leu
195 200 205

Cys Phe Leu Glu Asn His Trp Asn Gln Glu Asn Phe Trp Leu Asn Pro
210 215 220

Asp Ser Asn Glu Val Thr Asp Ile Gln Glu Ile Ala His Tyr His Ile
225 230 235 240

Lys Lys Asn Asn Leu Gln Gln Ala Lys Glu Ile Leu Glu Asn Leu Glu
245 250 255

Gln Gln Pro Asn Ile His Asn Asp Phe Gly Ile His Phe Tyr Leu Lys
260 265 270

Gly Leu Ala Tyr Glu Asp Lys Arg Phe Phe Tyr Glu Ser Ile Lys His
275 280 285

Phe Lys Leu Ser Gly Asp Leu Tyr Ser Val Arg Leu Pro Leu Asp Lys
290 295 300

Leu Arg Glu Met Gly Glu Asp Glu Gln Ile Leu Asp Leu Leu Ala Leu
305 310 315 320

<210> SEQ ID NO 163
<211> LENGTH: 320
<212> TYPE: PRT
<213> ORGANISM: Bacillus amyloliquefaciens

<400> SEQUENCE: 163

Met Leu Val Lys Glu Arg Glu Val Lys Lys Pro Glu Val Asp Ala Lys
1 5 10 15

Val Arg Leu Glu Met Ser Asp Ile Asn Glu Gln Tyr Glu Leu Thr Asp

```
            20                  25                  30

Thr Leu Ile Asp Gln Leu Ile Asn Ser Thr Cys Ser Ile Glu Arg Glu
        35                  40                  45

Trp Ala Ala Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Met Ile Val Asp
            100                 105                 110

Leu Asp Phe Ile Glu Asn Asn Glu Gln Ile Lys Ser Ser Phe Tyr Tyr
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Leu Gly Asn Thr Tyr Leu
                165                 170                 175

Leu Asp Asp Tyr Glu Lys Ala Lys Glu Tyr Tyr Leu Thr Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asn Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320


<210> SEQ ID NO 164
<211> LENGTH: 320
<212> TYPE: PRT
<213> ORGANISM: Bacillus amyloliquefaciens

<400> SEQUENCE: 164

Met Leu Val Lys Glu Arg Glu Val Lys Lys Pro Glu Val Asp Ala Lys
1               5                   10                  15

Val Arg Leu Glu Met Ser Asp Ile Asn Glu Gln Tyr Glu Leu Thr Asp
            20                  25                  30

Thr Leu Ile Asp Gln Leu Ile Asn Ser Thr Cys Ser Ile Glu Arg Glu
        35                  40                  45

Trp Ala Ala Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80
```

```
Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Met Ile Val Asp
            100                 105                 110

Leu Asp Phe Ile Glu Asn Asn Glu Gln Ile Lys Ser Ser Phe Tyr Tyr
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Leu Gly Asn Thr Tyr Leu
                165                 170                 175

Leu Asp Asp Tyr Glu Lys Ala Lys Glu Tyr Tyr Leu Thr Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asn Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320


<210> SEQ ID NO 165
<211> LENGTH: 320
<212> TYPE: PRT
<213> ORGANISM: Bacillus amyloliquefaciens

<400> SEQUENCE: 165

Met Ile Ala Lys Glu Arg Glu Val Lys Lys Pro Glu Val Asp Ala Lys
1               5                   10                  15

Val Arg Leu Glu Met Ser Asp Ile Asn Glu Gln Tyr Glu Gln Thr Asp
            20                  25                  30

Ala Leu Ile Asp Gln Leu Ile Asn Ser Ser Cys Ser Ile Glu Arg Glu
        35                  40                  45

Trp Ala Ala Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Met Ile Val Asp
            100                 105                 110

Leu Asp Phe Ile Glu Asn Asn Glu Gln Ile Lys Ser Ser Phe Tyr Tyr
        115                 120                 125

Arg Leu Met Ala Leu Leu Gly Ala Ser Ala Phe Ser Gln Asn Lys Met
    130                 135                 140
```

```
Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Met Gly Asn Thr Tyr Leu
                165                 170                 175

Leu Asp Asp Tyr Glu Lys Ala Lys Glu Tyr Tyr Leu Ala Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asp Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Gln
    290                 295                 300

Leu Arg Glu Met Gly Glu Asp Glu Gln Ile Leu Asp Leu Leu Ala Leu
305                 310                 315                 320


<210> SEQ ID NO 166
<211> LENGTH: 320
<212> TYPE: PRT
<213> ORGANISM: Bacillus methylotrophicus

<400> SEQUENCE: 166

Met Ile Ala Lys Glu Arg Glu Ala Lys Lys Pro Glu Val Asp Ala Lys
1               5                   10                  15

Val Arg Leu Glu Met Ser Asp Ile Asn Glu Gln Tyr Glu Gln Thr Asp
            20                  25                  30

Ala Leu Ile Asp Gln Leu Ile Asn Ser Ser Cys Ser Ile Glu Arg Glu
        35                  40                  45

Trp Ala Ala Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Thr Val Val Asp
            100                 105                 110

Leu Asp Phe Ile Glu Asn Asn Glu Gln Ile Lys Ser Ser Phe Tyr Asn
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Leu Gly Asn Thr Tyr Leu
                165                 170                 175

Leu Asp Asp Tyr Glu Lys Ala Lys Glu Tyr Tyr Leu Ala Gly Leu Lys
            180                 185                 190

His Thr Glu Asn Asn Pro Leu Ala Lys Leu Gln Leu Thr Arg Ser Leu
```

```
        195                 200                 205

Cys Phe Leu Glu Asn His Trp Asn Gln Glu Asn Phe Trp Leu Asn Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320


<210> SEQ ID NO 167
<211> LENGTH: 320
<212> TYPE: PRT
<213> ORGANISM: Bacillus amyloliquefaciens

<400> SEQUENCE: 167

Met Ile Ala Lys Glu Arg Glu Ala Lys Lys Pro Lys Val Asp Ala Lys
1               5                   10                  15

Val Arg Leu Glu Met Ser Asp Ile Asn Glu Gln Tyr Glu Gln Thr Asp
            20                  25                  30

Val Leu Ile Asp Gln Leu Ile Asn Ser Asn Cys Ser Ile Glu Arg Glu
        35                  40                  45

Trp Ala Val Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Thr Val Val Asp
            100                 105                 110

Leu Asp Phe Ile Glu Asn Asn Glu Gln Ile Lys Ser Ser Phe Tyr Asn
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Leu Gly Asn Thr Tyr Leu
                165                 170                 175

Leu Asp Asp Tyr Glu Lys Ala Lys Glu Tyr Tyr Leu Ala Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asn Pro
    210                 215                 220

Asp Ser Asn Glu Ile Thr Asp Met Gln Glu Ile Ala His Tyr His Ile
225                 230                 235                 240

Lys Arg Asn Asn Leu Gln Gln Ala Lys Glu Ile Leu Glu Asn Leu Glu
                245                 250                 255
```

-continued

```
Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Phe Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320


<210> SEQ ID NO 168
<211> LENGTH: 320
<212> TYPE: PRT
<213> ORGANISM: Bacillus amyloliquefaciens

<400> SEQUENCE: 168

Met Ile Ala Lys Glu Arg Glu Ala Lys Lys Pro Lys Val Asp Ala Lys
1               5                   10                  15

Val Arg Leu Glu Met Ser Asp Ile Asn Glu Gln Tyr Glu Gln Thr Asp
            20                  25                  30

Val Leu Ile Asp Gln Leu Ile Asn Ser Asn Cys Ser Ile Glu Arg Glu
        35                  40                  45

Trp Ala Val Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Thr Val Val Asp
            100                 105                 110

Leu Asp Phe Ile Glu Asn Asn Glu Gln Ile Lys Ser Ser Phe Tyr Asn
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Leu Gly Asn Thr Tyr Leu
                165                 170                 175

Leu Asp Asp Tyr Glu Lys Ala Lys Glu Tyr Tyr Leu Ala Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asn Pro
    210                 215                 220

Asp Ser Asn Glu Ile Thr Asp Met Gln Glu Ile Ala His Tyr His Ile
225                 230                 235                 240

Lys Arg Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Phe Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320
```

<210> SEQ ID NO 169
<211> LENGTH: 320
<212> TYPE: PRT
<213> ORGANISM: Bacillus amyloliquefaciens

<400> SEQUENCE: 169

Met Ile Ala Lys Glu Arg Glu Ala Lys Lys Pro Lys Val Asp Ala Lys
1 5 10 15

Val Arg Leu Glu Met Ser Asp Ile Asn Glu Gln Tyr Glu Leu Thr Asp
20 25 30

Thr Leu Ile Asn Gln Leu Ile Asn Ser Thr Cys Ser Ile Glu Arg Glu
35 40 45

Trp Ala Ala Met Tyr Gln Ile Lys Arg Lys Gln Asp Arg Gly Glu Ile
50 55 60

Asn Ala His Gln Ala Leu Lys Ala Ile Gly Lys Leu Asp Pro Lys Ser
65 70 75 80

Gln Glu Met Arg Val Phe Thr Tyr Ile Ile Pro Leu Tyr Tyr Tyr Leu
85 90 95

Arg Met Ala Glu Tyr Ser Asn Leu Ala Glu Met Ser Thr Val Val Asp
100 105 110

Leu Asp Phe Ile Glu Asn Asn Glu Gln Ile Lys Ser Ser Phe Tyr Asn
115 120 125

Arg Leu Met Ala Leu Leu Gly Ala Ser Ala Phe Ser Gln Asn Asn Met
130 135 140

Thr Gln Ala Arg Phe Tyr Cys Ser Tyr Gly Ile Asn Val Thr Asn Ile
145 150 155 160

Asp Arg Leu Val Ala Tyr Ser Tyr Leu Thr Leu Gly Asn Thr Tyr Leu
165 170 175

Leu Asp Asp Tyr Glu Lys Ala Lys Glu Asn Tyr Leu Ala Gly Leu Lys
180 185 190

His Thr Glu Asn Asn Pro Leu Ala Lys Leu Gln Leu Thr Arg Ser Leu
195 200 205

Cys Phe Leu Glu Asn His Trp Asn Gln Glu Asn Phe Trp Leu Asn Pro
210 215 220

Asp Ser Asn Glu Val Thr Asp Ile Gln Glu Ile Ala His Tyr His Ile
225 230 235 240

Lys Lys Asn Asn Leu Gln Gln Ala Lys Glu Ile Leu Glu Asn Leu Glu
245 250 255

Gln Gln Pro Asn Ile His Asn Asp Phe Gly Ile His Phe Tyr Leu Lys
260 265 270

Gly Leu Ala Tyr Glu Asp Lys Arg Phe Phe Tyr Glu Ser Ile Lys His
275 280 285

Phe Lys Leu Ser Gly Asp Leu Tyr Ser Val Arg Leu Pro Leu Asp Lys
290 295 300

Leu Arg Glu Met Gly Glu Asp Glu Gln Ile Leu Asp Leu Leu Ala Leu
305 310 315 320

<210> SEQ ID NO 170
<211> LENGTH: 387
<212> TYPE: PRT
<213> ORGANISM: Bacillus sp.

<400> SEQUENCE: 170

Met Ser Lys Leu Lys Ala Phe Ile Lys Ser Lys Cys Glu Asp Asp Ser
1 5 10 15

Ser Met Ala Met Lys Leu Ala Lys Ile Ala Gly Tyr Thr Asp Arg Ser
20 25 30

Gly Phe Tyr Arg Phe Leu Asn Asp Gly Arg Lys Glu Thr Thr Asp Ile
35 40 45

Gln Ser Ile Ile Asn Ile Val Lys Glu Ile Asp Pro Ala Asn Glu Arg
50 55 60

Val Val Met Gly Glu Tyr Ile Met Thr Leu Asp Pro Asn Lys Ser Ala
65 70 75 80

Ala Arg Gln Ala Leu Glu Tyr Leu Asp Val Asn Lys Tyr Tyr Ile Glu
85 90 95

Arg Asn Ala Leu Leu Asp Lys Met Lys Tyr Ala His Asn Gly Lys Ser
100 105 110

Gln Glu Trp Tyr Lys Ile Tyr Ser Ile His Ser Glu Val Gln Asp Gly
115 120 125

Asn Leu Thr Tyr Leu Glu Ala Met Asn Lys Val Gly Ser Val Asn Thr
130 135 140

Lys Thr Pro Glu Met Asn Val Phe Lys Asn Ile Leu Leu Leu Tyr Pro
145 150 155 160

Leu Cys Ser Lys Gly Glu Phe Gly Leu Met Ser Glu Ile Ala Asp Leu
165 170 175

Ile Asp Val Asp Ser Leu His Ile Thr Gly Tyr Val Asn Asp Ser Tyr
180 185 190

Arg Cys Arg Leu Leu Ile Met Ser Ala Ser Ala Ala Val Ser Gln Asn
195 200 205

Lys Leu Lys Arg Ala Arg Phe Asn Ala Gly Met Ala Leu Ser Glu Thr
210 215 220

Lys Ile Asp Arg Phe Ala Val Phe Ala Cys Leu His Leu Gly Asn Ser
225 230 235 240

Tyr Ile Tyr Thr Ser Tyr Glu Lys Ala Lys Glu Asn Phe Phe Lys Gly
245 250 255

Leu Gly Tyr Ala Asn Ala Asn Ser Glu Tyr Lys Arg Glu Ile Lys Arg
260 265 270

Ser Leu Ala Met Leu Glu Asn Val Trp Asn Lys Glu Glu Asn Glu Trp
275 280 285

Leu Asp Leu Asp Ser Arg Asp Thr Thr Asp Met Gln Glu Val Ala Phe
290 295 300

His His Ile Val Asn Lys Arg Asn Asp Gln Ala Arg Ser Ile Leu Asn
305 310 315 320

Gln Leu Asp Glu Arg Asp Ser Ser Asn His Glu Leu Ala Tyr Asn Thr
325 330 335

Phe Leu Arg Gly Phe Leu Met Asn Asp Phe Asn Cys Tyr Cys Gln Ser
340 345 350

Val Lys Leu Phe Lys Asp Thr Gly Asp Lys Tyr Thr Leu Gln Leu Pro
355 360 365

Leu Arg Asn Ile Glu Arg Leu Gly Ala Asp Lys Ser Leu Val Glu Leu
370 375 380

Ile Ala His
385

<210> SEQ ID NO 171
<211> LENGTH: 320
<212> TYPE: PRT
<213> ORGANISM: Bacillus amyloliquefaciens

<400> SEQUENCE: 171

Met Lys Leu Leu Lys Asp Glu Asn Arg Gln Ser Thr Leu Lys Lys Val
1 5 10 15

Arg Leu Leu Glu Gln Ala Asp Leu Asn Glu Asn Tyr Glu Glu Met Asp
20 25 30

Cys Ile Ile Glu Lys Phe Arg Tyr Ser Ile Asp Pro Ile Leu Asn Glu
35 40 45

Phe Gly Asn Val Tyr Gln Ile His Arg Gln Leu Gln Lys Gly Glu Ile
50 55 60

Asn Arg Ile Glu Ala Ser Arg Lys Phe Gly Lys Met Asp Leu Lys Thr
65 70 75 80

Pro Glu Cys Lys Val Phe Ser Arg Leu Met Ile Leu Pro Ile Cys Leu
85 90 95

Gln Thr Ala Glu Tyr Arg Leu Met Tyr Glu Val Gly Asn Glu Ile Asp
100 105 110

Leu Asp Ile Ile Glu Glu Glu Ser Tyr Ile Lys Ser Ser Tyr Arg Cys
115 120 125

Arg Leu Leu Ser Met Leu Ala Asn Ala Glu Leu Gly Ile Gly Asp Leu
130 135 140

Lys Lys Ala Gln Leu Tyr Ala Gly Leu Thr Ile Asn Cys Ala Ile Ser
145 150 155 160

Asp Asn Phe Phe Ala Ser Gly Tyr Leu Ile His Gly Asn Thr Leu Leu
165 170 175

Phe Ser Asp Tyr Glu Ala Ala Lys Gln Ser Phe Met His Gly Leu Asn
180 185 190

Phe Thr Glu Glu Gly Lys Phe His Tyr Lys Glu Leu Arg Arg Ser Leu
195 200 205

Ser Phe Leu Glu Asn Tyr Tyr Gly Val Glu Asn Glu Phe Leu Asp His
210 215 220

Asp Ser Glu Glu Val Gly Glu Gln Gln Gly Val Val Phe Ser Leu Ile
225 230 235 240

Lys Gln Gly Lys Lys Ser Glu Ala Leu Arg Ile Leu Glu Ser Leu Glu
245 250 255

Asn Arg Glu Gln Asn Lys Asn Ile Leu Ala Phe His Phe Phe Tyr Lys
260 265 270

Gly Leu Cys Thr Asp Ser Lys Glu Tyr Phe Phe Lys Ser Val Arg Tyr
275 280 285

Phe Lys Glu Ser Asp Asp Thr Phe Cys Ile Lys Leu Pro Leu Asp Glu
290 295 300

Leu Glu Arg Leu Gly Glu Asn Lys Ala Leu Leu Glu Leu Ile Thr Val
305 310 315 320

<210> SEQ ID NO 172
<211> LENGTH: 320
<212> TYPE: PRT
<213> ORGANISM: Bacillus amyloliquefaciens

<400> SEQUENCE: 172

Met Lys Leu Leu Lys Asp Glu Asn Arg Gln Ser Thr Leu Lys Lys Val
1 5 10 15

Arg Leu Leu Glu Gln Ala Asp Leu Asn Glu Asn Tyr Glu Glu Met Asp
20 25 30

Cys Ile Ile Glu Lys Phe Arg Tyr Ser Ile Asp Pro Ile Leu Asn Glu
35 40 45

-continued

```
Phe Gly Asn Val Tyr Gln Ile His Arg Gln Leu Gln Lys Gly Glu Ile
    50                  55                  60

Asn Arg Ile Glu Ala Ser Arg Lys Phe Gly Lys Met Asp Leu Lys Thr
65                  70                  75                  80

Pro Glu Cys Lys Val Phe Ser Arg Leu Met Ile Leu Pro Ile Cys Leu
                85                  90                  95

Gln Thr Ala Glu Tyr Arg Leu Met Tyr Glu Val Gly Asn Glu Ile Asp
            100                 105                 110

Leu Asp Ile Ile Glu Glu Glu Ser Tyr Ile Lys Ser Ser Tyr Arg Cys
        115                 120                 125

Arg Leu Leu Ser Met Leu Ala Asn Ala Glu Leu Gly Ile Gly Asp Leu
    130                 135                 140

Lys Lys Ala Gln Leu Tyr Ala Gly Leu Thr Ile Asn Cys Ala Ile Ser
145                 150                 155                 160

Asp Asn Phe Phe Ala Ser Gly Tyr Leu Ile His Gly Asn Thr Leu Leu
                165                 170                 175

Phe Ser Asp Tyr Glu Ala Ala Lys Gln Ser Phe Met His Gly Leu Asn
            180                 185                 190

Phe Thr Glu Glu Gly Lys Phe His Tyr Lys Glu Leu Arg Arg Ser Leu
        195                 200                 205

Ser Phe Leu Glu Asn Tyr Tyr Gly Val Glu Asn Glu Phe Leu Asp His
    210                 215                 220

Asp Ser Glu Glu Val Gly Glu Gln Gln Gly Val Val Phe Ser Leu Ile
225                 230                 235                 240

Lys Gln Gly Lys Lys Ser Glu Ala Leu Arg Ile Leu Glu Ser Leu Glu
                245                 250                 255

Asn Arg Glu Gln Asn Lys Asn Ile Leu Ala Phe His Phe Phe Tyr Lys
            260                 265                 270

Gly Leu Cys Thr Asp Ser Lys Glu Tyr Phe Phe Lys Ser Val Arg Tyr
        275                 280                 285

Phe Lys Glu Ser Asp Asp Thr Phe Cys Ile Lys Leu Pro Leu Asp Glu
    290                 295                 300

Leu Glu Arg Leu Gly Glu Asn Lys Ala Leu Leu Glu Leu Ile Thr Val
305                 310                 315                 320


<210> SEQ ID NO 173
<211> LENGTH: 390
<212> TYPE: PRT
<213> ORGANISM: Bacillus subtilis

<400> SEQUENCE: 173

Met Gly Val Asn Val Gln Leu Arg Lys Lys Leu Lys Asn Gly Ile Glu
1               5                   10                  15

Asn Lys Arg Leu Thr Val Gln Gln Leu Asn Glu Tyr Leu Glu Leu Lys
            20                  25                  30

Asn Cys Asn Pro Ile Tyr Asp Phe Leu Asn Asp Lys Lys Asp Thr Phe
        35                  40                  45

His Asp Phe Gly Ala Leu Ile Arg Leu Val Lys Gly Ile Phe Pro Glu
    50                  55                  60

Glu Glu Tyr Glu Leu Met Ser Asp Tyr Ile Leu His Leu Asp Pro Asn
65                  70                  75                  80

Lys His Ser Gln Val Leu Arg Cys Gly Met Glu Tyr Ala Asp Val Asn
                85                  90                  95

Gln Leu Asp Glu Leu Ala Asp Glu Val Ala Tyr Arg Leu Leu Asn Ser
            100                 105                 110
```

Ser Asn Asn His Ser Lys Glu Trp Gly Ser Ile Tyr Thr Leu His Arg
115 120 125

Lys Leu Ser Lys Gly Glu Met Glu Ile His Asp Ala Ile Arg Gln Thr
130 135 140

Gly Arg Ile Arg Ile His Thr Pro Glu Met Leu Val Phe Ser Asn Ala
145 150 155 160

Met Leu Met Tyr Ala Tyr Leu Asn Ile Gly Asp Phe His Leu Leu Lys
165 170 175

Ser Thr Phe Asp Leu Leu Asp Ile Asp Glu Leu Pro Glu Gly Tyr Val
180 185 190

Lys Glu Ser Tyr Tyr Gly Arg Thr Ala Leu Leu His Ala Asn Val Ser
195 200 205

Leu Asn Glu Asn Asn Leu Leu Ser Ala Arg His Tyr Ser Ser Tyr Val
210 215 220

Leu Glu Lys Ala Asn Asn Asn Arg Phe Met Val Phe Gly His Leu Thr
225 230 235 240

Ser Gly Asn Thr Tyr Val Phe Glu Asp Tyr Asp Lys Ala Lys Asp His
245 250 255

Tyr Leu Lys Gly Leu Gln Tyr Ala Asn Thr Asn Pro Phe His Tyr Tyr
260 265 270

Lys Leu Arg Leu Ala Leu Cys Phe Leu Asn Asn Val Trp Lys Lys Glu
275 280 285

Asn Glu Trp Val Asp Phe Glu Ser Asn Glu Ile Thr Asp Arg Ile Glu
290 295 300

Val Ala Tyr Tyr Tyr Val Asn Gln Asn Glu Glu Gln Lys Ala Ile Lys
305 310 315 320

Val Phe Gln Glu Leu Asp Ser Arg Lys Ile Pro Lys Asp Asp Leu Gly
325 330 335

Phe Leu Phe Tyr Val Lys Gly Leu Leu Tyr Gln Glu Lys Ser Tyr Phe
340 345 350

Tyr Glu Ser Ile Glu Tyr Phe Lys Lys Ser Gly Asp Lys Met Phe Val
355 360 365

Asn Leu Pro Leu Met Glu Leu Lys Lys Gln Gly Glu Asn Glu Arg Leu
370 375 380

Leu Gln Leu Leu Thr Ile
385 390

<210> SEQ ID NO 174
<211> LENGTH: 386
<212> TYPE: PRT
<213> ORGANISM: Bacillus subtilis

<400> SEQUENCE: 174

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Ser Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile

```
                85                  90                  95

Glu Asp Val Leu Ile Asp Ser Met Ile Ser Cys Ser Asn Leu Lys Ser
            100                 105                 110

Lys Glu Tyr Gly Lys Val Tyr Lys Ile His Arg Glu Leu Ser Asn Cys
        115                 120                 125

Asp Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Glu Ser Ile Met Asp Leu Gln Glu Gln Ala His Cys
    290                 295                 300

Phe Ile Asn Phe Asn Glu Asn Ser Lys Ala Lys Lys Val Leu Asp Lys
305                 310                 315                 320

Leu Asp Leu Leu Arg His Asn Asp Asn Glu Leu Ala Met His His Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 175
<211> LENGTH: 379
<212> TYPE: PRT
<213> ORGANISM: Bacillus methylotrophicus

<400> SEQUENCE: 175

Met Asn Leu Lys Gln Met Ile Lys Asn Glu Cys Glu Lys Asp Asn Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60
```

Leu Leu Ser Asp Tyr Phe Leu Ser Leu Asp Pro Asn Lys Lys Cys Ala
65 70 75 80

Arg Gln Ser Val Glu Tyr Ser Asp Ile Asn Gln Trp Asp Thr Leu Thr
85 90 95

Asp Lys Ile Ile Leu Asn Leu Ser Asn Ser Lys Asn Thr Thr Ser Gln
100 105 110

Glu Trp Gly Asn Ile Tyr Ser Ile His Arg Lys Leu Tyr Lys Asn Glu
115 120 125

Ile Ser Ile Pro Glu Ala Ile Arg Glu Cys Gly Arg Cys Lys Ala Pro
130 135 140

Glu Met Ser Phe Phe Ser Asp Ala Met Leu Met Tyr Lys Tyr Leu Asn
145 150 155 160

Ile Gly Glu Phe Gly Leu Met Lys Ser Thr Leu Thr Leu Leu Asp Phe
165 170 175

Lys Ser Leu Pro Glu Gly Phe Ile Lys Asp Ser Tyr Lys Ser Arg Val
180 185 190

Ser Met Leu Gln Ala Asn Ile Ser Leu Asn Glu Asn Asn Leu Ile Glu
195 200 205

Ala Arg Lys His Ser Asn Ile Ala Ile Met Gln Ser Asn Val Asn Arg
210 215 220

Ile Cys Phe Phe Ala His Leu Thr Ile Gly Asn Thr Leu Ile Phe Glu
225 230 235 240

Asn Tyr Glu Glu Ala Met Leu Ala Tyr Asn Glu Ala Lys Lys Tyr Val
245 250 255

Leu Asn Asp Thr His Lys Glu Met Leu Asn Gly Ala Leu Cys Phe Leu
260 265 270

Ala Asn Val Trp Asp Lys Gly Asn Pro Trp Val Asn Tyr Glu Ser Asp
275 280 285

Asp Ile Lys Tyr Gln Gln Leu Arg Ala Phe Tyr Tyr Ile Lys Asn Asn
290 295 300

Asn Leu Asp Lys Ala Asn Glu Leu Leu Glu Ser Leu Ser Thr Arg Asp
305 310 315 320

Gln Asp Glu Asn Glu Leu Gly Phe Tyr Phe Tyr Tyr Lys Gly Leu Ile
325 330 335

Ser Lys Gln Lys Ser Asp Phe Tyr Lys Ser Ile Thr Tyr Phe Lys Lys
340 345 350

Ser Asp Asp Lys Tyr Phe Ile Gln Leu Thr Ile Met Glu Leu Glu Lys
355 360 365

Leu Gly Cys Asp Pro Glu Leu Leu Asn Leu Ile
370 375

<210> SEQ ID NO 176
<211> LENGTH: 379
<212> TYPE: PRT
<213> ORGANISM: Bacillus methylotrophicus

<400> SEQUENCE: 176

Met Asn Leu Lys Gln Met Ile Lys Asn Glu Cys Glu Lys Asp Asn Gln
1 5 10 15

Leu Ala Ala Lys Leu Ser Lys Ile Ala Gly Tyr Glu Lys Val Asn Gly
20 25 30

Phe Tyr Lys Phe Ile Asn Thr Pro Glu Lys Glu Met Asp Asn Leu Gly
35 40 45

Gly Leu Ile Asn Ile Val Lys Ser Leu Phe Pro Asp Asn Glu Glu Gln
50 55 60

```
Leu Leu Ser Asp Tyr Phe Leu Ser Leu Asp Pro Asn Lys Lys Cys Ala
65                  70                  75                  80

Arg Gln Ser Val Glu Tyr Ser Asp Ile Asn Gln Trp Asp Thr Leu Thr
                85                  90                  95

Asp Lys Ile Ile Leu Asn Leu Ser Asn Ser Lys Asn Thr Thr Ser Gln
            100                 105                 110

Glu Trp Gly Asn Ile Tyr Ser Ile His Arg Lys Leu Tyr Lys Asn Glu
        115                 120                 125

Ile Ser Ile Pro Glu Ala Ile Arg Glu Cys Gly Arg Cys Lys Ala Pro
    130                 135                 140

Glu Met Ser Phe Phe Ser Asp Ala Met Leu Met Tyr Lys Tyr Leu Asn
145                 150                 155                 160

Ile Gly Glu Phe Gly Leu Met Lys Ser Thr Leu Thr Leu Leu Asp Phe
                165                 170                 175

Lys Ser Leu Pro Glu Gly Phe Ile Lys Asp Ser Tyr Lys Ser Arg Val
            180                 185                 190

Ser Met Leu Gln Ala Asn Ile Ser Leu Asn Glu Asn Asn Leu Ile Glu
        195                 200                 205

Ala Arg Lys His Ser Asn Ile Ala Ile Met Gln Ser Asn Val Asn Arg
    210                 215                 220

Ile Cys Phe Phe Ala His Leu Thr Ile Gly Asn Thr Leu Ile Phe Glu
225                 230                 235                 240

Asn Tyr Glu Glu Ala Met Leu Ala Tyr Asn Glu Ala Lys Lys Tyr Val
                245                 250                 255

Leu Asn Asp Thr His Lys Glu Met Leu Asn Gly Ala Leu Cys Phe Leu
            260                 265                 270

Ala Asn Val Trp Asp Lys Gly Asn Pro Trp Val Asn Tyr Glu Ser Asp
        275                 280                 285

Asp Ile Lys Tyr Gln Gln Leu Arg Ala Phe Tyr Tyr Ile Lys Asn Asn
    290                 295                 300

Asn Leu Asp Lys Ala Asn Glu Leu Leu Glu Ser Leu Ser Thr Arg Asp
305                 310                 315                 320

Gln Asp Glu Asn Glu Leu Gly Phe Tyr Phe Tyr Tyr Lys Gly Leu Ile
                325                 330                 335

Ser Lys Gln Lys Ser Asp Phe Tyr Lys Ser Ile Thr Tyr Phe Lys Lys
            340                 345                 350

Ser Asp Asp Lys Tyr Phe Ile Gln Leu Thr Ile Met Glu Leu Glu Lys
        355                 360                 365

Leu Gly Cys Asp Pro Glu Leu Leu Asn Leu Ile
    370                 375
```

<210> SEQ ID NO 177
<211> LENGTH: 320
<212> TYPE: PRT
<213> ORGANISM: Bacillus amyloliquefaciens

<400> SEQUENCE: 177

```
Met Ile Ala Lys Glu Arg Glu Ala Lys Lys Pro Glu Val Asp Ala Lys
1               5                   10                  15

Val Arg Leu Glu Met Ser Asp Ile Asn Glu Gln Tyr Glu Gln Thr Asp
            20                  25                  30

Ala Leu Ile Asp Gln Leu Ile Asn Ser Ser Cys Ser Ile Glu Arg Glu
        35                  40                  45

Trp Ala Ala Met Tyr Gln Ile Lys Arg Lys Gln Asp Arg Gly Glu Ile
```

-continued 50 55 60

Asn Ala His Gln Ala Leu Lys Ala Ile Gly Lys Leu Asp Pro Lys Ser
65 70 75 80

Gln Glu Met Arg Val Phe Thr Tyr Ile Ile Pro Leu Tyr Tyr Tyr Leu
85 90 95

Arg Met Ala Glu Tyr Ser Asn Leu Ala Glu Met Ser Thr Ile Val Asp
100 105 110

Leu Asp Phe Ile Glu Asn Asn Glu Gln Ile Lys Ser Ser Phe Tyr Asn
115 120 125

Arg Leu Met Ala Leu Leu Gly Ala Ser Ala Phe Ser Gln Asn Lys Met
130 135 140

Thr Gln Ala Arg Phe Tyr Cys Ser Tyr Gly Ile Asn Val Thr Asn Ile
145 150 155 160

Asp Arg Leu Val Ala Tyr Ser Tyr Leu Thr Met Gly Asn Thr Tyr Leu
165 170 175

Leu Asp Asp Tyr Glu Lys Ala Lys Glu Tyr Tyr Leu Ala Gly Leu Lys
180 185 190

His Thr Glu Asn Asn Pro Leu Ala Lys Leu Gln Leu Thr Arg Ser Leu
195 200 205

Cys Phe Leu Glu Asn His Trp Asp Gln Glu Asn Phe Trp Leu Asn Pro
210 215 220

Asp Ser Asn Glu Val Thr Asp Ile Gln Glu Ile Ala His Tyr His Ile
225 230 235 240

Lys Lys Asn Asn Leu Gln Gln Ala Lys Glu Ile Leu Glu Asn Leu Glu
245 250 255

Gln Gln Pro Asn Ile His Asn Asp Phe Gly Ile His Phe Tyr Leu Lys
260 265 270

Gly Ile Ala Tyr Glu Asp Lys Arg Phe Phe Tyr Glu Ser Ile Lys His
275 280 285

Phe Lys Leu Ser Gly Asp Leu Tyr Ser Val Arg Leu Pro Leu Asp Lys
290 295 300

Leu Arg Glu Met Gly Glu Asp Glu Gln Ile Leu Asp Leu Leu Ala Leu
305 310 315 320

<210> SEQ ID NO 178
<211> LENGTH: 379
<212> TYPE: PRT
<213> ORGANISM: Bacillus amyloliquefaciens

<400> SEQUENCE: 178

Met Asn Leu Lys Gln Met Ile Lys Asn Glu Cys Glu Lys Asp Asn Gln
1 5 10 15

Leu Ala Ala Lys Leu Ser Lys Ile Ala Gly Tyr Glu Lys Val Asn Gly
20 25 30

Phe Tyr Lys Phe Ile Asn Thr Pro Glu Lys Glu Met Asp Asn Leu Gly
35 40 45

Gly Leu Ile Asn Ile Val Lys Ser Leu Phe Pro Asp Asn Glu Glu Gln
50 55 60

Leu Leu Ser Asp Tyr Phe Leu Ser Leu Asp Pro Asn Lys Lys Cys Ala
65 70 75 80

Arg Gln Ser Val Glu Tyr Ser Asp Ile Asn Gln Trp Asp Ser Leu Thr
85 90 95

Asp Lys Ile Ile Leu Asn Leu Cys His Ser Lys Asn Thr Thr Ser Gln
100 105 110

```
Glu Trp Gly Asn Ile Tyr Asn Ile His Arg Lys Leu Tyr Lys Asn Glu
        115                 120                 125

Ile Ser Ile Pro Glu Ala Ile Arg Glu Cys Gly Arg Cys Lys Ala Pro
    130                 135                 140

Glu Met Ser Phe Phe Ser Asp Ala Met Leu Met Tyr Lys Tyr Leu Asn
145                 150                 155                 160

Ile Gly Glu Phe Gly Leu Met Lys Ser Thr Leu Thr Leu Leu Asp Phe
                165                 170                 175

Lys Ser Leu Pro Glu Gly Phe Ile Lys Asp Ser Tyr Lys Ser Arg Val
            180                 185                 190

Ser Met Leu Lys Ala Asn Ile Ser Leu Asn Glu Asn Asn Leu Ile Glu
        195                 200                 205

Ala Arg Lys His Ser Asn Ile Ala Ile Met Gln Ser Asn Val Asn Arg
    210                 215                 220

Ile Cys Phe Phe Ala His Leu Thr Ile Gly Asn Thr Leu Ile Phe Glu
225                 230                 235                 240

Asn Tyr Glu Glu Ala Met Leu Ala Tyr Val Glu Ala Lys Lys Tyr Val
                245                 250                 255

Leu Asn Asp Thr His Glu Glu Met Leu Asn Gly Ala Leu Cys Phe Leu
            260                 265                 270

Ala Asn Val Trp Asn Lys Glu Asn Leu Trp Val Asn Tyr Glu Ser Asn
        275                 280                 285

Glu Ile Lys Tyr Gln Gln Leu Arg Ala Phe Tyr Tyr Ile Lys Ser Asn
    290                 295                 300

Asn Leu Asp Lys Ala Asn Glu Leu Leu Glu Ser Leu Ser Lys Arg Asp
305                 310                 315                 320

Gln Asp Glu Asn Glu Leu Gly Phe Tyr Phe Tyr Tyr Lys Gly Leu Ile
                325                 330                 335

Ser Arg Gln Lys Ser Asp Phe Phe Lys Ser Ile Thr Tyr Phe Lys Glu
            340                 345                 350

Ser Asp Asp Lys Tyr Phe Ile Gln Leu Ala Ile Ile Glu Leu Glu Lys
        355                 360                 365

Leu Gly Cys Asp Pro Glu Leu Leu Asn Leu Ile
    370                 375
```

<210> SEQ ID NO 179
<211> LENGTH: 379
<212> TYPE: PRT
<213> ORGANISM: Bacillus amyloliquefaciens

<400> SEQUENCE: 179

```
Met Asn Leu Lys Gln Met Ile Lys Asn Glu Cys Glu Lys Asp Ser Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Cys Ala
65                  70                  75                  80

Arg Gln Ser Val Glu Tyr Ser Asp Ile Asn Gln Trp Asp Ser Leu Thr
                85                  90                  95

Asp Lys Ile Ile Leu Asn Leu Cys His Ser Lys Asn Thr Thr Ser Gln
            100                 105                 110
```

Glu Trp Gly Asn Ile Tyr Asn Ile His Arg Lys Leu Tyr Lys Asn Glu
115 120 125

Ile Ser Ile Pro Glu Ala Ile Arg Glu Cys Gly Arg Cys Lys Ala Pro
130 135 140

Glu Met Ser Phe Phe Ser Asp Ala Met Leu Met Tyr Lys Tyr Leu Asn
145 150 155 160

Ile Gly Glu Phe Gly Leu Met Lys Ser Thr Leu Thr Leu Leu Asp Phe
165 170 175

Lys Ser Leu Pro Glu Gly Phe Ile Lys Asp Ser Tyr Lys Ser Arg Val
180 185 190

Ser Met Leu Lys Ala Asn Ile Ser Leu Asn Glu Asn Asn Leu Ile Glu
195 200 205

Ala Arg Lys His Ser Asn Ile Ala Ile Met Gln Ser Asn Val Asn Arg
210 215 220

Ile Cys Phe Phe Ala His Leu Thr Ile Gly Asn Thr Leu Ile Phe Glu
225 230 235 240

Asn Tyr Glu Glu Ala Met Leu Ala Tyr Val Glu Ala Lys Lys Tyr Val
245 250 255

Leu Asn Asp Thr His Glu Glu Met Leu Asn Gly Ala Leu Cys Phe Leu
260 265 270

Ala Asn Val Trp Ile Lys Glu Asn Leu Trp Val Asn Tyr Glu Ser Asn
275 280 285

Glu Ile Lys Tyr Gln Gln Leu Arg Ala Phe Tyr Tyr Ile Lys Ser Asn
290 295 300

Asn Leu Asp Lys Ala Asn Glu Leu Leu Glu Asn Leu Ser Lys Arg Asp
305 310 315 320

Gln Asp Glu Asn Glu Leu Gly Phe Tyr Phe Tyr Tyr Lys Gly Leu Ile
325 330 335

Ser Arg Gln Lys Ser Asp Phe Phe Lys Ser Ile Thr Tyr Phe Lys Glu
340 345 350

Ser Asp Asp Lys Tyr Phe Ile Gln Leu Ala Ile Ile Glu Leu Glu Lys
355 360 365

Leu Gly Cys Asp Pro Glu Leu Leu Asn Leu Ile
370 375

<210> SEQ ID NO 180
<211> LENGTH: 379
<212> TYPE: PRT
<213> ORGANISM: Bacillus amyloliquefaciens

<400> SEQUENCE: 180

Met Asn Leu Lys Gln Met Ile Lys Asn Glu Cys Glu Lys Asp Asn Gln
1 5 10 15

Leu Ala Ala Lys Leu Ser Lys Ile Ala Gly Tyr Glu Lys Val Asn Gly
20 25 30

Phe Tyr Lys Phe Ile Asn Thr Pro Glu Lys Glu Met Asp Asn Leu Gly
35 40 45

Gly Leu Ile Asn Ile Val Lys Ser Leu Phe Pro Asp Asn Glu Glu Gln
50 55 60

Leu Leu Ser Asp Tyr Phe Leu Ser Leu Asp Pro Asn Lys Lys Cys Ala
65 70 75 80

Arg Gln Ser Val Glu Tyr Ser Asp Ile Asn Gln Trp Asp Ser Leu Thr
85 90 95

Asp Lys Ile Ile Leu Asn Leu Cys His Ser Lys Asn Thr Thr Ser Gln

```
            100                 105                 110

Glu Trp Gly Asn Ile Tyr Asn Ile His Arg Lys Leu Tyr Lys Asn Glu
        115                 120                 125

Ile Ser Ile Pro Glu Ala Ile Arg Glu Cys Gly Arg Cys Lys Ala Pro
    130                 135                 140

Glu Met Ser Phe Phe Ser Asp Ala Met Leu Met Tyr Lys Tyr Leu Asn
145                 150                 155                 160

Ile Gly Glu Phe Gly Leu Met Lys Ser Thr Leu Thr Leu Leu Asp Phe
                165                 170                 175

Lys Ser Leu Pro Glu Gly Phe Ile Lys Asp Ser Tyr Lys Ser Arg Val
            180                 185                 190

Ser Met Leu Lys Ala Asn Ile Ser Leu Asn Glu Asn Asn Leu Ile Glu
        195                 200                 205

Ala Arg Lys His Ser Asn Ile Ala Ile Met Gln Ser Asn Val Asn Arg
    210                 215                 220

Ile Cys Phe Phe Ala His Leu Thr Ile Gly Asn Thr Leu Ile Phe Glu
225                 230                 235                 240

Asn Tyr Glu Glu Ala Met Leu Ala Tyr Val Glu Ala Lys Lys Tyr Val
                245                 250                 255

Leu Asn Asp Thr His Glu Glu Met Leu Asn Gly Ala Leu Cys Phe Leu
            260                 265                 270

Ala Asn Val Trp Asn Lys Glu Asn Leu Trp Val Asn Tyr Glu Ser Asn
        275                 280                 285

Glu Ile Lys Tyr Gln Gln Leu Arg Ala Phe Tyr Tyr Ile Lys Ser Asn
    290                 295                 300

Asn Leu Asp Lys Ala Asn Glu Leu Leu Glu Ser Leu Ser Lys Arg Asp
305                 310                 315                 320

Gln Asp Glu Asn Glu Leu Gly Phe Tyr Phe Tyr Tyr Lys Gly Leu Ile
                325                 330                 335

Ser Arg Gln Lys Ser Asp Phe Phe Lys Ser Ile Thr Tyr Phe Lys Glu
            340                 345                 350

Ser Asp Asp Lys Tyr Phe Ile Gln Leu Ala Ile Ile Glu Leu Glu Lys
        355                 360                 365

Leu Gly Cys Asp Pro Glu Leu Leu Asn Leu Ile
    370                 375


<210> SEQ ID NO 181
<211> LENGTH: 321
<212> TYPE: PRT
<213> ORGANISM: Bacillus amyloliquefaciens

<400> SEQUENCE: 181

Met Asn Leu Leu Asp Arg Gly Leu Glu Lys Glu Ser Leu Asn Glu Asp
1               5                   10                  15

Ile Arg Phe Leu Glu Leu Ala Asp Leu Asn Glu Asn Phe Asp Glu Met
            20                  25                  30

Glu Leu Leu Ile Glu Lys Leu Arg Phe Ser Lys Asn Thr Glu Ala Lys
        35                  40                  45

Gln Tyr Ser Glu Val Tyr Ser Ile His Arg Lys Leu Ala Lys Gly Glu
    50                  55                  60

Leu Thr Val Asn Glu Ala Ser Lys Met Ile Gly Arg Met Asp Ile Asn
65                  70                  75                  80

Ile Pro Glu Leu Lys Val Phe Ser Glu Leu Met Leu Leu Pro Glu Tyr
                85                  90                  95
```

Leu Asn Leu Ser Glu Tyr Lys Val Met Asn Gly Ile Ala Asn Lys Ile
                100                 105                 110

Asp Leu Asp Thr Ile Glu Asn Glu Asn Phe Phe Lys Ser Ser Tyr Arg
            115                 120                 125

Cys Arg Leu Leu Ile Met Ser Ala Asn Ala Tyr Leu Gly Leu Gly Asp
        130                 135                 140

Leu Lys Lys Ala Gln Phe Tyr Ala Gly Leu Thr Ile Glu His Ala Thr
145                 150                 155                 160

Asp Ser Arg Phe Leu Ala Tyr Gly Tyr Leu Ile His Gly Asn Thr Leu
                165                 170                 175

Leu Phe Ser Asp Tyr Lys Glu Ala Lys Lys Ser Phe Leu Lys Gly Leu
            180                 185                 190

Glu His Ser Glu Lys Gly Lys Ser His Tyr Lys Glu Leu Arg Arg Ser
        195                 200                 205

Leu Ser Phe Leu Glu Asn Tyr Tyr Gly Glu Lys Asn Glu Tyr Leu Asp
210                 215                 220

Tyr Asn Ser Leu Glu Val Gly Glu Gln Gln Gly Val Ala Tyr Ser Phe
225                 230                 235                 240

Ile Asn Glu Gly Lys Ile Val Glu Ala Leu Gln Ile Leu Asp Arg Ile
                245                 250                 255

Glu Asn Glu Lys Gln Asn Asn Asn Leu Leu Gly Phe His Phe Phe Tyr
            260                 265                 270

Lys Gly Leu Ala Thr Lys Ser Lys Asp Tyr Phe Phe Lys Ser Val Lys
        275                 280                 285

His Phe Lys Leu Ser Asp Asp Lys Tyr Cys Val Lys Leu Pro Leu Asp
290                 295                 300

Glu Leu Glu Lys Leu Gly Glu Asn Lys Ala Leu Leu Glu Leu Ile Thr
305                 310                 315                 320

Leu

<210> SEQ ID NO 182
<211> LENGTH: 379
<212> TYPE: PRT
<213> ORGANISM: Bacillus amyloliquefaciens

<400> SEQUENCE: 182

Met Asn Leu Lys Gln Met Ile Lys Asn Glu Cys Glu Lys Asp Ser Gln
1                   5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Cys Ala
65                  70                  75                  80

Arg Gln Ser Val Glu Tyr Ser Asp Ile Asn Gln Trp Asp Ser Leu Thr
                85                  90                  95

Asp Lys Ile Ile Leu Asn Leu Cys His Ser Lys Asn Thr Thr Ser Gln
            100                 105                 110

Glu Trp Gly Asn Ile Tyr Asn Ile His Arg Lys Leu Tyr Lys Asn Glu
        115                 120                 125

Ile Ser Ile Pro Glu Ala Ile Arg Glu Cys Gly Arg Cys Lys Ala Pro
    130                 135                 140

-continued

Glu Met Ser Phe Phe Ser Asp Ala Met Leu Met Tyr Lys Tyr Leu Asn
145 150 155 160

Ile Gly Glu Phe Gly Leu Met Lys Ser Thr Leu Thr Leu Leu Asp Phe
165 170 175

Lys Ser Leu Pro Glu Gly Phe Ile Lys Asp Ser Tyr Lys Ser Arg Val
180 185 190

Ser Met Leu Lys Ala Asn Ile Ser Leu Asn Glu Asn Asn Leu Ile Glu
195 200 205

Ala Arg Lys His Ser Asn Ile Ala Ile Met Gln Ser Asn Val Asn Arg
210 215 220

Ile Cys Phe Phe Ala His Leu Thr Ile Gly Asn Thr Leu Ile Phe Glu
225 230 235 240

Asn Tyr Glu Glu Ala Met Leu Ala Tyr Val Glu Ala Lys Lys Tyr Val
245 250 255

Leu Asn Asp Thr His Glu Glu Met Leu Asn Gly Ala Leu Cys Phe Leu
260 265 270

Ala Asn Val Trp Ile Lys Glu Asn Leu Trp Val Asn Tyr Glu Ser Asn
275 280 285

Glu Ile Lys Tyr Gln Gln Leu Arg Ala Phe Tyr Tyr Ile Lys Ser Asn
290 295 300

Asn Leu Asp Lys Ala Asn Glu Leu Leu Glu Asn Leu Ser Lys Arg Asp
305 310 315 320

Gln Asp Glu Asn Glu Leu Gly Phe Tyr Phe Tyr Tyr Lys Gly Leu Ile
325 330 335

Ser Arg Gln Lys Ser Asp Phe Phe Lys Ser Ile Thr Tyr Phe Lys Glu
340 345 350

Ser Asp Asp Lys Tyr Phe Ile Gln Leu Ala Ile Ile Glu Leu Glu Lys
355 360 365

Leu Gly Cys Asp Pro Glu Leu Leu Asn Leu Ile
370 375

<210> SEQ ID NO 183
<211> LENGTH: 388
<212> TYPE: PRT
<213> ORGANISM: Bacillus licheniformis

<400> SEQUENCE: 183

Met Lys Glu Leu Glu Leu Lys Asn Phe Leu Lys Asn Lys Cys Glu Glu
1 5 10 15

Glu Arg Gly Leu Glu Lys Glu Leu Ala Arg Ile Ala Gly Tyr Ser Asn
20 25 30

Ser Ser Gly Phe His His Phe Ile Tyr Asn Glu Lys Lys Glu Met Asp
35 40 45

Asn Ile Gln Gly Ile Ile Glu Val Ile Gln Lys Ile Ser Pro Glu Tyr
50 55 60

Glu Phe Asp Leu Met Ser Glu Tyr Ile Leu Thr Leu Asp Ile Asn Lys
65 70 75 80

Ser Ala Ala Arg Gln Gly Leu Glu Tyr Leu Ser Val Asn Gln Leu Tyr
85 90 95

Asp Thr Leu Asp Lys His Ile Lys Lys Met Val Ser Ala Lys Asn Ser
100 105 110

Val Ser Lys Glu Trp Gly Lys Val Tyr Ala Ala Gln Arg Glu Leu Asp
115 120 125

Lys Gly Asn Ile Gly Ile Glu Glu Cys Ile Arg Leu Leu Ala Glu Val
130 135 140

His Pro Lys Ser Ser Glu Met Lys Val Tyr Ser Arg Ile Ile Pro Met
145 150 155 160

Tyr Ala Ile Leu Pro Leu Lys Gln Phe Gly Arg Leu Lys Asp Met Ser
165 170 175

Asp Ile Val Leu Ile Asp Thr Ile Ser Ser Gln Asn Tyr Val Tyr His
180 185 190

Ser Phe Lys Ser Arg Tyr Met Leu Leu Leu Ala Asn Cys Phe Phe Gly
195 200 205

Asn Asn Glu Ile Glu Lys Ala Gln Glu Tyr Ala Arg His Gly Ile Glu
210 215 220

Asn Ser Asn Val Lys Arg Ile Ile Phe Phe Ser Tyr Leu Thr Tyr Gly
225 230 235 240

Ser Ser Leu Met Leu Asp Asp Tyr Glu Lys Ser Lys Ser Ser Phe Leu
245 250 255

Lys Gly Leu Glu Val Gly Lys Gly Asn Lys Ile Tyr Glu Gln His Ala
260 265 270

Ile Arg Asn Leu Cys Phe Leu Glu Asn Leu Trp Gly Lys Glu Asn Gln
275 280 285

Tyr Leu Asn Ile Gln Ser Asn Glu Ile Met Asp Arg Gln Glu Val Val
290 295 300

His Tyr Leu Ile Arg Lys Gly Ser Lys Gln Gln Ala Lys Lys Met Leu
305 310 315 320

Asp Gln Leu Asp Leu Val Glu Gln Asp Asp Asn Asp Leu Gly Leu His
325 330 335

Tyr Tyr Leu Lys Gly Leu Leu Glu Asn Ser Arg Asp Tyr Phe Leu Glu
340 345 350

Ser Val Lys Tyr Phe Lys Leu Ser Gly Asp Lys Phe Ser Cys Thr Leu
355 360 365

Pro Ile Ile Glu Leu Glu Lys Leu Gly Val Asp Lys Gln Ile Leu Glu
370 375 380

Met Ile Ser Ile
385

<210> SEQ ID NO 184
<211> LENGTH: 385
<212> TYPE: PRT
<213> ORGANISM: Bacillus sp.

<400> SEQUENCE: 184

Met Asn Leu Lys Thr Tyr Ile Lys Asn Lys Cys Glu Asp Asp Ser Ser
1 5 10 15

Leu Ala Met Lys Leu Ala Lys Ile Ala Gly Tyr Ser Asp Arg Thr Gly
20 25 30

Leu Tyr Lys Phe Leu Asn Ser Ser Asn Lys Glu Met Asp Asp Leu Ser
35 40 45

Asn Leu Ile Asn Leu Val Arg Glu Val Asp Gln Glu Arg Glu Ile Glu
50 55 60

Ile Ile Ser Thr Tyr Ile Thr Thr Leu Asp Pro Asn Lys Ser Ala Ala
65 70 75 80

Arg Gln Ala Val Glu Tyr Leu Asp Ala Asn Gln Leu Gly Glu Glu Thr
85 90 95

Asp Glu Leu Val Asp Lys Leu Cys Asn Ala Ser Asn Ala Leu Ser Lys
100 105 110

Glu Trp Gly Asn Val Tyr Arg Ile His Arg Met Leu Thr Lys Gly Glu

```
        115                 120                 125

Ile Asp Leu Thr Ser Ala Ile Lys Glu Thr Gly Thr Ile Lys Ile Lys
    130                 135                 140

Ser Glu Glu Met Phe Val Phe Ala Arg Met Met Thr Leu Tyr Glu Tyr
145                 150                 155                 160

Leu Asn Ser Gly Glu Phe Gly Leu Met Lys Ser Thr Ser Ala Tyr Ile
                165                 170                 175

Asp Leu Ser Asn Leu Lys Lys Gly Tyr Val Lys Asp Ser Phe Ser Ser
            180                 185                 190

Arg Tyr Leu Leu Leu Met Ala Asn Val Phe Leu Asn Asp Asn Asn Leu
        195                 200                 205

Lys Pro Leu Arg Asp Tyr Cys Asp Gln Ile Ile Thr Glu Asp Val Lys
    210                 215                 220

Val Asn Arg Phe Gln Val Phe Ala His Leu Thr Cys Gly Asn Ser Tyr
225                 230                 235                 240

Val Phe Asp Asp Tyr Lys Lys Ala Lys Thr Tyr Tyr Ile Asn Gly Leu
                245                 250                 255

Lys Phe Ala Lys Asn Ser Phe His Lys Tyr Lys Leu Thr Ser Ala Leu
            260                 265                 270

Ala Phe Leu Glu Asn Ile Trp Gly Val Lys Glu Asn Lys Tyr Leu Glu
        275                 280                 285

Gln Glu Pro Lys Asn Asp Ser Asp Phe Ile Glu Leu Ala His His Phe
    290                 295                 300

Met Leu Asn Asp Gln Ala Asp Lys Met Met Asp Val Phe Asn Lys Leu
305                 310                 315                 320

Asp Ser Thr Thr Met His Asp Asn Asp Leu Gly Phe Leu Tyr Tyr Val
                325                 330                 335

Lys Gly Ile Phe Tyr Lys Asp Lys Gly Cys Phe Leu Lys Ser Val Lys
            340                 345                 350

His Phe Lys Lys Ser Asp Asp Lys Tyr Phe Val Lys Leu Pro Leu Ile
        355                 360                 365

Lys Leu Lys Asn Met Gly Val Glu Asn Glu Ile Leu Glu Leu Leu Ala
    370                 375                 380

Ile
385


<210> SEQ ID NO 185
<211> LENGTH: 388
<212> TYPE: PRT
<213> ORGANISM: Bacillus sonorensis

<400> SEQUENCE: 185

Met Lys Glu Leu Glu Leu Lys Ser Leu Leu Lys Asn Lys Cys Glu Glu
1               5                   10                  15

Glu Arg Gly Leu Glu Lys Glu Leu Ala Lys Ile Ala Gly Tyr Ser Asn
            20                  25                  30

Ser Ser Gly Phe His Gln Phe Ile Phe Asn Asp Lys Lys Glu Met Asp
        35                  40                  45

Asn Ile Gln Gly Leu Ile Asn Val Val Gln Arg Val Ser Pro Asp Asn
    50                  55                  60

Glu Phe Glu Leu Met Ser Glu Tyr Ile Leu Thr Leu Asp Pro Asn Lys
65                  70                  75                  80

Ser Ala Ala Arg Gln Gly Leu Glu Tyr Leu Ser Val Asn Gln Leu Tyr
                85                  90                  95
```

```
Asp Thr Leu Asp Thr His Ile Glu Asn Leu Arg Ala Ala Lys Asn Thr
            100                 105                 110

Ile Ser Lys Glu Trp Gly Lys Val Tyr Ser Leu Gln Arg Glu Leu Asp
        115                 120                 125

Cys Gly Lys Ile Ser Ile Glu Glu Cys Ile Arg Ile Leu Gly Glu Ile
    130                 135                 140

Asn Pro Lys Ser Pro Glu Met Lys Val Tyr Ser Arg Leu Ile Pro Met
145                 150                 155                 160

Tyr Ala Ala Leu Ser Leu Asn Gln Phe Thr Arg Leu Met Ala Met Ser
                165                 170                 175

Glu Asp Val Ile Leu Asn Arg Ile Thr Thr Gln Asn Tyr Val Tyr Tyr
            180                 185                 190

Ser Tyr Lys Ser Arg Tyr Met Leu Leu Leu Ala Asn Cys Cys Phe Gly
        195                 200                 205

Ser Asn Asp Leu Lys Lys Ala Arg Glu Tyr Ala Lys Tyr Gly Ile Asn
    210                 215                 220

Asn Ser Asn Val Lys Arg Ile Ile Phe Phe Ser Tyr Leu Thr Tyr Gly
225                 230                 235                 240

Thr Thr Leu Met Phe Ser Asp Tyr Ser Ser Ala Lys Glu Ile Phe Leu
                245                 250                 255

Lys Gly Met Glu Ile Ala Lys Gly Asn Asp Phe Tyr Glu Gln Gln Ile
            260                 265                 270

Lys Arg Ser Leu Cys Phe Leu Glu Asn Val Trp Asn Lys Glu Asn Gln
        275                 280                 285

Tyr Leu Asn Ile Glu Ser Asn Glu Ile Met Asp Lys Gln Glu Val Ile
    290                 295                 300

His Tyr Leu Ile Arg Lys Gly Asn Ile Asp Glu Ala Lys Arg Met Leu
305                 310                 315                 320

Glu Gln Ile Glu Lys Leu His His Asp Asp Tyr Glu Leu Gly Met His
                325                 330                 335

Phe Tyr Leu Lys Gly Leu Ile Asp Asn Ser Gln Ser His Phe Leu Arg
            340                 345                 350

Ser Ile Lys His Phe Lys Ile Ser Gly Asp Lys Phe Ser Thr Thr Leu
        355                 360                 365

Pro Ile Ile Glu Leu Glu Lys Leu Gly Leu Asp Lys Ala Ile Leu Asp
    370                 375                 380

Val Leu Thr Leu
385
```

<210> SEQ ID NO 186
<211> LENGTH: 389
<212> TYPE: PRT
<213> ORGANISM: Bacillus licheniformis

<400> SEQUENCE: 186

```
Val Val Lys Glu Leu Glu Leu Lys Asn Phe Leu Lys Asn Lys Cys Glu
1               5                   10                  15

Glu Glu Arg Gly Leu Glu Lys Glu Leu Ala Arg Ile Ala Gly Tyr Ser
            20                  25                  30

Asn Ser Ser Gly Phe His His Phe Ile Tyr Asn Glu Lys Lys Glu Met
        35                  40                  45

Asp Asn Ile Gln Gly Ile Ile Asp Val Ile Gln Lys Ile Ser Pro Glu
    50                  55                  60

Tyr Glu Phe Asp Leu Met Ser Glu Tyr Ile Phe Thr Leu Asp Ile Asn
65                  70                  75                  80
```

-continued

```
Lys Ser Ala Ala Arg Gln Gly Leu Glu Tyr Leu Ser Val Asn Gln Leu
                85                  90                  95

Tyr Asp Thr Leu Asp Lys His Ile Lys Lys Met Val Ser Ala Lys Asn
            100                 105                 110

Ser Val Ser Lys Glu Trp Gly Lys Val Tyr Ala Ala Gln Arg Glu Leu
        115                 120                 125

Asp Lys Gly Asn Ile Gly Ile Glu Glu Cys Ile Arg Leu Leu Ala Glu
    130                 135                 140

Ile Gln Pro Lys Ser Ser Glu Met Lys Val Tyr Ser Arg Ile Ile Pro
145                 150                 155                 160

Met Tyr Ala Ile Leu Pro Leu Lys Gln Phe Gly Arg Leu Lys Asp Met
                165                 170                 175

Ser Asp Ser Val Leu Ile Asp Thr Ile Ser Asn Gln Asn Tyr Val Tyr
            180                 185                 190

His Ser Phe Lys Ser Arg Tyr Met Leu Leu Leu Ala Asn Cys Phe Phe
        195                 200                 205

Gly Asn Asn Glu Ile Glu Lys Ala Gln Glu Tyr Ala Arg His Gly Ile
    210                 215                 220

Glu Asn Ser Asn Val Lys Arg Ile Ile Phe Phe Ser Tyr Leu Thr Tyr
225                 230                 235                 240

Gly Ser Ser Leu Met Leu Asp Asp Tyr Glu Lys Ser Lys Ser Ser Phe
                245                 250                 255

Leu Lys Gly Leu Glu Val Gly Lys Gly Asn Lys Ile Tyr Glu Gln His
            260                 265                 270

Ala Ile Arg Asn Leu Cys Phe Leu Glu Asn Leu Trp Gly Lys Glu Asn
        275                 280                 285

Gln Tyr Leu Asn Ile Gln Ser Asn Glu Ile Ile Asp Arg Gln Glu Val
    290                 295                 300

Val His Tyr Leu Ile Arg Lys Gly Ser Lys Gln Gln Ala Lys Lys Met
305                 310                 315                 320

Leu Asp Gln Leu Asp Leu Met Glu His Asp Asp Asn Asp Leu Gly Leu
                325                 330                 335

His Tyr Tyr Leu Lys Gly Leu Leu Glu Ser Ser Arg Glu Tyr Phe Leu
            340                 345                 350

Glu Ser Val Lys Tyr Phe Lys Leu Ser Gly Asp Lys Phe Ser Cys Thr
        355                 360                 365

Leu Pro Ile Ile Glu Leu Glu Lys Leu Gly Val Glu Lys Gln Ile Leu
    370                 375                 380

Glu Ile Ile Ser Ile
385
```

<210> SEQ ID NO 187
<211> LENGTH: 389
<212> TYPE: PRT
<213> ORGANISM: Bacillus licheniformis

<400> SEQUENCE: 187

```
Val Val Lys Glu Leu Glu Leu Lys Asn Phe Leu Lys Asn Lys Cys Glu
1               5                   10                  15

Glu Glu Arg Gly Leu Glu Lys Glu Leu Ala Arg Ile Ala Gly Tyr Ser
            20                  25                  30

Asn Ser Ser Gly Phe His His Phe Ile Tyr Asn Glu Lys Lys Glu Met
        35                  40                  45

Asp Asn Ile Gln Gly Ile Ile Asp Val Ile Gln Lys Ile Ser Pro Glu
```

```
    50                  55                  60

Tyr Glu Phe Asp Leu Met Ser Glu Tyr Ile Phe Thr Leu Asp Ile Asn
65                  70                  75                  80

Lys Ser Ala Ala Arg Gln Gly Leu Glu Tyr Leu Ser Val Asn Gln Leu
                85                  90                  95

Tyr Asp Thr Leu Asp Lys His Ile Lys Lys Met Val Ser Ala Lys Asn
            100                 105                 110

Ser Val Ser Lys Glu Trp Gly Lys Val Tyr Ala Ala Gln Arg Glu Leu
        115                 120                 125

Asp Lys Gly Asn Ile Gly Ile Glu Glu Cys Ile Arg Leu Leu Ala Glu
    130                 135                 140

Ile Gln Pro Lys Ser Ser Glu Met Lys Val Tyr Ser Arg Ile Ile Pro
145                 150                 155                 160

Met Tyr Ala Ile Leu Pro Leu Lys Gln Phe Gly Arg Leu Lys Asp Met
                165                 170                 175

Ser Asp Ser Val Leu Ile Asp Thr Ile Ser Asn Gln Asn Tyr Val Tyr
            180                 185                 190

His Ser Phe Lys Ser Arg Tyr Met Leu Leu Leu Ala Asn Cys Phe Phe
        195                 200                 205

Gly Asn Asn Glu Ile Glu Lys Ala Gln Glu Tyr Ala Arg His Gly Ile
    210                 215                 220

Glu Asn Ser Asn Val Lys Arg Ile Ile Phe Phe Ser Tyr Leu Thr Tyr
225                 230                 235                 240

Gly Ser Ser Leu Met Leu Asp Asp Tyr Glu Lys Ser Lys Ser Ser Phe
                245                 250                 255

Leu Lys Gly Leu Glu Val Gly Lys Gly Asn Lys Ile Tyr Glu Gln His
            260                 265                 270

Ala Ile Arg Asn Leu Cys Phe Leu Glu Asn Leu Trp Gly Lys Glu Asn
        275                 280                 285

Gln Tyr Leu Asn Ile Gln Ser Asn Glu Ile Ile Asp Arg Gln Glu Val
    290                 295                 300

Val His Tyr Leu Ile Arg Lys Gly Ser Lys Gln Gln Ala Lys Lys Met
305                 310                 315                 320

Leu Asp Gln Leu Asp Leu Met Glu His Asp Asp Asn Asp Leu Gly Leu
                325                 330                 335

His Tyr Tyr Leu Lys Gly Leu Leu Glu Ser Ser Arg Glu Tyr Phe Leu
            340                 345                 350

Glu Ser Val Lys Tyr Phe Lys Leu Ser Gly Asp Lys Phe Ser Cys Thr
        355                 360                 365

Leu Pro Ile Ile Glu Leu Glu Lys Leu Gly Val Glu Lys Gln Ile Leu
    370                 375                 380

Glu Ile Ile Ser Ile
385


<210> SEQ ID NO 188
<211> LENGTH: 389
<212> TYPE: PRT
<213> ORGANISM: Bacillus sp.

<400> SEQUENCE: 188

Val Val Lys Glu Leu Glu Leu Lys Asn Phe Leu Lys Asn Lys Cys Glu
1               5                   10                  15

Glu Glu Arg Gly Leu Glu Lys Glu Leu Ala Arg Ile Ala Gly Tyr Ser
            20                  25                  30
```

-continued

```
Asn Ser Ser Gly Phe His His Phe Ile Tyr Asn Glu Lys Lys Glu Met
        35                  40                  45

Asp Asn Ile Gln Gly Ile Ile Asp Val Ile Gln Lys Ile Ser Pro Glu
    50                  55                  60

Tyr Glu Phe Asp Leu Met Ser Glu Tyr Ile Leu Thr Leu Asp Ile Asn
65                  70                  75                  80

Lys Ser Ala Ala Arg Gln Gly Leu Glu Tyr Leu Ser Val Asn Gln Leu
                85                  90                  95

Tyr Asp Thr Leu Asp Lys His Ile Lys Lys Met Val Ser Ala Lys Asn
            100                 105                 110

Ser Val Ser Lys Glu Trp Gly Lys Val Tyr Ala Ala Gln Arg Glu Leu
        115                 120                 125

Asp Lys Gly Asn Ile Gly Ile Glu Glu Cys Ile Arg Leu Leu Ala Glu
    130                 135                 140

Ile His Pro Lys Ser Ser Glu Met Lys Val Tyr Ser Arg Ile Ile Pro
145                 150                 155                 160

Met Tyr Ala Ile Leu Pro Leu Lys Gln Phe Gly Arg Leu Lys Asp Met
                165                 170                 175

Ser Asp Ile Val Leu Ile Asp Thr Ile Ser Asn Gln Asn Tyr Val Tyr
            180                 185                 190

His Ser Phe Lys Ser Arg Tyr Met Leu Leu Leu Ala Asn Cys Phe Phe
        195                 200                 205

Gly Asn Asn Glu Ile Glu Lys Ala Gln Glu Tyr Ala Arg His Gly Ile
    210                 215                 220

Glu Asn Ser Asn Val Lys Arg Ile Ile Phe Phe Ser Tyr Leu Thr Tyr
225                 230                 235                 240

Gly Ser Ser Leu Met Leu Asp Asp Tyr Glu Lys Ser Lys Ser Ser Phe
                245                 250                 255

Leu Lys Gly Leu Glu Val Gly Lys Gly Asn Lys Ile Tyr Glu Gln His
            260                 265                 270

Ala Ile Arg Asn Leu Cys Phe Leu Glu Asn Leu Trp Gly Lys Glu Asn
        275                 280                 285

Gln Tyr Leu Asn Ile Gln Ser Asn Glu Ile Met Asp Arg Gln Glu Val
    290                 295                 300

Val His Tyr Leu Ile Arg Lys Gly Ser Lys Gln Gln Ala Lys Lys Met
305                 310                 315                 320

Leu Asp Gln Leu Asp Leu Met Glu His Asp Asp Asn Asp Leu Gly Leu
                325                 330                 335

His Tyr Tyr Leu Lys Gly Leu Leu Glu Ser Ser Arg Glu Tyr Phe Leu
            340                 345                 350

Glu Ser Val Lys Tyr Phe Lys Leu Ser Gly Asp Lys Phe Ser Cys Thr
        355                 360                 365

Leu Pro Ile Ile Glu Leu Glu Lys Leu Gly Val Glu Lys Gln Ile Leu
    370                 375                 380

Glu Ile Ile Ser Ile
385
```

<210> SEQ ID NO 189
<211> LENGTH: 351
<212> TYPE: PRT
<213> ORGANISM: Bacillus licheniformis

<400> SEQUENCE: 189

```
Val Val Lys Glu Leu Glu Leu Lys Asn Phe Leu Lys Asn Lys Cys Glu
1               5                   10                  15
```

```
Glu Glu Arg Gly Leu Glu Lys Glu Leu Ala Arg Ile Ala Gly Tyr Ser
            20                  25                  30

Asn Ser Ser Gly Phe His His Phe Ile Tyr Asn Glu Lys Lys Glu Met
        35                  40                  45

Asp Asn Ile Gln Gly Ile Ile Asp Val Ile Gln Lys Ile Ser Pro Glu
    50                  55                  60

Tyr Glu Phe Asp Leu Met Ser Glu Tyr Ile Leu Thr Leu Asp Ile Asn
65                  70                  75                  80

Lys Ser Ala Ala Arg Gln Gly Leu Glu Tyr Leu Ser Val Asn Gln Leu
                85                  90                  95

Tyr Asp Thr Leu Asp Lys His Ile Lys Lys Met Val Ser Ala Lys Asn
            100                 105                 110

Ser Val Ser Lys Glu Trp Gly Lys Val Tyr Ala Ala Gln Arg Glu Leu
        115                 120                 125

Asp Lys Gly Asn Ile Gly Ile Glu Glu Cys Ile Arg Leu Leu Ala Glu
    130                 135                 140

Ile His Pro Lys Ser Ser Glu Met Lys Val Tyr Ser Arg Ile Ile Pro
145                 150                 155                 160

Met Tyr Ala Ile Leu Pro Leu Lys Gln Phe Gly Arg Leu Lys Asp Met
                165                 170                 175

Ser Asp Ser Val Leu Ile Asp Thr Ile Ser Asn Gln Asn Tyr Val Tyr
            180                 185                 190

His Ser Phe Lys Ser Arg Tyr Met Leu Leu Leu Ala Asn Cys Phe Phe
        195                 200                 205

Gly Asn Asn Glu Ile Glu Lys Ala Gln Glu Tyr Ala Arg His Gly Ile
    210                 215                 220

Glu Asn Ser Asn Val Lys Arg Ile Ile Phe Phe Ser Tyr Leu Thr Tyr
225                 230                 235                 240

Gly Ser Ser Leu Met Leu Asp Asp Tyr Glu Lys Ser Lys Ser Ser Phe
                245                 250                 255

Leu Lys Gly Leu Glu Val Gly Lys Gly Asn Lys Ile Tyr Glu Gln His
            260                 265                 270

Ala Ile Arg Asn Leu Cys Phe Leu Glu Asn Leu Trp Gly Lys Glu Asn
        275                 280                 285

Gln Tyr Leu Asn Ile Gln Ser Asn Glu Ile Met Asp Arg Gln Glu Val
    290                 295                 300

Val His Tyr Leu Ile Arg Lys Gly Ser Lys Gln Gln Ala Lys Lys Met
305                 310                 315                 320

Leu Asp Gln Leu Asp Phe Met Glu His Asp Asp Asn Asp Leu Gly Leu
                325                 330                 335

His Tyr Tyr Leu Lys Gly Leu Leu Glu Ser Ser Arg Glu Tyr Phe
            340                 345                 350


<210> SEQ ID NO 190
<211> LENGTH: 389
<212> TYPE: PRT
<213> ORGANISM: Bacillus sp.

<400> SEQUENCE: 190

Met Val Lys Glu Leu Glu Leu Lys Asn Phe Leu Lys Asn Lys Cys Glu
1               5                   10                  15

Glu Glu Arg Gly Leu Glu Lys Glu Leu Ala Arg Ile Ala Gly Tyr Ser
            20                  25                  30

Asn Ser Ser Gly Phe His His Phe Ile Tyr Asn Glu Lys Lys Glu Met
```

```
        35                  40                  45

Asp Asn Ile Gln Gly Ile Ile Asp Val Ile Gln Lys Ile Ser Pro Glu
    50                  55                  60

Tyr Glu Phe Asp Leu Met Ser Glu Tyr Ile Leu Thr Leu Asp Ile Asn
65                  70                  75                  80

Lys Ser Ala Ala Arg Gln Gly Leu Glu Tyr Leu Ser Val Asn Gln Leu
                85                  90                  95

Tyr Gly Thr Leu Asp Lys His Ile Lys Lys Met Met Ser Ala Lys Asn
            100                 105                 110

Ser Val Ser Lys Glu Trp Gly Lys Val Tyr Ala Ala Gln Arg Glu Leu
        115                 120                 125

Asp Lys Gly Asn Ile Gly Ile Glu Glu Cys Ile Arg Leu Leu Ala Glu
    130                 135                 140

Ile His Pro Lys Ser Ser Glu Met Lys Val Tyr Ser Arg Ile Ile Pro
145                 150                 155                 160

Met Tyr Ala Ile Leu Pro Leu Lys Gln Phe Gly Arg Leu Lys Asp Met
                165                 170                 175

Ser Asp Ile Val Leu Ile Asp Thr Ile Ser Asn Gln Asn Tyr Val Tyr
            180                 185                 190

His Ser Phe Lys Ser Arg Tyr Met Leu Leu Leu Ala Asn Cys Phe Phe
        195                 200                 205

Gly Asn Asn Glu Ile Glu Lys Ala Gln Glu Tyr Ala Arg His Gly Ile
    210                 215                 220

Glu Asn Ser Asn Val Lys Arg Ile Ile Phe Phe Ser Tyr Leu Thr His
225                 230                 235                 240

Gly Ser Ser Leu Met Leu Asp Asp Tyr Glu Lys Ser Lys Ser Ser Phe
                245                 250                 255

Leu Lys Gly Leu Glu Val Gly Lys Gly Asn Lys Ile Tyr Glu Gln His
            260                 265                 270

Ala Ile Arg Asn Leu Cys Phe Leu Glu Asn Leu Trp Gly Lys Glu Asn
        275                 280                 285

Lys Tyr Leu Asn Ile Gln Ser Asn Glu Ile Met Asp Arg Gln Glu Val
    290                 295                 300

Val His Tyr Leu Ile Arg Lys Gly Ser Lys Gln Gln Ala Lys Lys Met
305                 310                 315                 320

Leu Asp Gln Leu Asp Leu Met Glu His Asp Asp Asn Asp Leu Gly Leu
                325                 330                 335

His Tyr Tyr Leu Lys Gly Leu Leu Glu Ser Ser Arg Glu Tyr Phe Leu
            340                 345                 350

Glu Ser Val Lys Tyr Phe Lys Leu Ser Gly Asp Lys Phe Ser Cys Thr
        355                 360                 365

Leu Pro Ile Ile Glu Leu Glu Lys Leu Gly Val Glu Lys Gln Ile Leu
    370                 375                 380

Glu Ile Ile Ser Ile
385
```

<210> SEQ ID NO 191
<211> LENGTH: 385
<212> TYPE: PRT
<213> ORGANISM: Bacillus licheniformis

<400> SEQUENCE: 191

```
Met Glu Leu Lys Arg Phe Ile Lys Asn Lys Cys Glu Glu Glu Arg Gly
1               5                   10                  15
```

-continued

```
Leu Glu Lys Glu Leu Ala Arg Ile Ala Gly Tyr Ser Asn Ser Ser Gly
            20                  25                  30

Phe His His Phe Ile Tyr Asn Glu Lys Lys Glu Met Asp Asn Ile Gln
        35                  40                  45

Gly Ile Ile Asp Val Ile Gln Lys Val Ser Pro Glu Tyr Glu Phe Asp
    50                  55                  60

Leu Met Ser Glu Tyr Ile Leu Thr Leu Asp Ile Asn Lys Ser Ala Ala
65                  70                  75                  80

Arg Gln Gly Leu Glu Tyr Leu Ser Val Asn Gln Leu Tyr Asp Thr Leu
                85                  90                  95

Asp Lys His Ile Lys Lys Met Val Ser Ala Lys Asn Ser Val Ser Lys
            100                 105                 110

Glu Trp Gly Lys Val Tyr Ala Ala Gln Arg Glu Leu Asp Lys Gly Ser
        115                 120                 125

Ile Gly Ile Glu Glu Cys Ile Arg Leu Leu Ser Glu Ile His Pro Lys
    130                 135                 140

Ser Ser Glu Met Arg Val Tyr Ser Arg Ile Ile Pro Met Tyr Ala Ile
145                 150                 155                 160

Leu Pro Leu Lys Gln Phe Gly Arg Leu Lys Asp Met Ser Asp Ile Val
                165                 170                 175

Leu Ile Asp Thr Ile Ser Asn Gln Asn Tyr Val Tyr His Ser Phe Lys
            180                 185                 190

Ser Arg Tyr Met Leu Leu Leu Ala Asn Cys Phe Phe Gly Asn Asn Glu
        195                 200                 205

Ile Glu Lys Ala Gln Lys Tyr Ala Arg His Gly Ile Glu Asn Ser Asn
    210                 215                 220

Val Lys Arg Ile Ile Phe Phe Ser Tyr Leu Thr Tyr Gly Ser Ser Leu
225                 230                 235                 240

Met Leu Asp Asp Tyr Glu Lys Ser Lys Ser Ser Phe Leu Lys Gly Leu
                245                 250                 255

Glu Val Gly Lys Gly Asn Lys Ile Tyr Glu Gln His Ala Ile Arg Asn
            260                 265                 270

Leu Cys Phe Leu Glu Asn Leu Trp Gly Lys Glu Asn Gln Tyr Leu Asn
        275                 280                 285

Ile Glu Ser Asn Glu Ile Val Asp Lys Gln Glu Val Val His Tyr Leu
    290                 295                 300

Ile Arg Lys Gly Ser Lys Gln Gln Ala Lys Lys Met Leu Asp Gln Leu
305                 310                 315                 320

Asp Leu Val Glu His Asp Asp Asn Asp Leu Gly Leu His Tyr Tyr Leu
                325                 330                 335

Lys Gly Leu Leu Glu Asn Ser Arg Glu Tyr Phe Leu Glu Ser Val Lys
            340                 345                 350

Tyr Phe Lys Leu Ser Gly Asp Lys Phe Ser Cys Thr Leu Pro Ile Ile
        355                 360                 365

Glu Leu Glu Lys Leu Gly Val Asp Lys Gln Ile Leu Glu Ile Ile Ser
    370                 375                 380

Ile
385
```

<210> SEQ ID NO 192
<211> LENGTH: 385
<212> TYPE: PRT
<213> ORGANISM: Bacillus licheniformis

<400> SEQUENCE: 192

```
Leu Glu Leu Lys Asn Leu Leu Lys Asn Lys Cys Glu Glu Glu Arg Gly
1               5                   10                  15

Leu Glu Lys Glu Leu Ala Arg Ile Ala Gly Tyr Ser Asn Ser Ser Gly
            20                  25                  30

Phe His His Phe Ile Tyr Asn Glu Lys Lys Glu Met Asp Asn Ile Gln
        35                  40                  45

Gly Ile Ile Asp Val Ile Gln Lys Val Ser Pro Glu Tyr Glu Phe Asp
    50                  55                  60

Leu Met Ser Glu Tyr Ile Leu Thr Leu Asp Ile Asn Lys Ser Ala Ala
65                  70                  75                  80

Arg Gln Gly Leu Glu Tyr Leu Ser Val Asn Gln Leu Tyr Asp Thr Leu
                85                  90                  95

Asp Lys His Ile Lys Lys Met Val Ser Ala Lys Asn Ser Val Ser Lys
            100                 105                 110

Glu Trp Gly Lys Val Tyr Ala Ala Gln Arg Glu Leu Asp Lys Gly Asn
        115                 120                 125

Ile Cys Ile Glu Glu Cys Ile Arg Leu Leu Ala Glu Ile His Pro Lys
    130                 135                 140

Ser Ser Glu Met Lys Val Tyr Ser Arg Ile Ile Pro Met Tyr Ala Ile
145                 150                 155                 160

Leu Pro Leu Lys Gln Phe Gly Arg Leu Lys Asp Met Ser Asp Ile Val
                165                 170                 175

Leu Ile Asp Thr Ile Ser Asn His Asn Tyr Val Tyr His Ser Phe Lys
            180                 185                 190

Ser Arg Tyr Met Leu Leu Leu Ala Asn Cys Phe Phe Gly Asn Asn Glu
        195                 200                 205

Thr Glu Lys Ala Gln Lys Tyr Ala Arg His Gly Ile Glu Asn Ser Asn
    210                 215                 220

Val Lys Arg Ile Ile Phe Phe Ser Tyr Leu Thr Tyr Gly Ser Ser Leu
225                 230                 235                 240

Met Leu Asp Asp Tyr Glu Lys Ser Lys Ser Ser Phe Leu Lys Gly Leu
                245                 250                 255

Glu Val Gly Lys Gly Asn Lys Ile Tyr Glu Gln His Ala Ile Arg Asn
            260                 265                 270

Leu Cys Phe Leu Glu Asn Leu Trp Gly Lys Glu Asn Gln Tyr Leu Asn
        275                 280                 285

Ile Glu Ser Asn Glu Ile Val Asp Lys Gln Glu Val Val His Tyr Leu
    290                 295                 300

Ile Lys Lys Gly Ser Lys Gln Gln Ala Lys Lys Met Leu Asp Gln Leu
305                 310                 315                 320

Asp Leu Val Glu Gln Asp Asp Asn Asp Leu Gly Leu His Tyr Tyr Leu
                325                 330                 335

Lys Gly Leu Leu Glu Asn Ser Arg Asp Tyr Phe Leu Glu Ser Val Lys
            340                 345                 350

Tyr Phe Lys Leu Ser Gly Asp Lys Phe Ser Cys Thr Leu Pro Ile Ile
        355                 360                 365

Glu Leu Glu Lys Leu Gly Val Asp Lys Gln Ile Leu Glu Val Ile Ser
    370                 375                 380

Ile
385
```

<210> SEQ ID NO 193
<211> LENGTH: 297

<212> TYPE: PRT
<213> ORGANISM: Bacillus subtilis

<400> SEQUENCE: 193

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295

<210> SEQ ID NO 194
<211> LENGTH: 297
<212> TYPE: PRT
<213> ORGANISM: Bacillus atrophaeus

<400> SEQUENCE: 194

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

```
Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295


<210> SEQ ID NO 195
<211> LENGTH: 320
<212> TYPE: PRT
<213> ORGANISM: Bacillus subtilis

<400> SEQUENCE: 195

Met Ser Thr Asn Thr Lys Glu Val Glu Ser Asn Val Ser Glu Glu Ile
1               5                   10                  15

Lys Leu Leu Glu Leu Ala Asp Leu Asp Glu Asn Tyr Glu Glu Met Asp
            20                  25                  30

Leu Ile Ile Glu Arg Leu Arg Phe Ser Ser Asp Ser Val Leu Asn Glu
        35                  40                  45

Phe Gly Asn Val Tyr Gln Ile His Arg Gln Leu Gln Lys Gly Gln Ile
    50                  55                  60

Asn Arg Ile Glu Ala Ser Arg Lys Leu Gly Lys Met Asp Leu Lys Thr
65                  70                  75                  80

Pro Glu Cys Lys Val Phe Ser Arg Leu Met Ile Leu Pro Ile Cys Leu
                85                  90                  95

Gln Thr Ala Glu Tyr Lys Leu Met Tyr Glu Val Gly Asn Glu Ile Asp
            100                 105                 110

Leu Asp Ile Ile Glu Glu Glu Ser Phe Leu Lys Lys Ser Tyr Arg Ser
        115                 120                 125
```

```
Arg Leu Leu Ser Met Leu Ala Asn Ala Glu Leu Gly Ile Gly Asn Leu
    130                 135                 140

Lys Lys Ala Gln Phe Tyr Ala Ser Leu Thr Val Asp Ser Ala Ile Thr
145                 150                 155                 160

Asp Asn Phe Tyr Ala Ser Gly Tyr Leu Ile His Gly Asn Thr Leu Leu
                165                 170                 175

Phe Ser Asp Tyr Asn Glu Ala Lys Leu Ser Phe Leu Gln Gly Leu Glu
            180                 185                 190

Tyr Thr Glu Glu Gly Lys Phe His Tyr Arg Glu Leu Arg Arg Ser Leu
        195                 200                 205

Ser Phe Leu Glu Asn Tyr His Gly Glu Glu Asn Ile Tyr Leu Asp His
    210                 215                 220

Asn Ser Asn Glu Val Gly Glu Arg Gln Gly Val Ala Tyr Ala Leu Ile
225                 230                 235                 240

Lys Glu Gly Lys Lys Ser Glu Ala Leu Lys Ile Leu Glu Glu Leu Glu
                245                 250                 255

Asn Arg Glu Gln Asn Lys Asn Ile Leu Ala Phe His Tyr Tyr Tyr Lys
            260                 265                 270

Gly Leu Cys Thr Asp Ser Lys Asp Tyr Phe Phe Lys Ser Val Arg Tyr
        275                 280                 285

Phe Lys Glu Ser Asp Asp Thr Tyr Cys Val Lys Leu Pro Leu Asp Glu
    290                 295                 300

Leu Glu Arg Leu Gly Glu Asn Lys Thr Leu Leu Asp Leu Ile Thr Ile
305                 310                 315                 320


<210> SEQ ID NO 196
<211> LENGTH: 386
<212> TYPE: PRT
<213> ORGANISM: Bacillus amyloliquefaciens

<400> SEQUENCE: 196

Met Glu Leu Ile Arg Ile Ala Met Arg Lys Asp Leu Glu Asn Asp Lys
1               5                   10                  15

Ser Leu Met Ser Lys Trp Ala Ala Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Asn Ser Ile Val Asn Ile Val Lys Thr His Tyr Pro Asp Gln Glu Tyr
    50                  55                  60

Glu Leu Met Glu Asn Tyr Cys Leu Leu Leu Asp Pro Asn Thr Lys Ala
65                  70                  75                  80

Ala Arg Ser Ala Leu Glu Tyr Ala Asp Ala Asn Ser Phe Asn Thr Leu
                85                  90                  95

Thr Asp Lys Leu Val Glu Lys Met Ser Ile Ala Ser Asn Leu Lys Ser
            100                 105                 110

Lys Glu Tyr Gly Lys Ile Tyr Glu Ile His Arg Lys Leu Ser Arg Gly
        115                 120                 125

Glu Ile Asp Val Leu Glu Ala Ser Lys Asn Ile Gly Lys Tyr Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Ser Leu Leu Lys Gln
                165                 170                 175

Ile Asp Leu Asn Asp Ile Lys Glu Asn Asn Tyr Leu Lys Lys Ser Phe
```

```
            180                 185                 190

Glu Thr Arg Ile Tyr Val Leu Leu Ser Asn Ile Tyr Leu Asn Glu Asn
        195                 200                 205

Glu Leu Glu Leu Ser Arg Lys Tyr Ala Glu Lys Ala Ile Lys Ser Thr
    210                 215                 220

Asp Thr Lys Arg Phe Leu Val Phe Ser Tyr Leu Thr Ile Gly Thr Ser
225                 230                 235                 240

Tyr Ile Phe Ser Asp Tyr Ala Leu Ser Lys Gln Asn Tyr Leu Ser Gly
                245                 250                 255

Tyr Glu Ile Ala Lys Gly Asn Ser Val Phe Glu Glu Phe Phe Lys Arg
            260                 265                 270

Asn Leu Ser Phe Leu Asn Asn Phe Trp Asn Lys Glu Asn Pro Trp Ile
        275                 280                 285

Asn Tyr Asp Ser Asn Ala Val Thr Asp Val Gln Glu Val Ile Phe Glu
    290                 295                 300

Leu Ile Asn Gln Lys Lys Leu Glu Arg Ala Leu Thr Leu Leu Lys Ser
305                 310                 315                 320

Leu Glu Arg Lys Lys Gln Asn Glu Asn Asp Leu Gly Phe His Tyr Tyr
                325                 330                 335

Leu Glu Gly Leu Ile Thr Asn Asp Lys Glu Ala Phe Tyr Lys Ser Val
            340                 345                 350

Glu Tyr Phe Lys Leu Ser Gln Asp Lys Leu Phe Ile Lys Met Pro Leu
        355                 360                 365

Ile Lys Leu Glu Ser Leu Gly Glu Asn Pro Arg Leu Leu Lys Ile Ile
    370                 375                 380

Ser Met
385


<210> SEQ ID NO 197
<211> LENGTH: 386
<212> TYPE: PRT
<213> ORGANISM: Bacillus subtilis

<400> SEQUENCE: 197

Met Glu Leu Ile Arg Ile Ala Met Arg Lys Asp Leu Glu Asn Asp Lys
1               5                   10                  15

Ser Leu Met Ser Lys Trp Ala Ala Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Asn Ser Ile Val Asn Ile Val Lys Thr His Tyr Pro Asp Gln Glu Tyr
    50                  55                  60

Glu Leu Met Glu Asn Tyr Cys Leu Leu Leu Asp Pro Asn Thr Lys Ala
65                  70                  75                  80

Ala Arg Ser Ala Leu Glu Tyr Ala Asp Ala Asn Ser Phe Asn Thr Leu
                85                  90                  95

Thr Asp Lys Leu Val Glu Lys Met Ser Ile Ala Ser Asn Leu Lys Ser
            100                 105                 110

Lys Glu Tyr Gly Lys Ile Tyr Glu Ile His Arg Lys Leu Ser Arg Gly
        115                 120                 125

Glu Ile Asp Val Leu Glu Ala Ser Lys Asn Ile Gly Lys Tyr Arg Ile
    130                 135                 140

Lys Thr Asp Glu Met Asn Ile Phe Ser Lys Met Ile Pro Met Tyr Asp
145                 150                 155                 160
```

-continued

Tyr Leu Ser Lys Gly Asn Phe Ser Pro Met Lys Ser Leu Leu Lys Gln
165 170 175

Ile Asp Leu Asn Asp Ile Lys Glu Asn Asn Tyr Leu Lys Lys Ser Phe
180 185 190

Glu Thr Arg Ile Tyr Val Leu Leu Ser Asn Ile Tyr Leu Asn Glu Asn
195 200 205

Glu Leu Glu Leu Ser Arg Lys Tyr Ala Glu Lys Ala Ile Lys Ser Thr
210 215 220

Asp Thr Lys Arg Phe Leu Val Phe Ser Tyr Leu Thr Ile Gly Thr Ser
225 230 235 240

Tyr Ile Phe Ser Asp Tyr Ala Leu Ser Lys Gln Asn Tyr Leu Ser Gly
245 250 255

Tyr Glu Ile Ala Lys Gly Asn Ser Val Phe Glu Glu Phe Phe Lys Arg
260 265 270

Asn Leu Ser Phe Leu Asn Asn Phe Trp Asn Lys Glu Asn Pro Trp Ile
275 280 285

Asn Tyr Asp Ser Asn Ala Val Thr Asp Val Gln Glu Val Ile Phe Glu
290 295 300

Leu Ile Asn Gln Lys Lys Leu Glu Arg Ala Leu Thr Leu Leu Lys Ser
305 310 315 320

Leu Glu Arg Lys Lys Gln Asn Glu Asn Asp Leu Gly Phe His Tyr Tyr
325 330 335

Leu Glu Gly Leu Ile Thr Asn Asp Lys Glu Ala Phe Tyr Lys Ser Val
340 345 350

Glu Tyr Phe Lys Leu Ser Gln Asp Lys Leu Phe Ile Lys Met Pro Leu
355 360 365

Ile Lys Leu Glu Ser Leu Gly Glu Asn Pro Arg Leu Leu Lys Ile Ile
370 375 380

Ser Met
385

<210> SEQ ID NO 198
<211> LENGTH: 238
<212> TYPE: PRT
<213> ORGANISM: Bacillus subtilis

<400> SEQUENCE: 198

Met Arg Val Phe Thr Tyr Ile Ile Pro Leu Tyr Tyr Tyr Leu Glu Val
1 5 10 15

Ala Glu Tyr Ser Asn Leu Ala Glu Met Ser Thr Ile Val Asp Leu Asp
20 25 30

Leu Ile Glu Asn Asn Asp Asp Ile Lys Ser Tyr Phe Tyr Asn Arg Leu
35 40 45

Met Ala Leu Leu Gly Ala Ser Ala Phe Ser Gln Asn Lys Met Thr Gln
50 55 60

Ala Arg Phe Tyr Cys Ser Tyr Gly Ile Asn Leu Lys Asn Ile Asp Arg
65 70 75 80

Leu Val Ala Tyr Ser Cys Leu Thr Met Gly Asn Thr Tyr Ile Leu Asp
85 90 95

Asp Tyr Glu Arg Ala Lys Glu Tyr Phe Leu Lys Gly Leu Asn His Thr
100 105 110

Asp Asn Asn His Leu Ala Glu Leu Gln Leu Thr Arg Ser Leu Cys Phe
115 120 125

Leu Glu Asn His Trp Arg Lys Glu Asn Phe Trp Leu Asn Pro Asp Ser
130 135 140

Glu Glu Thr Thr Asp Ile Gln Glu Ile Ala His Tyr His Ile Lys Arg
145 150 155 160

Asn Asn Leu Asp Tyr Ala Lys Glu Ile Leu Asp Tyr Leu Glu Glu Ile
165 170 175

Pro Ser Ile Asp Asn Asp Tyr Gly Ile His Phe Tyr Leu Lys Gly Leu
180 185 190

Ala Tyr Lys Asp Lys Arg Tyr Phe Tyr Lys Ser Ile Lys His Phe Lys
195 200 205

Leu Ser Gly Asp Leu Phe Cys Val Arg Leu Pro Leu Asp Gln Leu Arg
210 215 220

Glu Met Gly Glu Asp Ala Gln Ile Leu Asp Leu Leu Ala Leu
225 230 235

<210> SEQ ID NO 199
<211> LENGTH: 320
<212> TYPE: PRT
<213> ORGANISM: Bacillus subtilis

<400> SEQUENCE: 199

Leu Thr Val Lys Glu Arg Glu Val Glu Lys Thr Asn Val Asp Val Lys
1 5 10 15

Val Gln Leu Glu Met Ser Asp Ile Asn Glu Gln Cys Glu Gln Thr Asp
20 25 30

Thr Leu Ile Glu Gln Leu Ser Asn Ser Ser Cys Pro Ile Glu Arg Glu
35 40 45

Trp Ala Ala Met Tyr Gln Ile Lys Arg Arg Gln Asp Lys Gly Glu Leu
50 55 60

Asn Ala His Gln Ala Leu Lys Ala Ile Gly Lys Leu Asp Pro Lys Thr
65 70 75 80

Gln Glu Met Arg Val Phe Thr Tyr Ile Ile Pro Leu Tyr Tyr Tyr Leu
85 90 95

Glu Val Ala Gly Tyr Ser Asn Leu Ala Glu Met Ser Thr Ile Val Asp
100 105 110

Leu Asp Leu Ile Glu Asn Asn Asp Asp Ile Lys Ser Tyr Phe Tyr Asn
115 120 125

Arg Leu Met Ala Leu Leu Gly Ala Ser Ala Phe Ser Gln Asn Lys Met
130 135 140

Thr Gln Ala Arg Phe Tyr Cys Ser Tyr Gly Ile Asn Leu Lys Asn Ile
145 150 155 160

Asp Arg Leu Val Ala Cys Ser Cys Leu Thr Met Gly Asn Thr Tyr Ile
165 170 175

Leu Asp Asp Tyr Glu Arg Ala Lys Glu Tyr Phe Leu Lys Gly Leu Asn
180 185 190

His Thr Asp Asn Asn His Leu Ala Glu Leu Gln Leu Thr Arg Ser Leu
195 200 205

Cys Phe Leu Glu Asn His Trp Arg Lys Glu Asn Phe Trp Leu Asn Pro
210 215 220

Asp Ser Glu Glu Thr Thr Asp Ile Gln Glu Ile Ala His Tyr His Ile
225 230 235 240

Lys Arg Asn Asn Leu Asp Tyr Ala Lys Glu Ile Leu Asp Tyr Leu Glu
245 250 255

Glu Ile Pro Ser Ile Asp Asn Asp Tyr Gly Ile His Phe Tyr Leu Lys
260 265 270

Gly Leu Ala Tyr Lys Asp Lys Arg Tyr Phe Tyr Lys Ser Ile Lys His

```
        275                 280                 285

Phe Lys Leu Ser Gly Asp Leu Phe Cys Val Arg Leu Pro Leu Asp Gln
    290                 295                 300

Leu Arg Glu Met Gly Glu Asp Ala Gln Ile Leu Asp Leu Leu Ala Leu
305                 310                 315                 320


<210> SEQ ID NO 200
<211> LENGTH: 386
<212> TYPE: PRT
<213> ORGANISM: Bacillus aerophilus

<400> SEQUENCE: 200

Met Ser Lys Leu Lys Ala Phe Ile Lys Ser Lys Cys Glu Asp Asp Ser
1               5                   10                  15

Ser Met Ala Met Lys Leu Ala Lys Ile Ala Gly Tyr Thr Asp Arg Ser
            20                  25                  30

Gly Phe Tyr Arg Phe Leu Asn Asp Arg Arg Lys Glu Thr Thr Asp Ile
        35                  40                  45

Gln Ser Ile Ile Asp Ile Val Lys Glu Ile Asp Pro Gly Lys Glu Met
    50                  55                  60

Glu Met Met Ser Glu Tyr Ile Pro Thr Leu Asp Pro Gly Lys Gln Cys
65                  70                  75                  80

Ser Arg Gln Ala Leu Glu Tyr Phe Ser Val Asn Ala Glu Ile Glu Lys
                85                  90                  95

Leu Asp Thr His Ile Glu Asn Ile Leu Asn Asn Thr Ala Asn Ile Lys
            100                 105                 110

Ser Leu Glu Trp Ala Lys Thr Tyr Lys Ala Gln Arg Asp Ala Glu Lys
        115                 120                 125

Gly Leu Val Asn Ser Glu Asp Leu Val Arg Leu Leu Gly Ser Phe Lys
    130                 135                 140

Leu Lys Thr Asp Glu Met Lys Val Tyr Ser Arg Ile Ile Pro Met Tyr
145                 150                 155                 160

Phe Ala Leu Trp Asn Asn Gln Phe Asn Arg Leu Asp Ser Leu Ser Glu
                165                 170                 175

Asp Val Val Ile Glu Ser Leu Glu Glu Ser Tyr Val Lys Gln Ser Phe
            180                 185                 190

His Ser Arg Leu Met Leu Leu Leu Ala Asn Cys Ser Leu Arg Gln Asn
        195                 200                 205

Lys Leu Glu Arg Val Leu His Tyr Ser Ser Tyr Gly Ile Leu Asn Ser
    210                 215                 220

Asn Val Lys Arg Ile Thr Ala Tyr Ser Tyr Leu Ala Gln Gly Asn Ser
225                 230                 235                 240

Gln Met Phe Thr Asp Tyr Asp Ser Ser Lys Lys Cys Phe Leu Phe Ala
                245                 250                 255

Leu Glu His Ser Thr Glu Asn Arg Glu Arg Ser Ile Gln Ala Leu Arg
            260                 265                 270

Ser Leu Cys Phe Leu Glu Asn Leu Trp Gly Lys Glu Asn Lys Trp Leu
        275                 280                 285

His His Asp Ser Glu Glu Ile Ser Asp Arg Gln Glu Val Ala His Ser
    290                 295                 300

Tyr Ile Arg Lys Gly Glu Met Ser Ile Ala Lys Ser Ile Leu Glu Ala
305                 310                 315                 320

Leu Glu Ala Glu Glu His Asp Asp Asn Gln Leu Gly Met His Met Tyr
                325                 330                 335
```

```
Leu Lys Gly Leu Ala Tyr Gly Ser Asp Gly Tyr Phe Tyr Lys Ser Ile
            340                 345                 350

Lys His Phe Lys Leu Ser Gly Asp Lys Phe Ser Ala Asn Leu Pro Leu
        355                 360                 365

Leu Glu Leu Glu Lys Leu Gly Thr Asp Lys Leu Ile Leu Glu Val Leu
    370                 375                 380

Ala Val
385


<210> SEQ ID NO 201
<211> LENGTH: 386
<212> TYPE: PRT
<213> ORGANISM: Bacillus sp.

<400> SEQUENCE: 201

Leu Ser Lys Leu Lys Ala Phe Ile Lys Ser Lys Cys Glu Asp Asp Ser
1               5                   10                  15

Ser Leu Ala Ala Lys Leu Ala Ser Ile Ala Gly Tyr Ser Gln Thr Ser
            20                  25                  30

Gly Leu Tyr Lys Phe Leu Asn Ile Ser Gly Lys Glu Thr Ser Asp Leu
        35                  40                  45

Gln Met Ile Ile Asp Met Ile Lys Glu Ile Asp Pro Asp Arg Glu Ile
    50                  55                  60

Asp Leu Met Cys Asp Tyr Ile Phe Thr Leu Asp Pro Gly Lys Gln Cys
65                  70                  75                  80

Ala Arg Gln Ala Leu Glu Tyr Leu Ser Val Asn Ala Gln Ser Glu Lys
                85                  90                  95

Leu Asp Asp Tyr Ile Glu Phe Val Leu Ser Asn Thr Gly Asn Gly Lys
            100                 105                 110

Thr Ile Glu Trp Ala Lys Thr Tyr Lys Leu Gln Arg Asp Ala Glu Lys
        115                 120                 125

Gly Leu Val Asn Phe Glu Asn Leu Ile Arg Ser Leu Gly Asn Leu Lys
    130                 135                 140

Leu Lys Thr Glu Glu Met Gln Val Tyr Ser Met Ile Ile Pro Met Tyr
145                 150                 155                 160

Pro Ala Leu Trp Asn Asn Tyr Phe Asn Arg Leu Glu Ser Leu Ser Glu
                165                 170                 175

Asn Val Phe Ile Asp Asn Leu Glu Asp Ser Tyr Val Lys Gln Ser Phe
            180                 185                 190

His Ser Arg Leu Leu Leu Leu Leu Ala Asn Cys Ala Phe Asn Gln Asn
        195                 200                 205

Gln Leu Gly Lys Val Gln His Tyr Thr Asp Tyr Cys Ile Leu Asn Ser
    210                 215                 220

Asn Val Arg Arg Ile Thr Ala Tyr Ser Tyr Leu Thr Gln Gly Asn Ser
225                 230                 235                 240

Leu Met Leu Thr Asp Tyr Ser Thr Ser Lys Arg Cys Phe Leu Ser Ala
                245                 250                 255

Leu Glu His Ser Thr Glu Asn Arg Glu Arg Ser Ile Gln Ala Leu Arg
            260                 265                 270

Ser Leu Cys Phe Leu Glu Asn Leu Trp Ser Lys Glu Asn Lys Trp Leu
        275                 280                 285

Gln Tyr Asp Ser Asp Glu Ile Thr Asp Arg Gln Glu Val Ala His Ala
    290                 295                 300

Tyr Ile Arg Lys Gly Glu Leu Glu Leu Ala Lys Ser Ile Leu Asp Ser
305                 310                 315                 320
```

```
Leu Glu Ala Glu Glu His Asp Asp Asn Gln Leu Gly Met His Met Tyr
                325                 330                 335

Leu Lys Gly Leu Leu His Arg Ser Glu Asp Tyr Phe Tyr Lys Ser Ile
            340                 345                 350

Arg His Phe Lys Leu Ser Gly Asp Lys Phe Ser Val Gly Phe Pro Leu
        355                 360                 365

Leu Glu Leu Glu Lys Leu Gly Ala Asp Lys Leu Ile Leu Glu Val Leu
    370                 375                 380

Ala Ile
385


<210> SEQ ID NO 202
<211> LENGTH: 392
<212> TYPE: PRT
<213> ORGANISM: Bacillus amyloliquefaciens

<400> SEQUENCE: 202

Met Ser Gln Tyr Thr Lys Phe Ala Gln Glu Leu Lys Tyr Leu Leu Asp
1               5                   10                  15

Asn Glu Lys Ile Thr Met Asn Gly Ile Leu Asp Ser Thr Asn Leu Lys
            20                  25                  30

Thr Arg Ser Arg Leu Tyr Glu Met Val Asn Gly Lys Arg Glu Thr Leu
        35                  40                  45

Lys Asp Phe Glu Asn Ile Leu Asn Ile Ala Lys Tyr Ala Phe Pro Asp
    50                  55                  60

Thr Phe Glu Glu Gln Leu Glu Asp Tyr Ile Cys Ser Leu Ala Glu Ser
65                  70                  75                  80

Asp Pro Ser Arg Met Ile Val Val Glu Ala Met Glu Trp Ala Asp Ala
                85                  90                  95

Ser Gln Arg Asp Glu Leu Thr Asp Phe Val Val Asp Lys Leu Lys Asn
            100                 105                 110

Cys Asn Asn Ile Lys Cys Lys Glu Tyr Gly Asn Val Tyr Tyr Leu His
        115                 120                 125

Arg Gln Leu Thr Lys Gly Glu Ile Thr Ala His Glu Ala Leu Val Ala
    130                 135                 140

Ser Gly Lys Leu Gly Leu Lys Gln Met Glu Thr Val Val Phe Ser Arg
145                 150                 155                 160

Leu Met Val Leu Tyr Lys Tyr Leu Glu Leu Arg Gln Phe Asp Thr Leu
                165                 170                 175

Ser Asp Met Ala Arg Asp Ile His Ser Glu Ile Val Glu Asn Glu Ser
            180                 185                 190

Phe Ile Ser Arg Ser Tyr Ser Ser Arg Ile Gln Thr Leu Leu Ala Asn
        195                 200                 205

Met Ser Leu Thr Gln Gly Asp Leu Val Asn Thr Arg Lys His Ala Glu
    210                 215                 220

Leu Ala Val Tyr Glu Ser Asn Asn Pro Arg Phe Leu Ala Phe Gly Tyr
225                 230                 235                 240

Leu His Leu Gly Asn Ser Tyr Leu Phe Glu Ser Phe Glu Lys Ser Lys
                245                 250                 255

Glu Lys Leu Leu Met Gly Met Glu His Ala Glu Arg Tyr Pro Glu Arg
            260                 265                 270

Tyr Lys Gln Leu Arg Arg Ser Met Val Phe Leu Asp Asn Tyr Trp Asn
        275                 280                 285

Lys Gly Gln Ala Tyr Leu Asn His Asp Ser Asp Glu Ile Glu Asp Ile
```

```
    290                 295                 300

Gln Gly Ile Ile Tyr Asn His Ile Gln Asn Gly Arg Lys Glu Val Ala
305                 310                 315                 320

Leu Asp Met Leu Leu Lys Leu Glu Asp Arg Asn Gln Asn Asp Asn Leu
                325                 330                 335

Lys Gly Tyr His Tyr Tyr Phe Lys Gly Leu Ile Asp Glu Asn Ile Ser
            340                 345                 350

Asn Phe Tyr Leu Ser Val Lys His Phe Lys Leu Ser Gly Asp Lys Phe
        355                 360                 365

Cys Val Thr Leu Pro Leu Val Glu Leu Gln Lys Arg Gly Glu Asn Thr
    370                 375                 380

Gln Leu Leu Asp Leu Leu Thr Ile
385                 390


<210> SEQ ID NO 203
<211> LENGTH: 392
<212> TYPE: PRT
<213> ORGANISM: Bacillus amyloliquefaciens

<400> SEQUENCE: 203

Met Ser Gln Tyr Thr Lys Phe Ala Gln Glu Leu Lys Tyr Leu Leu Asp
1               5                   10                  15

Asn Glu Lys Ile Thr Met Asn Gly Ile Leu Asp Ser Thr Asn Leu Lys
            20                  25                  30

Thr Arg Ser Arg Leu Tyr Glu Met Val Asn Gly Lys Arg Glu Thr Leu
        35                  40                  45

Lys Asp Phe Glu Asn Ile Leu Asn Ile Ala Lys Tyr Ala Phe Pro Asp
    50                  55                  60

Thr Phe Glu Glu Gln Leu Glu Asp Tyr Ile Cys Ser Leu Ala Glu Ser
65                  70                  75                  80

Asp Pro Ser Arg Met Ile Val Val Glu Ala Met Glu Trp Ala Asp Ala
                85                  90                  95

Ser Gln Arg Asp Glu Leu Thr Asp Phe Val Val Asp Lys Leu Lys Asn
            100                 105                 110

Cys Asn Asn Ile Lys Cys Lys Glu Tyr Gly Asn Val Tyr Tyr Leu His
        115                 120                 125

Arg Gln Leu Thr Lys Gly Glu Ile Thr Ala His Glu Ala Leu Val Ala
    130                 135                 140

Ser Gly Lys Leu Gly Leu Lys Gln Met Glu Thr Val Val Phe Ser Arg
145                 150                 155                 160

Leu Met Val Leu Tyr Lys Tyr Leu Glu Leu Arg Gln Phe Asp Thr Leu
                165                 170                 175

Ser Asp Met Ala Arg Asp Ile His Ser Glu Ile Val Glu Asn Glu Ser
            180                 185                 190

Phe Ile Ser Arg Ser Tyr Ser Ser Arg Ile Gln Thr Leu Leu Ala Asn
        195                 200                 205

Met Ser Leu Thr Gln Gly Asp Leu Val Asn Thr Arg Lys His Ala Glu
    210                 215                 220

Leu Ala Val Tyr Glu Ser Asn Asn Pro Arg Phe Leu Ala Phe Gly Tyr
225                 230                 235                 240

Leu His Leu Gly Asn Ser Tyr Leu Phe Glu Ser Phe Glu Lys Ser Lys
                245                 250                 255

Glu Lys Leu Leu Met Gly Met Glu His Ala Glu Arg Tyr Pro Glu Arg
            260                 265                 270
```

```
Tyr Lys Gln Leu Arg Arg Ser Met Val Phe Leu Asp Asn Tyr Trp Asn
        275                 280                 285

Lys Gly Gln Ala Tyr Leu Asn His Asp Ser Asp Glu Ile Glu Asp Ile
    290                 295                 300

Gln Gly Ile Ile Tyr Asn His Ile Gln Asn Gly Arg Lys Glu Val Ala
305                 310                 315                 320

Leu Asp Met Leu Leu Lys Leu Glu Asp Arg Asn Gln Asn Asp Asn Leu
                325                 330                 335

Lys Gly Tyr His Tyr Tyr Phe Lys Gly Leu Ile Asp Glu Asn Ile Ser
            340                 345                 350

Asn Phe Tyr Leu Ser Val Lys His Phe Lys Leu Ser Gly Asp Lys Phe
        355                 360                 365

Cys Val Thr Leu Pro Leu Val Glu Leu Gln Lys Arg Gly Glu Asn Thr
    370                 375                 380

Gln Leu Leu Asp Leu Leu Thr Ile
385                 390


<210> SEQ ID NO 204
<211> LENGTH: 384
<212> TYPE: PRT
<213> ORGANISM: Bacillus subtilis

<400> SEQUENCE: 204

Leu Lys Leu Lys Gln Met Ile Lys Asn Glu Cys Glu Lys Asp Asn Gln
1               5                   10                  15

Leu Ala Ala Arg Leu Ala Lys Leu Ala Gly Tyr Glu Lys Val Asn Gly
            20                  25                  30

Phe Tyr Lys Phe Val Asn Thr Pro Glu Lys Glu Met Glu Asn Leu Gly
        35                  40                  45

Gly Leu Ile Lys Ile Val Lys Ser Leu Phe Ser Glu Lys Glu Glu Gln
    50                  55                  60

Leu Leu Ser Glu Tyr Phe Leu Gln Leu Asp Pro Asn Lys Lys Cys Ala
65                  70                  75                  80

Arg Gln Ser Val Glu Tyr Ser Asp Ile Asn Gln Trp Asp Ser Leu Thr
                85                  90                  95

Asp Lys Ile Ile Leu Asn Leu Cys Asn Ser Lys Asn Ala Thr Ser Gln
            100                 105                 110

Glu Trp Gly Asn Ile Tyr Ser Ile His Arg Lys Leu Asn Lys Ser Glu
        115                 120                 125

Leu Gly Leu Asn Asp Ala Ile Arg Glu Thr Gly Lys Cys Lys Ile Lys
    130                 135                 140

Thr Pro Glu Met Leu Phe Phe Ser Asn Ala Met Leu Met Tyr Glu Tyr
145                 150                 155                 160

Leu Asn Ile Gly Glu Phe Gly Leu Met Lys Ser Thr Ala Lys Leu Leu
                165                 170                 175

Asp Leu Asp Glu Leu Pro Asn Gly Phe Ile Lys Asp Ser Tyr Ala Ser
            180                 185                 190

Arg Val Ala Leu Leu Lys Ala Asn Ile Tyr Leu Asn Asp Asn Asp Leu
        195                 200                 205

Glu Lys Ser Arg Tyr Tyr Ser Glu Glu Val Ile Thr Asn Thr Asp Ile
    210                 215                 220

Glu Arg Leu Lys Val Phe Gly Tyr Leu Thr Tyr Gly Asn Thr Leu Ile
225                 230                 235                 240

Phe Glu Ser Tyr Asp Lys Ala Lys Glu Ser Tyr Glu Leu Gly Arg Thr
                245                 250                 255
```

Phe Ala Lys Thr Asn Thr His His Asp Tyr Lys Leu Arg Leu Ala Leu
260 265 270

Cys Phe Leu Asn Asn Val Trp Asn Lys Glu Asn Gln Trp Val Asp Phe
275 280 285

Asn Ser Asn Leu Val Ala Asp Gln Ile Glu Val Ala Tyr Tyr Tyr Thr
290 295 300

Asn Lys Lys Gln Tyr Asp Lys Ala Ile Ser Val Ile Ser Ser Leu Glu
305 310 315 320

Lys Arg Asp Leu Tyr Leu Tyr Asp Ala Gly Ile Leu Asp Tyr Ile Lys
325 330 335

Gly Leu Ile Tyr Gln Glu Lys Ser Tyr Phe Tyr Glu Ser Thr Ala Lys
340 345 350

Leu Lys Lys Ser Gly Asp Lys Met Phe Ile Asn Leu Pro Leu Gly Lys
355 360 365

Leu Arg Lys Met Gly Cys Asp Glu Asn Leu Leu Glu Leu Ile Leu Ile
370 375 380

<210> SEQ ID NO 205
<211> LENGTH: 346
<212> TYPE: PRT
<213> ORGANISM: Bacillus cellulosilyticus

<400> SEQUENCE: 205

Met Asn Ile Met Val Gln Lys Asp Thr Ser Phe Asn Asn Pro Asp Asn
1 5 10 15

Ile Phe Arg Thr Ser Asp Asn Leu Asp Glu Tyr Ile Lys Gly Leu Asp
20 25 30

Pro Asn Ser Tyr Leu Ala Arg Val Ala Leu Glu Tyr Thr Val Ser Asn
35 40 45

Ser Lys Ile Glu Leu His Glu Glu Leu Ile Asp Cys Leu Leu His Ser
50 55 60

Gly Asn Gln Glu Ser Lys Glu Trp Ala Glu Val Tyr Lys Ile Asp Asn
65 70 75 80

Leu Val Ser Lys Gln Glu Leu Ser Leu Pro Asp Ser Ile Thr Gln Leu
85 90 95

Thr Tyr Ile Leu Cys Ser Ser Lys Glu Met Ser Val Leu Gln Lys Ile
100 105 110

Phe Gln Leu Tyr Asn Tyr Tyr Asp Leu Lys Ala Phe Gln Met Ile Glu
115 120 125

Ile Val Ser Glu Leu Ile Asn Lys Glu Leu Lys Glu Ile Pro Asp Gly
130 135 140

Tyr Met Lys Asp Ser Leu Gln Ser Arg Leu Asp Leu Ala Met Gln Ser
145 150 155 160

Val Tyr Thr His Leu Asn Glu Leu Glu Lys Ala Arg Ile Tyr Gly Glu
165 170 175

Asn Leu Lys Asp Ile Ala Leu Thr Pro Val Met Lys Ala Ile Ala Tyr
180 185 190

Lys Asn Leu Gly Met Thr Tyr Leu Tyr Glu Asp Tyr Asp Lys Leu Cys
195 200 205

Thr Tyr Phe Glu Met Ser Leu Lys Ile Phe Lys Glu Met Asp Asn Ser
210 215 220

Asp Arg Leu Tyr Asn Val Gln Ser Lys Tyr Asn Phe Ala Gln Thr Phe
225 230 235 240

Trp Ser Tyr Pro Asp Lys Thr Val Trp Leu Arg Lys Glu Thr Ile Asp

-continued

```
            245                 250                 255

Glu Leu Gln Ile Tyr Ala Tyr Ser Leu Ile Lys Ser Gly Asn Lys Glu
            260                 265                 270

Glu Ala His Lys Ile Leu Asp Ser Thr Lys Asn Ser Leu Ser Asn Asp
        275                 280                 285

Phe Gln Phe Gly Tyr His Tyr Tyr Phe Leu Gly Leu Leu Asn Asp Asn
    290                 295                 300

Glu Lys Asn Tyr Tyr Glu Ser Val Lys Tyr Phe Ser Lys Ser Gly Asp
305                 310                 315                 320

Arg Phe Phe Arg Gln Leu Pro Leu Ile Ala Leu Lys Glu Lys Gly Val
                325                 330                 335

Asp Thr Ser Leu Leu Ser Ala Leu Ser Val
            340                 345


<210> SEQ ID NO 206
<211> LENGTH: 386
<212> TYPE: PRT
<213> ORGANISM: Bacillus subtilis

<400> SEQUENCE: 206

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270
```

```
Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 207
<211> LENGTH: 379
<212> TYPE: PRT
<213> ORGANISM: Bacillus amyloliquefaciens

<400> SEQUENCE: 207

Met Asn Leu Lys Gln Met Ile Lys Asn Glu Cys Glu Lys Asp Asn Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Ser Ala
65                  70                  75                  80

Arg Gln Ser Val Glu Tyr Ser Asp Ile Asn Gln Trp Asp Thr Leu Thr
                85                  90                  95

Asp Lys Ile Ile Leu Asn Leu Ser Asn Ser Lys Asn Thr Thr Ser Gln
            100                 105                 110

Glu Trp Gly Asn Ile Tyr Ser Ile His Arg Lys Leu Tyr Lys Asn Glu
        115                 120                 125

Ile Ser Ile Pro Glu Ala Ile Arg Glu Cys Gly Arg Cys Lys Ala Pro
    130                 135                 140

Glu Met Ser Phe Phe Ser Asp Ala Met Leu Met Tyr Lys Tyr Leu Asn
145                 150                 155                 160

Ile Gly Glu Phe Gly Leu Met Lys Ser Thr Leu Thr Leu Leu Asp Phe
                165                 170                 175

Ser Ser Leu Pro Glu Gly Phe Ile Lys Asp Ser Tyr Lys Ser Arg Val
            180                 185                 190

Ser Met Leu Gln Ala Asn Ile Ser Leu Asn Glu Asn Asn Leu Ile Glu
        195                 200                 205

Ala Arg Lys His Ser Asn Ile Ala Ile Met Gln Ser Asn Val Asn Arg
    210                 215                 220

Ile Cys Phe Phe Ala His Leu Thr Ile Gly Asn Thr Leu Ile Phe Glu
225                 230                 235                 240

Asn Tyr Glu Glu Ala Met Leu Ala Tyr Ile Glu Ala Lys Lys Tyr Val
                245                 250                 255
```

```
Leu Asn Asp Thr His Lys Glu Met Leu Asn Gly Ala Leu Cys Phe Leu
            260                 265                 270

Ala Asn Val Trp Asn Lys Glu Asn Pro Trp Val Asn Tyr Glu Ser Asp
        275                 280                 285

Asp Ile Lys Tyr Gln Gln Leu Arg Ala Phe Tyr Tyr Ile Lys Asn Asn
    290                 295                 300

Asn Leu Asp Lys Ala Asn Glu Leu Leu Glu Ser Leu Ser Asn Arg Asp
305                 310                 315                 320

Gln Asp Glu Asn Glu Leu Gly Phe Tyr Phe Tyr Tyr Lys Gly Leu Ile
                325                 330                 335

Ser Lys Gln Lys Ser Asp Phe Tyr Lys Ser Ile Thr Tyr Phe Lys Lys
            340                 345                 350

Ser Asp Asp Lys Tyr Phe Ile Gln Leu Thr Ile Ile Glu Leu Glu Lys
        355                 360                 365

Leu Gly Cys Asp Pro Glu Leu Leu Asn Leu Ile
    370                 375


<210> SEQ ID NO 208
<211> LENGTH: 386
<212> TYPE: PRT
<213> ORGANISM: Bacillus subtilis

<400> SEQUENCE: 208

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Val Leu Ile Asp Ser Met Ile Ser Cys Ser Asn Met Lys Ser
            100                 105                 110

Lys Glu Tyr Gly Lys Val Tyr Lys Ile His Arg Glu Leu Ser Asn Ser
        115                 120                 125

Val Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
```

-continued

```
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Glu Ser Ile Met Asp Leu Gln Glu Gln Ala His Cys
    290                 295                 300

Phe Ile Asn Phe Asn Glu Asn Ser Lys Ala Lys Lys Val Leu Asp Lys
305                 310                 315                 320

Leu Asp Leu Leu Arg His Asn Asp Asn Glu Leu Ala Met His His Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385


<210> SEQ ID NO 209
<211> LENGTH: 386
<212> TYPE: PRT
<213> ORGANISM: Bacillus amyloliquefaciens

<400> SEQUENCE: 209

Met Glu Leu Ile Arg Ile Ala Met Arg Lys Asp Leu Glu Asn Asp Lys
1               5                   10                  15

Ser Leu Met Ser Lys Trp Ala Ala Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Asn Ser Ile Val Asn Ile Val Lys Thr His Tyr Pro Asp Gln Glu Tyr
    50                  55                  60

Glu Leu Met Glu Asn Tyr Cys Leu Leu Leu Asp Pro Asn Thr Lys Ala
65                  70                  75                  80

Ala Arg Ser Ala Leu Glu Tyr Ala Asp Ala Asn Ser Phe Asn Thr Leu
                85                  90                  95

Thr Asp Lys Leu Val Glu Lys Met Ser Ile Ala Ser Asn Leu Lys Ser
            100                 105                 110

Lys Glu Tyr Gly Lys Ile Tyr Glu Ile His Arg Lys Leu Ser Arg Gly
        115                 120                 125

Glu Ile Asp Val Leu Glu Ala Ser Lys Asn Ile Gly Lys Tyr Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Ser Leu Leu Lys Gln
                165                 170                 175

Ile Asp Leu Asn Asp Ile Lys Glu Asn Asn Tyr Leu Lys Lys Ser Phe
            180                 185                 190

Glu Thr Arg Ile Tyr Val Leu Leu Ser Asn Ile Tyr Leu Asn Glu Asn
        195                 200                 205

Glu Leu Glu Leu Ser Arg Lys Tyr Ala Glu Lys Ala Ile Lys Ser Thr
    210                 215                 220
```

Asp Thr Lys Arg Phe Leu Val Phe Ser Tyr Leu Thr Ile Gly Thr Ser
225 230 235 240

Tyr Ile Phe Ser Asp Tyr Ala Leu Ser Lys Gln Asn Tyr Leu Ser Gly
245 250 255

Tyr Glu Ile Ala Lys Gly Asn Ser Val Phe Glu Glu Phe Phe Lys Arg
260 265 270

Asn Leu Ser Phe Leu Asn Asn Phe Trp Asn Lys Glu Asn Pro Trp Ile
275 280 285

Asn Tyr Asp Ser Asn Ala Val Thr Asp Val Gln Glu Val Ile Phe Glu
290 295 300

Leu Ile Asn Gln Lys Lys Leu Glu Arg Ala Leu Thr Leu Leu Lys Ser
305 310 315 320

Leu Glu Arg Lys Lys Gln Asn Glu Asn Asp Leu Gly Phe His Tyr Tyr
325 330 335

Leu Glu Gly Leu Ile Thr Asn Asp Lys Glu Ala Phe Tyr Lys Ser Val
340 345 350

Glu Tyr Phe Lys Leu Ser Gln Asp Lys Leu Phe Ile Lys Met Pro Leu
355 360 365

Ile Lys Leu Glu Ser Leu Gly Glu Asn Pro Arg Leu Leu Lys Ile Ile
370 375 380

Ser Met
385

<210> SEQ ID NO 210
<211> LENGTH: 320
<212> TYPE: PRT
<213> ORGANISM: Bacillus amyloliquefaciens

<400> SEQUENCE: 210

Met Ile Ala Lys Glu Arg Glu Ala Lys Lys Pro Lys Val Asp Ala Lys
1 5 10 15

Val Arg Leu Glu Met Ser Asp Ile Asn Glu Gln Tyr Glu Leu Thr Asp
20 25 30

Thr Leu Ile Asp Gln Leu Ile Asn Ser Thr Cys Ser Ile Glu Arg Glu
35 40 45

Trp Ala Ala Met Tyr Gln Ile Lys Arg Lys Gln Asp Arg Gly Glu Ile
50 55 60

Asn Ala His Gln Ala Leu Lys Ala Ile Gly Lys Leu Asp Pro Lys Ser
65 70 75 80

Gln Glu Met Arg Val Phe Thr Tyr Ile Ile Pro Leu Tyr Tyr Tyr Leu
85 90 95

Arg Met Ala Glu Tyr Ser Asn Leu Ala Glu Met Ser Met Ile Val Asp
100 105 110

Leu Asp Phe Ile Glu Asn Asn Glu Gln Ile Lys Ser Ser Phe Tyr Tyr
115 120 125

Arg Leu Met Ala Leu Leu Gly Ala Ser Ala Phe Ser Gln Asn Lys Met
130 135 140

Thr Gln Ala Arg Phe Tyr Cys Ser Tyr Gly Ile Asn Val Thr Asn Ile
145 150 155 160

Asp Arg Leu Val Ala Tyr Ser Tyr Leu Thr Met Gly Asn Thr Tyr Leu
165 170 175

Leu Asp Asp Tyr Glu Lys Ala Lys Glu Tyr Tyr Leu Ala Gly Leu Lys
180 185 190

His Thr Glu Asn Asn Pro Leu Ala Lys Leu Gln Leu Thr Arg Ser Leu
195 200 205

```
Cys Phe Leu Glu Asn His Trp Asn Gln Glu Asn Phe Trp Leu Asn Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Lys
    290                 295                 300

Leu Arg Glu Met Gly Glu Asp Glu Gln Ile Leu Asp Leu Leu Ala Leu
305                 310                 315                 320


<210> SEQ ID NO 211
<211> LENGTH: 320
<212> TYPE: PRT
<213> ORGANISM: Bacillus amyloliquefaciens

<400> SEQUENCE: 211

Met Leu Thr Lys Glu Arg Glu Val Glu Lys Lys Val Asn Asp Leu Lys
1               5                   10                  15

Val Gln Leu Glu Met Ser Asp Ile Asn Glu Glu Tyr Glu Thr Thr Asp
            20                  25                  30

Lys Leu Ile Asp Gln Leu Asn Asn Ser Lys Cys Pro Ile Glu Arg Glu
        35                  40                  45

Trp Ala Thr Leu Tyr Gln Ile Lys Arg Lys Gln Asp Arg Gly Glu Ile
    50                  55                  60

Asn Ala His Glu Ala Leu Lys Ala Ile Gly Gln Phe Asp Pro Lys Thr
65                  70                  75                  80

Pro Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Thr Ile Val Asp
            100                 105                 110

Val Asp Ser Ile Glu Gln Asn Gln Val Ile Arg Asp Ser Tyr Tyr Asn
        115                 120                 125

Arg Leu Gln Ala Leu Leu Ala Ala Ser Ala Phe Ser Gln His Lys Leu
    130                 135                 140

Thr Arg Ala Arg Phe His Cys Thr Tyr Gly Ile Asn Cys Thr Asn Thr
145                 150                 155                 160

Asp Arg Leu Ile Ala Tyr Ser Tyr Leu Thr Met Gly Asn Thr Tyr Ile
                165                 170                 175

Leu Ser Asn Tyr Glu Lys Ala Lys Glu Asn Phe Ile Lys Gly Leu Glu
            180                 185                 190

Lys Ser Met Lys Asn Pro Glu Arg Lys Thr Gln Leu Thr Arg Ser Leu
        195                 200                 205

Ala Phe Leu Glu Asn Tyr Trp Gly Lys Glu Asn Lys Trp Ile Asn Arg
    210                 215                 220

Gln Ser Lys Glu Gln Asp Asp Leu Tyr Gly Gln Val Phe Glu Leu Ile
225                 230                 235                 240

Val Lys Lys Glu Asn Asp Gln Ala Ile Ala Leu Leu Asp Glu Leu Phe
                245                 250                 255

Glu Ser Gly Leu Ser Asp Asn Gln Leu Gly Phe His Tyr Tyr Tyr Leu
```

```
            260                 265                 270

Gly Leu Ile His Asp Lys Glu Asp Tyr Phe Leu Lys Ser Val Glu His
        275                 280                 285

Phe Lys Lys Ser Gly Glu Lys His Phe Leu Glu Cys Pro Ile Thr Glu
    290                 295                 300

Leu Arg Arg Leu Gly Thr Asp Ser Arg Leu Leu Asp Leu Leu Val Leu
305                 310                 315                 320


<210> SEQ ID NO 212
<211> LENGTH: 384
<212> TYPE: PRT
<213> ORGANISM: Bacillus amyloliquefaciens

<400> SEQUENCE: 212

Met Asn Leu Lys Gln Met Ile Lys Asn Glu Cys Glu Lys Asp Asn Gln
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Ser Ala
65                  70                  75                  80

Arg Gln Ser Val Glu Tyr Ala Asp Leu Asn Gln Trp Asn Ala Leu Thr
                85                  90                  95

Asp Lys Ile Val Ser Asn Leu Cys Glu Ser Ser Asn Ser Ile Ser Arg
            100                 105                 110

Glu Trp Gly Gln Val Tyr Ser Leu His Arg Lys Leu Asn Asn Asn Lys
        115                 120                 125

Ile Ser Ile Asn Glu Ala Ile Arg Glu Thr Gly Lys Tyr Arg Ile Lys
    130                 135                 140

Ser Pro Glu Met Tyr Ser Phe Ser Asn Ile Met Ile Met Tyr Glu Tyr
145                 150                 155                 160

Leu Lys Ile Gly Glu Phe Gly Leu Met Lys Ser Thr Ala Gln Phe Leu
                165                 170                 175

Glu Ile Asp Glu Leu Ser Asp Gly Phe Ile Lys Asp Ser Tyr Ser Gly
            180                 185                 190

Arg Ile Glu Leu Leu Lys Ala Asn Ile Ser Leu Asn Asp Tyr Glu Leu
        195                 200                 205

Glu Glu Thr Arg Lys His Cys Ser Ala Val Ile Glu Glu Cys Asn Asn
    210                 215                 220

Asn Arg Leu Ile Val Phe Ser Tyr Leu Thr Leu Gly Asn Thr Tyr Ile
225                 230                 235                 240

Phe Glu Asp Tyr Ala Lys Ala Lys Leu Cys Tyr Glu Lys Gly Leu Asn
                245                 250                 255

Phe Ala Lys Asp Asn Ser His His His Tyr Lys Leu Arg Leu Ala Leu
            260                 265                 270

Cys Phe Leu Asp Asn Val Trp Ala Arg Glu Asn Lys Trp Val Asp Phe
        275                 280                 285

Glu Ser Gln Glu Ile Pro Asp Met Ile Glu Ala Ala Phe Tyr Leu Thr
    290                 295                 300

Asn Thr Lys Glu Thr Lys Lys Ala Glu Asp Val Ile Lys Lys Ile Glu
305                 310                 315                 320
```

```
Glu His Asp Val Leu Asp Asp Asp Leu Gly Phe Leu Tyr His Val Lys
                325                 330                 335

Gly Leu Leu Tyr Asn Asp Met Ser His Phe His Glu Ser Ile Lys Lys
            340                 345                 350

Phe Lys Lys Ser Gly Asp Arg Leu Cys Leu Asn Leu Pro Leu Ile Glu
        355                 360                 365

Leu Lys Lys Arg Gly Tyr Ser Asp Glu Ile Leu Asn Leu Ile Ala Leu
    370                 375                 380


<210> SEQ ID NO 213
<211> LENGTH: 379
<212> TYPE: PRT
<213> ORGANISM: Bacillus subtilis

<400> SEQUENCE: 213

Met Lys Lys Asp Leu Glu Asn Asp Asn Ser Leu Met Asn Lys Trp Ala
1               5                   10                  15

Thr Val Ala Gly Leu Lys Asn Pro Asn Pro Leu Tyr Asp Phe Leu Asn
            20                  25                  30

His Asp Gly Lys Thr Phe Asn Glu Phe Ser Ser Ile Val Asn Ile Val
        35                  40                  45

Lys Ser Gln Tyr Pro Asp Arg Glu Tyr Glu Leu Met Lys Asp Tyr Cys
    50                  55                  60

Leu Asn Leu Asp Val Lys Thr Lys Ala Ala Arg Ser Ala Leu Glu Tyr
65                  70                  75                  80

Ala Asp Ala Asn Met Phe Phe Glu Ile Glu Asp Val Leu Ile Asp Ser
                85                  90                  95

Met Ile Ser Cys Ser Asn Met Lys Ser Lys Glu Tyr Gly Lys Val Tyr
            100                 105                 110

Lys Ile His Arg Glu Leu Ser Asn Ser Val Ile Thr Glu Phe Glu Ala
        115                 120                 125

Val Lys Arg Leu Gly Lys Leu Asn Ile Lys Thr Pro Glu Met Asn Ser
    130                 135                 140

Phe Ser Arg Leu Leu Leu Leu Tyr His Tyr Leu Ser Thr Gly Asn Phe
145                 150                 155                 160

Ser Pro Met Ala Gln Leu Ile Lys Gln Ile Asp Leu Ser Glu Ile Ser
                165                 170                 175

Glu Asn Met Tyr Ile Arg Asn Thr Tyr Gln Thr Arg Val His Val Leu
            180                 185                 190

Met Ser Asn Ile Lys Leu Asn Glu Asn Ser Leu Glu Glu Cys Arg Glu
        195                 200                 205

Tyr Ser Lys Lys Ala Leu Glu Ser Thr Asn Ile Leu Arg Phe Gln Val
    210                 215                 220

Phe Ser Tyr Leu Thr Ile Gly Asn Ser Leu Leu Phe Ser Asn Tyr Glu
225                 230                 235                 240

Leu Ala Gln Glu Asn Phe Leu Lys Gly Leu Ser Ile Ser Val Gln Asn
                245                 250                 255

Glu Asn Tyr Asn Met Ile Phe Gln Gln Ala Leu Cys Phe Leu Asn Asn
            260                 265                 270

Val Trp Arg Lys Glu Asn Lys Trp Ile Asn Phe Glu Ser Asp Ser Ile
        275                 280                 285

Met Asp Leu Gln Glu Gln Ala His Cys Phe Ile Asn Phe Asn Glu Asn
    290                 295                 300

Ser Lys Ala Lys Glu Val Leu Asp Lys Leu Asp Leu Leu Val His Asn
305                 310                 315                 320
```

```
Asp Asn Glu Leu Ala Met His Tyr Tyr Leu Lys Gly Arg Leu Glu Gln
                325                 330                 335

Asn Lys Ala Cys Phe Tyr Ser Ser Ile Glu Tyr Phe Lys Lys Ser Asn
            340                 345                 350

Asp Lys Phe Leu Ile Arg Leu Pro Leu Leu Glu Leu Gln Lys Met Gly
        355                 360                 365

Glu Asn Gln Lys Leu Leu Glu Leu Leu Leu Leu
    370                 375


<210> SEQ ID NO 214
<211> LENGTH: 320
<212> TYPE: PRT
<213> ORGANISM: Bacillus amyloliquefaciens

<400> SEQUENCE: 214

Met Ile Ala Lys Glu Arg Glu Ala Lys Lys Pro Lys Val Asp Ala Lys
1               5                   10                  15

Val Arg Leu Glu Met Ser Asp Ile Asn Glu Gln Tyr Glu Leu Thr Asp
            20                  25                  30

Thr Leu Ile Asp Gln Leu Ile Asn Ser Thr Cys Ser Ile Glu Arg Glu
        35                  40                  45

Trp Ala Ala Met Tyr Gln Ile Lys Arg Lys Gln Asp Arg Gly Glu Ile
    50                  55                  60

Asn Ala His Gln Ala Leu Lys Ala Ile Gly Lys Leu Asp Pro Lys Ser
65                  70                  75                  80

Gln Glu Met Arg Val Phe Thr Tyr Ile Ile Pro Leu Tyr Tyr Tyr Leu
                85                  90                  95

Arg Met Ala Glu Tyr Ser Asn Leu Ala Glu Met Ser Met Ile Val Asp
            100                 105                 110

Leu Asp Phe Ile Glu Asn Asn Glu Gln Ile Lys Ser Ser Phe Tyr Tyr
        115                 120                 125

Arg Leu Met Ala Leu Leu Gly Ala Ser Ala Phe Ser Gln Asn Lys Met
    130                 135                 140

Thr Gln Ala Arg Phe Tyr Cys Ser Tyr Gly Ile Asn Val Thr Asn Ile
145                 150                 155                 160

Asp Arg Leu Val Ala Tyr Ser Tyr Leu Thr Met Gly Asn Thr Tyr Leu
                165                 170                 175

Leu Asp Asp Tyr Glu Lys Ala Lys Glu Tyr Tyr Leu Ala Gly Leu Lys
            180                 185                 190

His Thr Glu Asn Asn Pro Leu Ala Lys Leu Gln Leu Thr Arg Ser Leu
        195                 200                 205

Cys Phe Leu Glu Asn His Trp Asn Gln Glu Asn Phe Trp Leu Asn Pro
    210                 215                 220

Asp Ser Asn Glu Val Thr Asp Ile Gln Glu Ile Ala His Tyr His Ile
225                 230                 235                 240

Lys Lys Asn Asn Leu Gln Gln Ala Lys Glu Ile Leu Glu Asn Leu Glu
                245                 250                 255

Gln Gln Pro Asn Ile His Asn Asp Phe Gly Ile His Phe Tyr Leu Lys
            260                 265                 270

Gly Leu Ala Tyr Glu Asp Lys Arg Phe Phe Tyr Glu Ser Ile Lys His
        275                 280                 285

Phe Lys Leu Ser Gly Asp Leu Tyr Ser Val Arg Leu Pro Leu Asp Lys
    290                 295                 300

Leu Arg Glu Met Gly Glu Asp Glu Gln Ile Leu Asp Leu Leu Ala Leu
```

305 310 315 320

<210> SEQ ID NO 215
<211> LENGTH: 320
<212> TYPE: PRT
<213> ORGANISM: Bacillus amyloliquefaciens

<400> SEQUENCE: 215

Met Leu Thr Lys Glu Arg Glu Val Glu Lys Lys Val Asn Asp Leu Lys
1 5 10 15

Val Gln Leu Glu Met Ser Asp Ile Asn Glu Glu Tyr Glu Thr Thr Asp
20 25 30

Lys Leu Ile Asp Gln Leu Asn Asn Ser Lys Cys Pro Ile Glu Arg Glu
35 40 45

Trp Ala Thr Leu Tyr Gln Ile Lys Arg Lys Gln Asp Arg Gly Glu Ile
50 55 60

Asn Ala His Glu Ala Leu Lys Ala Ile Gly Gln Phe Asp Pro Lys Thr
65 70 75 80

Pro Glu Met Arg Val Phe Thr Tyr Ile Ile Pro Leu Tyr Tyr Tyr Leu
85 90 95

Arg Met Ala Glu Tyr Ser Asn Leu Ala Glu Met Ser Thr Ile Val Asp
100 105 110

Val Asp Ser Ile Glu Gln Asn Gln Val Ile Arg Asp Ser Tyr Tyr Asn
115 120 125

Arg Leu Gln Ala Leu Leu Ala Ala Ser Ala Phe Ser Gln His Lys Leu
130 135 140

Thr Arg Ala Arg Phe His Cys Thr Tyr Gly Ile Asn Cys Thr Asn Thr
145 150 155 160

Asp Arg Leu Ile Ala Tyr Ser Tyr Leu Thr Met Gly Asn Thr Tyr Ile
165 170 175

Leu Ser Asn Tyr Glu Lys Ala Lys Glu Asn Phe Ile Lys Gly Leu Glu
180 185 190

Lys Ser Met Lys Asn Pro Glu Arg Lys Thr Gln Leu Thr Arg Ser Leu
195 200 205

Ala Phe Leu Glu Asn Tyr Trp Gly Lys Glu Asn Lys Trp Ile Asn Arg
210 215 220

Gln Ser Lys Glu Gln Asp Asp Leu Tyr Gly Gln Val Phe Glu Leu Ile
225 230 235 240

Val Lys Lys Glu Asn Asp Gln Ala Ile Ala Leu Leu Asp Glu Leu Phe
245 250 255

Glu Ser Gly Leu Ser Asp Asn Gln Leu Gly Phe His Tyr Tyr Tyr Leu
260 265 270

Gly Leu Ile His Asp Lys Glu Asp Tyr Phe Leu Lys Ser Val Glu His
275 280 285

Phe Lys Lys Ser Gly Glu Lys His Phe Leu Glu Cys Pro Ile Thr Glu
290 295 300

Leu Arg Arg Leu Gly Thr Asp Ser Arg Leu Leu Asp Leu Leu Val Leu
305 310 315 320

<210> SEQ ID NO 216
<211> LENGTH: 384
<212> TYPE: PRT
<213> ORGANISM: Bacillus amyloliquefaciens

<400> SEQUENCE: 216

Met Asn Leu Lys Gln Met Ile Lys Asn Glu Cys Glu Lys Asp Asn Gln

-continued

```
1               5                   10                  15

Leu Ala Ala Lys Leu Ser Lys Ile Ala Gly Tyr Glu Lys Val Asn Gly
            20                  25                  30

Phe Tyr Lys Phe Ile Asn Thr Pro Glu Lys Glu Met Asp Asn Leu Gly
        35                  40                  45

Gly Leu Ile Asn Ile Val Lys Ser Leu Phe Pro Asp Asn Glu Glu Gln
    50                  55                  60

Leu Leu Ser Asp Tyr Phe Leu Ser Leu Asp Pro Asn Lys Lys Ser Ala
65                  70                  75                  80

Arg Gln Ser Val Glu Tyr Ala Asp Leu Asn Gln Trp Asn Ala Leu Thr
                85                  90                  95

Asp Lys Ile Val Ser Asn Leu Cys Glu Ser Ser Asn Ser Ile Ser Arg
            100                 105                 110

Glu Trp Gly Gln Val Tyr Ser Leu His Arg Lys Leu Asn Asn Asn Lys
        115                 120                 125

Ile Ser Ile Asn Glu Ala Ile Arg Glu Thr Gly Lys Tyr Arg Ile Lys
    130                 135                 140

Ser Pro Glu Met Tyr Ser Phe Ser Asn Ile Met Ile Met Tyr Glu Tyr
145                 150                 155                 160

Leu Lys Ile Gly Glu Phe Gly Leu Met Lys Ser Thr Ala Gln Phe Leu
                165                 170                 175

Glu Ile Asp Glu Leu Ser Asp Gly Phe Ile Lys Asp Ser Tyr Ser Gly
            180                 185                 190

Arg Ile Glu Leu Leu Lys Ala Asn Ile Ser Leu Asn Asp Tyr Glu Leu
        195                 200                 205

Glu Glu Thr Arg Lys His Cys Ser Ala Val Ile Glu Glu Cys Asn Asn
    210                 215                 220

Asn Arg Leu Ile Val Phe Ser Tyr Leu Thr Leu Gly Asn Thr Tyr Ile
225                 230                 235                 240

Phe Glu Asp Tyr Ala Lys Ala Lys Leu Cys Tyr Glu Lys Gly Leu Asn
                245                 250                 255

Phe Ala Lys Asp Asn Ser His His His Tyr Lys Leu Arg Leu Ala Leu
            260                 265                 270

Cys Phe Leu Asp Asn Val Trp Ala Arg Glu Asn Lys Trp Val Asp Phe
        275                 280                 285

Glu Ser Gln Glu Ile Pro Asp Met Ile Glu Ala Ala Phe Tyr Leu Thr
    290                 295                 300

Asn Thr Lys Glu Thr Lys Lys Ala Glu Asp Val Ile Lys Lys Ile Glu
305                 310                 315                 320

Glu His Asp Val Leu Asp Asp Asp Leu Gly Phe Leu Tyr His Val Lys
                325                 330                 335

Gly Leu Leu Tyr Asn Asp Met Ser His Phe His Glu Ser Ile Lys Lys
            340                 345                 350

Phe Lys Lys Ser Gly Asp Arg Leu Cys Leu Asn Leu Pro Leu Ile Glu
        355                 360                 365

Leu Lys Lys Arg Gly Tyr Ser Asp Glu Ile Leu Asn Leu Ile Ala Leu
    370                 375                 380
```

<210> SEQ ID NO 217
<211> LENGTH: 336
<212> TYPE: PRT
<213> ORGANISM: Bacillus vallismortis

<400> SEQUENCE: 217

-continued

Met Asp Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asn Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Ala Leu Ile Glu Ser Met Ile Ser Cys Ser Asn Met Lys Ser
            100                 105                 110

Lys Glu Tyr Gly Lys Val Tyr Lys Ile His Arg Glu Leu Ser Asn Phe
        115                 120                 125

Asp Ile Thr Glu Phe Glu Ala Val Lys Arg Leu Gly Lys Leu Asn Ile
    130                 135                 140

Lys Thr Pro Glu Met Asn Ser Phe Ser Arg Leu Leu Leu Leu Tyr His
145                 150                 155                 160

Tyr Leu Ser Thr Gly Asn Phe Ser Pro Met Ala Gln Leu Ile Lys Gln
                165                 170                 175

Ile Asp Leu Ser Glu Ile Ser Glu Asn Met Tyr Ile Arg Asn Thr Tyr
            180                 185                 190

Gln Thr Arg Val His Val Leu Met Ser Asn Ile Lys Leu Asn Glu Asn
        195                 200                 205

Ser Leu Glu Glu Cys Arg Glu Tyr Ser Arg Met Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Val Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Glu Ser Ile Met Asp Leu Gln Glu Gln Ala His Cys
    290                 295                 300

Phe Ile Asn Phe Asn Glu Asn Ser Lys Ala Lys Lys Phe Trp Ile Asn
305                 310                 315                 320

Tyr Ile Phe Tyr Val Ile Thr Ile Met Ser Leu Gln Cys Ile Ile Ile
                325                 330                 335

<210> SEQ ID NO 218
<211> LENGTH: 297
<212> TYPE: PRT
<213> ORGANISM: Bacillus atrophaeus

<400> SEQUENCE: 218

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

```
Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295


<210> SEQ ID NO 219
<211> LENGTH: 297
<212> TYPE: PRT
<213> ORGANISM: Bacillus atrophaeus

<400> SEQUENCE: 219

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
```

```
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295


<210> SEQ ID NO 220
<211> LENGTH: 297
<212> TYPE: PRT
<213> ORGANISM: Bacillus atrophaeus

<400> SEQUENCE: 220

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190
```

```
Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295
```

<210> SEQ ID NO 221
<211> LENGTH: 297
<212> TYPE: PRT
<213> ORGANISM: Bacillus atrophaeus

<400> SEQUENCE: 221

```
Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270
```

```
Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295
```

<210> SEQ ID NO 222
<211> LENGTH: 297
<212> TYPE: PRT
<213> ORGANISM: Bacillus atrophaeus

<400> SEQUENCE: 222

```
Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
        115                 120                 125

Glu Ile Asp Val Leu Glu Ala Thr Lys Asn Ile Gly Lys Gln Arg Ile
    130                 135                 140

Lys Thr Asp Glu Met Asn Ile Phe Ser Lys Met Ile Pro Met Tyr Asp
145                 150                 155                 160

Tyr Leu Ser Lys Gly Asn Phe Ser Pro Met Lys Pro Leu Leu Lys Gln
                165                 170                 175

Ile Asn Leu Asn Glu Ile Lys Glu Asn Lys Tyr Leu Lys Lys Ser Phe
            180                 185                 190

Glu Thr Arg Ile His Val Leu Leu Ser Asn Met Tyr Leu Asn Glu Asn
        195                 200                 205

Lys Leu Glu Leu Cys Arg Glu Tyr Ala Lys Lys Ala Ile Gln Ser Thr
    210                 215                 220

Ser Thr Lys Arg Phe Leu Val Phe Ser Tyr Leu Thr Ile Gly Thr Ser
225                 230                 235                 240

Tyr Ile Phe Leu Asp Tyr Asn Leu Ser Arg Gln Asn Tyr Leu Ser Gly
                245                 250                 255

Tyr Glu Ile Ser Lys Gly Asn Asn Val Phe Glu Glu Phe Phe Lys Arg
            260                 265                 270

Asn Leu Ser Phe Leu Asn Asn Tyr Trp Asn Lys Glu Asn Ser Trp Ile
        275                 280                 285

Asn Tyr Asp Ser Asp Arg Arg Ser Asp
    290                 295
```

<210> SEQ ID NO 223
<211> LENGTH: 386
<212> TYPE: PRT
<213> ORGANISM: Bacillus subtilis

<400> SEQUENCE: 223

Met Glu Leu Ile Arg Ile Ala Met Lys Lys Asp Leu Glu Asn Asp Asn
1               5                   10                  15

Ser Leu Met Asn Lys Trp Ala Thr Val Ala Gly Leu Lys Asn Pro Asn
            20                  25                  30

Pro Leu Tyr Asp Phe Leu Asn His Asp Gly Lys Thr Phe Asn Glu Phe
        35                  40                  45

Ser Ser Ile Val Asn Ile Val Lys Ser Gln Tyr Pro Asp Arg Glu Tyr
    50                  55                  60

Glu Leu Met Lys Asp Tyr Cys Leu Asn Leu Asp Val Lys Thr Lys Ala
65                  70                  75                  80

Ala Arg Ser Ala Leu Glu Tyr Ala Asp Ala Asn Met Phe Phe Glu Ile
                85                  90                  95

Glu Asp Ala Leu Ile Asp Ser Met Ile Ser Cys Ser Asn Met Lys Ser
            100                 105                 110

Lys Glu Tyr Gly Lys Val Tyr Lys Ile His Arg Glu Leu Ser Lys Gly
        115                 120                 125

Glu Ile Asp Val Phe Glu Ala Ser Ala Asn Ile Gly Lys Gln Arg Ile
    130                 135                 140

Lys Thr Ala Glu Met Asn Ile Phe Ser Lys Met Leu Leu Met Tyr Asp
145                 150                 155                 160

Cys Leu Asn Lys Gly Asn Phe Ala Pro Met Met Leu Leu Phe Gln Gln
                165                 170                 175

Ile Asp Leu Ser Glu Ile Lys Glu Asn Arg Tyr Leu Lys Asn Ser Phe
            180                 185                 190

Glu Thr Arg Ile Asn Val Leu Leu Ser Asn Ile Tyr Leu Asn Glu Asn
        195                 200                 205

Asn Leu Glu Leu Cys Arg Glu Tyr Ala Gln Lys Ala Ile Ser Ser Thr
    210                 215                 220

Asp Thr Gln Arg Phe Leu Val Phe Ser Tyr Leu Thr Ile Gly Thr Ser
225                 230                 235                 240

Tyr Ile Phe Ser Asp Phe Asn Leu Ser Lys Gln Asn Tyr Leu Ile Gly
                245                 250                 255

Leu Lys Phe Ala Lys Gly Asn Pro Gly Phe Glu Glu Phe Phe Lys Arg
            260                 265                 270

Asn Leu Ser Phe Leu Asn Asn Phe Trp Asn Lys Glu Asn Glu Trp Ile
        275                 280                 285

Asn Tyr Asp Ser Asp Ala Val Thr Asp Met Gln Glu Val Ile Phe Glu
    290                 295                 300

Leu Ile Asn His Lys Glu Leu Ser Lys Ala Leu Gln Leu Leu Asn Lys
305                 310                 315                 320

Leu Glu Glu Arg Asp Gln Asn Glu Asn Glu Leu Gly Phe His Tyr Tyr
                325                 330                 335

Leu Lys Gly Leu Ile Thr Asn Glu Lys Glu Ala Phe Phe Lys Ser Val
            340                 345                 350

Glu Tyr Phe Lys Ala Ser Gln Asp Lys Leu Ser Ile Lys Met Pro Leu
        355                 360                 365

Ile Gln Leu Glu Lys Met Gly Glu Asn Pro Arg Leu Leu Lys Ile Ile
    370                 375                 380

Thr Met
385

<210> SEQ ID NO 224
<211> LENGTH: 238

<212> TYPE: PRT
<213> ORGANISM: Bacillus subtilis

<400> SEQUENCE: 224

Glu Met Leu Val Phe Ser Asn Ala Met Leu Met Tyr Ala Tyr Leu Asn
1               5                   10                  15

Ile Gly Asp Phe His Leu Leu Lys Ser Thr Phe Asp Leu Leu Asp Ile
            20                  25                  30

Asp Glu Leu Pro Glu Gly Tyr Val Lys Glu Ser Tyr Tyr Gly Arg Ala
        35                  40                  45

Ala Leu Leu His Ala Asn Val Ser Leu Asn Glu Asn Asp Ile Leu Ser
    50                  55                  60

Ala Arg His Tyr Ser Ser Tyr Val Leu Glu Lys Ala Asn Asn Asp Arg
65                  70                  75                  80

Phe Met Val Phe Gly His Leu Thr Ser Gly Asn Thr Tyr Val Phe Glu
                85                  90                  95

Asp Tyr Asp Lys Ala Lys Asp His Tyr Leu Lys Gly Leu Arg Tyr Ala
            100                 105                 110

Asn Thr Asn Pro Phe His Tyr Tyr Lys Leu Arg Leu Ala Leu Cys Phe
        115                 120                 125

Leu Asn Asn Val Trp Lys Lys Glu Asn Lys Trp Val Asp Phe Glu Ser
    130                 135                 140

Asn Glu Ile Thr Asp Arg Ile Glu Val Ala Tyr Tyr Tyr Val Asn Gln
145                 150                 155                 160

Asn Glu Glu Gln Lys Ala Ile Lys Val Phe Gln Glu Leu Asp Ser Arg
                165                 170                 175

Lys Ile Pro Lys Asp Asp Leu Gly Phe Leu Phe Tyr Val Lys Gly Leu
            180                 185                 190

Leu His Gln Glu Lys Ser Tyr Phe Tyr Glu Ser Ile Glu Phe Phe Lys
        195                 200                 205

Lys Ser Gly Asp Lys Met Phe Val Asn Leu Pro Leu Met Glu Leu Lys
    210                 215                 220

Lys Gln Gly Glu Asn Glu Arg Leu Leu Gln Leu Leu Thr Ile
225                 230                 235

<210> SEQ ID NO 225
<211> LENGTH: 297
<212> TYPE: PRT
<213> ORGANISM: Bacillus atrophaeus

<400> SEQUENCE: 225

Met Glu Leu Ile Arg Lys Ala Met Arg Lys Asp Leu Glu Asn Asp Lys
1               5                   10                  15

Thr Leu Met Ser Lys Trp Ala Thr Val Ala Gly Leu Lys Asn Pro Asn
            20                  25                  30

Pro Leu Tyr Asp Phe Leu Asn His Asp Gly Lys Thr Phe Ser Glu Phe
        35                  40                  45

Ser Thr Leu Val Asn Ile Val Lys Ser Gln Tyr Pro Asp Arg Glu Tyr
    50                  55                  60

Glu Leu Met Glu Asp Tyr Cys Leu Ile Leu Asp Pro Lys Thr Lys Ala
65                  70                  75                  80

Ala Arg Ser Ala Leu Lys Tyr Ala Asp Ala Asn Ser Phe Asn Asp Leu
                85                  90                  95

Thr Asp Lys Leu Val Asp Lys Met Ser Ile Ser Ser Asn Leu Lys Ser
            100                 105                 110

Lys Glu Tyr Gly Lys Ile Tyr Gly Ile His Arg Lys Leu Ser Lys Gly
115 120 125

Glu Ile Asp Val Leu Glu Ala Thr Lys Asn Ile Gly Lys Gln Arg Ile
130 135 140

Lys Thr Asp Glu Met Asn Ile Phe Ser Lys Met Ile Pro Met Tyr Asp
145 150 155 160

Tyr Leu Ser Lys Gly Asn Phe Ser Pro Met Lys Pro Leu Leu Lys Gln
165 170 175

Ile Asn Leu Asn Glu Ile Lys Glu Asn Lys Tyr Leu Lys Lys Ser Phe
180 185 190

Glu Thr Arg Ile His Val Leu Leu Ser Asn Met Tyr Leu Asn Glu Asn
195 200 205

Lys Leu Glu Leu Cys Arg Glu Tyr Ala Lys Lys Ala Ile Gln Ser Thr
210 215 220

Ser Thr Lys Arg Phe Leu Val Phe Ser Tyr Leu Thr Ile Gly Thr Ser
225 230 235 240

Tyr Ile Phe Leu Asp Tyr Asn Leu Ser Arg Gln Asn Tyr Leu Ser Gly
245 250 255

Tyr Glu Ile Ser Lys Gly Asn Asn Val Phe Glu Glu Phe Phe Lys Arg
260 265 270

Asn Leu Ser Phe Leu Asn Asn Tyr Trp Asn Lys Glu Asn Ser Trp Ile
275 280 285

Asn Tyr Asp Ser Asp Arg Arg Ser Asp
290 295

<210> SEQ ID NO 226
<211> LENGTH: 386
<212> TYPE: PRT
<213> ORGANISM: Bacillus sp.

<400> SEQUENCE: 226

Met Glu Leu Ile Arg Ile Ala Met Lys Lys Asp Leu Glu Asn Asp Asn
1 5 10 15

Ser Leu Met Asn Lys Trp Ala Thr Val Ala Gly Leu Lys Asn Pro Asn
20 25 30

Pro Leu Tyr Asp Phe Leu Asn His Asp Gly Lys Thr Phe Asn Glu Phe
35 40 45

Ser Ser Ile Val Asn Ile Val Lys Ser Gln Tyr Pro Asp Arg Glu Tyr
50 55 60

Glu Leu Met Lys Asp Tyr Cys Leu Asn Leu Asp Val Lys Thr Lys Ala
65 70 75 80

Ala Arg Ser Ala Leu Glu Tyr Ala Asp Ala Asn Met Phe Phe Glu Ile
85 90 95

Glu Asp Val Leu Ile Asp Ser Met Ile Ser Cys Ser Asn Met Lys Ser
100 105 110

Lys Glu Tyr Gly Lys Val Tyr Lys Ile His Arg Glu Leu Ser Asn Ser
115 120 125

Val Ile Thr Glu Phe Glu Ala Val Lys Arg Leu Gly Lys Leu Asn Ile
130 135 140

Lys Thr Pro Glu Met Asn Ser Phe Ser Arg Leu Leu Leu Leu Tyr His
145 150 155 160

Tyr Leu Ser Thr Gly Asn Phe Ser Pro Met Ala Gln Leu Ile Lys Gln
165 170 175

Ile Asp Leu Ser Glu Ile Ser Glu Asn Met Tyr Ile Arg Asn Thr Tyr
180 185 190

Gln Thr Arg Val His Val Leu Met Ser Asn Ile Lys Leu Asn Glu Asn
        195                 200                 205

Ser Leu Glu Glu Cys Arg Glu Tyr Ser Lys Lys Ala Leu Glu Ser Thr
    210                 215                 220

Asn Ile Leu Arg Phe Gln Val Phe Ser Tyr Leu Thr Ile Gly Asn Ser
225                 230                 235                 240

Leu Leu Phe Ser Asn Tyr Glu Leu Ala Gln Glu Asn Phe Leu Lys Gly
                245                 250                 255

Leu Ser Ile Ser Val Gln Asn Glu Asn Tyr Asn Met Ile Phe Gln Gln
            260                 265                 270

Ala Leu Cys Phe Leu Asn Asn Val Trp Arg Lys Glu Asn Lys Trp Ile
        275                 280                 285

Asn Phe Glu Ser Asp Ser Ile Met Asp Leu Gln Glu Gln Ala His Cys
    290                 295                 300

Phe Ile Asn Phe Asn Glu Asn Ser Lys Ala Lys Glu Val Leu Asp Lys
305                 310                 315                 320

Leu Asp Leu Leu Val His Asn Asp Asn Glu Leu Ala Met His Tyr Tyr
                325                 330                 335

Leu Lys Gly Arg Leu Glu Gln Asn Lys Ala Cys Phe Tyr Ser Ser Ile
            340                 345                 350

Glu Tyr Phe Lys Lys Ser Asn Asp Lys Phe Leu Ile Arg Leu Pro Leu
        355                 360                 365

Leu Glu Leu Gln Lys Met Gly Glu Asn Gln Lys Leu Leu Glu Leu Leu
    370                 375                 380

Leu Leu
385

<210> SEQ ID NO 227
<211> LENGTH: 43
<212> TYPE: PRT
<213> ORGANISM: Artificial sequence
<220> FEATURE:
<223> OTHER INFORMATION: Associated AimP amino acid sequence

<400> SEQUENCE: 227

Met Lys Lys Val Phe Phe Gly Leu Val Ile Leu Thr Ala Leu Ala Ile
1               5                   10                  15

Ser Phe Val Ala Gly Gln Gln Ser Val Ser Thr Ala Ser Ala Ser Asp
            20                  25                  30

Glu Val Thr Val Ala Ser Ala Ile Arg Gly Ala
        35                  40

<210> SEQ ID NO 228
<211> LENGTH: 43
<212> TYPE: PRT
<213> ORGANISM: Artificial sequence
<220> FEATURE:
<223> OTHER INFORMATION: Associated AimP amino acid sequence

<400> SEQUENCE: 228

Leu Lys Lys Thr Ile Leu Gly Val Ala Ile Ile Ala Ala Leu Ala Leu
1               5                   10                  15

Ser Phe Val Ala Gly Gln Lys Ser Val Ser Thr Ala Ala Pro Asn Asp
            20                  25                  30

Glu Ile Ser Val Ala Ser Ile Ile Arg Gly Ala
        35                  40

<210> SEQ ID NO 229
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 229

Met Lys Lys Leu Ile Met Ala Leu Val Ile Leu Gly Ala Leu Gly Thr
1 5 10 15

Ser Phe Ile Ser Ala Asp Ser Ser Ile Arg Gln Ala Ser Gly Asp Tyr
20 25 30

Glu Val Ala Gly Met Pro Arg Gly Ala
35 40

<210> SEQ ID NO 230
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 230

Met Lys Lys Leu Ile Met Ala Leu Val Ile Leu Gly Ala Leu Gly Thr
1 5 10 15

Ser Tyr Ile Ser Ala Asp Ser Ser Ile Gln Gln Ala Ser Gly Asp Tyr
20 25 30

Glu Val Ala Gly Met Pro Arg Gly Ala
35 40

<210> SEQ ID NO 231
<211> LENGTH: 44
<212> TYPE: PRT
<213> ORGANISM: Artificial sequence
<220> FEATURE:
<223> OTHER INFORMATION: Associated AimP amino acid sequence

<400> SEQUENCE: 231

Met Lys Lys Val Phe Ile Gly Leu Thr Ile Val Ala Ser Leu Ala Val
1 5 10 15

Gly Phe Val Ala Gly Gln Gln Thr Thr Ile His Ser Ala Ser Gly Glu
20 25 30

Gly Thr Phe His Val Ala Gly Phe Gly Arg Gly Ala
35 40

<210> SEQ ID NO 232
<211> LENGTH: 38
<212> TYPE: PRT
<213> ORGANISM: Artificial sequence
<220> FEATURE:
<223> OTHER INFORMATION: Associated AimP amino acid sequence

<400> SEQUENCE: 232

Met Lys Lys Leu Leu Ile Gly Ile Phe Val Ser Ala Thr Leu Leu Ala
1 5 10 15

Val Gly Tyr Val Ala Ser Gln Val Asn Asn Ser Gly Tyr Ser Ile Ala
20 25 30

Gly Phe Thr Val Gly Ala
35

<210> SEQ ID NO 233
<211> LENGTH: 43
<212> TYPE: PRT

<213> ORGANISM: Artificial sequence
<220> FEATURE:
<223> OTHER INFORMATION: Associated AimP amino acid sequence

<400> SEQUENCE: 233

Met Lys Lys Lys Ile Thr Met Ser Val Ile Val Leu Ala Ala Ile Val
1 5 10 15

Thr Val Val Leu Gly Ser Val Gln His Gln Glu Ala Lys Ser His Thr
20 25 30

Val Asn Gln Leu Ala Asp Pro Gly Arg Gly Gly
35 40

<210> SEQ ID NO 234
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 234

Met Lys Lys Leu Val Met Ala Leu Val Leu Leu Ala Ala Val Ala Gly
1 5 10 15

Val Phe Ser Gly Thr Gln Gln Ser Ile Ala Leu Asp Asp Glu Lys Val
20 25 30

Ser Thr Ser Ser Ala Ser Arg Gly Ala
35 40

<210> SEQ ID NO 235
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 235

Met Lys Lys Phe Asn Cys Ala Ile Val Ile Leu Leu Ala Leu Thr Val
1 5 10 15

Gly Phe Val Ser Gly Gln Gln Ser Val Gln Thr Ala Asn Gly Asp Ile
20 25 30

Thr Val Ala Ser Ala Ser Arg Gly Ala
35 40

<210> SEQ ID NO 236
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 236

Met Lys Lys Phe Asn Cys Ala Ile Val Ile Leu Leu Ala Leu Ala Val
1 5 10 15

Gly Phe Val Ser Gly Gln Gln Ser Val Gln Thr Ala Asn Gly Asp Ile
20 25 30

Thr Val Ala Ser Ala Ser Arg Gly Ala
35 40

<210> SEQ ID NO 237
<211> LENGTH: 42
<212> TYPE: PRT
<213> ORGANISM: Artificial sequence
<220> FEATURE:
<223> OTHER INFORMATION: Associated AimP amino acid sequence

<400> SEQUENCE: 237

Met Lys Lys Ile Phe Met Gly Ile Thr Ile Ala Ala Val Leu Met Phe
1               5                   10                  15

Ser Tyr Ala Ser Val Lys Leu Ala Ser Asn Glu Gln Thr Leu Gly Asp
            20                  25                  30

Tyr Glu Val Ala Gly Val Val Arg Gly Ala
        35                  40

<210> SEQ ID NO 238
<211> LENGTH: 46
<212> TYPE: PRT
<213> ORGANISM: Artificial sequence
<220> FEATURE:
<223> OTHER INFORMATION: Associated AimP amino acid sequence

<400> SEQUENCE: 238

Met Lys Asn Ile Ile Leu Gly Ile Val Ile Leu Leu Ala Met Ala Val
1               5                   10                  15

Gly Phe Val Ala Gly Gln Gln Ser Ile Glu Thr Ala Ser Val Asp His
            20                  25                  30

Val Asp Gln Pro Val Lys Val Ala Ser Pro Ser Arg Gly Ala
        35                  40                  45

<210> SEQ ID NO 239
<211> LENGTH: 44
<212> TYPE: PRT
<213> ORGANISM: Artificial sequence
<220> FEATURE:
<223> OTHER INFORMATION: Associated AimP amino acid sequence

<400> SEQUENCE: 239

Met Lys Lys Val Phe Ile Gly Leu Thr Ile Val Ala Ser Leu Ala Val
1               5                   10                  15

Gly Phe Val Ala Gly Gln Gln Thr Thr Ile His Thr Ala Ser Gly Glu
            20                  25                  30

Glu Thr Phe His Val Ala Gly Phe Gly Arg Gly Ala
        35                  40

<210> SEQ ID NO 240
<211> LENGTH: 44
<212> TYPE: PRT
<213> ORGANISM: Artificial sequence
<220> FEATURE:
<223> OTHER INFORMATION: Associated AimP amino acid sequence

<400> SEQUENCE: 240

Met Lys Lys Val Phe Ile Gly Leu Thr Ile Val Ala Ser Leu Ala Val
1               5                   10                  15

Gly Phe Val Ala Gly Gln Gln Thr Thr Ile His Ser Ala Ser Gly Glu
            20                  25                  30

Glu Thr Phe His Val Ala Gly Phe Gly Arg Gly Ala
        35                  40

<210> SEQ ID NO 241
<211> LENGTH: 45
<212> TYPE: PRT
<213> ORGANISM: Artificial sequence
<220> FEATURE:
<223> OTHER INFORMATION: Associated AimP amino acid sequence

<400> SEQUENCE: 241

Met Lys Lys Val Phe Ile Gly Leu Thr Ile Val Ala Ser Leu Ala Val
1 5 10 15

Gly Phe Val Ala Gly Gln Gln Thr Thr Ile His Asn Ala Ala Ser Gly
20 25 30

Glu Glu Thr Phe His Val Ala Gly Phe Gly Arg Gly Ala
35 40 45

<210> SEQ ID NO 242
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 242

Met Lys Lys Thr Ala Leu Phe Leu Ile Val Ala Val Thr Ile Phe Ser
1 5 10 15

Val Gly Phe Ala Ser Gly Gln Thr Ser Glu Gln Ala Ile Glu Phe Ile
20 25 30

Lys Thr Ala Ala Met Gly Asn Gly Gly
35 40

<210> SEQ ID NO 243
<211> LENGTH: 46
<212> TYPE: PRT
<213> ORGANISM: Artificial sequence
<220> FEATURE:
<223> OTHER INFORMATION: Associated AimP amino acid sequence

<400> SEQUENCE: 243

Met Ser Met Lys Ile Lys Leu Gly Leu Ala Ala Gly Ala Val Ala Leu
1 5 10 15

Phe Val Ala Gly Tyr Ala Thr Asn Gln Ala Val Lys Asp Val Ala Ala
20 25 30

Gly Gln Asp Thr Val Phe Lys Val Ala Thr Ile Gly Arg Gly
35 40 45

<210> SEQ ID NO 244
<211> LENGTH: 42
<212> TYPE: PRT
<213> ORGANISM: Artificial sequence
<220> FEATURE:
<223> OTHER INFORMATION: Associated AimP amino acid sequence

<400> SEQUENCE: 244

Met Lys Lys Val Phe Ile Gly Leu Thr Ile Val Ala Ala Leu Ala Val
1 5 10 15

Ala Phe Val Ala Gly Gln His Ser Gln Val Asp Thr Ala Ser Gly Ser
20 25 30

Val Ser Val Ala Ser Ala Ser Arg Gly Ala
35 40

<210> SEQ ID NO 245
<211> LENGTH: 43
<212> TYPE: PRT
<213> ORGANISM: Artificial sequence
<220> FEATURE:
<223> OTHER INFORMATION: Associated AimP amino acid sequence

<400> SEQUENCE: 245

Met Lys Lys Ile Ile Phe Gly Thr Ala Ile Leu Ala Ala Leu Ala Ile
1 5 10 15

Ser Phe Ile Ala Gly Gln His Ser Val Asn Thr Ala Ser Val Ser Asp
20 25 30

Glu Ile Ser Val Ala Ser Ala Ile Arg Gly Ala
35 40

<210> SEQ ID NO 246
<211> LENGTH: 43
<212> TYPE: PRT
<213> ORGANISM: Artificial sequence
<220> FEATURE:
<223> OTHER INFORMATION: Associated AimP amino acid sequence

<400> SEQUENCE: 246

Met Lys Lys Ile Ile Phe Gly Thr Ala Ile Leu Ala Ser Leu Ala Ile
1 5 10 15

Ser Phe Ile Ala Gly Gln His Ser Val Asn Thr Ala Ser Ala Ser Asp
20 25 30

Glu Ile Ser Val Ala Ser Ala Ile Arg Gly Ala
35 40

<210> SEQ ID NO 247
<211> LENGTH: 47
<212> TYPE: PRT
<213> ORGANISM: Artificial sequence
<220> FEATURE:
<223> OTHER INFORMATION: Associated AimP amino acid sequence

<400> SEQUENCE: 247

Met Lys Asn Lys Leu Lys Ile Gly Leu Ala Val Ala Val Leu Ser Val
1 5 10 15

Ser Val Ile Gly Phe Val Ala Asn Lys Ala Met Asn Ala Ala Ala Asp
20 25 30

Ala Lys Glu Pro Gln Phe Lys Val Ala Thr Ile Gly Arg Gly Gly
35 40 45

<210> SEQ ID NO 248
<211> LENGTH: 37
<212> TYPE: PRT
<213> ORGANISM: Artificial sequence
<220> FEATURE:
<223> OTHER INFORMATION: Associated AimP amino acid sequence

<400> SEQUENCE: 248

Met Lys Lys Leu Phe Val Gly Ile Val Val Ser Val Ser Leu Leu Ala
1 5 10 15

Val Gly Ile Ala Ala Ala Gln Ile Asn Ser Gly Phe Ser Val Ala Gly
20 25 30

Phe Thr Val Gly Ala
35

<210> SEQ ID NO 249
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 249

Met Lys Lys Leu Val Met Ala Leu Val Leu Val Ala Ala Val Ala Gly
1 5 10 15

Val Phe Ser Gly Thr Gln Gln Ser Ile Ala Met Asp Ala Glu Lys Val
20 25 30

```
Ser Thr Ser Ser Ala Ser Arg Gly Ala
        35                  40


<210> SEQ ID NO 250
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 250

Met Lys Lys Trp Leu Phe Ser Ile Ala Val Val Ala Ala Leu Leu Ile
1               5                   10                  15

Thr Gly Val Ala Val Ala Glu Ser Thr His Gln Ala Glu Gly Gly Tyr
            20                  25                  30

Tyr Ile Ala Gly Phe Pro Arg Gly Ala
        35                  40


<210> SEQ ID NO 251
<211> LENGTH: 37
<212> TYPE: PRT
<213> ORGANISM: Artificial sequence
<220> FEATURE:
<223> OTHER INFORMATION: Associated AimP amino acid sequence

<400> SEQUENCE: 251

Met Lys Lys Leu Phe Val Gly Ile Val Val Ser Val Ser Leu Leu Ala
1               5                   10                  15

Val Gly Ile Ala Ala Ala Gln Val Asn Ser Gly Phe Ser Val Ala Gly
            20                  25                  30

Phe Thr Val Gly Ala
        35


<210> SEQ ID NO 252
<211> LENGTH: 37
<212> TYPE: PRT
<213> ORGANISM: Artificial sequence
<220> FEATURE:
<223> OTHER INFORMATION: Associated AimP amino acid sequence

<400> SEQUENCE: 252

Met Lys Lys Leu Phe Val Gly Ile Val Val Ser Val Thr Leu Leu Ala
1               5                   10                  15

Val Gly Ile Ala Ala Ala Lys Ile Asn Ser Gly Phe Ser Val Ala Gly
            20                  25                  30

Phe Thr Val Gly Ala
        35


<210> SEQ ID NO 253
<211> LENGTH: 37
<212> TYPE: PRT
<213> ORGANISM: Artificial sequence
<220> FEATURE:
<223> OTHER INFORMATION: Associated AimP amino acid sequence

<400> SEQUENCE: 253

Met Lys Lys Leu Phe Val Gly Ile Val Val Ser Val Ser Leu Leu Ala
1               5                   10                  15

Val Gly Ile Ala Ala Ser Gln Ile Asn Ser Gly Phe Ser Val Ala Gly
            20                  25                  30

Phe Thr Val Gly Ala
        35
```

<210> SEQ ID NO 254
<211> LENGTH: 46
<212> TYPE: PRT
<213> ORGANISM: Artificial sequence
<220> FEATURE:
<223> OTHER INFORMATION: Associated AimP amino acid sequence

<400> SEQUENCE: 254

Met Ala Lys Lys Met Lys Leu Gly Leu Ala Thr Ala Ala Val Ala Leu
1 5 10 15

Phe Leu Ala Gly Tyr Ala Thr Asn Leu Val Val Ser Asp Val Ala Ala
20 25 30

Gly Lys Gly Asp Val Phe Lys Val Ala Thr Ile Gly Arg Gly
35 40 45

<210> SEQ ID NO 255
<211> LENGTH: 42
<212> TYPE: PRT
<213> ORGANISM: Artificial sequence
<220> FEATURE:
<223> OTHER INFORMATION: Associated AimP amino acid sequence

<400> SEQUENCE: 255

Met Lys Lys Leu Phe Met Gly Ile Thr Ile Ala Ala Val Leu Met Phe
1 5 10 15

Ser Tyr Ala Ser Val Lys Leu Val Ser Asn Glu Gln Ala Ser Gly Asp
20 25 30

Tyr Glu Val Ala Gly Val Val Arg Gly Ala
35 40

<210> SEQ ID NO 256
<211> LENGTH: 44
<212> TYPE: PRT
<213> ORGANISM: Artificial sequence
<220> FEATURE:
<223> OTHER INFORMATION: Associated AimP amino acid sequence

<400> SEQUENCE: 256

Met Lys Lys Val Thr Ile Gly Leu Thr Ile Val Ala Ala Leu Ala Ile
1 5 10 15

Gly Phe Val Ala Gly Gln Gln Ser Gly Leu His Ser Ala Ser Gly Asn
20 25 30

Glu Thr Phe His Val Ala Gly Phe Gly Arg Gly Ala
35 40

<210> SEQ ID NO 257
<211> LENGTH: 44
<212> TYPE: PRT
<213> ORGANISM: Artificial sequence
<220> FEATURE:
<223> OTHER INFORMATION: Associated AimP amino acid sequence

<400> SEQUENCE: 257

Met Lys Lys Val Thr Ile Gly Leu Thr Ile Val Ala Ala Leu Thr Ile
1 5 10 15

Gly Phe Val Ala Gly Gln Gln Ser Gly Leu His Ser Ala Ser Gly Asn
20 25 30

Lys Thr Phe His Val Ala Gly Phe Gly Arg Gly Ala
35 40

<210> SEQ ID NO 258
<211> LENGTH: 40

<212> TYPE: PRT
<213> ORGANISM: Artificial sequence
<220> FEATURE:
<223> OTHER INFORMATION: Associated AimP amino acid sequence

<400> SEQUENCE: 258

```
Met Lys Lys Val Phe Ala Leu Thr Ile Val Ala Ala Ala Ile Phe Phe
1               5                   10                  15

Gly Gly Val Val Thr Gly Thr Gln Ile Asn Ser Ala Ser Asp Phe Asn
            20                  25                  30

Thr Ala Gly Phe Gly His Gly Ala
        35                  40
```

<210> SEQ ID NO 259
<211> LENGTH: 40
<212> TYPE: PRT
<213> ORGANISM: Artificial sequence
<220> FEATURE:
<223> OTHER INFORMATION: Associated AimP amino acid sequence

<400> SEQUENCE: 259

```
Met Lys Lys Val Phe Ala Leu Thr Ile Val Val Ala Ala Ile Phe Phe
1               5                   10                  15

Gly Gly Val Ala Thr Gly Thr Gln Ile Asp Thr Ala Ser Asp Tyr Ser
            20                  25                  30

Thr Ala Gly Phe Gly Arg Gly Ala
        35                  40
```

<210> SEQ ID NO 260
<211> LENGTH: 41
<212> TYPE: PRT
<213> ORGANISM: Artificial sequence
<220> FEATURE:
<223> OTHER INFORMATION: Associated AimP amino acid sequence

<400> SEQUENCE: 260

```
Met Lys Lys Val Leu Ile Gly Leu Thr Ile Val Ala Ala Leu Thr Val
1               5                   10                  15

Gly Phe Val Gly Gly Gln Tyr Ser Val Asn Asn Ala Ser Gly Asp Val
            20                  25                  30

Gln Val Ala Ser Ile Gly His Gly Ala
        35                  40
```

<210> SEQ ID NO 261
<211> LENGTH: 43
<212> TYPE: PRT
<213> ORGANISM: Artificial sequence
<220> FEATURE:
<223> OTHER INFORMATION: Associated AimP amino acid sequence

<400> SEQUENCE: 261

```
Met Lys Lys Val Leu Tyr Ser Leu Ile Ile Val Ile Ala Leu Ala Val
1               5                   10                  15

Gly Phe Val Gly Gly Gln Lys Ser Met Glu Thr Ala Ser Val Asp Gln
            20                  25                  30

Pro Ile Lys Val Ala Ser Pro Ser Arg Gly Ala
        35                  40
```

<210> SEQ ID NO 262
<211> LENGTH: 71
<212> TYPE: PRT
<213> ORGANISM: Artificial sequence
<220> FEATURE:

<223> OTHER INFORMATION: Associated AimP amino acid sequence

<400> SEQUENCE: 262

```
Met Lys Lys Phe Ile Lys Gly Leu Ile Ile Ala Val Thr Leu Val Ala
1               5                   10                  15

Ala Ser Thr Ser Ile Pro Thr Ser Ser Val Ala Tyr Asp Val Asp Phe
            20                  25                  30

Arg Val Arg Ser Ile Glu Val Val Asp Val Gln Pro Leu Tyr Asp Val
        35                  40                  45

Asp Phe Arg Val Arg Ser Val Glu Gln Phe Asp Val Gln Pro Leu Tyr
    50                  55                  60

Asp Val Asp Phe Arg Val Arg
65                  70
```

<210> SEQ ID NO 263
<211> LENGTH: 43
<212> TYPE: PRT
<213> ORGANISM: Artificial sequence
<220> FEATURE:
<223> OTHER INFORMATION: Associated AimP amino acid sequence

<400> SEQUENCE: 263

```
Met Lys Lys Ile Ile Phe Gly Thr Ala Ile Leu Ala Ala Leu Ala Ile
1               5                   10                  15

Ser Phe Ile Ala Gly Gln His Ser Val Asn Thr Ala Ser Ala Ser Asp
            20                  25                  30

Glu Ile Ser Val Ala Ser Ala Ile Arg Gly Ala
        35                  40
```

<210> SEQ ID NO 264
<211> LENGTH: 44
<212> TYPE: PRT
<213> ORGANISM: Artificial sequence
<220> FEATURE:
<223> OTHER INFORMATION: Associated AimP amino acid sequence

<400> SEQUENCE: 264

```
Met Lys Lys Val Phe Ile Cys Leu Thr Ile Val Ala Ser Leu Ala Val
1               5                   10                  15

Gly Phe Ile Ala Gly Gln Gln Thr Thr Ile His Ser Ala Ser Gly Glu
            20                  25                  30

Glu Thr Phe His Val Ala Gly Phe Gly Arg Gly Ala
        35                  40
```

<210> SEQ ID NO 265
<211> LENGTH: 40
<212> TYPE: PRT
<213> ORGANISM: Artificial sequence
<220> FEATURE:
<223> OTHER INFORMATION: Associated AimP amino acid sequence

<400> SEQUENCE: 265

```
Met Lys Lys Val Leu Ile Gly Leu Ala Ile Val Ala Ala Leu Ala Val
1               5                   10                  15

Gly Phe Val Gly Gly Gln His Phe Lys Thr Ala Ser Gly Asp Ile Gln
            20                  25                  30

Met Ala Asn Pro Gly Arg Gly Ala
        35                  40
```

<210> SEQ ID NO 266
<211> LENGTH: 41

<212> TYPE: PRT
<213> ORGANISM: Artificial sequence
<220> FEATURE:
<223> OTHER INFORMATION: Associated AimP amino acid sequence

<400> SEQUENCE: 266

Met Lys Lys Leu Ile Met Ala Leu Val Ile Leu Gly Ala Leu Gly Thr
1               5                   10                  15

Ser Tyr Ile Ser Ala Asp Ser Ser Asn Gln Gln Ala Ser Gly Asp Tyr
            20                  25                  30

Glu Val Ala Gly Met Pro Arg Gly Ala
        35                  40

<210> SEQ ID NO 267
<211> LENGTH: 48
<212> TYPE: PRT
<213> ORGANISM: Artificial sequence
<220> FEATURE:
<223> OTHER INFORMATION: Associated AimP amino acid sequence

<400> SEQUENCE: 267

Met Lys Gly Gly Asp Lys Met Lys Lys Phe Ile Met Ala Ile Thr Ile
1               5                   10                  15

Ala Ala Val Leu Ser Ile Ser Phe Val Gly Ala Lys Ala Ser Ser Asn
            20                  25                  30

Glu Gln Ala Ser Gly Asp Tyr Gln Val Ala Gly Ile Val Arg Gly Ala
        35                  40                  45

<210> SEQ ID NO 268
<211> LENGTH: 42
<212> TYPE: PRT
<213> ORGANISM: Artificial sequence
<220> FEATURE:
<223> OTHER INFORMATION: Associated AimP amino acid sequence

<400> SEQUENCE: 268

Met Lys Lys Val Phe Ile Gly Leu Ala Ile Val Ala Ala Leu Ala Val
1               5                   10                  15

Ala Phe Val Ala Gly Gln His Ser Gln Thr Asp Asn Ala Ser Gly Asn
            20                  25                  30

Val Ser Val Ala Ser Ala Ser Arg Gly Ala
        35                  40

<210> SEQ ID NO 269
<211> LENGTH: 6
<212> TYPE: PRT
<213> ORGANISM: Artificial sequence
<220> FEATURE:
<223> OTHER INFORMATION: peptide

<400> SEQUENCE: 269

Ser Ala Ile Arg Gly Ala
1               5

<210> SEQ ID NO 270
<211> LENGTH: 6
<212> TYPE: PRT
<213> ORGANISM: Artificial sequence
<220> FEATURE:
<223> OTHER INFORMATION: peptide

<400> SEQUENCE: 270

Ser Ile Ile Arg Gly Ala
1               5

<210> SEQ ID NO 271
<211> LENGTH: 6
<212> TYPE: PRT
<213> ORGANISM: Artificial sequence
<220> FEATURE:
<223> OTHER INFORMATION: peptide

<400> SEQUENCE: 271

Gly Met Pro Arg Gly Ala
1               5

<210> SEQ ID NO 272
<211> LENGTH: 6
<212> TYPE: PRT
<213> ORGANISM: Artificial sequence
<220> FEATURE:
<223> OTHER INFORMATION: peptide

<400> SEQUENCE: 272

Gly Phe Gly Arg Gly Ala
1               5

<210> SEQ ID NO 273
<211> LENGTH: 6
<212> TYPE: PRT
<213> ORGANISM: Artificial sequence
<220> FEATURE:
<223> OTHER INFORMATION: peptide

<400> SEQUENCE: 273

Gly Phe Thr Val Gly Ala
1               5

<210> SEQ ID NO 274
<211> LENGTH: 6
<212> TYPE: PRT
<213> ORGANISM: Artificial sequence
<220> FEATURE:
<223> OTHER INFORMATION: peptide

<400> SEQUENCE: 274

Asp Pro Gly Arg Gly Gly
1               5

<210> SEQ ID NO 275
<211> LENGTH: 6
<212> TYPE: PRT
<213> ORGANISM: Artificial sequence
<220> FEATURE:
<223> OTHER INFORMATION: peptide

<400> SEQUENCE: 275

Ser Ala Ser Arg Gly Ala
1               5

<210> SEQ ID NO 276
<211> LENGTH: 6
<212> TYPE: PRT
<213> ORGANISM: Artificial sequence
<220> FEATURE:
<223> OTHER INFORMATION: peptide

<400> SEQUENCE: 276

Gly Val Val Arg Gly Ala
1               5

<210> SEQ ID NO 277
<211> LENGTH: 6
<212> TYPE: PRT
<213> ORGANISM: Artificial sequence
<220> FEATURE:
<223> OTHER INFORMATION: peptide

<400> SEQUENCE: 277

Ser Pro Ser Arg Gly Ala
1               5

<210> SEQ ID NO 278
<211> LENGTH: 6
<212> TYPE: PRT
<213> ORGANISM: Artificial sequence
<220> FEATURE:
<223> OTHER INFORMATION: peptide

<400> SEQUENCE: 278

Ala Met Gly Asn Gly Gly
1               5

<210> SEQ ID NO 279
<211> LENGTH: 5
<212> TYPE: PRT
<213> ORGANISM: Artificial sequence
<220> FEATURE:
<223> OTHER INFORMATION: peptide

<400> SEQUENCE: 279

Thr Ile Gly Arg Gly
1               5

<210> SEQ ID NO 280
<211> LENGTH: 6
<212> TYPE: PRT
<213> ORGANISM: Artificial sequence
<220> FEATURE:
<223> OTHER INFORMATION: peptide

<400> SEQUENCE: 280

Thr Ile Gly Arg Gly Gly
1               5

<210> SEQ ID NO 281
<211> LENGTH: 6
<212> TYPE: PRT
<213> ORGANISM: Artificial sequence
<220> FEATURE:
<223> OTHER INFORMATION: peptide

<400> SEQUENCE: 281

Gly Phe Pro Arg Gly Ala
1               5

<210> SEQ ID NO 282
<211> LENGTH: 6
<212> TYPE: PRT
<213> ORGANISM: Artificial sequence
<220> FEATURE:
<223> OTHER INFORMATION: peptide

<400> SEQUENCE: 282

Gly Phe Gly His Gly Ala
1               5

-continued

<210> SEQ ID NO 283
<211> LENGTH: 6
<212> TYPE: PRT
<213> ORGANISM: Artificial sequence
<220> FEATURE:
<223> OTHER INFORMATION: peptide

<400> SEQUENCE: 283

Ser Ile Gly His Gly Ala
1               5

<210> SEQ ID NO 284

<400> SEQUENCE: 284

000

<210> SEQ ID NO 285
<211> LENGTH: 6
<212> TYPE: PRT
<213> ORGANISM: Artificial sequence
<220> FEATURE:
<223> OTHER INFORMATION: peptide

<400> SEQUENCE: 285

Asn Pro Gly Arg Gly Ala
1               5

<210> SEQ ID NO 286
<211> LENGTH: 6
<212> TYPE: PRT
<213> ORGANISM: Artificial sequence
<220> FEATURE:
<223> OTHER INFORMATION: peptide

<400> SEQUENCE: 286

Gly Ile Val Arg Gly Ala
1               5

<210> SEQ ID NO 287
<211> LENGTH: 110
<212> TYPE: DNA
<213> ORGANISM: Artificial sequence
<220> FEATURE:
<223> OTHER INFORMATION: DNA bind region nucleic acid sequence

<400> SEQUENCE: 287
ttaaataatt gaataggtaa tacataatac tatcatagac gtttgatcca ttggatcagg     60
cgtcttttct aattttaagg gaaagttcca gaaattcaaa aatcaaaaaa               110

<210> SEQ ID NO 288
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 288
aaaatcacaa cagcgatact acataatcaa tggttagacg tttgatccag tggatcaggc     60
gtcttttcta attttaagag aatgttccag aaattcataa                           100

<210> SEQ ID NO 289
<211> LENGTH: 100
<212> TYPE: DNA
<213> ORGANISM: Artificial sequence
<220> FEATURE:

<223> OTHER INFORMATION: DNA bind region nucleic acid sequence

<400> SEQUENCE: 289
aatccattga cacataaagt tattagtatt attatttact caactttcgc agagtgaaat 60
cggcaaataa gccttgatat aattaggaag gctagagatc 100

<210> SEQ ID NO 290
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 290
aatccattga cacataaagt tattagtatt attatttatt taattaaatt aaacagagaa 60
aaggaagacg tttggctctt ttgagctaag cgtcttttgt 100

<210> SEQ ID NO 291
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 291
aatccattga cacataaagt tattagtatt attatttatt taattaaatt aaacagagaa 60
aagtaagacg tttggctctt ttgagctaag cgtcttttgt 100

<210> SEQ ID NO 292
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 292
aatccattga cacataaagt tattagtatt attatttatt taattaaatt agaaaaggaa 60
gacgtttggc tcttttgagc taagcgtctt ttgtagtttt 100

<210> SEQ ID NO 293
<211> LENGTH: 100
<212> TYPE: DNA
<213> ORGANISM: Artificial sequence
<220> FEATURE:
<223> OTHER INFORMATION: DNA bind region nucleic acid sequence
<220> FEATURE:
<221> NAME/KEY: misc_feature
<222> LOCATION: (38)..(38)
<223> OTHER INFORMATION: n is a, c, g, or t

<400> SEQUENCE: 293
aatccattga cacataaagt tattagtatt attatttntt taattaaatt aaacagagaa 60
aaggaagacg tttggctctt ttgagctaag cgtcttttgt 100

<210> SEQ ID NO 294
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 294
aattaaataa aagcacttta tacataactg gacgtttgac atttaagtca agcgtctttt 60
ccattttctt ataattttta ttgaaattca agttcaccat 100

<210> SEQ ID NO 295
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 295
agctacatag tgtatccaac aaaataccgg agggctattt cttagctctc ccctttatta 60
cagtttttta gaataaaaat aaaataacga ttttattcaa 100

<210> SEQ ID NO 296
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 296
atgcatagtt ggaacttagg gatagaaata tccccttttt cttgataatt ctagaattaa 60
agtatataat tatttgaata attgttgtac ataatatgac 100

<210> SEQ ID NO 297
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 297
cacaactagg aatttacata gtcaacggtt agacgtttga tccaaaggat caggcgtctt 60
ttctaattta aaggggaagt tcctatattt tataaaacca 100

<210> SEQ ID NO 298
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 298
cacaactagg aatttacata gtcaatggtt agacgtttga tccaaaggat caggcgtctt 60
ttctaattta aaggggaagt tcctatattt tataaaacca 100

<210> SEQ ID NO 299
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 299
ccattgacac atataatgac atagagtatc atttacttaa ttaaattaac caaaggaaca 60
agtggaagag acgtttggct cattgagcta agcgtctttt 100

<210> SEQ ID NO 300
<211> LENGTH: 100
<212> TYPE: DNA
<213> ORGANISM: Artificial sequence
<220> FEATURE:

<223> OTHER INFORMATION: DNA bind region nucleic acid sequence

<400> SEQUENCE: 300
cttcaaagat gatacataac ttggctagac gtttgatcca ctggatcagg cgtcttttct 60
aattttaaga gaatgttcca gaaattcata atataaaaaa 100

<210> SEQ ID NO 301
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 301
gcattacata tccatttgaa ggggtgagcg atacgttcac cccttattaa ttgtaggatg 60
gattttaact tgttatctgt cttataagtg gtgggcaaat 100

<210> SEQ ID NO 302
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 302
gcattacata tccatttgaa ggggtgagcg attcgttcac tccttattaa tcgtaggatt 60
gattttaact ggttatctgt cttataagtg gtgggcaaat 100

<210> SEQ ID NO 303
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 303
gcattacata tccatttgaa ggggtgagcg attcgttcac tccttctcat tacatatttt 60
taggataaaa ataaaataag tgaataaaag gagaaatgtt 100

<210> SEQ ID NO 304
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 304
gcattacata tctatttgaa ggggtgagcg attcgttcac tccttctcat tacatatttt 60
taggataaaa ataaaataag tggaggatca atgatgaaaa 100

<210> SEQ ID NO 305
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 305
gcgttacata tccatttgaa ggggtgaacg attcgttcac tccttctcat tacatactta 60
aaggataaaa ataaaataag tggagtgata aaagtgggaa 100

-continued

<210> SEQ ID NO 306
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 306
ggcaacggtg gatgatttac atattagaaa ggtggggaga ttgaatccct gcctttttga 60
tatatcaaga aatgatctga aaaggagaaa ttgaaatgat 100

<210> SEQ ID NO 307
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 307
gtagtagcta catagggga agtcttaaat ggctttccta ctttttaaa actttttaga 60 gtaaaaataa aataagtgaa taaaaggaga aatgttattt 100

<210> SEQ ID NO 308
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 308
gtcatacata gtaggggaag ccttaattgg ctttcctttc tattgaacta tttaggataa 60
aaataaaata agtggagaat tgttatgaca aacgaattat 100

<210> SEQ ID NO 309
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 309
taaaatccat tgacacataa agttattagt attatcattt acttaattaa attaagcaga 60
gaaaaggaag acgtttggct cttttaatga gctaagcgtc 100

<210> SEQ ID NO 310
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 310
taacacaaca ggatactaca ctacataatc aatggttagg cgtttgatcc actggatcag 60
gcgtcttttc taattttaag agaatgttcc agaaattcat 100

<210> SEQ ID NO 311
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 311
taagcattac atatccattt gaaggggtga acgattcgtt cactccttct cattacatat 60
ttttaggata aaaataaaat aagtggagga tgatgatggg 100

<210> SEQ ID NO 312
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 312
taatacaaca ggatactaca taatcaatgg ttagacgttt gatccagtgg atcaggcgtc 60
ttttctaatt ttaagagaat gttccagaaa ttcataatat 100

<210> SEQ ID NO 313
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 313
taatacatag caattaaaag tttagtttca gtacataatt aggcgtttga ctcttttgag 60
ttaagcgtct tttccatttt aaagagtttt ttatcaaaat 100

<210> SEQ ID NO 314
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 314
taatcgtttg tagtcaaggg atagaaatat ccccttttc ttgaaatttt aagaatgaca 60
atatataatc taatgaataa ttgttgtaca taatatgacg 100

<210> SEQ ID NO 315
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 315
taatgtaaat taaaagtgga atattgagta cataactgga cgtttgacac tttagtcaag 60
cgtcttttcc attttcttag aaattttatt aaaattcaaa 100

<210> SEQ ID NO 316
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 316
tacataacaa ttaaaagttt agtttcacta cataattaga cgtttgactc ttttgagtta 60
agcgtctttt ccattttaaa gagtttttta tcaaaattgc 100

<210> SEQ ID NO 317
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 317
tacatagcaa ttaaaagttt agtttcacta cataattaga cgtttgactc ttttgagtta 60
agcgtctttt ccattttaaa gagtttttta tcaaaattgc 100

<210> SEQ ID NO 318
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 318
tacatagcaa ttaaaagttt ggtttcagta cataattgga cgtttgactc tttgagttaa 60
gcgtcttttc cattttaaag agtttttat caaaattgca 100

<210> SEQ ID NO 319
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 319
tagccattga cacatataat gacatagagt atcatttact taattaaatt aaccaaagga 60
acaagtggaa gagacgtttg gctcattgag ctaagcgtct 100

<210> SEQ ID NO 320
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 320
tcaattacat atcagagcaa acggacaaat tgaccttttg ctctgattat aaggagaata 60
ttatgaacga attatcaaca gagttcaagt atgatttagt 100

<210> SEQ ID NO 321
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 321
tcattgacac ataaggggat atttagtatc atttacttaa tttaataact tagaaatgga 60
agacgtttgg ctctatcgag ctaagcgtct tttgtacttt 100

<210> SEQ ID NO 322
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 322
tccatacagc ctttaatggc tttcgttcct attaaactat ttagaataaa aataaaatta 60
gtggagattt atttgattgt aagaagaagc gtatgaattg 100

<210> SEQ ID NO 323
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 323
tccttacagc ctttaatggc tttcgttccc attaaactat ttagaataaa aataaaatta 60
gtggagattt atttgattgt aagaagaagc gtatgaattg 100

<210> SEQ ID NO 324
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 324
ttaaatgctt tacatattag aaaggtgggg agattgaatc cctgcctttt tgatatatca 60
agaaatgacc tgaaaaggag aacttgaaat gattttaaat 100

<210> SEQ ID NO 325
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 325
ttaaatgctt tacatattag aaaggtgggg agattgaatc cctgcctttt tgatatatga 60
gcgctcaggc gcacatttga tcttaaaaca aaaggagaat 100

<210> SEQ ID NO 326
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 326
ttacataggg gaaagtctta aaaggctttc ctattttttt aaaatgtttt tagagtaaaa 60
ataaaataag tggagaaatg ttatgacaaa cgaattatca 100

<210> SEQ ID NO 327
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 327
ttagaaaatt taatacatat ttgtaagacg tttgatccat tggatcaggc gtcttttcta 60
attttaaggg aaagttccag aaattcaaaa atcaaaaaat 100

<210> SEQ ID NO 328
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 328
ttcgtttatt tgaaagcaaa tggatcaaag acccatttgc tttttttgaa ctatagctca 60
ttaaaaaaac atgagataaa ttggttatct taaacctgct 100

<210> SEQ ID NO 329
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 329
tacaacagga tactacataa tcaatggtta gacgtttgat ccagtggatc aggcgtcttt 60
tctaatttta agagaatgtt ccagaaattc ataatataaa 100

<210> SEQ ID NO 330
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 330
gcattacata tccatttgaa ggggtgagcg attcgttcac tccttctcat tacatatttt 60
taggataaaa ataaaataag tggaggatta aatgtcggct 100

<210> SEQ ID NO 331
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 331
gcattacata ttcatctgga gggctacatc ttagctctcc cctttattac agttttttag 60
aataaaaata aaataacgat tttatttaaa aatgaaataa 100

<210> SEQ ID NO 332
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 332
aatccattga cacataaagt tattagtatt attatttact taattaaatt aaccagaaaa 60
ggaagacgtt tggctctttt gagctaagcg tcttttgtag 100

<210> SEQ ID NO 333
<211> LENGTH: 100
<212> TYPE: DNA
<213> ORGANISM: Artificial sequence
<220> FEATURE:
<223> OTHER INFORMATION: DNA bind region nucleic acid sequence

<400> SEQUENCE: 333
ttaaacattg acacatagaa ttattagtat tattatttac ttaattaaat taaccaaagg 60
aatggaagac gtttggctct tttgagctaa gcgtcttttg 100

<210> SEQ ID NO 334
<211> LENGTH: 100
<212> TYPE: DNA

<213> ORGANISM: Artificial sequence
<220> FEATURE:
<223> OTHER INFORMATION: DNA bind region nucleic acid sequence

<400> SEQUENCE: 334
gaaggttaca taataaaatt ccgcaacaaa aacggagagt ctttttggct ctcctcattt 60
aaaaatatta agaattaaaa taaaatgaca attttatttg 100

<210> SEQ ID NO 335
<211> LENGTH: 20
<212> TYPE: PRT
<213> ORGANISM: Artificial Sequence
<220> FEATURE:
<223> OTHER INFORMATION: consensus sequence for a helix-turn domain
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X is a hydrophobic amino acid (ALA, ILE, LEU, PHE, VAL, PRO, GLY)
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X is a hydrophobic amino acid (ALA, ILE, LEU, PHE, VAL, PRO, GLY)
<220> FEATURE:
<221> NAME/KEY: MISC_FEATURE
<222> LOCATION: (10)..(10)
<223> OTHER INFORMATION: X is a hydrophobic amino acid (ALA, ILE, LEU, PHE, VAL, PRO, GLY)
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X is a hydrophobic amino acid (ALA, ILE, LEU, PHE, VAL, PRO, GLY)
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: X is a hydrophobic amino acid (ALA, ILE, LEU, PHE, VAL, PRO, GLY)
<220> FEATURE:
<221> NAME/KEY: misc_feature
<222> LOCATION: (19)..(20)
<223> OTHER INFORMATION: Xaa can be any naturally occurring amino acid

<400> SEQUENCE: 335

```
Xaa Xaa Xaa Xaa Ala Xaa Xaa Xaa Gly Xaa Xaa Xaa Xaa Xaa Xaa Xaa
1               5                   10                  15

Xaa Xaa Xaa Xaa
            20
```

<210> SEQ ID NO 336
<211> LENGTH: 350
<212> TYPE: DNA
<213> ORGANISM: Artificial Sequence
<220> FEATURE:
<223> OTHER INFORMATION: AimX Nucleic Acid sequence

<400> SEQUENCE: 336
ttaaataatt gaataggtaa tacataatac tatcatagac gtttgatcca ttggatcagg 60
cgtcttttct aattttaagg gaaagttcca gaaattcaaa aatcaaaaaa taagaacatg 120
ggggttatta gaatgaaaag agcattaggt aaagcaatat cttatgaaga aatggcaaaa 180
gggtacgagg aaatggctgc aatcaattca ataattgctc aagaggacaa ccatcttgag 240
aatgaagcgg aaatgattaa aacaaggtat aaaaccctgg cttcatgagc atattgaaac 300
taaataaaat agacatttta aacacatcga gcacatgtgt ttatttgtct 350

<210> SEQ ID NO 337
<211> LENGTH: 25
<212> TYPE: PRT
<213> ORGANISM: Artificial sequence
<220> FEATURE:
<223> OTHER INFORMATION: peptide

<400> SEQUENCE: 337

Met Lys Ser Lys Trp Met Ser Gly Leu Leu Leu Val Ala Val Gly Phe
1 5 10 15

Ser Phe Thr Gln Val Met Val His Ala
20 25

<210> SEQ ID NO 338
<211> LENGTH: 27
<212> TYPE: PRT
<213> ORGANISM: Artificial sequence
<220> FEATURE:
<223> OTHER INFORMATION: peptide

<400> SEQUENCE: 338

Met Lys Leu Lys Ser Lys Leu Phe Val Ile Cys Leu Ala Ala Ala Ile
1 5 10 15

Phe Thr Ala Ala Gly Val Ala Ser Ala Asn Ala
20 25

<210> SEQ ID NO 339
<211> LENGTH: 26
<212> TYPE: PRT
<213> ORGANISM: Artificial sequence
<220> FEATURE:
<223> OTHER INFORMATION: peptide

<400> SEQUENCE: 339

Met Lys Leu Lys Ser Lys Leu Leu Leu Ser Cys Leu Ala Leu Ser Thr
1 5 10 15

Val Gly Val Ala Thr Thr Ile Ala Asn Ala
20 25

<210> SEQ ID NO 340
<211> LENGTH: 21
<212> TYPE: PRT
<213> ORGANISM: Artificial sequence
<220> FEATURE:
<223> OTHER INFORMATION: peptide

<400> SEQUENCE: 340

Met Lys Arg Phe Leu Ile Gly Ala Gly Val Ala Ala Val Ile Leu Ser
1 5 10 15

Gly Trp Phe Ile Ala
20

<210> SEQ ID NO 341
<211> LENGTH: 24
<212> TYPE: PRT
<213> ORGANISM: Artificial sequence
<220> FEATURE:
<223> OTHER INFORMATION: peptide

<400> SEQUENCE: 341

```
Met Lys Phe Lys Gly Leu Phe Ser Ala Val Leu Ile Val Ser Leu Leu
1               5                   10                  15

Val Gly Ala Gly Tyr Ser Phe Val
            20
```

<210> SEQ ID NO 342
<211> LENGTH: 30
<212> TYPE: PRT
<213> ORGANISM: Artificial sequence
<220> FEATURE:
<223> OTHER INFORMATION: peptide

<400> SEQUENCE: 342

```
Met Lys Lys Val Phe Phe Gly Leu Val Ile Leu Thr Ala Leu Ala Ile
1               5                   10                  15

Ser Phe Val Ala Gly Gln Gln Ser Val Ser Thr Ala Ser Ala
            20                  25                  30
```

<210> SEQ ID NO 343
<211> LENGTH: 14
<212> TYPE: PRT
<213> ORGANISM: Artificial sequence
<220> FEATURE:
<223> OTHER INFORMATION: peptide

<400> SEQUENCE: 343

```
Gly Glu Thr Ala Asn Thr Glu Gly Lys Thr Phe His Ile Ala
1               5                   10
```

<210> SEQ ID NO 344
<211> LENGTH: 8
<212> TYPE: PRT
<213> ORGANISM: Artificial sequence
<220> FEATURE:
<223> OTHER INFORMATION: peptide

<400> SEQUENCE: 344

```
Glu Ala Leu Asp Phe His Val Thr
1               5
```

<210> SEQ ID NO 345
<211> LENGTH: 8
<212> TYPE: PRT
<213> ORGANISM: Artificial sequence
<220> FEATURE:
<223> OTHER INFORMATION: peptide

<400> SEQUENCE: 345

```
Pro Thr His Gln Ile Glu Val Ala
1               5
```

<210> SEQ ID NO 346
<211> LENGTH: 12
<212> TYPE: PRT
<213> ORGANISM: Artificial sequence
<220> FEATURE:
<223> OTHER INFORMATION: peptide

<400> SEQUENCE: 346

Asp His Gln Thr His Ser Gln Glu Met Lys Val Ala
1 5 10

<210> SEQ ID NO 347
<211> LENGTH: 8
<212> TYPE: PRT
<213> ORGANISM: Artificial sequence
<220> FEATURE:
<223> OTHER INFORMATION: peptide

<400> SEQUENCE: 347

His His Asp Glu Val Ser Val Ala
1 5

<210> SEQ ID NO 348
<211> LENGTH: 7
<212> TYPE: PRT
<213> ORGANISM: Artificial sequence
<220> FEATURE:
<223> OTHER INFORMATION: peptide

<400> SEQUENCE: 348

Ser Asp Glu Val Thr Val Ala
1 5

<210> SEQ ID NO 349
<211> LENGTH: 5
<212> TYPE: PRT
<213> ORGANISM: Artificial sequence
<220> FEATURE:
<223> OTHER INFORMATION: peptide

<400> SEQUENCE: 349

Ala Arg Asn Gln Thr
1 5

<210> SEQ ID NO 350
<211> LENGTH: 5
<212> TYPE: PRT
<213> ORGANISM: Artificial sequence
<220> FEATURE:
<223> OTHER INFORMATION: peptide

<400> SEQUENCE: 350

Glu Arg Gly Met Thr
1 5

<210> SEQ ID NO 351
<211> LENGTH: 5
<212> TYPE: PRT
<213> ORGANISM: Artificial sequence
<220> FEATURE:
<223> OTHER INFORMATION: peptide

<400> SEQUENCE: 351

Gln Arg Gly Met Ile
1 5

<210> SEQ ID NO 352
<211> LENGTH: 5
<212> TYPE: PRT
<213> ORGANISM: Artificial sequence
<220> FEATURE:
<223> OTHER INFORMATION: peptide

<400> SEQUENCE: 352

Glu Lys Met Ile Gly
1 5

<210> SEQ ID NO 353
<211> LENGTH: 5
<212> TYPE: PRT
<213> ORGANISM: Artificial sequence
<220> FEATURE:
<223> OTHER INFORMATION: peptide

<400> SEQUENCE: 353

Ser Arg Asn Ala Thr
1 5

<210> SEQ ID NO 354
<211> LENGTH: 5
<212> TYPE: PRT
<213> ORGANISM: Artificial sequence
<220> FEATURE:
<223> OTHER INFORMATION: peptide

<400> SEQUENCE: 354

Ser Ala Ile Arg Gly
1 5

<210> SEQ ID NO 355
<211> LENGTH: 5
<212> TYPE: PRT
<213> ORGANISM: Artificial sequence
<220> FEATURE:
<223> OTHER INFORMATION: peptide

<400> SEQUENCE: 355

Ala Ile Arg Gly Ala
1 5

<210> SEQ ID NO 356
<211> LENGTH: 54
<212> TYPE: DNA
<213> ORGANISM: Artificial sequence
<220> FEATURE:
<223> OTHER INFORMATION: Single strand DNA oligonucleotide

<400> SEQUENCE: 356
tttgtttaac tttaagaagg agatatacca tgattaagaa tgaatgcgaa aagg 54

<210> SEQ ID NO 357
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 357
ctttgttagc agccggatct tagtggtggt ggtggtggtg aatagagata aggtttaata 60
attcaag 67

<210> SEQ ID NO 358
<211> LENGTH: 20
<212> TYPE: DNA
<213> ORGANISM: Artificial sequence
<220> FEATURE:
<223> OTHER INFORMATION: Spacer targeting aimR

<400> SEQUENCE: 358
accatttact ttttcataac 20

<210> SEQ ID NO 359
<211> LENGTH: 20
<212> TYPE: DNA
<213> ORGANISM: Artificial sequence
<220> FEATURE:
<223> OTHER INFORMATION: spacer targeting aimX

<400> SEQUENCE: 359
tttccgcttc attctcaaga 20

<210> SEQ ID NO 360
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 360
aagaattcct cattgtgttt aggtaaaata agaaattc 38

<210> SEQ ID NO 361
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 361
aactgcagtt agtggtggtg gtggtggtga atagagataa ggtttaataa ttcaag 56

<210> SEQ ID NO 362
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 362
aaactagttt taagggaaag ttccagaaat tc 32

<210> SEQ ID NO 363
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 363
aactgcagtc cgttgccaat agattatgc 29

<210> SEQ ID NO 364
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 364
aatcgccatt cgccagggct gcaggaattc ccctcattgt gtttaggtaa aataagaa 58

<210> SEQ ID NO 365
<211> LENGTH: 42
<212> TYPE: DNA
<213> ORGANISM: Artificial sequence
<220> FEATURE:

<223> OTHER INFORMATION: Single strand DNA oligonucleotide

<400> SEQUENCE: 365
gtgtttaaaa tgtctatttt atttagtttc aatatgctca tg 42

<210> SEQ ID NO 366
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 366
gaaactaaat aaaatagaca ttttaaacac tgattaacta ataaggagga caaacatgtc 60

<210> SEQ ID NO 367
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 367
ggtaatggta gcgaccggcg ctcaggatcc taaatacgct tcacagtttc ttcttcatt 59

<210> SEQ ID NO 368
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 368
tattctcacc tcctttcaaa tttgtcaaac c 31

<210> SEQ ID NO 369
<211> LENGTH: 71
<212> TYPE: DNA
<213> ORGANISM: Artificial sequence
<220> FEATURE:
<223> OTHER INFORMATION: Single strand DNA oligonucleotide

<400> SEQUENCE: 369
gtttgacaaa tttgaaagga ggtgagaata ttaaataatt gaataggtaa tacataatac 60
tatcatagac g 71

<210> SEQ ID NO 370
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 370
tctaataacc cccatgttct tattttttga tttttg 36

<210> SEQ ID NO 371
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 371
tcaaaaaata agaacatggg ggttattaga gcatattgaa actaaataaa atagacattt 60
taaacac 67

<210> SEQ ID NO 372
<211> LENGTH: 1783
<212> TYPE: DNA
<213> ORGANISM: Artificial sequence
<220> FEATURE:
<223> OTHER INFORMATION: AimR-AimP-AimX locus

<400> SEQUENCE: 372
ccctcattgt gtttaggtaa aataagaaat tcattgattt aacaacaaat aaagaataaa 60
aataaaatat atacttgaaa ttctgacaac tatgaggtat attataaaca agggaagtga 120
taactgaata aagggggag acaattgaaa ttaaagcaga tgattaagaa tgaatgcgaa 180
aaggataatc agcttgcagc tcgacttgca aaattggccg gttatgaaaa agtaaatggt 240
ttttataagt ttgtgaacac cccagaaaaa gaaatggaaa acttgggtgg attactcaag 300
atcgtaaaaa acttgtttcc tgatagtgaa gagcaacttt taagtgaata cttcttagaa 360
ttagacccta ataaaaaatg tgcaaggcaa tcagttgagt actcagatat aaaccaatgg 420
gacacactta ctgataagat tatcattaac ttatgcaact caaaaaattc cacaagtcaa 480
gagtggggaa aagtttacag cttacataga aaattaaaca aaaacgaaat cagtttaaat 540
gatgctatta gggaatcagg gaaatgtaaa ataaaatccg cggaaatgct cttcttttca 600
aatgcaatgc tgatgtatgc gtatttaaac attggtgaat ttggattaat gaagagcact 660
tcaaaattgt tagaatttga tgatttaccc gaagggttca ttaaagagtc attcaaaagc 720
agagtatcta tgctcgaagc gaacataagc ttaaatgaaa atagcctact tgaagcgaga 780
cagcattcta accgcgcaat tgaaaattct aacgtgaatc gtatttgttt ttttgcatat 840
ttaacaattg gcaacacttt aatttttgag gattatgatg aggccaaaaa ggcgtacatt 900
aaaggtcaaa aatatgctaa aaatccagtg caccaagaaa tgcttgatgg tgcgttgtgc 960
tttttgtcaa acatctggaa aaaagaaaat caatgggtga attataactc tgataacatt 1020
aaatatttgc aattaagagc tttttattac ataaatcaag gtaacattga ggaagccacg 1080
gaaattttag atgaactgtc atcaagagat caagatgaga atgaattagg attctactat 1140
tactacaaag gattaatatc tcaggataag acagactatt ataaatcaat aagatatttc 1200
aaaaaatcag atgataaata ttttatacaa ttgccattac ttcaactcga acgaatgggg 1260
gctgatcttg aattattaaa ccttatctct atttaggttt gacaaatttg aaaggaggtg 1320
agaatattga aaaaagtatt ttttggttta gtaattctta cggctttagc aatttcattt 1380
gttgccggcc aacaatcagt aagcacagca tctgcttctg atgaagtaac tgtagcaagt 1440
gcaattcgtg gtgcttaatt aaataattga ataggtaata cataatacta tcatagacgt 1500
ttgatccatt ggatcaggcg tcttttctaa ttttaaggga aagttccaga aattcaaaaa 1560
tcaaaaaata agaacatggg ggttattaga atgaaaagag cattaggtaa agcaatatct 1620
tatgaagaaa tggcaaaagg gtacgaggaa atggctgcaa tcaattcaat aattgctcaa 1680
gaggacaacc atcttgagaa tgaagcggaa atgattaaaa caaggtataa aaccctggct 1740
tcatgagcat attgaaacta aataaaatag acattttaaa cac 1783

<210> SEQ ID NO 373
<211> LENGTH: 714
<212> TYPE: DNA
<213> ORGANISM: Artificial sequence
<220> FEATURE:

<223> OTHER INFORMATION: GFP reporter gene

<400> SEQUENCE: 373
atgtcaaaag gagaagaact tttacaggt gtagtaccta tcttggttga attggatggt 60
gatgttaacg gtcacaaatt ttctgtacgt ggtgaaggtg aaggtgatgc aactaacggt 120
aaattgacac ttaaattcat ttgtacaact ggaaaacttc ctgttccttg gcctactctt 180
gttacaacat tgacatatgg agtacaatgt ttttcacgtt atcctgatca tatgaaacgt 240
cacgattttt ttaaatctgc tatgccagaa ggttatgtac aagaacgtac aatttcattt 300
aaagatgacg gaacatataa aacacgtgct gaagtaaaat tcgaaggtga cactcttgtt 360
aatcgtatcg aattgaaagg aatcgatttc aaagaagatg gtaacatttt gggacacaaa 420
cttgaataca acttcaactc tcataatgtt tatatcacag ctgacaaaca aaaaaacggt 480
attaaagcta attttaaaat tcgtcacaat gttgaagatg gatctgttca attggctgat 540
cattatcaac aaaatacacc aatcggagac ggaccagtat tgcttccaga taaccactac 600
ctttctactc aatcagttct ttcaaaagat cctaacgaaa aacgtgacca tatggtactt 660
cttgaatttg ttacagcagc aggtatcact cacggtatgg acgaacttta taaa 714

<210> SEQ ID NO 374
<211> LENGTH: 2651
<212> TYPE: DNA
<213> ORGANISM: Artificial sequence
<220> FEATURE:
<223> OTHER INFORMATION: Construct 1

<400> SEQUENCE: 374
ccctcattgt gtttaggtaa aataagaaat tcattgattt aacaacaaat aaagaataaa 60
aataaaatat atacttgaaa ttctgacaac tatgaggtat attataaaca agggaagtga 120
taactgaata aagggggag acaattgaaa ttaaagcaga tgattaagaa tgaatgcgaa 180
aaggataatc agcttgcagc tcgacttgca aaattggccg gttatgaaaa agtaaatggt 240
ttttataagt ttgtgaacac cccagaaaaa gaaatggaaa acttgggtgg attactcaag 300
atcgtaaaaa acttgtttcc tgatagtgaa gagcaacttt taagtgaata cttcttagaa 360
ttagacccta ataaaaaatg tgcaaggcaa tcagttgagt actcagatat aaaccaatgg 420
gacacactta ctgataagat tatcattaac ttatgcaact caaaaaattc cacaagtcaa 480
gagtggggaa aagtttacag cttacataga aaattaaaca aaaacgaaat cagtttaaat 540
gatgctatta gggaatcagg gaaatgtaaa ataaaatccg cggaaatgct cttcttttca 600
aatgcaatgc tgatgtatgc gtatttaaac attggtgaat ttggattaat gaagagcact 660
tcaaaattgt tagaatttga tgatttaccc gaagggttca ttaaagagtc attcaaaagc 720
agagtatcta tgctcgaagc gaacataagc ttaaatgaaa atagcctact tgaagcgaga 780
cagcattcta accgcgcaat tgaaaattct aacgtgaatc gtatttgttt ttttgcatat 840
ttaacaattg gcaacacttt aatttttgag gattatgatg aggccaaaaa ggcgtacatt 900
aaaggtcaaa aatatgctaa aaatccagtg caccaagaaa tgcttgatgg tgcgttgtgc 960
tttttgtcaa acatctggaa aaaagaaaat caatgggtga attataactc tgataacatt 1020
aaatatttgc aattaagagc tttttattac ataaatcaag gtaacattga ggaagccacg 1080
gaaattttag atgaactgtc atcaagagat caagatgaga atgaattagg attctactat 1140
tactacaaag gattaatatc tcaggataag acagactatt ataaatcaat aagatatttc 1200
aaaaaatcag atgataaata ttttatacaa ttgccattac ttcaactcga acgaatgggg 1260
gctgatcttg aattattaaa ccttatctct atttaggttt gacaaatttg aaaggaggtg 1320
agaatattga aaaaagtatt ttttggttta gtaattctta cggctttagc aatttcattt 1380
gttgccggcc aacaatcagt aagcacagca tctgcttctg atgaagtaac tgtagcaagt 1440
gcaattcgtg gtgcttaatt aaataattga ataggtaata cataatacta tcatagacgt 1500
ttgatccatt ggatcaggcg tcttttctaa ttttaaggga aagttccaga aattcaaaaa 1560
tcaaaaaata agaacatggg ggttattaga atgaaaagag cattaggtaa agcaatatct 1620
tatgaagaaa tggcaaaagg gtacgaggaa atggctgcaa tcaattcaat aattgctcaa 1680
gaggacaacc atcttgagaa tgaagcggaa atgattaaaa caaggtataa aaccctggct 1740
tcatgagcat attgaaacta aataaaatag acattttaaa cactgattaa ctaataagga 1800
ggacaaacat gtcaaaagga gaagaacttt ttacaggtgt agtacctatc ttggttgaat 1860
tggatggtga tgttaacggt cacaaatttt ctgtacgtgg tgaaggtgaa ggtgatgcaa 1920
ctaacggtaa attgacactt aaattcattt gtacaactgg aaaacttcct gttccttggc 1980
ctactcttgt tacaacattg acatatggag tacaatgttt ttcacgttat cctgatcata 2040
tgaaacgtca cgattttttt aaatctgcta tgccagaagg ttatgtacaa gaacgtacaa 2100
tttcatttaa agatgacgga acatataaaa cacgtgctga agtaaaattc gaaggtgaca 2160
ctcttgttaa tcgtatcgaa ttgaaaggaa tcgatttcaa agaagatggt aacattttgg 2220
gacacaaact tgaatacaac ttcaactctc ataatgttta tatcacagct gacaaacaaa 2280
aaaacggtat taaagctaat tttaaaattc gtcacaatgt tgaagatgga tctgttcaat 2340
tggctgatca ttatcaacaa aatacaccaa tcggagacgg accagtattg cttccagata 2400
accactacct ttctactcaa tcagttcttt caaaagatcc taacgaaaaa cgtgaccata 2460
tggtacttct tgaatttgtt acagcagcag gtatcactca cggtatggac gaactttata 2520
aataataatg agcactagtc aaggtcggca attctgcagt actaggacgc cgccaagcca 2580
gcttaaaccc agctcaatga gctgggtttt ttgtttgtta aaaatgaaga agaaactgtg 2640
aagcgtattt a 2651

<210> SEQ ID NO 375
<211> LENGTH: 8727
<212> TYPE: DNA
<213> ORGANISM: Artificial sequence
<220> FEATURE:
<223> OTHER INFORMATION: pDR111 plasmid containing Construct 1

<400> SEQUENCE: 375
atttcatttg ttgccggcca acaatcagta agcacagcat ctgcttctga tgaagtaact 60
gtagcaagtg caattcgtgg tgcttaatta aataattgaa taggtaatac ataatactat 120
catagacgtt tgatccattg gatcaggcgt cttttctaat tttaagggaa agttccagaa 180
attcaaaaat caaaaaataa gaacatgggg gttattagaa tgaaaagagc attaggtaaa 240
gcaatatctt atgaagaaat ggcaaaaggg tacgaggaaa tggctgcaat caattcaata 300
attgctcaag aggacaacca tcttgagaat gaagcggaaa tgattaaaac aaggtataaa 360
accctggctt catgagcata ttgaaactaa ataaaataga cattttaaac actgattaac 420
taataaggag gacaaacatg tcaaaaggag aagaactttt tacaggtgta gtacctatct 480
tggttgaatt ggatggtgat gttaacggtc acaaattttc tgtacgtggt gaaggtgaag 540
gtgatgcaac taacggtaaa ttgacactta aattcatttg tacaactgga aaacttcctg 600

-continued

```
ttccttggcc tactcttgtt acaacattga catatggagt acaatgtttt tcacgttatc    660
ctgatcatat gaaacgtcac gatttttttta aatctgctat gccagaaggt tatgtacaag    720
aacgtacaat ttcatttaaa gatgacggaa catataaaac acgtgctgaa gtaaaattcg    780
aaggtgacac tcttgttaat cgtatcgaat tgaaaggaat cgatttcaaa gaagatggta    840
acattttggg acacaaactt gaatacaact tcaactctca taatgtttat atcacagctg    900
acaaacaaaa aaacggtatt aaagctaatt ttaaaattcg tcacaatgtt gaagatggat    960
ctgttcaatt ggctgatcat tatcaacaaa atacaccaat cggagacgga ccagtattgc   1020
ttccagataa ccactacctt tctactcaat cagttctttc aaaagatcct aacgaaaaac   1080
gtgaccatat ggtacttctt gaatttgtta cagcagcagg tatcactcac ggtatggacg   1140
aactttataa ataataatga gcactagtca aggtcggcaa ttctgcagta ctaggacgcc   1200
gccaagccag cttaaaccca gctcaatgag ctgggttttt tgtttgttaa aaatgaagaa   1260
gaaactgtga agcgtattta ggatcctgag cgccggtcgc taccattacc agttggtctg   1320
gtgtcaaaaa taataataac cgggcaggcc atgtctgccc gtatttcgcg taaggaaatc   1380
cattatgtac tatttcgatc agaccagttt ttaatttgtg tgtttccatg tgtccagttt   1440
ggaatactct taacctcatt ggaaatcgcg gcataatcac tggtggtatg attgatgacc   1500
gcgtcaacaa tgacctttat gccatattct tcagcggctg cacacatttc tttaaattct   1560
tgttcagtac ctaagtaacg gttgccaatt tgatacgatg tcggctgata cagccagtac   1620
cagttcgaca tgcttttatc tccttgattc ccttccttta cttggttaat cggagatgtc   1680
tgaatggctg tatatcctgc atcatgaata tccttcatat tgtgttttaa cgtattgaac   1740
gaccaattcc atgcatgaag aatggttccg cttttgatcg acggtgctgt aagctcattc   1800
gatttgttcg ccgtttcagc actcgcagcc gccggtcctg ccagaaccaa atgaaacagc   1860
aataaaaatc cagcgaataa cggcagtaaa gaggttttga atcgttttgc aaacattctt   1920
gacactcctt atttgatttt ttgaagactt acttcggagt caaaaatccc tcttacttca   1980
ttcttccgct tcctcctttc aaaccgatgt gaagactgga gaattttgtt aattcttgaa   2040
gacgaaaggg cctcgtgata cgcctatttt tataggttaa tgtcatgata ataatggttt   2100
cttagacgtc aggtggcact tttcggggaa atgtgcgcgg aacccctatt tgtttatttt   2160
tctaaataca ttcaaatatg tatccgctca tgagacaata accctgataa atgcttcaat   2220
aatattgaaa aaggaagagt atgagtattc aacatttccg tgtcgccctt attccctttt   2280
ttgcggcatt ttgccttcct gtttttgctc acccagaaac gctggtgaaa gtaaaagatg   2340
ctgaagatca gttgggtgca cgagtgggtt acatcgaact ggatctcaac agcggtaaga   2400
tccttgagag ttttcgcccc gaagaacgtt ttccaatgat gagcactttt aaagttctgc   2460
tatgtggcgc ggtattatcc cgtgttgacg ccgggcaaga gcaactcggt cgccgcatac   2520
actattctca gaatgacttg gttgagtact caccagtcac agaaaagcat cttacggatg   2580
gcatgacagt aagagaatta tgcagtgctg ccataaccat gagtgataac actgcggcca   2640
acttacttct gacaacgatc ggaggaccga aggagctaac cgcttttttg cacaacatgg   2700
gggatcatgt aactcgcctt gatcgttggg aaccggagct gaatgaagcc ataccaaacg   2760
acgagcgtga caccacgatg cctgcagcaa tggcaacaac gttgcgcaaa ctattaactg   2820
gcgaactact tactctagct tcccggcaac aattaataga ctggatggag gcggataaag   2880
ttgcaggacc acttctgcgc tcggcccttc cggctggctg gtttattgct gataaatctg   2940
gagccggtga gcgtgggtct cgcggtatca ttgcagcact ggggccagat ggtaagccct   3000
```

cccgtatcgt agttatctac acgacgggga gtcaggcaac tatggatgaa cgaaatagac 3060
agatcgctga gataggtgcc tcactgatta agcattggta actgtcagac caagtttact 3120
catatatact ttagattgat ttaaaacttc atttttaatt taaaaggatc taggtgaaga 3180
tcctttttga taatctcatg accaaaatcc cttaacgtga gttttcgttc cactgagcgt 3240
cagaccccgt agaaaagatc aaaggatctt cttgagatcc tttttttctg cgcgtaatct 3300
gctgcttgca aacaaaaaaa ccaccgctac cagcggtggt ttgtttgccg gatcaagagc 3360
tatcaactct ttttccgaag gtaactggct tcagcagagc gcagatacca aatactgtcc 3420
ttctagtgta gccgtagtta ggccaccact tcaagaactc tgtagcaccg cctacatacc 3480
tcgctctgct aatcctgtta ccagtggctg ctgccagtgg cgataagtcg tgtcttaccg 3540
ggttggactc aagacgatag ttaccggata aggcgcagcg gtcgggctga acggggggtt 3600
cgtgcacaca gcccagcttg gagcgaacga cctacaccga actgagatac ctacagcgtg 3660
agctatgaga aagcgccacg cttcccgaag ggagaaaggc ggacaggtat ccggtaagcg 3720
gcagggtcgg aacaggagag cgcacgaggg agcttccagg gggaaacgcc tggtatcttt 3780
atagtcctgt cgggtttcgc cacctctgac ttgagcgtcg atttttgtga tgctcgtcag 3840
gggggcggag cctatggaaa aacgccagca acgcggcccg acctcgagct ggatacttcc 3900
cgtccgccag gggacatgc cggcgatgct gaaggtcgcg cgcattcccg atgaagaggc 3960
cggttaccgc ctgtttgagg atatagtaat ctttctaaat agctttggat tggaggagta 4020
tggccactaa tactaagttc agctaataaa aaaatttgct aaagaactcc agctggattt 4080
cactgatgag aatatcgtcg gagataaata taataattcc acggactata gactatacta 4140
gtatactccg tctactgtac gatacacttc cgctcaggtc cttgtccttt aacgaggatt 4200
gttacgtacg ctaatggcgt caaaacaaag actctagacc taggccttaa gatctgatca 4260
tatgcatccg cgggcccggg ttaacgcgta atccatggat caagagacag gatgaggatc 4320
gtttcgcatg attgaacaag atggattgca cgcaggttct ccggtgccct gaatgaactg 4380
cagaaagagc tggtagttgg cgcactgttc gaagaactgc cgatgtccag taagattctt 4440
actatgctgg ttgaaccgga tgctggtaaa gctacttggg ttgctgcttc tacttatggt 4500
accgatacaa ctactggtga ggaagttaaa ggagctctta aagaaatcca cttcagtagg 4560
tggcccggct ccatgcaccg cgacgcaacg cggggaggca gacaaggtat agggcggcgc 4620
ctacaatcca tgccaacccg ttccatgtgc tcgccgaggc ggcataaatc gccgtgacga 4680
tcagcggtcc agtgatcgaa gttaggctgg taagagccgc gagcgatcct tgaagctgtc 4740
cctgatggtc gtcatctacc tgcctggaca gcatggcctg caacgcgggc atcccgatgc 4800
cgccggaagc gagaagaatc ataatgggga aggccatcca gcctcgcgtc gcgactaaga 4860
aaatgccgtc aaatccgctc gccatgactt cactaacgat gcctttgaaa atcttcaagt 4920
tcttttctac taattcaagg cgtgtctcac caggtttttg gtttgctccg gcgcaaatgc 4980
agacaatatc agcatccttg cagggtatgt ttctctttga tgtctttttg tttgtgaagt 5040
atttcacatt tatattgtgc aacacttcac aaacttttgc aagagaaaag ttttgtctga 5100
tttatgaaca aaaaagaaac catcattgat ggtttctttc ggtaagtccc gtctagcctt 5160
gccctcaatg ggaagagaa ccgcttaagc ccgagtcatt atataaacca tttagcacgt 5220
aatcaaagcc aggctgattc tgaccgggca cttgggcgct gccattatta aaaatcactt 5280
ttgcgttggt tgtatccgtg tccgcaggca gcgtcagcgt gtaaattccg tctgcatttt 5340

-continued

```
tagtcattgg ttttccaggc caagatccgg tcaattcaat tactcggctc ccatcatgtt   5400
tatagatata agcatttacc tggctccaat gattcggatt ttgatagccg atggttttgg   5460
ccgacgctgg atctctttta acaaaactgt atttctcggt cctcgttaca ccatcactgt   5520
tcgttccttt taacatgatg gtgtatgttt tgccaaattg gatctccttt tccgattgtg   5580
aattgatctc catccttaaa cgcctgtcgt ctggtccatt attgatttga taaacggctt   5640
ttgttgtatt cgcatctgca cgcaaggtaa tcgtcagttg atcattgaaa gaatgtgtta   5700
cacctgtttt gtaattctca aggaaaacat gaggcgcttt tgcaatatca tcaggataaa   5760
gcacagctac agacctggca ttgatcgtgc ctgtcagttt accatcgttc acttgaaatg   5820
aacccgctcc agctttattg tcatacctgc catcaggcaa ttttgttgcc gtattgatag   5880
agacagagga tgaacctgca tttgccagca caacgccatg tgagccgcgc tgattcataa   5940
atatctggtt gtttccattc gggttcgaga gttcctcagg ctgtccagcc atcacattgt   6000
gaaatctatt gaccgcagtg atagcctgat cttcaaataa agcactcccg cgatcgccta   6060
tttggctttt ccccgggaac ctcacaccat ttccgcctcc ctcaggtctg gaaaagaaaa   6120
gaggcgtact gcctgaacga gaagctatca ccgcccagcc taaacggatg atccccctat   6180
gcaagggttt attgttttct aaaatctgat taccaattag aatgaatatt tcccaaatat   6240
taaataataa aacaaaaaaa ttgaaaaaag tgtttccacc atttttcaa tttttttata   6300
atttttttaa tctgttattt aaatagttta tagttaaatt tacattttca ttagtccatt   6360
caatattctc tccaagataa ctacgaactg ctaacaaaat tctctcccta tgttctaatg   6420
gagaagattc agccactgca tttcccgcaa tatcttttgg tatgatttta cccgtgtcca   6480
tagttaaaat catacggcat aaagttaata tagagttggt ttcatcatcc tgataattat   6540
ctattaattc ctctgacgaa tccataatgg ctcttctcac atcagaaaat ggaatatcag   6600
gtagtaattc ctctaagtca taatttccgt atattctttt attttttcgt tttgcttggt   6660
aaagcattat ggttaaatct gaatttaatt ccttctgagg aatgtatcct tgttcataaa   6720
gctcttgtaa ccattctcca taaataaatt cttgtttggg aggatgattc cacggtacca   6780
tttcttgctg aataataatt gttaattcaa tatatcgtaa gttgctttta tctcctattt   6840
tttttgaaat aggtctaatt ttttgtataa gtatttcttt actttgatct gtcaatggtt   6900
cagatacgac gactaaaaag tcaagatcac tatttggttt tagtccactc tcaactcctg   6960
atccaaacat gtaagtacca ataaggttat tttttaaatg tttccgaagt atttttttca   7020
ctttattaat ttgttcgtat gtattcaaat atatcctcct cactattttg attagtacct   7080
attttatatc catagttgtt aattaaataa acttaattta gtttatttat agatttcatt   7140
ggcttctaaa ttttttatct agataataat tattttagtt aattttattc tagattatat   7200
atgatatgat ctttcatttc cataaaacta aagtaagtgt aaacctattc attgttttaa   7260
aaatatctct tgccagtcac gttacgttat tagttatagt tattataaca tgtattcacg   7320
aacgaaaatc gccattcgcc agggctgcag gaattcccct cattgtgttt aggtaaaata   7380
agaaattcat tgatttaaca acaaataaag aataaaaata aaatatatac ttgaaattct   7440
gacaactatg aggtatatta taaacaaggg aagtgataac tgaataaagg ggggagacaa   7500
ttgaaattaa agcagatgat taagaatgaa tgcgaaaagg ataatcagct tgcagctcga   7560
cttgcaaaat tggccggtta tgaaaaagta aatggttttt ataagtttgt gaacacccca   7620
gaaaaagaaa tggaaaactt gggtggatta ctcaagatcg taaaaaactt gtttcctgat   7680
agtgaagagc aacttttaag tgaatacttc ttagaattag accctaataa aaaatgtgca   7740
```

aggcaatcag ttgagtactc agatataaac caatgggaca cacttactga taagattatc 7800
attaacttat gcaactcaaa aaattccaca agtcaagagt ggggaaaagt ttacagctta 7860
catagaaaat taaacaaaaa cgaaatcagt ttaaatgatg ctattaggga atcagggaaa 7920
tgtaaaataa aatccgcgga aatgctcttc ttttcaaatg caatgctgat gtatgcgtat 7980
ttaaacattg gtgaatttgg attaatgaag agcacttcaa aattgttaga atttgatgat 8040
ttacccgaag ggttcattaa agagtcattc aaaagcagag tatctatgct cgaagcgaac 8100
ataagcttaa atgaaaatag cctacttgaa gcgagacagc attctaaccg cgcaattgaa 8160
aattctaacg tgaatcgtat ttgttttttt gcatatttaa caattggcaa cactttaatt 8220
tttgaggatt atgatgaggc caaaaaggcg tacattaaag gtcaaaaata tgctaaaaat 8280
ccagtgcacc aagaaatgct tgatggtgcg ttgtgctttt tgtcaaacat ctggaaaaaa 8340
gaaaatcaat gggtgaatta taactctgat aacattaaat atttgcaatt aagagctttt 8400
tattacataa atcaaggtaa cattgaggaa gccacggaaa ttttagatga actgtcatca 8460
agagatcaag atgagaatga attaggattc tactattact acaaaggatt aatatctcag 8520
gataagacag actattataa atcaataaga tatttcaaaa aatcagatga taaatatttt 8580
atacaattgc cattacttca actcgaacga atgggggctg atcttgaatt attaaacctt 8640
atctctattt aggtttgaca aatttgaaag gaggtgagaa tattgaaaaa agtatttttt 8700
ggtttagtaa ttcttacggc tttagca 8727

<210> SEQ ID NO 376
<211> LENGTH: 2363
<212> TYPE: DNA
<213> ORGANISM: Artificial sequence
<220> FEATURE:
<223> OTHER INFORMATION: Construct 2

<400> SEQUENCE: 376
ccctcattgt gtttaggtaa aataagaaat tcattgattt aacaacaaat aaagaataaa 60
aataaaatat atacttgaaa ttctgacaac tatgaggtat attataaaca agggaagtga 120
taactgaata aagggggag acaattgaaa ttaaagcaga tgattaagaa tgaatgcgaa 180
aaggataatc agcttgcagc tcgacttgca aaattggccg gttatgaaaa agtaaatggt 240
ttttataagt ttgtgaacac cccagaaaaa gaaatggaaa acttgggtgg attactcaag 300
atcgtaaaaa acttgtttcc tgatagtgaa gagcaacttt taagtgaata cttcttagaa 360
ttagacccta ataaaaaatg tgcaaggcaa tcagttgagt actcagatat aaaccaatgg 420
gacacactta ctgataagat tatcattaac ttatgcaact caaaaaattc cacaagtcaa 480
gagtggggaa aagtttacag cttacataga aaattaaaca aaaacgaaat cagtttaaat 540
gatgctatta gggaatcagg gaaatgtaaa ataaaatccg cggaaatgct cttcttttca 600
aatgcaatgc tgatgtatgc gtatttaaac attggtgaat ttggattaat gaagagcact 660
tcaaaattgt tagaatttga tgatttaccc gaagggttca ttaaagagtc attcaaaagc 720
agagtatcta tgctcgaagc gaacataagc ttaaatgaaa atagcctact tgaagcgaga 780
cagcattcta accgcgcaat tgaaaattct aacgtgaatc gtatttgttt ttttgcatat 840
ttaacaattg gcaacacttt aatttttgag gattatgatg aggccaaaaa ggcgtacatt 900
aaaggtcaaa aatatgctaa aaatccagtg caccaagaaa tgcttgatgg tgcgttgtgc 960
tttttgtcaa acatctggaa aaaagaaaat caatgggtga attataactc tgataacatt 1020

```
aaatatttgc aattaagagc tttttattac ataaatcaag gtaacattga ggaagccacg   1080
gaaattttag atgaactgtc atcaagagat caagatgaga atgaattagg attctactat   1140
tactacaaag gattaatatc tcaggataag acagactatt ataaatcaat aagatatttc   1200
aaaaaatcag atgataaata ttttatacaa ttgccattac ttcaactcga acgaatgggg   1260
gctgatcttg aattattaaa ccttatctct atttaggttt gacaaatttg aaaggaggtg   1320
agaatattaa ataattgaat aggtaataca taatactatc atagacgttt gatccattgg   1380
atcaggcgtc ttttctaatt ttaagggaaa gttccagaaa ttcaaaaatc aaaaaataag   1440
aacatggggg ttattagagc atattgaaac taaataaaat agacatttta aacactgatt   1500
aactaataag gaggacaaac atgtcaaaag gagaagaact tttacaggt gtagtaccta   1560
tcttggttga attggatggt gatgttaacg gtcacaaatt ttctgtacgt ggtgaaggtg   1620
aaggtgatgc aactaacggt aaattgacac ttaaattcat ttgtacaact ggaaaacttc   1680
ctgttccttg gcctactctt gttacaacat tgacatatgg agtacaatgt tttcacgtt   1740
atcctgatca tatgaaacgt cacgattttt ttaaatctgc tatgccagaa ggttatgtac   1800
aagaacgtac aatttcattt aaagatgacg gaacatataa aacacgtgct gaagtaaaat   1860
tcgaaggtga cactcttgtt aatcgtatcg aattgaaagg aatcgatttc aaagaagatg   1920
gtaacatttt gggacacaaa cttgaataca acttcaactc tcataatgtt tatatcacag   1980
ctgacaaaca aaaaaacggt attaaagcta attttaaaat tcgtcacaat gttgaagatg   2040
gatctgttca attggctgat cattatcaac aaaatacacc aatcggagac ggaccagtat   2100
tgcttccaga taaccactac ctttctactc aatcagttct ttcaaaagat cctaacgaaa   2160
aacgtgacca tatggtactt cttgaatttg ttacagcagc aggtatcact cacggtatgg   2220
acgaacttta taaataataa tgagcactag tcaaggtcgg caattctgca gtactaggac   2280
gccgccaagc cagcttaaac ccagctcaat gagctgggtt ttttgtttgt taaaaatgaa   2340
gaagaaactg tgaagcgtat tta                                           2363
```

<210> SEQ ID NO 377
<211> LENGTH: 8439
<212> TYPE: DNA
<213> ORGANISM: Artificial sequence
<220> FEATURE:
<223> OTHER INFORMATION: pDR111 plasmid containing Construct 2

<400> SEQUENCE: 377

```
acctattcat tgttttaaaa atatctcttg ccagtcacgt tacgttatta gttatagtta     60
ttataacatg tattcacgaa cgaaaatcgc cattcgccag ggctgcagga attcccctca    120
ttgtgtttag gtaaaataag aaattcattg atttaacaac aaataaagaa taaaaataaa    180
atatatactt gaaattctga caactatgag gtatattata aacaagggaa gtgataactg    240
aataaagggg ggagacaatt gaaattaaag cagatgatta agaatgaatg cgaaaaggat    300
aatcagcttg cagctcgact tgcaaaattg gccggttatg aaaaagtaaa tggtttttat    360
aagtttgtga acaccccaga aaaagaaatg gaaaacttgg gtggattact caagatcgta    420
aaaaacttgt ttcctgatag tgaagagcaa cttttaagtg aatacttctt agaattagac    480
cctaataaaa aatgtgcaag gcaatcagtt gagtactcag atataaacca atgggacaca    540
cttactgata agattatcat taacttatgc aactcaaaaa attccacaag tcaagagtgg    600
ggaaaagttt acagcttaca tagaaaatta aacaaaaacg aaatcagttt aaatgatgct    660
attagggaat cagggaaatg taaaataaaa tccgcggaaa tgctcttctt ttcaaatgca    720
```

```
atgctgatgt atgcgtattt aaacattggt gaatttggat taatgaagag cacttcaaaa    780
ttgttagaat ttgatgattt acccgaaggg ttcattaaag agtcattcaa aagcagagta    840
tctatgctcg aagcgaacat aagcttaaat gaaaatagcc tacttgaagc gagacagcat    900
tctaaccgcg caattgaaaa ttctaacgtg aatcgtattt gtttttttgc atatttaaca    960
attggcaaca ctttaatttt tgaggattat gatgaggcca aaaaggcgta cattaaaggt   1020
caaaaatatg ctaaaaatcc agtgcaccaa gaaatgcttg atggtgcgtt gtgctttttg   1080
tcaaacatct ggaaaaaaga aaatcaatgg gtgaattata actctgataa cattaaatat   1140
ttgcaattaa gagcttttta ttacataaat caaggtaaca ttgaggaagc cacggaaatt   1200
ttagatgaac tgtcatcaag agatcaagat gagaatgaat taggattcta ctattactac   1260
aaaggattaa tatctcagga taagacagac tattataaat caataagata tttcaaaaaa   1320
tcagatgata aatattttat acaattgcca ttacttcaac tcgaacgaat gggggctgat   1380
cttgaattat taaaccttat ctctatttag gtttgacaaa tttgaaagga ggtgagaata   1440
ttaaataatt gaataggtaa tacataatac tatcatagac gtttgatcca ttggatcagg   1500
cgtcttttct aattttaagg gaaagttcca gaaattcaaa aatcaaaaaa taagaacatg   1560
ggggttatta gagcatattg aaactaaata aaatagacat tttaaacact gattaactaa   1620
taaggaggac aaacatgtca aaaggagaag aactttttac aggtgtagta cctatcttgg   1680
ttgaattgga tggtgatgtt aacggtcaca aattttctgt acgtggtgaa ggtgaaggtg   1740
atgcaactaa cggtaaattg acacttaaat tcatttgtac aactggaaaa cttcctgttc   1800
cttggcctac tcttgttaca acattgacat atggagtaca atgtttttca cgttatcctg   1860
atcatatgaa acgtcacgat ttttttaaat ctgctatgcc agaaggttat gtacaagaac   1920
gtacaatttc atttaaagat gacggaacat ataaaacacg tgctgaagta aaattcgaag   1980
gtgacactct tgttaatcgt atcgaattga aaggaatcga tttcaaagaa gatggtaaca   2040
ttttgggaca caaacttgaa tacaacttca actctcataa tgtttatatc acagctgaca   2100
aacaaaaaaa cggtattaaa gctaatttta aaattcgtca caatgttgaa gatggatctg   2160
ttcaattggc tgatcattat caacaaaata caccaatcgg agacggacca gtattgcttc   2220
cagataacca ctacctttct actcaatcag ttctttcaaa agatcctaac gaaaaacgtg   2280
accatatggt acttcttgaa tttgttacag cagcaggtat cactcacggt atggacgaac   2340
tttataaata ataatgagca ctagtcaagg tcggcaattc tgcagtacta ggacgccgcc   2400
aagccagctt aaacccagct caatgagctg ggtttttttgt ttgttaaaaa tgaagaagaa   2460
actgtgaagc gtatttagga tcctgagcgc cggtcgctac cattaccagt tggtctggtg   2520
tcaaaaataa taataaccgg gcaggccatg tctgcccgta tttcgcgtaa ggaaatccat   2580
tatgtactat ttcgatcaga ccagttttta atttgtgtgt ttccatgtgt ccagtttgga   2640
atactcttaa cctcattgga aatcgcggca taatcactgg tggtatgatt gatgaccgcg   2700
tcaacaatga cctttatgcc atattcttca gcggctgcac acatttcttt aaattcttgt   2760
tcagtaccta agtaacggtt gccaatttga tacgatgtcg gctgatacag ccagtaccag   2820
ttcgacatgc ttttatctcc ttgattccct tcctttactt ggttaatcgg agatgtctga   2880
atggctgtat atcctgcatc atgaatatcc ttcatattgt gttttaacgt attgaacgac   2940
caattccatg catgaagaat ggttccgctt ttgatcgacg gtgctgtaag ctcattcgat   3000
ttgttcgccg tttcagcact cgcagccgcc ggtcctgcca gaaccaaatg aaacagcaat   3060
```

-continued

```
aaaaatccag cgaataacgg cagtaaagag gttttgaatc gttttgcaaa cattcttgac   3120
actccttatt tgatttttg aagacttact tcggagtcaa aaatccctct tacttcattc   3180
ttccgcttcc tcctttcaaa ccgatgtgaa gactggagaa ttttgttaat tcttgaagac   3240
gaaagggcct cgtgatacgc ctatttttat aggttaatgt catgataata atggtttctt   3300
agacgtcagg tggcactttt cggggaaatg tgcgcggaac ccctatttgt ttatttttct   3360
aaatacattc aaatatgtat ccgctcatga gacaataacc ctgataaatg cttcaataat   3420
attgaaaaag gaagagtatg agtattcaac atttccgtgt cgcccttatt cccttttttg   3480
cggcattttg ccttcctgtt tttgctcacc cagaaacgct ggtgaaagta aaagatgctg   3540
aagatcagtt gggtgcacga gtgggttaca tcgaactgga tctcaacagc ggtaagatcc   3600
ttgagagttt tcgccccgaa gaacgttttc caatgatgag cacttttaaa gttctgctat   3660
gtggcgcggt attatcccgt gttgacgccg ggcaagagca actcggtcgc cgcatacact   3720
attctcagaa tgacttggtt gagtactcac cagtcacaga aaagcatctt acggatggca   3780
tgacagtaag agaattatgc agtgctgcca taaccatgag tgataacact gcggccaact   3840
tacttctgac aacgatcgga ggaccgaagg agctaaccgc ttttttgcac aacatggggg   3900
atcatgtaac tcgccttgat cgttgggaac cggagctgaa tgaagccata ccaaacgacg   3960
agcgtgacac cacgatgcct gcagcaatgg caacaacgtt gcgcaaacta ttaactggcg   4020
aactacttac tctagcttcc cggcaacaat taatagactg gatggaggcg gataaagttg   4080
caggaccact tctgcgctcg gcccttccgg ctggctggtt tattgctgat aaatctggag   4140
ccggtgagcg tgggtctcgc ggtatcattg cagcactggg gccagatggt aagccctccc   4200
gtatcgtagt tatctacacg acggggagtc aggcaactat ggatgaacga aatagacaga   4260
tcgctgagat aggtgcctca ctgattaagc attggtaact gtcagaccaa gtttactcat   4320
atatacttta gattgattta aaacttcatt tttaatttaa aaggatctag gtgaagatcc   4380
tttttgataa tctcatgacc aaaatccctt aacgtgagtt ttcgttccac tgagcgtcag   4440
accccgtaga aaagatcaaa ggatcttctt gagatccttt ttttctgcgc gtaatctgct   4500
gcttgcaaac aaaaaaacca ccgctaccag cggtggtttg tttgccggat caagagctat   4560
caactctttt tccgaaggta actggcttca gcagagcgca gataccaaat actgtccttc   4620
tagtgtagcc gtagttaggc caccacttca agaactctgt agcaccgcct acatacctcg   4680
ctctgctaat cctgttacca gtggctgctg ccagtggcga taagtcgtgt cttaccgggt   4740
tggactcaag acgatagtta ccggataagg cgcagcggtc gggctgaacg gggggttcgt   4800
gcacacagcc cagcttggag cgaacgacct acaccgaact gagataccta cagcgtgagc   4860
tatgagaaag cgccacgctt cccgaaggga gaaaggcgga caggtatccg gtaagcggca   4920
gggtcggaac aggagagcgc acgagggagc ttccaggggg aaacgcctgg tatctttata   4980
gtcctgtcgg gtttcgccac ctctgacttg agcgtcgatt tttgtgatgc tcgtcagggg   5040
ggcggagcct atggaaaaac gccagcaacg cggcccgacc tcgagctgga tacttcccgt   5100
ccgccagggg gacatgccgg cgatgctgaa ggtcgcgcgc attcccgatg aagaggccgg   5160
ttaccgcctg tttgaggata tagtaatctt tctaaatagc tttggattgg aggagtatgg   5220
ccactaatac taagttcagc taataaaaaa atttgctaaa gaactccagc tggatttcac   5280
tgatgagaat atcgtcggag ataaatataa taattccacg gactatagac tatactagta   5340
tactccgtct actgtacgat acacttccgc tcaggtcctt gtcctttaac gaggattgtt   5400
acgtacgcta atggcgtcaa aacaaagact ctagacctag gccttaagat ctgatcatat   5460
```

-continued

```
gcatccgcgg gcccgggtta acgcgtaatc catggatcaa gagacaggat gaggatcgtt   5520
tcgcatgatt gaacaagatg gattgcacgc aggttctccg gtgccctgaa tgaactgcag   5580
aaagagctgg tagttggcgc actgttcgaa gaactgccga tgtccagtaa gattcttact   5640
atgctggttg aaccggatgc tggtaaagct acttgggttg ctgcttctac ttatggtacc   5700
gatacaacta ctggtgagga agttaaagga gctcttaaag aaatccactt cagtaggtgg   5760
cccggctcca tgcaccgcga cgcaacgcgg ggaggcagac aaggtatagg gcggcgccta   5820
caatccatgc caacccgttc catgtgctcg ccgaggcggc ataaatcgcc gtgacgatca   5880
gcggtccagt gatcgaagtt aggctggtaa gagccgcgag cgatccttga agctgtccct   5940
gatggtcgtc atctacctgc ctggacagca tggcctgcaa cgcgggcatc ccgatgccgc   6000
cggaagcgag aagaatcata atggggaagg ccatccagcc tcgcgtcgcg actaagaaaa   6060
tgccgtcaaa tccgctcgcc atgacttcac taacgatgcc tttgaaaatc ttcaagttct   6120
tttctactaa ttcaaggcgt gtctcaccag gtttttggtt tgctccggcg caaatgcaga   6180
caatatcagc atccttgcag ggtatgtttc tctttgatgt ctttttgttt gtgaagtatt   6240
tcacatttat attgtgcaac acttcacaaa cttttgcaag agaaaagttt tgtctgattt   6300
atgaacaaaa aagaaaccat cattgatggt ttctttcggt aagtcccgtc tagccttgcc   6360
ctcaatgggg aagagaaccg cttaagcccg agtcattata taaaccattt agcacgtaat   6420
caaagccagg ctgattctga ccgggcactt gggcgctgcc attattaaaa atcacttttg   6480
cgttggttgt atccgtgtcc gcaggcagcg tcagcgtgta aattccgtct gcatttttag   6540
tcattggttt tccaggccaa gatccggtca attcaattac tcggctccca tcatgtttat   6600
agatataagc atttacctgg ctccaatgat tcggattttg atagccgatg gttttggccg   6660
acgctggatc tcttttaaca aaactgtatt tctcggtcct cgttacacca tcactgttcg   6720
ttccttttaa catgatggtg tatgttttgc caaattggat ctccttttcc gattgtgaat   6780
tgatctccat ccttaaacgc ctgtcgtctg gtccattatt gatttgataa acggcttttg   6840
ttgtattcgc atctgcacgc aaggtaatcg tcagttgatc attgaaagaa tgtgttacac   6900
ctgttttgta attctcaagg aaaacatgag gcgcttttgc aatatcatca ggataaagca   6960
cagctacaga cctggcattg atcgtgcctg tcagtttacc atcgttcact tgaaatgaac   7020
ccgctccagc tttattgtca tacctgccat caggcaattt tgttgccgta ttgatagaga   7080
cagaggatga acctgcattt gccagcacaa cgccatgtga gccgcgctga ttcataaata   7140
tctggttgtt tccattcggg ttcgagagtt cctcaggctg tccagccatc acattgtgaa   7200
atctattgac cgcagtgata gcctgatctt caaataaagc actcccgcga tcgcctattt   7260
ggcttttccc cgggaacctc acaccatttc cgcctccctc aggtctggaa aagaaaagag   7320
gcgtactgcc tgaacgagaa gctatcaccg cccagcctaa acggatgatc cccctatgca   7380
agggtttatt gttttctaaa atctgattac caattagaat gaatatttcc caaatattaa   7440
ataataaaac aaaaaaattg aaaaaagtgt ttccaccatt ttttcaattt ttttataatt   7500
tttttaatct gttatttaaa tagtttatag ttaaatttac attttcatta gtccattcaa   7560
tattctctcc aagataacta cgaactgcta acaaaattct ctccctatgt tctaatggag   7620
aagattcagc cactgcattt cccgcaatat cttttggtat gattttaccc gtgtccatag   7680
ttaaaatcat acggcataaa gttaatatag agttggtttc atcatcctga taattatcta   7740
ttaattcctc tgacgaatcc ataatggctc ttctcacatc agaaaatgga atatcaggta   7800
```

-continued

```
gtaattcctc taagtcataa tttccgtata ttcttttatt ttttcgtttt gcttggtaaa   7860

gcattatggt taaatctgaa tttaattcct tctgaggaat gtatccttgt tcataaagct   7920

cttgtaacca ttctccataa ataaattctt gtttgggagg atgattccac ggtaccattt   7980

cttgctgaat aataattgtt aattcaatat atcgtaagtt gcttttatct cctatttttt   8040

ttgaaatagg tctaattttt tgtataagta tttctttact ttgatctgtc aatggttcag   8100

atacgacgac taaaaagtca agatcactat ttggttttag tccactctca actcctgatc   8160

caaacatgta agtaccaata aggttatttt ttaaatgttt ccgaagtatt tttttcactt   8220

tattaatttg ttcgtatgta ttcaaatata tcctcctcac tattttgatt agtacctatt   8280

ttatatccat agttgttaat taaataaact taatttagtt tatttataga tttcattggc   8340

ttctaaattt tttatctaga taataattat tttagttaat tttattctag attatatatg   8400

atatgatctt tcatttccat aaaactaaag taagtgtaa                          8439


<210> SEQ ID NO 378
<211> LENGTH: 40
<212> TYPE: DNA
<213> ORGANISM: Artificial sequence
<220> FEATURE:
<223> OTHER INFORMATION: AimR responsive element

<400> SEQUENCE: 378

cagaaattca aaaatcaaaa aataagaaca tgggggttat                            40
```

ISOLATED POLYNUCLEOTIDES AND POLYPEPTIDES AND METHODS OF USING SAME FOR EXPRESSING AN EXPRESSION PRODUCT OF INTEREST

RELATED APPLICATIONS

This application is a National Phase of PCT Patent Application No. PCT/IL2017/051293 having International filing date of Nov. 28, 2017, which claims the benefit of priority under 35 USC § 119(e) of U.S. Provisional Patent Application No. 62/426,669 filed on Nov. 28, 2016. The contents of the above applications are all incorporated by reference as if fully set forth herein in their entirety.

SEQUENCE LISTING STATEMENT

The ASCII file, entitled 77331SequenceListing.txt, created on Apr. 30, 2019, comprising 605,369 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to isolated polynucleotides and polypeptides and methods of using same for expressing an expression product of interest.

Recombinant DNA technologies, including inducible gene expression and genome editing technologies have provided opportunities for control of gene expression and precise, targeted modifications to genome sequences in many types of organisms, including plants and animals. Rational gene expression in general, and genome editing in particular, have an enormous potential across basic research, drug discovery and cell based medicine by inserting or removing a specific genetic trait. This includes the correction of mutations that cause disease, the addition of therapeutic genes to specific sites in the genome, the removal of deleterious genes or genome sequences and alteration of plant genomes in order to generate improved crops. Existing methods for genome editing include, for example, the use of zinc finger nucleases, TALENs, and CRISPR-Cas9 systems.

SUMMARY OF THE INVENTION

According to an aspect of some embodiments of the present invention there is provided a method of expressing an expression product of interest, the method comprising:

(i) introducing into a cell a polynucleotide comprising an AimR responsive element operatively linked to a nucleic acid sequence encoding the expression product of interest, wherein the AimR comprises a DNA binding domain for binding the AimR responsive element, the AimR comprising a helix-turn-helix (HTH) motif and a tetratricopeptide repeat (TPR) domain; and (ii) contacting the cell with an AimP peptide comprising an amino acid sequence of XXXXGG/A, wherein the AimP peptide is capable of binding the AimR polypeptide and dissociating the AimR polypeptide from the AimR responsive element, thereby expressing the expression product of interest.

According to an aspect of some embodiments of the present invention there is provided a method of expressing an expression product of interest, the method comprising introducing into a cell a polynucleotide comprising an AimR responsive element operatively linked to a heterologous nucleic acid sequence encoding the expression product of interest, wherein the AimR comprises a DNA binding domain for binding the AimR responsive element, the AimR comprising a helix-turn-helix (HTH) motif and a tetratricopeptide repeat (TPR) domain, thereby expressing the expression product of interest.

According to an aspect of some embodiments of the present invention there is provided a method of expressing an expression product of interest, the method comprising introducing into a cell a polynucleotide comprising an AimR responsive element operatively linked to a nucleic acid sequence encoding the expression product of interest; and a nucleic acid construct comprising an AimR polynucleotide and a cis-acting regulatory element heterologous to the AimR for directing expression of the AimR polynucleotide, wherein the AimR comprises a DNA binding domain for binding the AimR responsive element, the AimR comprising a helix-turn-helix (HTH) motif and a tetratricopeptide repeat (TPR) domain, thereby expressing the expression product of interest.

According to some embodiments of the invention, the method comprising introducing into the cell a polynucleotide encoding the AimR.

According to some embodiments of the invention, the method comprising contacting the cell with an AimP peptide or a nucleic acid sequence encoding same, the AimP peptide comprising an amino acid sequence of XXXXGG/A, wherein the AimP peptide is capable of binding the AimR polypeptide and dissociating the AimR polypeptide from the AimR responsive element.

According to some embodiments of the invention, the method comprising contacting the cell with an agent capable of downregulating expression and/or activity of the AimR responsive element.

According to some embodiments of the invention, the expression product of interest is endogenous to the cell.

According to some embodiments of the invention, the expression product of interest is exogenous to the cell.

According to an aspect of some embodiments of the present invention there is provided an article of manufacture identified for expressing an expression product of interest comprising a packaging material packaging at least two of:

(i) a polynucleotide comprising an AimR responsive element, wherein the AimR comprises a DNA binding domain for binding the AimR responsive element, the AimR comprising a helix-turn-helix (HTH) motif and a tetratricopeptide repeat (TPR) domain;

(ii) a polynucleotide encoding the AimR;

(iii) an AimP peptide comprising an amino acid sequence of XXXXGG/A or a nucleic acid sequence encoding same, wherein the AimP peptide is capable of binding the AimR polypeptide and dissociating the AimR polypeptide from the AimR responsive element; and/or (iv) an agent capable of downregulating expression and/or activity of the AimR responsive element.

According to some embodiments of the invention, the polynucleotide encoding the AimR is comprised in a nucleic acid construct comprising a cis-acting regulatory element heterologous to the AimR for directing expression of the AimR polynucleotide.

According to some embodiments of the invention, the article of manufacture comprising a multiple cloning site (MCS).

According to some embodiments of the invention, the article of manufacture comprising a polynucleotide encoding the expression product of interest.

According to some embodiments of the invention, the expression product of interest is a DNA editing agent.

According to some embodiments of the invention, the AimR responsive element comprises a nucleic acid sequence for binding said AimR and an AimX polynucleotide, wherein the AimX polynucleotide or an AimX polypeptide encoded by the AimX polynucleotide is capable of inhibiting lysogeny of a temperate phage expressing the AimR in a host bacteria.

According to some embodiments of the invention, the expression product of interest is an AimX dependent DNA editing agent.

According to some embodiments of the invention, the method comprising introducing into the cell a nucleic acid sequence to be integrated into a genome of the cell by the DNA editing agent.

According to some embodiments of the invention, the DNA editing agent is an integrase.

According to some embodiments of the invention, the DNA editing agent is selected from the group consisting of zinc finger nuclease, an effector protein of Class 2 CRISPR/Cas (e.g. Cas9, Cpf1, C2c1, C2c3) and TALEN.

According to an aspect of some embodiments of the present invention there is provided an isolated AimP peptide comprising an amino acid sequence of XXXXGG/A, wherein the peptide is capable of binding an AimR polypeptide comprising a DNA binding domain for binding an AimR responsive element, the AimR comprising a helix-turn-helix (HTH) motif and a tetratricopeptide repeat (TPR) domain; and dissociating the AimR polypeptide from an AimR responsive element.

According to some embodiments of the invention, there is provided an isolated polynucleotide encoding the peptide of the invention.

According to an aspect of some embodiments of the present invention there is provided an isolated AimR polypeptide comprising a DNA binding domain for binding an AimR responsive element, the AimR comprising a helix-turn-helix (HTH) motif and a tetratricopeptide repeat (TPR) domain.

According to some embodiments of the invention, there is provided an isolated polynucleotide encoding the polypeptide of the invention.

According to an aspect of some embodiments of the present invention there is provided an isolated polynucleotide comprising an AimR responsive element, wherein the AimR comprises a DNA binding domain for binding the AimR responsive element, the AimR comprising a helix-turn-helix (HTH) motif and a tetratricopeptide repeat (TPR) domain.

According to some embodiments of the invention, AimR responsive element comprises a nucleic acid sequence for binding said AimR and an AimX polynucleotide, wherein the AimX polynucleotide or an AimX polypeptide encoded by the AimX polynucleotide is capable of inhibiting lysogeny of a temperate phage expressing the AimR in a host bacteria.

According to some embodiments of the invention, there is provided an isolated polypeptide encoded by the polynucleotide of the present invention.

According to some embodiments of the invention, there is provided an isolated polynucleotide comprising the polynucleotides of the present invention.

According to some embodiments of the invention, there is provided an isolated polynucleotide encoding an arbitrium system comprising the polynucleotides of the present invention, wherein the arbitrium system is capable of regulating lysogeny of a phage expressing the arbitrium system in a host bacteria.

According to some embodiments of the invention, there is provided a nucleic acid construct comprising the polynucleotide of the present invention and a multiple cloning site (MCS).

According to some embodiments of the invention, there is provided a nucleic acid construct comprising the polynucleotide of the present invention and a multiple cloning site (MCS).

According to some embodiments of the invention, there is provided a nucleic acid construct comprising the polynucleotide of the present invention or the nucleic acid construct of the present invention and a cis-acting regulatory element heterologous to the AimP, the AimR, the AimR responsive element and/or the AimX for directing expression of the polynucleotide.

According to some embodiments of the invention, the nucleic acid construct of the present invention being a nucleic acid construct system comprising at least two nucleic acid constructs each expressing at least one of the polynucleotides.

According to some embodiments of the invention, the construct encodes a polycistronic mRNA comprising the polynucleotide.

According to an aspect of some embodiments of the present invention there is provided an isolated nucleic acid agent capable of downregulating expression and/or activity of AimR responsive element, wherein the AimR comprises a DNA binding domain for binding the AimR responsive element, the AimR comprising a helix-turn-helix (HTH) motif and a tetratricopeptide repeat (TPR) domain.

According to some embodiments of the invention, there is provided an article of manufacture identified for expressing an expression product of interest comprising a packaging material packaging at least one of:

(a)(i) the isolated polynucleotide of the present invention, (a)(ii) a nucleic acid construct comprising the polynucleotide of the present invention and a multiple cloning site (MCS), and or (a)(iii) a nucleic acid construct comprising the polynucleotide of the present invention and a cis-acting regulatory element heterologous to the AimR or the AimX for directing expression of the polynucleotide;

and at least one of:

(b)(i) the isolated peptide of the present invention, (b)(ii) the isolated polynucleotide of the present invention, (b)(iii) a nucleic acid construct comprising the polynucleotide of the present invention and a MCS, (b)(iv) a nucleic acid construct comprising the polynucleotide of the present invention and a cis-acting regulatory element heterologous to the AimP for directing expression of the polynucleotide, and/or (b)(v) the isolated agent of the present invention.

According to some embodiments of the invention, the isolated polynucleotide, the nucleic acid construct or the article of manufacture of the present invention comprising a nucleic acid sequence encoding an expression product of interest.

According to some embodiments of the invention, the expression product of interest is a DNA editing agent.

According to some embodiments of the invention, the AimP peptide is capable of leading to lysogeny of a temperate phage expressing the AimR in a host bacteria.

According to some embodiments of the invention, the AimP comprises an amino acid sequence selected from the group consisting of SEQ ID NOs: 269-283 and 285-286.

According to some embodiments of the invention, the AimR comprises a nucleic acid sequence having at least 80% identity to a sequence selected from the group consisting of SEQ ID NO: 1-113 and/or an amino acid sequence having at least 80% identity to a sequence selected from the group consisting of SEQ ID NOs: 114-226.

According to some embodiments of the invention, the AimR comprises a nucleic acid sequence selected from the group consisting of 1-113 and/or an amino acid sequence selected from the group consisting of SEQ ID NOs: 114-226.

According to some embodiments of the invention, the AimR responsive element comprises a nucleic acid sequence selected from the group consisting of SEQ ID NOs: 287-334.

According to some embodiments of the invention, the AimR responsive element comprises SEQ ID NO: 378.

According to some embodiments of the invention, the AimX comprises a nucleic acid sequence as set forth in SEQ ID NO: 336.

According to some embodiments of the invention, the AimR and the AimP and/or the AimR responsive element are positioned sequentially 5' to 3' on a nucleic acid molecule of a temperate phage expressing same.

According to some embodiments of the invention, the AimP and the AimR responsive element are positioned sequentially 5' to 3' on a nucleic acid molecule of a temperate phage expressing same.

According to some embodiments of the invention, the AimR and the AimP and/or the AimR responsive element are positioned sequentially 5' to 3' in a genome of a temperate phage.

According to some embodiments of the invention, the AimP and the AimR responsive element are positioned sequentially 5' to 3' in a genome of a temperate phage.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1E:
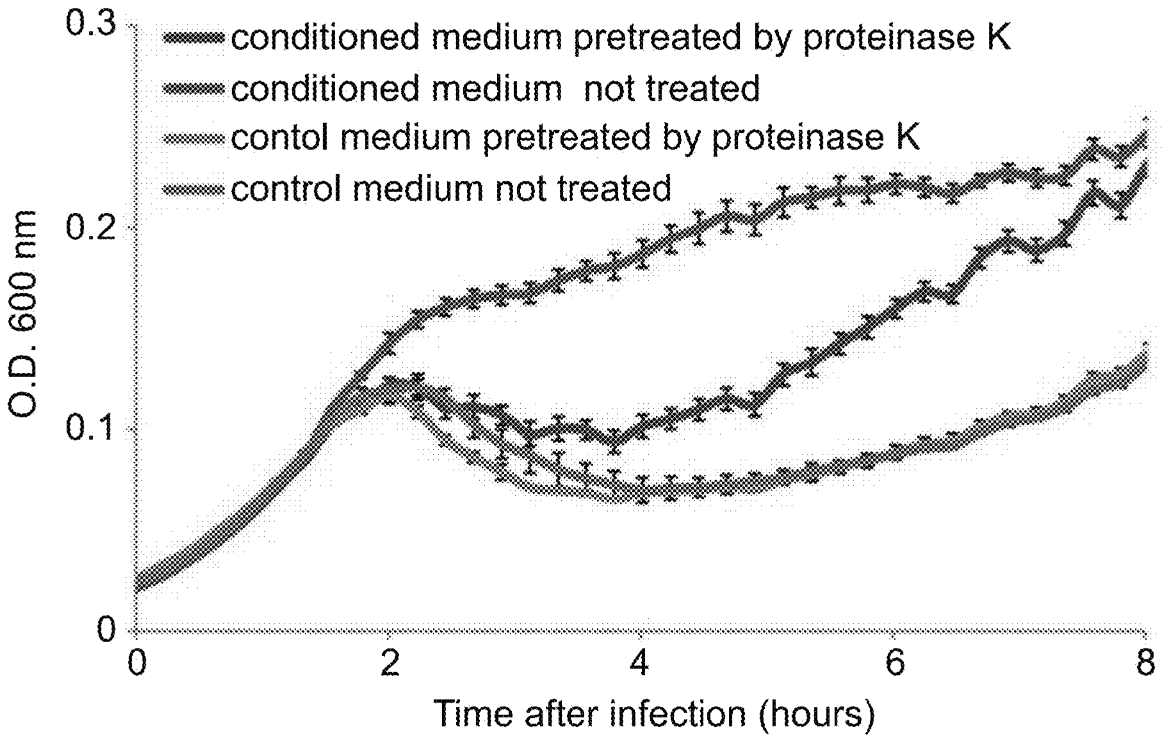

FIGS. 1A-E demonstrate the effect of conditioned media on infection dynamics of phage phi3T. FIG. 1A is a schematic representation of the preparation protocol of control and conditioned media. FIG. 1B is a graph showing the growth curves of *B. subtilis* 168 infected by phi3T at multiplicity of infection (MOI)=0.1, in control and conditioned media. FIG. 1C is a graph showing the growth curves of *B. subtilis* strain DS4979[5] (oppD::kan) infected by phi3T at MOI=0.1, in control and conditioned media. For FIGS. 1B-C, data represents average of 3 biological replicates, each with 3 technical replicates, and error bars represent standard error. FIG. 1D is a semi-quantitative PCR photograph demonstrating phage lysogeny during an infection time course of *B. subtilis* 168 with phi3T in control and conditioned media. FIG. 1E is a graph showing the growth curves of *B. subtilis* 168 infected by phi3T at MOI=0.1, in control and conditioned media, with and without pre-treatment with proteinase K. Data represents average of 3 technical replicates, and error bars represent standard error.

Figure 2A:
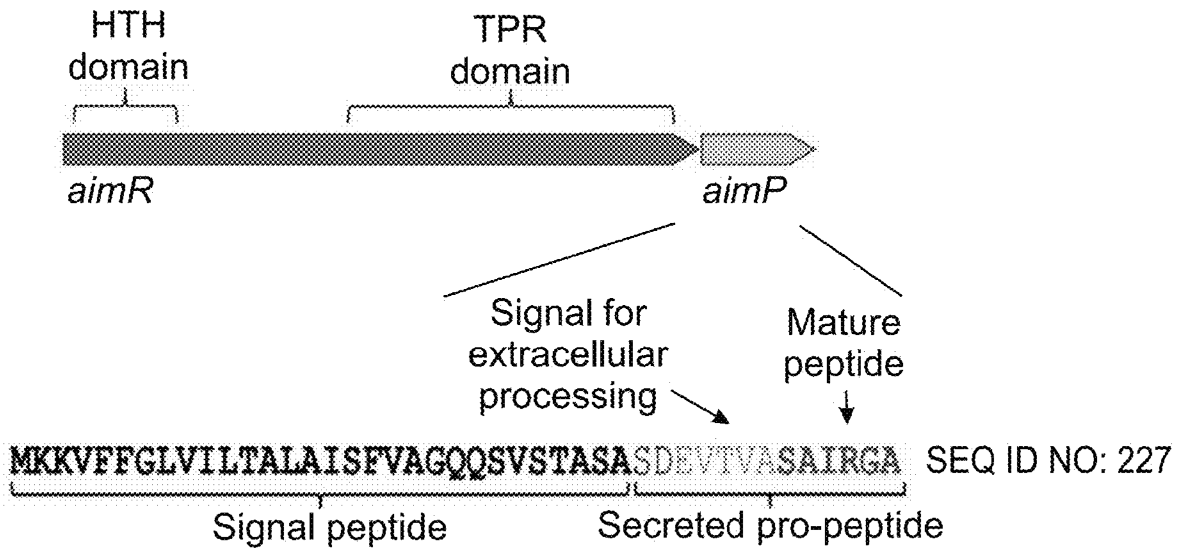
Figure 2D:
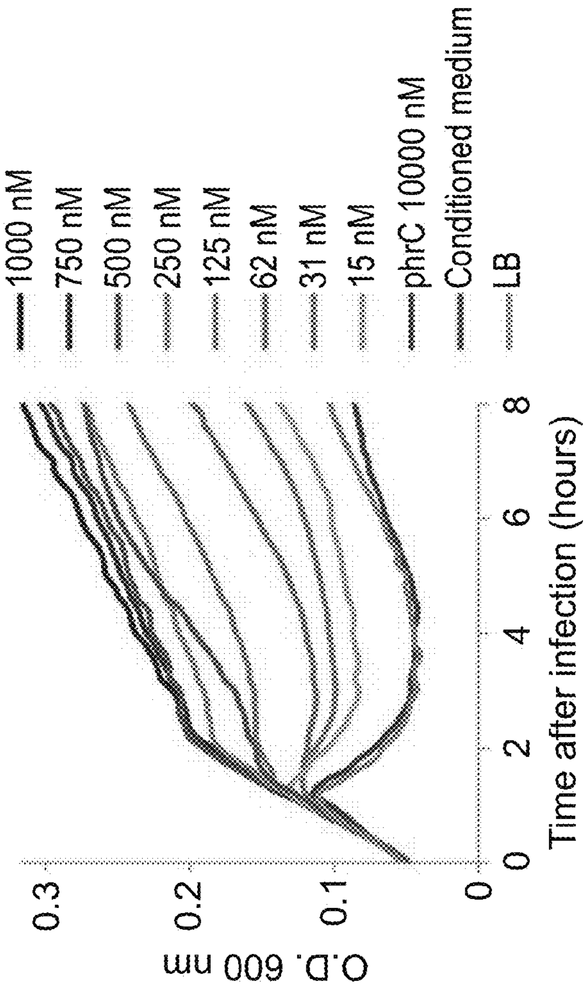
Figure 2E:
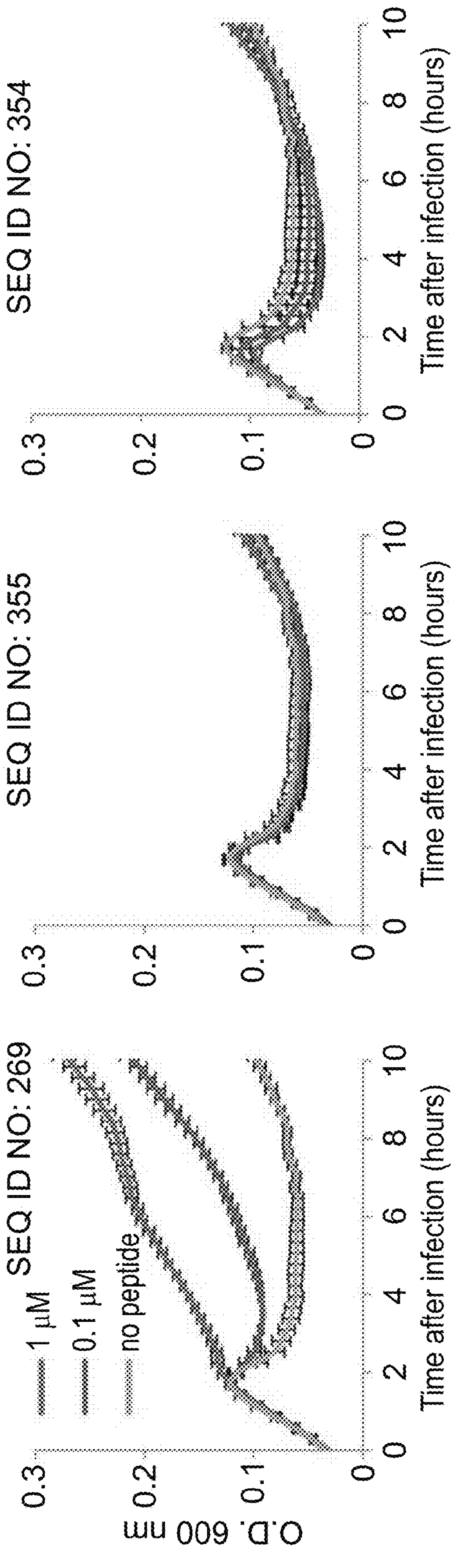
Figure 2F:
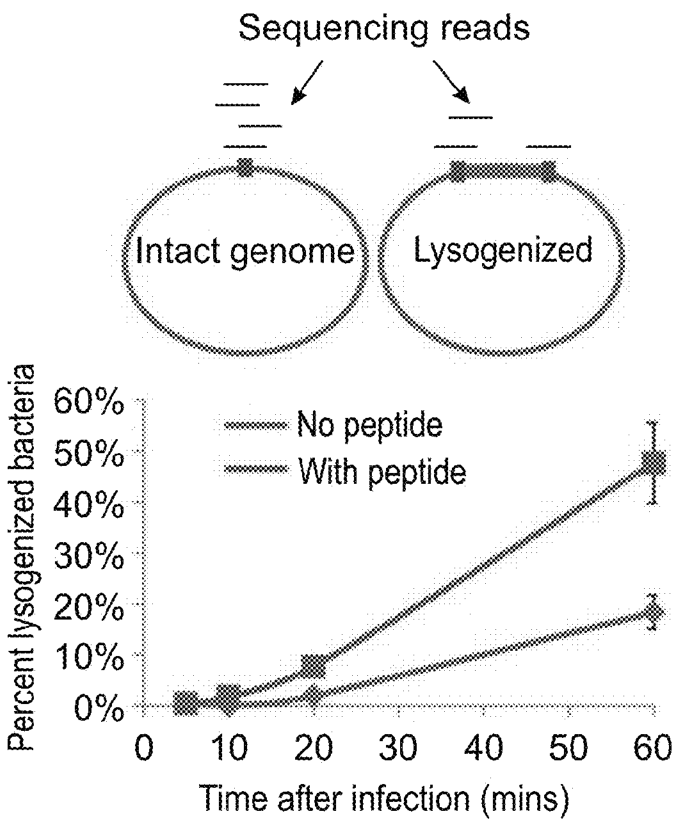
Figure 2G:
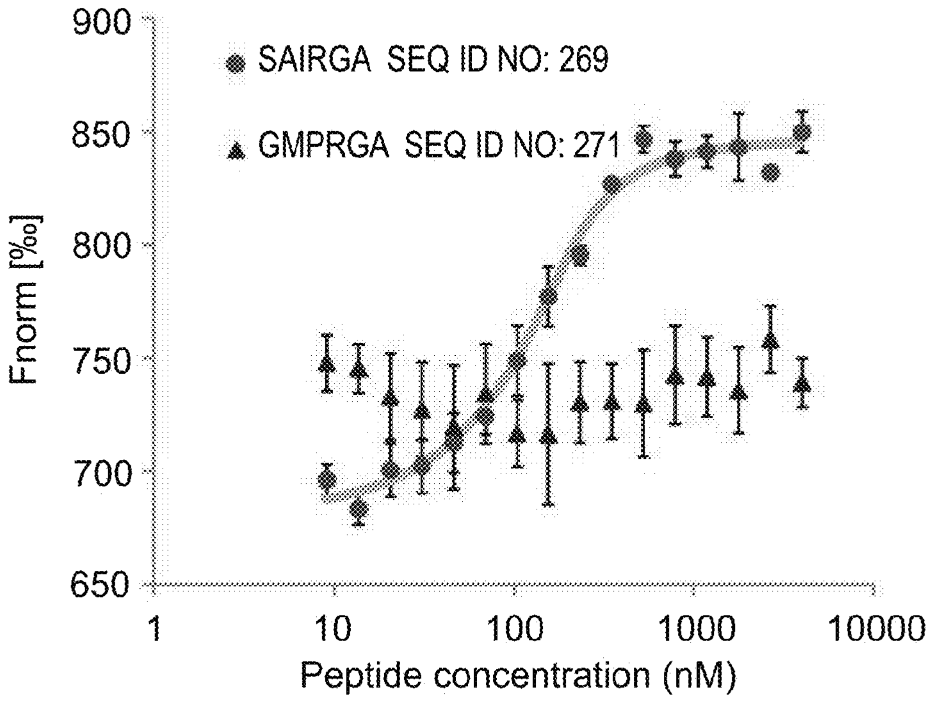

FIGS. 2A-G demonstrate the arbitrium peptide and its receptor. FIG. 2A is a schematic representation of the arbitrium locus in the phi3T phage genome. FIG. 2B demonstrate the signal for cleavage by extracellular proteases in the AimP pre-pro-peptide. Shown are the amino acid sequences of *B. subtilis* quorum sensing Phr genes divided to their domains[1]. The recognition signal for *B. subtilis* extracellular proteases in each sequence is marked in green. The signal peptide in the phi3T AimP protein was predicted by the SignalP 4.1 web server[8]. SEQ ID NOs on the right represent the sequences of the signal peptide, the pro-peptide and the mature peptide, respectively. FIG. 2C demonstrate mass spectrometry histograms verifying the presence of the SAIRGA (SEQ ID NO: 269) peptide in conditioned medium. The left panel shows reference synthesized SAIRGA peptide at 100 nM concentration in LB. B2, Y3, Y4 and Y5 are the peptide fragment ions. The middle panel shows control medium and the right panel shows conditioned medium. In all panels, arrowhead depicts the expected retention time of the SAIRGA peptide. FIG. 2D is a graph demonstrating the growth curves of *B. subtilis* 168 infected by phi3T at MOI=0.1, in LB media supplemented with synthesized SAIRGA (SEQ ID NO: 269) peptide. Numbers represent peptide concentrations. Shown is the average of 3 biological replicates, each with 3 technical replicates. FIG. 2E show graphs demonstrating that 5 amino acids versions of the 6 amino acids arbitrium peptide do not guide lysogeny. Shown are growth curves of *B. subtilis* 168 infected by phi3T at MOI=0.1, in LB media supplemented with synthesized SAIRGA (SEQ ID NO: 269, left panel), AIRGA (SEQ ID NO: 335, middle panel) or SAIRG (SEQ ID NO: 355) peptide. Shown is the average of 3 biological replicates, each with 3 technical replicates. Error bars represent standard error. FIG. 2F demonstrate the sequencing-based quantitative determination of the fraction of lysogenized bacteria. Top—schematics of the analysis: total DNA was extracted from cells during infection and was subjected to Illumina whole genome sequencing. Percent lysogeny was calculated as the fraction of reads spanning the phage/bacteria integration junction out of total reads covering this junction. Integration junction is marked red; integrated phage DNA is green. Bottom—percent lysogenized bacteria at four time points during infection of *B. subtilis* 168 with phi3T at MOI=2. Shown is the average of three biological replicates with error bars denoting standard error. FIG. 2G is a graph demonstrating microscale thermophoresis (MST) analysis of the binding between purified AimR (C-terminal 6×His-tag, at concentration of 200 nM) and synthesized SAIRGA (SEQ ID NO: 269) or GMPRGA (SEQ ID NO: 271) peptides (at a concentration range of 9-4000 nM). Average and standard error of three replicates is shown.

Figure 3A:
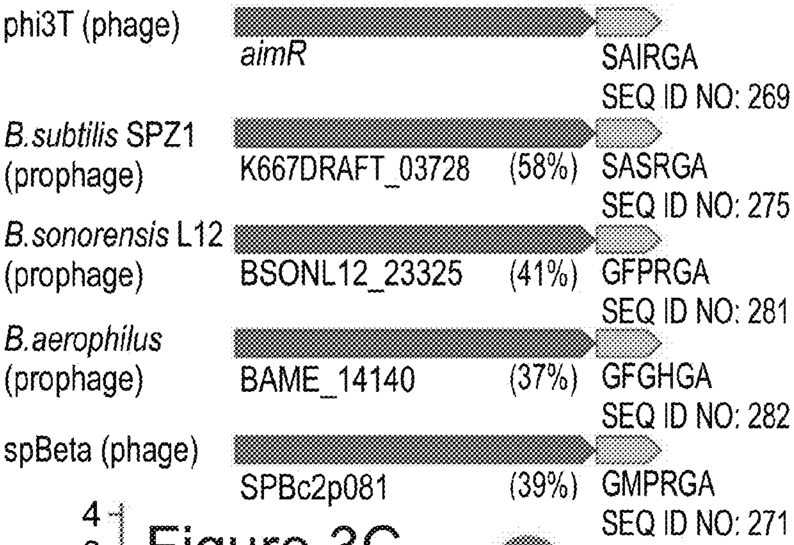
Figure 3B:
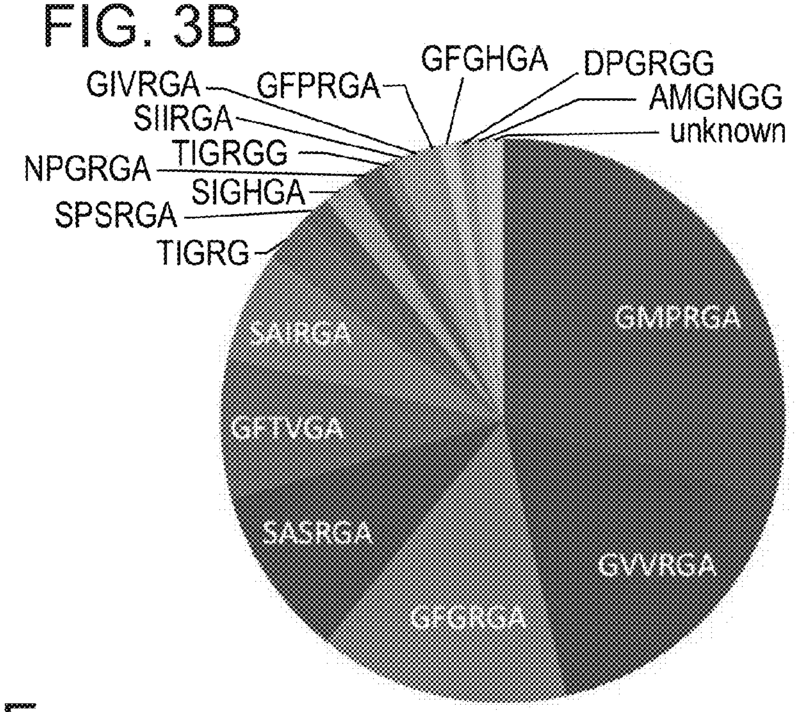
Figure 3C:
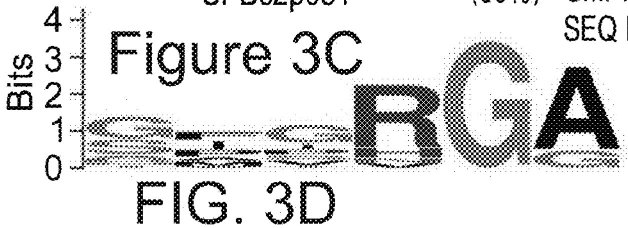
Figure 3D:
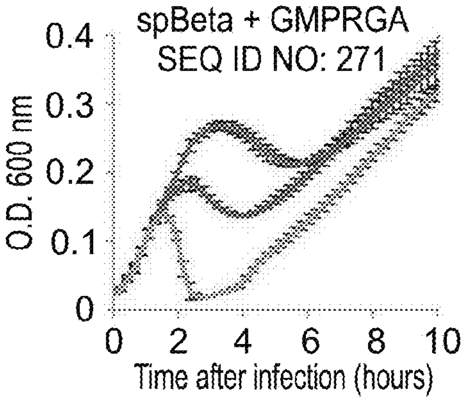
Figure 3E:
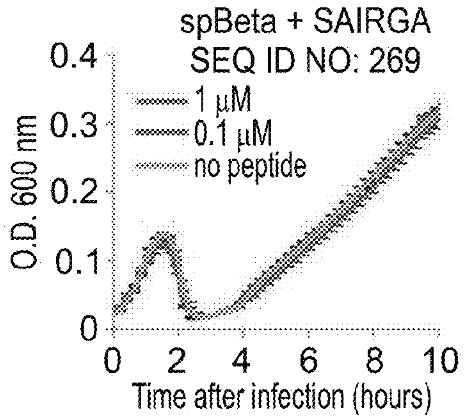
Figure 3F:
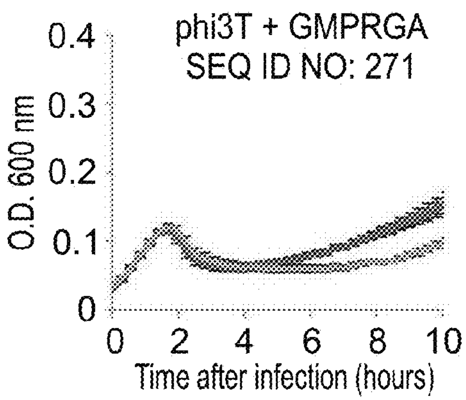

FIGS. 3A-F demonstrate a conserved peptide communication code guiding lysogeny in *Bacillus* phages. FIG. 3A is a schematic representation of selected instances of AimR homologs in sequenced genomes (marked in red). Locus tags are indicated for AimR homologs, along with the percent identity to the phi3T AimR. Mature arbitrium peptide (the last 6 amino acids of AimP ORF) is indicated below the AimP homolog (marked in orange). FIG. 3B is a pie chart demonstrating the distribution of arbitrium peptides among 112 homologs of AimP (see Table 3). The peptides shown are SAIRGA (SEQ ID NO: 269), GFTVGA (SEQ ID NO: 273), SASRGA (SEQ ID NO: 275), GFGRGA (SEQ ID NO: 272), GVVRGA (SEQ ID NO: 276), GMPRGA (SEQ ID NO: 271), AMGNGG (SEQ ID NO: 278), DPGRGG (SEQ ID NO: 274), GFGHGA (SEQ ID NO: 282), GFPRGA (SEQ ID NO: 281), GIVRGA (SEQ ID NO: 286), SIIRGA (SEQ ID NO: 270), TIGRGG (SEQ ID NO: 280), NPGRGA (SEQ ID NO: 285), SIGHGA (SEQ ID NO: 283), SPSRGA (SEQ ID NO: 277) and TIGRG (SEQ ID NO: 279). FIG. 3C shows the amino acid profile of arbitrium peptide types. FIGS. 3D-E are graphs demonstrating growth curves of *B. subtilis* BEST7003 infected by spBeta at MOI=0.1, in LB media supplemented with synthesized GMPRGA (SEQ ID NO: 271, FIG. 3D) and SAIRGA (SEQ ID NO: 269, FIG. 3E) peptides. FIG. 3F is a graph demonstrating the growth curves of *B. subtilis* 168 infected by phi3T at MOI=0.1, in LB media supplemented with synthesized GMPRGA (SEQ ID NO: 271) peptide. Data in FIGS. 3D-F represent average of 3 biological replicates, each with 3 technical replicates. Error bars represent standard error.

Figure 4A:
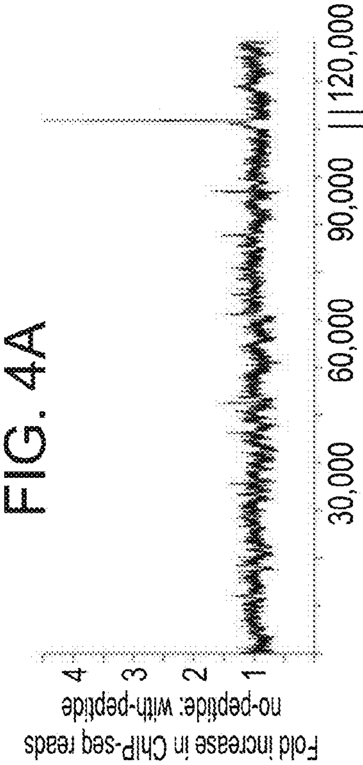
Figure 4B:
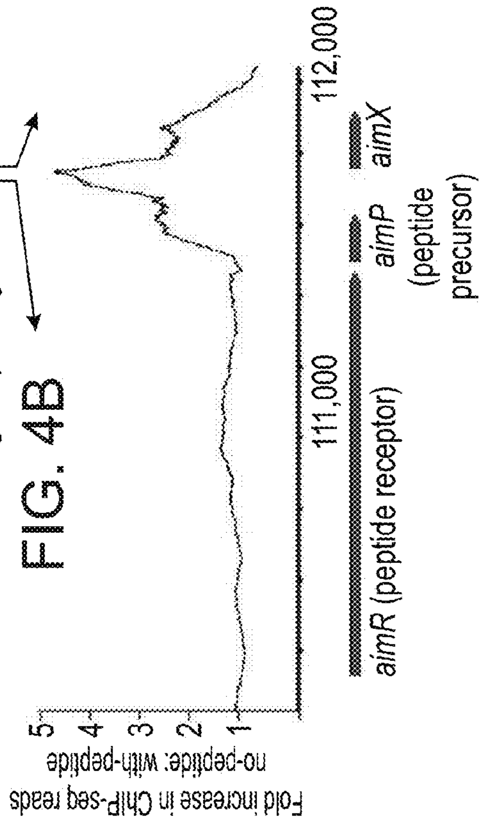
Figure 4C:
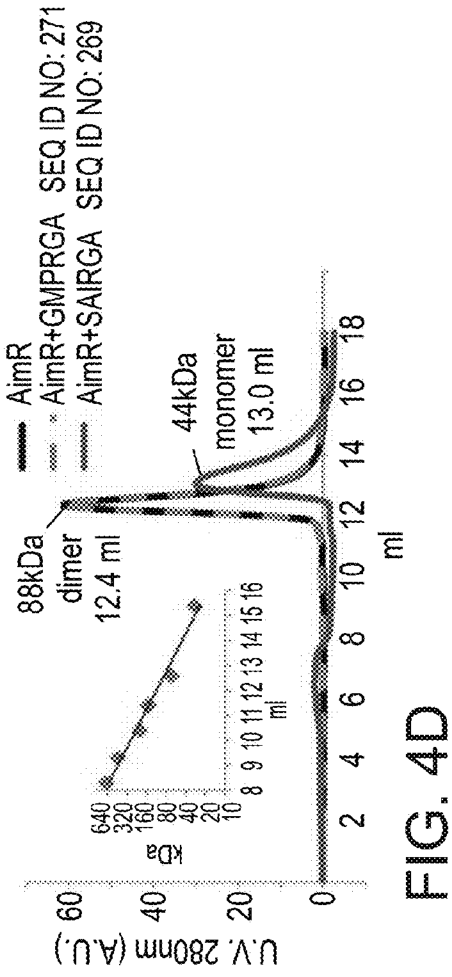
Figure 4D:
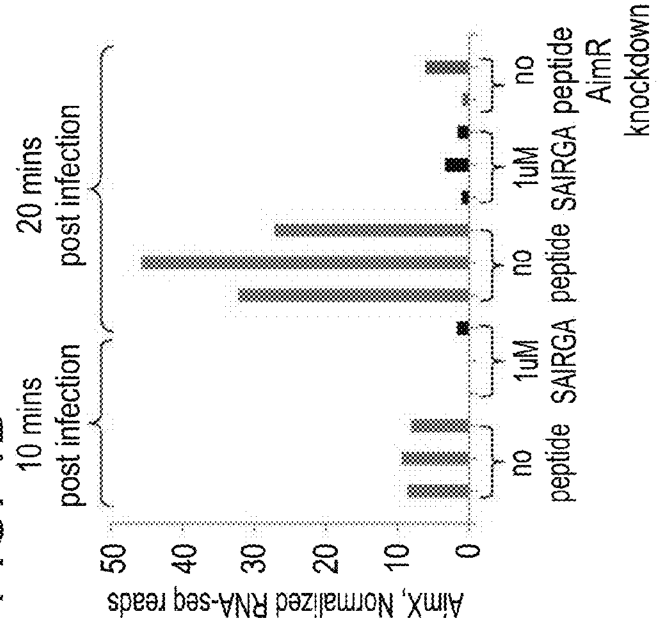
Figure 4I:
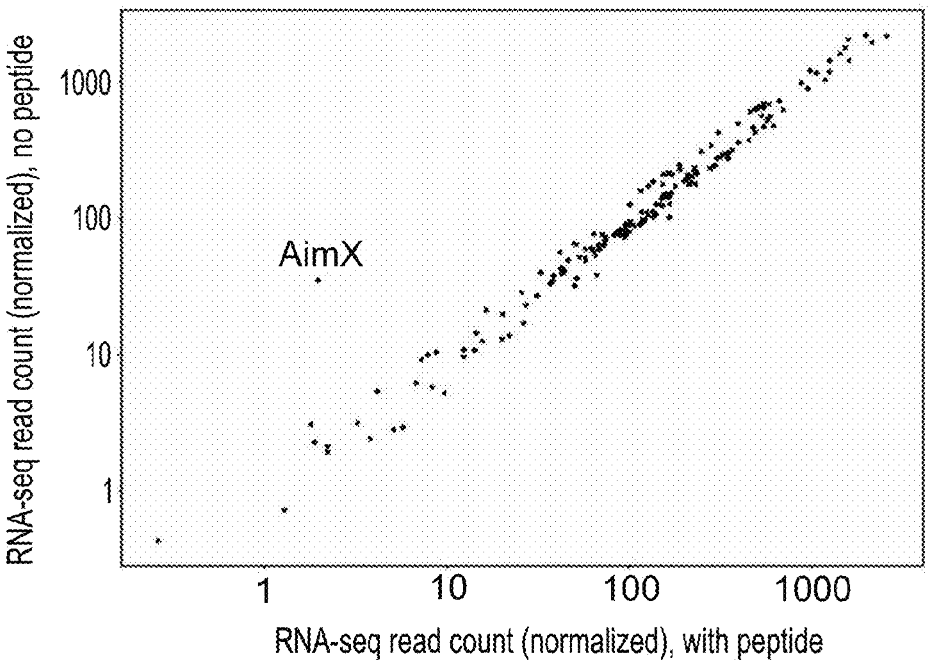

FIGS. 4A-I demonstrate DNA binding and transcription regulation in the arbitrium system. FIG. 4A is a graph demonstrating ChIP-seq of His-tagged AimR 15 minutes post-infection with or without 1 μM of SAIRGA (SEQ ID NO: 269) peptide. For each nucleotide in the phage genome, the ratio between the amount of sequenced pulled-down DNA during infection without the peptide to the amount of DNA pulled-down when the peptide was present in the medium is shown. The ratio was normalized to the amount of sequenced reads in each library. FIG. 4B shows a zoomed-in region in the phage genome of the graph presented in FIG. 4A. FIG. 4C is a graph demonstrating gel-filtration results of purified AimR with or without the presence of either SAIRGA (SEQ ID NO: 269) or GMPRGA (SEQ ID NO: 271) peptide. Inset presents a calibration curve for the gel filtration using proteins of known sizes. FIG. 4D is a bar graph demonstrating expression of the AimX gene during infection. RNA-seq read counts were normalized to the number of reads hitting the phage genome in each RNA-seq library. Normalization was performed separately for the two time points. Data presented for individual biological replicates (3 for each experiment with wild type bacteria and 2 for AimR knockdown strains). FIGS. 4E-G show RNA-seq coverage of the arbitrium locus at 5 min (FIG. 4E), 10 min (FIG. 4F) and 20 min (FIG. 4G) post infection. RNA-seq coverage was normalized to the number of reads hitting the phage genome in each RNA-seq library. FIG. 4H is a graph demonstrating growth curves of wild type and dCas9-silenced bacterial strains during phi3T-infection. Strains were infected at t=0 at MOI=0.1. dCas9 was induced by xylose 0.2%. The aimX gene (purple line) was cloned also under a xylose promoter. Shown is the average of 3 biological replicates, each with 3 technical replicates. Error bars represent standard error. FIG. 4I demonstrates phage gene expression 20 minutes post infection. Each dot represents a single phage gene. Axes represent average RNA-seq read count per gene from 3 replicates, after normalization to control for RNA-seq library size. X axis represent expression when phage infection was in the presence of 1 μM of SAIRGA (SEQ ID NO: 269) peptide; and Y axis represent expression in the absence of peptide.

Figure 5A:
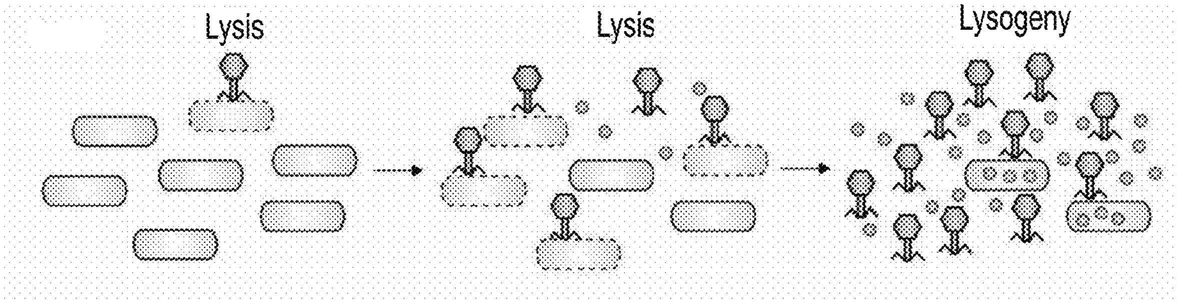
Figure 5B:
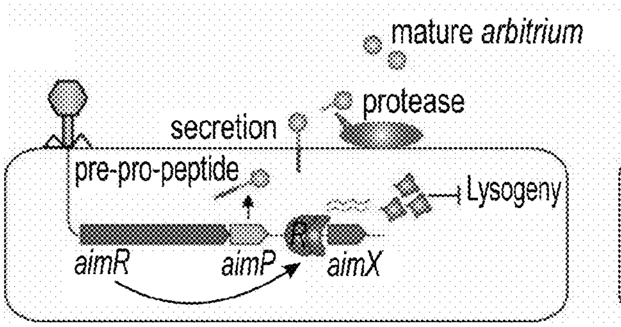
Figure 5C:
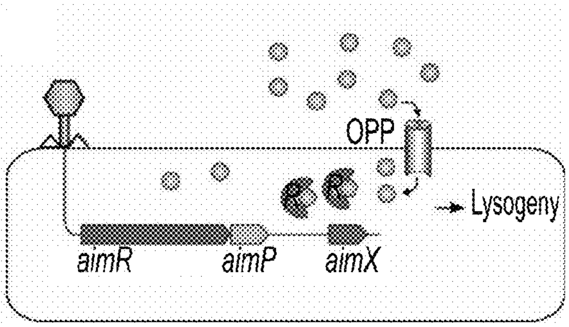

FIGS. 5A-C are schematic representations of the proposed mechanistic model for communication-based lysis-lysogeny decisions. FIG. 5A demonstrates the dynamics of arbitrium accumulation during infection of a bacterial culture by phage. FIG. 5B shows that at the first encounter of a phage with a bacterial population, there is no arbitrium in the medium. The early genes aimR and aimP are expressed immediately upon infection. AimR binds, as a dimer, the phage DNA upstream of aimX, and activates AimX expression. AimX is an inhibitor of lysogeny, directing the phage to a lytic cycle. At the same time AimP is expressed, secreted and processed extracellularly to produce the mature peptide. FIG. 5C shows that at later stages of the infection dynamics, the arbitrium peptide accumulates in the medium and is internalized into the bacteria by the OPP transporter. At this stage when the phage infects the bacterium, the expressed AimR receptor binds the arbitrium molecules and cannot activate the expression of AimX, leading to lysogeny preference.

Figure 6:
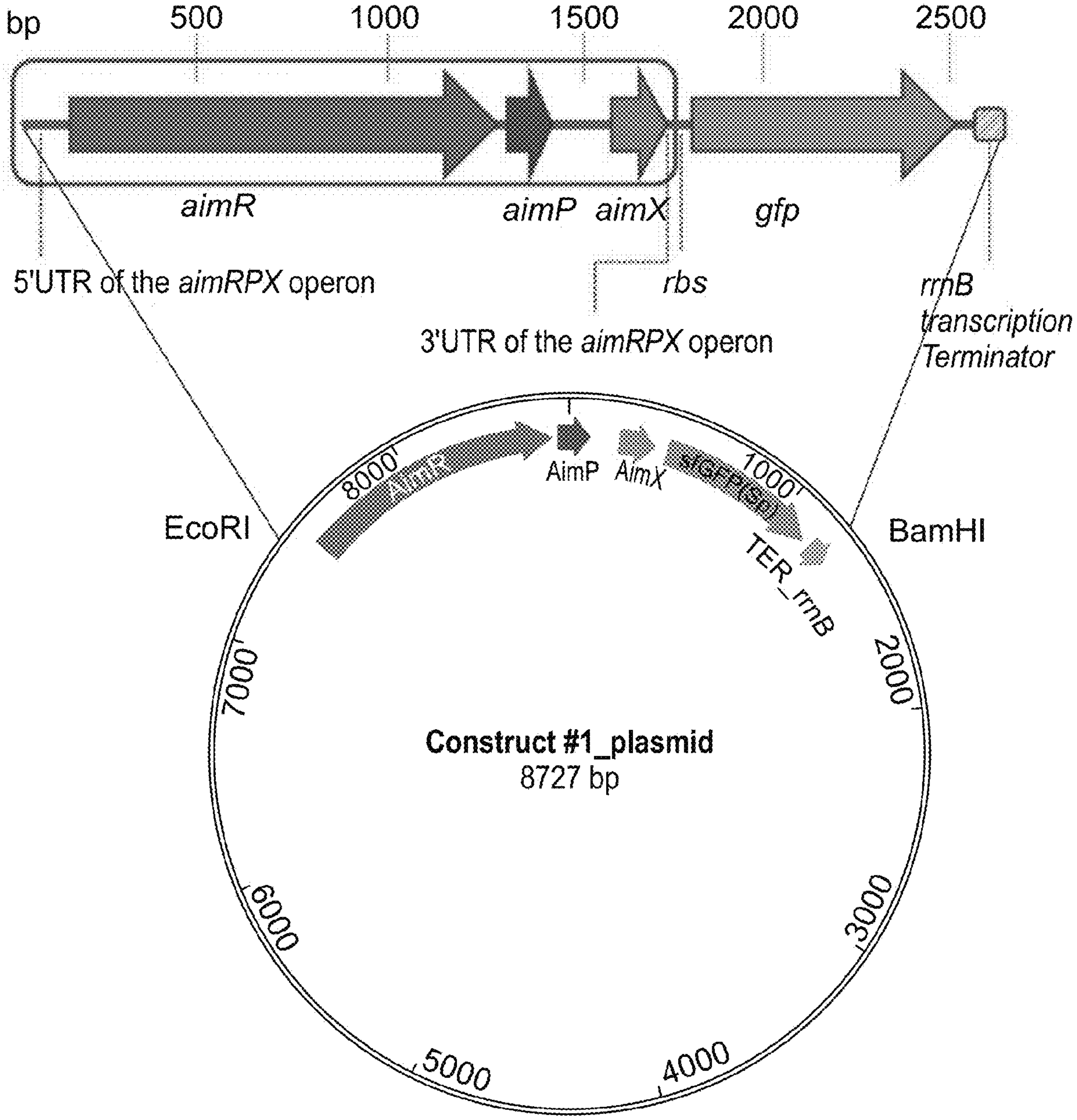

FIG. 6 is a schematic representation of Construct #1: bacteriophage Phi3T AimR-AimP-AimX locus (red rectangle) was genetically fused to the fluorescent reporter gene (gfp) and inserted within the EcoRI/BamHI-cleavage sites of the pDR111 plasmid yielding pDR111-Construct #1.

Figure 7:
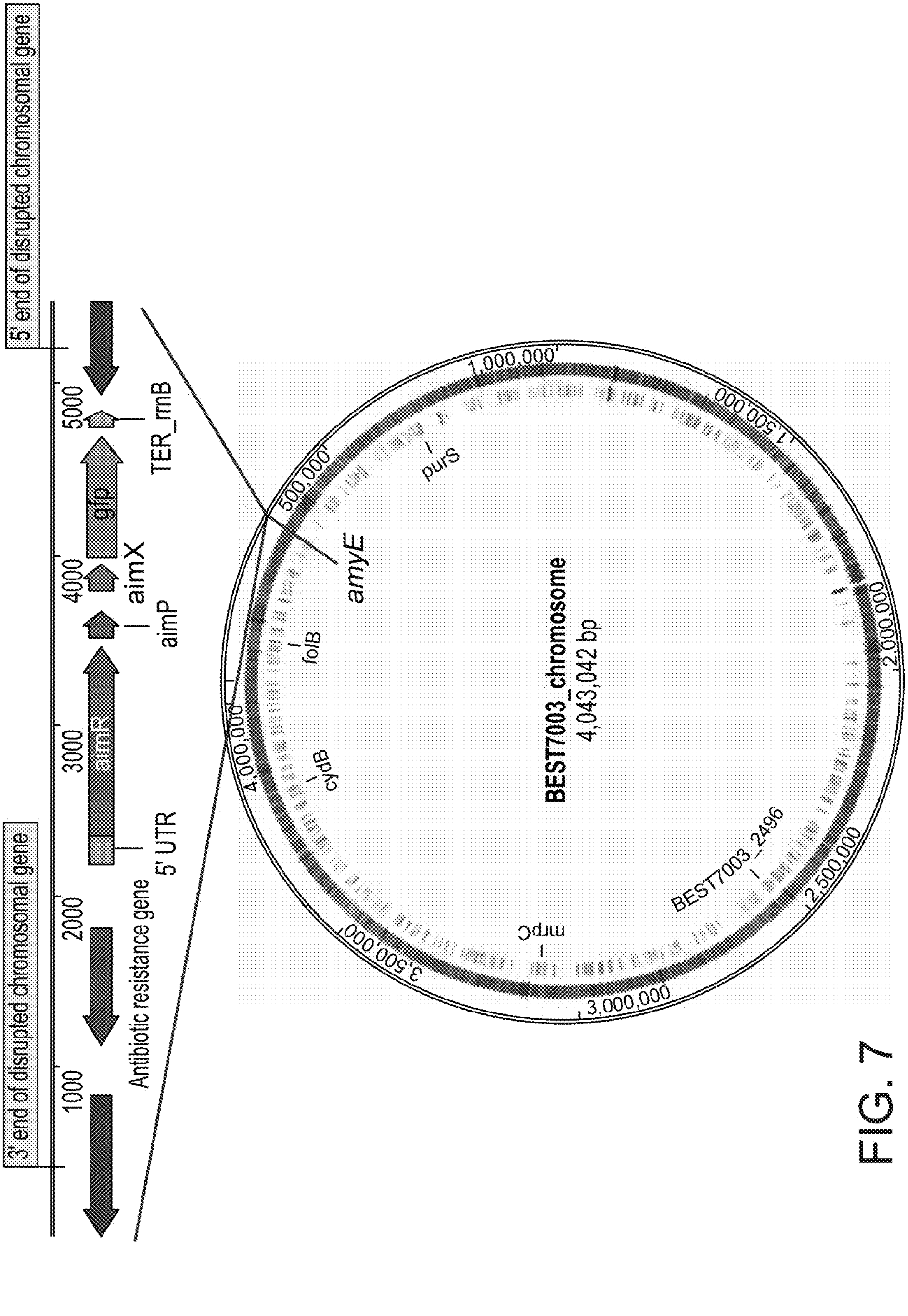

FIG. 7 is a schematic representation of Construct #1 with an antibiotic-resistance gene inserted into the *Bacillus subtilis* BEST7003 chromosome within the amyE gene.

Figure 8:
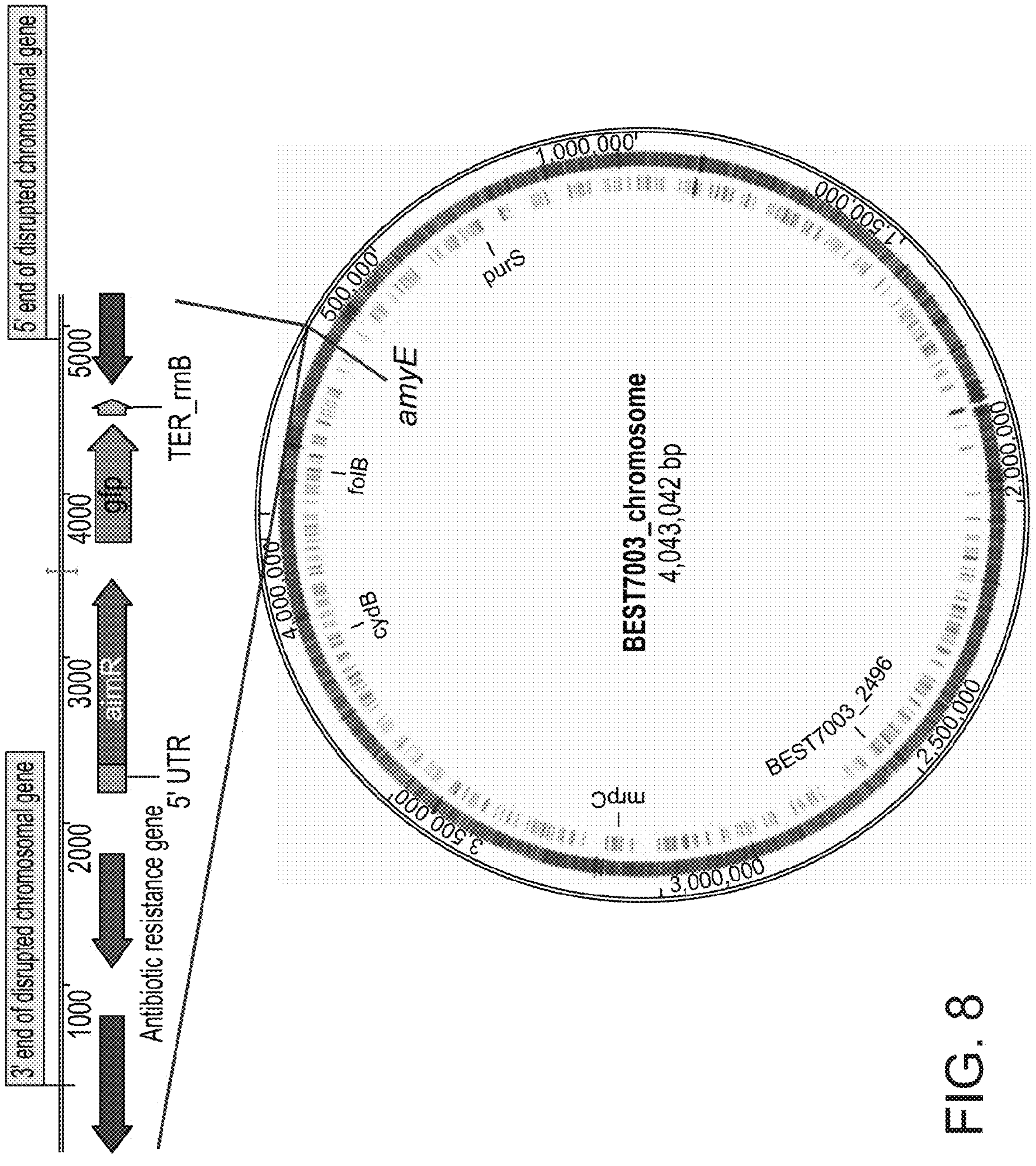

FIG. 8 is a schematic representation of Construct #2 with an antibiotic-resistance gene inserted into the *Bacillus subtilis* BEST7003 chromosome within the amyE gene.

Figure 9B:
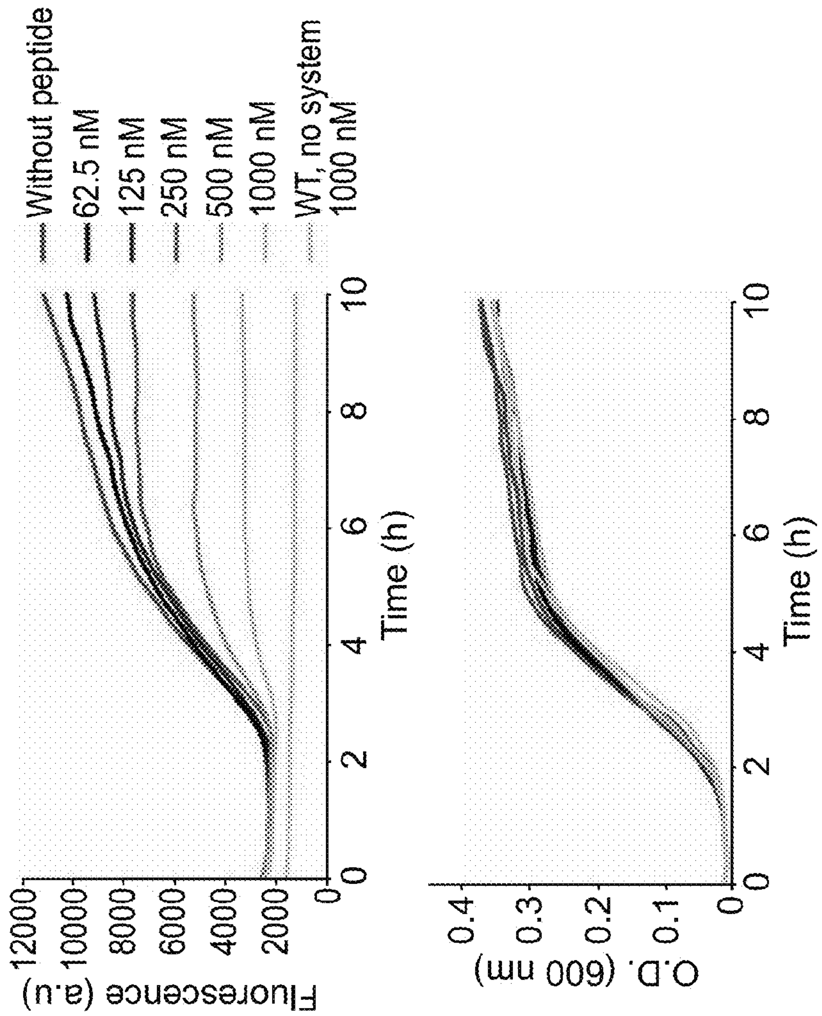
Figure 9A:
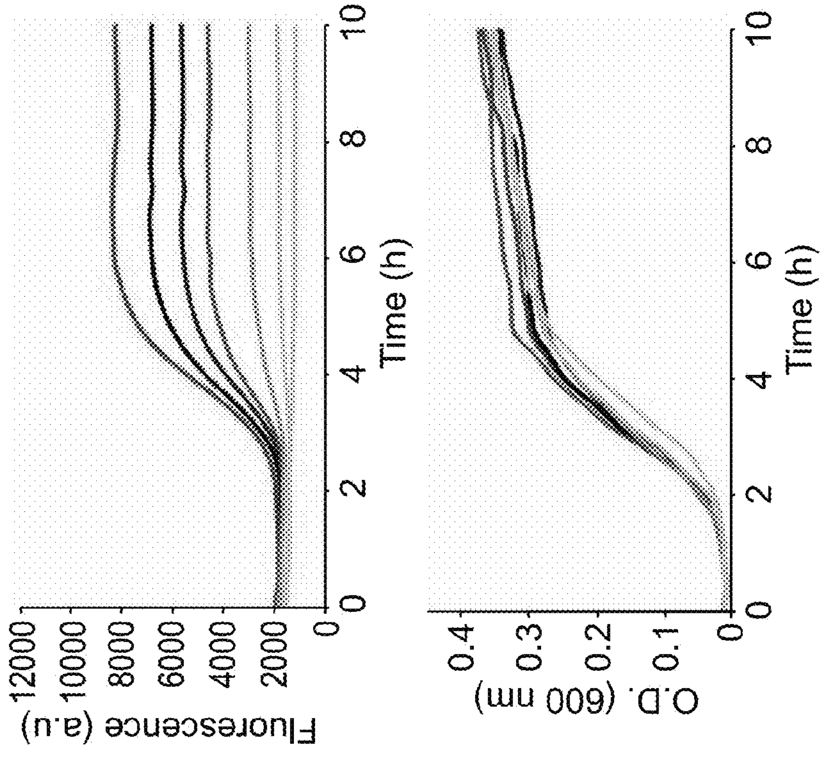

FIGS. 9A-B are graphs demonstrating growth curves and GFP fluorescence levels of wild-type *Bacillus subtilis* BEST7003 (WT) and of *Bacillus subtilis* BEST7003 containing Construct #1 (FIG. 9A) or Construct #2 (FIG. 9B) following culture in LB growth medium supplemented with the indicated concentrations of SAIRGA (SEQ ID NO: 269) peptide. Shown is the mean value of technical replicates (n=3). Fluorescence is shown in arbitrary units (a.u).

DESCRIPTION OF SPECIFIC EMBODIMENTS OF THE INVENTION

The present invention, in some embodiments thereof, relates to isolated polynucleotides and polypeptides and methods of using same for expressing an expression product of interest.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Recombinant DNA technologies, including inducible gene expression and genome editing technologies developed in recent years allow control of gene expression and precise and targeted modifications to genome sequences in many types of organisms, including plants and animals.

Whilst conceiving embodiments of the invention and reducing to practice, the present inventors have devised a novel expression tool which is based on a newly uncovered communication system utilized by temperate viruses to coordinate lytic-lysogenic decisions.

As is illustrated hereinunder and in the Examples section, which follows, the present inventors show that during infection of its *Bacillus* host cell, the virus (spBeta family phage) produces a 6 amino acids long peptide that is released to the medium (Examples 1-2, FIGS. 1A-E and 2A-F). This peptide leads to lysogeny of the phage in its infected host in a concentration-dependent manner (Example 2, FIG. 2D). Following, the inventors were able to identify a shared motif in the peptides encoded by different species of the phage family; a glycine residue at the $5^{th}$ position, glycine or alanine at the $6^{th}$ position, and optionally a positively charged residue at the $4^{th}$ position (Example 3, FIGS. 2G and 3A-C). The inventors further demonstrate that this novel communication system, which the present inventors denoted as the "arbitrium" system, is encoded by 3 phage genes denoted herein as: AimP, producing the peptide; AimR, the intracellular peptide receptor; and AimX, a negative regulator of lysogeny (Example 2-4, FIGS. 2A-G, 3A-C and 4A-I and Table 3). AimR, as a homodimer, is a transcriptional activator of AimX; when bound by the peptide AimR becomes a monomer and the transcription of AimX is repressed, leading to lysogeny. Without being bound by theory it is suggested that the arbitrium system enables an offspring phage particle to communicate with its predecessors, i.e., to estimate the amount of recent prior infections and hence decide whether to employ the lytic or lysogenic cycle (Example 4, FIGS. 5A-C).

Taken together, the present teachings suggest that the arbitrium system and functional fragments thereof can be used for e.g. controlling expression of an expression product of interest in general and controlling the integration of DNA sequences into a target genome in particular. As is further described hereinbelow and in the Examples section that follows, AimR can bind an AimR responsive element thereby leading to activation of transcription of an expression product of interest operatively linked to the AimR responsive element (e.g. AimR binding site); while binding of AimP to AimR represses the transcription of the expression product of interest.

The present inventors further show that an AimR-AimP system can function to control the expression of a GFP reporter gene operatively linked to AimR binding site in *Bacillus subtilis* BEST7003 in a phage-independent context (Example 5, FIGS. 6-8 and 9A-B). Thus, according to a first aspect of the present invention, there is provided an isolated AimP peptide comprising an amino acid sequence of XXXXGG/A, wherein said peptide is capable of binding an AimR polypeptide comprising a DNA binding domain for binding an AimR responsive element, said AimR comprising a helix-turn-helix (HTH) motif and a tetratricopeptide repeat (TPR) domain; and dissociating said AimR polypeptide from said AimR responsive element.

According to another aspect of the present invention, there is provided an isolated AimR polypeptide comprising a DNA binding domain for binding an AimR responsive element, said AimR comprising a helix-turn-helix (HTH) motif and a tetratricopeptide repeat (TPR) domain.

As used herein the term "isolated" refers to at least partially separated from the natural environment, physiological environment e.g., a microorganism or e.g., phage.

As used herein, the term "AimR" refers to the polynucleotide and expression product e.g. polypeptide of the AimR gene. The product of the AimR gene contains a DNA binding domain for binding an AimR responsive element. The product of the AimR gene contains a helix-turn-helix (HTH) motif and a tetratricopeptide repeat (TPR) domain.

As used herein, the phrase "DNA binding domain (DBD)" refers to a motif that can recognize and bind to a specific nucleic acid sequence (e.g. AimR responsive element). The DBD can recognize and bind to a double-stranded nucleic acid sequence (e.g. DNA) in a sequence specific manner. Typically, a DBD is a structural motif in a protein domain. According to specific embodiments the DBD comprises a helix-turn-helix (HTH) motif.

As used herein the term "helix-turn-helix (HTH) motif" refers to a well-known DNA binding motif which complements the shape of the DNA major groove, having the mfap number IPR000047 (see e.g. Ann Rev. of Biochem. (1984) 53:293 and Brunelle and Schleif J. Mol. Biol. (1989) 209: 607). The domain can be illustrated by the sequence XXX-PhoAlaXXPhoGlyPhoXXXXPhoXXPhoXX (SEQ ID NO: 335), wherein X is any amino acid and Pho is a hydrophobic amino acid.

As used herein, the term "tetratricopeptide repeat (TPR) domain" refers to a degenerate 34 amino acid consensus sequence found in tandem arrays of 3-16 motifs that is believed to mediate protein-protein binding Family: TPR_1 (PF00515). TPR domain forms two anti-parallel α-helices separated by a turn, to form a structure with an amphipathic groove [see e.g. Hirano et al. (1990), *Cell,* 60:319-328].

According to specific embodiments, the AimR polynucleotide has at least 80% identity to a nucleic acid selected from the group consisting of SEQ ID NO: 1-113.

According to specific embodiments, the AimR polynucleotide has at least 85%, at least 90%, at least 95% identity to a nucleic acid selected from the group consisting of SEQ ID NO: 1-113.

According to specific embodiments, the AimR polypeptide has at least 80% identity to an amino acid sequence selected from the group consisting of SEQ ID NOs: 114-226.

According to specific embodiments, the AimR polypeptide has at least at least 85%, at least 90%, at least 95% identity to an amino acid sequence selected from the group consisting of SEQ ID NOs: 114-226.

According to specific embodiments, the AimR polypeptide has at least 35%, at least 40%, at least 45%, at least 50%, at least 55%, at least 60%, at least 70%, at least 80%, at least 85%, at least 90% or 100% identity to SEQ ID NO: 114.

Sequence identity can be determined using any protein alignment algorithm or any nucleic acid sequence alignment algorithm based on the polynucleotide sequence encoding the polypeptide such as Blast, ClustalW, MUSCLE, and HHpred.

According to specific embodiments, AimR amino acid sequence is selected from the group consisting of SEQ ID NOs: 114-226.

According to specific embodiments, AimR nucleic acid sequence is selected from the group consisting of SEQ ID NOs: 1-113.

According to a specific embodiment, AimR comprises SEQ ID NO: 114.

The present inventors have uncovered that AimR binds the phage DNA as a dimer in the absence of the AimP peptide and functions as a transcriptional activator of e.g. AimX. Upon binding to the AimP peptide, the AimR changes its oligomeric state from the active dimer to the inactive monomer leading to a decrease in the transcription of e.g. AimX.

Hence, an AimR polypeptide according to some embodiments is capable of binding an AimP peptide comprising an amino acid sequence of XXXXGG/A (as further described hereinbelow); and in the absence of AimP binding DNA (i.e. AimR responsive element) and activating gene expression (i.e. a transcription factor).

Methods of determining binding of a transcription factor (e.g. AimR) to DNA (e.g. AimR Responsive element) are well known in the art and include, but not limited to, Chromatin Immunoprecipitation (ChIP) Assay, DNA Electrophoretic Mobility Shift Assay (EMSA), DNA Pull-down Assay and Microplate Capture and Detection Assay.

According to specific embodiments, the AimR binds DNA as a dimer. Methods of evaluating dimerization are well known in the art and are further described in the Examples section which follows and include migration on a gel filtration column.

According to specific embodiments, the term "AimR" refers to a full length AimR. According to other specific embodiments, the term "AimR" refers to a fragment of AimR which maintains the activity as described herein.

The term "AimR", also refers to functional AimR homologues which exhibit the desired activity as described herein. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NOs: 114-226, or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide encoding same (as further described hereinabove and below). The homolog may also refer to an ortholog, a deletion, insertion, or substitution variant, including an amino acid substitution.

Sequence identity or homology can be determined using any protein or nucleic acid sequence alignment algorithm such as Blast, ClustalW, MUSCLE, and HHpred.

As used herein, the term "operatively linked" refers to a nucleic acid sequence having a functional relationship with another nucleic acid sequence. According to specific embodiments, a nucleic acid sequence is "operatively linked" to a regulatory sequence when the regulatory sequence (e.g. AimR binding site) controls and regulates the transcription and/or translation of that nucleic acid sequence. According to one embodiment, the regulatory element act in cis on the nucleic acid sequence it regulates. According to another embodiment, the regulatory element act in trans on the nucleic acid sequence it regulates. According to specific embodiments, the regulatory sequence is placed upstream to the nucleic acid sequence it regulates. According to specific embodiments, the term "operatively linked" includes having an appropriate start signal (e.g., ATG) upstream of the nucleic acid sequence to be expressed and maintaining the correct reading frame to allow expression of the nucleic acid sequence under the control of the regulatory sequence and expression of the desired product encoded by the nucleic acid sequence.

According to specific embodiments, the term "AimR responsive element" refers to a full length AimR responsive element. According to other specific embodiments, the term "AimR responsive element" refers to a fragment of AimR responsive element which maintains the activity as described herein. According to specific embodiments, the AimR responsive element is 4-100, 4-50, 4-30 or 4-10 nucleic acids long.

According to specific embodiment, the AimR responsive element comprises a nucleic acid sequence for binding AimR (i.e. AimR binding site).

According to specific embodiments, the AimR responsive element comprises a nucleic acid sequence selected from the group consisting of SEQ ID NOs: 287-334.

According to specific embodiments, the AimR responsive element is comprised in a nucleic acid sequence selected from the group consisting of SEQ ID NOs: 287-334.

According to specific embodiments, the AimR responsive element comprises SEQ ID NO: 378.

According to specific embodiments, the AimR responsive element is comprised in SEQ ID NO: 378.

According to specific embodiments, the AimR responsive element comprises a fragment of SEQ ID NOs: 287-334 or 378 which maintains SEQ ID NOs: 287-334 or 378 activity as a nucleic acid sequence for binding AimR (i.e. AimR binding site), as determined by e.g. Chromatin Immunoprecipitation (ChIP) Assay, DNA Electrophoretic Mobility Shift Assay (EMSA), Microplate Capture and Detection Assay, or DNA Pull-down Assay.

According to specific embodiments, the AimR responsive element comprises a nucleic acids sequence for binding AimR (i.e. AimR binding site) and AimX. Hence, specific embodiments of the present invention disclose that binding of AimR to its binding site controls expression of AimX, which in turn controls expression of an expression product of interest.

The term "AimR responsive element", also refers to functional AimR responsive element homologues which exhibit the desired activity (i.e., binding an AimR). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polynucleotide SEQ ID NOs: 287-334 and 378. The homolog may also refer to an ortholog, a deletion, insertion, or substitution variant, including an amino acid substitution.

AimRs and their cognate sequences comprising AimR responsive elements which can be used in accordance with some embodiments are listed in Table 3 hereinbelow.

As used herein, the term "AimP" refers to a peptide having an amino acid sequence of XXXXGG/A, wherein X is any amino acid or a nucleic acid encoding same. According to specific embodiments, the AimP has an amino acid sequence of $XXXX_1GG/A$, wherein X is any amino acid and wherein $X_1$ is a positively charged amino acid. According to a specific embodiment, the AimP is the product of the AimP gene.

The peptide can be long e.g., more than 50 amino acids (e.g., 51-80 amino acids, 51-100 amino acids, 100-200 amino acids) or short e.g., 6-50 amino acids long. According to specific embodiments, the peptide is 6 amino acids long.

According to specific embodiments, AimP comprises an amino acid sequence selected from the group consisting of SEQ ID NOs: 269-283 and 285-286.

According to specific embodiments, the AimP peptide comprises a SAIRGA (SEQ ID NO: 269) or GMPRGA (SEQ ID NO: 271) amino acid sequence.

According to specific embodiments, the AimP peptide comprises a SAIRGA (SEQ ID NO: 269) amino acid sequence.

A functional AimP peptide can bind an AimR polypeptide and dissociate the AimR polypeptide from DNA and specifically from an AimR responsive element.

As used herein, the terms "dissociating" and "dissociate" refer to at least 30% reduction in complexes comprising the AimR and AimR responsive element, as evidenced by an assay known in the art e.g., Chromatin Immunoprecipitation (ChIP) Assay, DNA Electrophoretic Mobility Shift Assay (EMSA), DNA Pull-down Assay and Microplate Capture and Detection Assay.

According to specific embodiments, a functional AimP can lead to lysogeny of a temperate phage expressing AimR in a host bacteria. Methods of analyzing phage lysogeny are described hereinbelow.

The term "AimP", also refers to functional AimP homologues which exhibit the desired activity as described herein. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the peptide SEQ ID NOs: 269-283 and 285-286. The homolog may also refer to an ortholog, a deletion, insertion, or substitution variant, including an amino acid substitution.

AimPs and their cognate AimRs which can be used in accordance with some embodiments are listed in Table 3 hereinbelow.

Binding assays for qualifying peptide binding to AimR are well known in the art and include e.g. western blot, BiaCore, high-performance liquid chromatography (HPLC) or flow cytometry.

Binding assays for qualifying the ability of the peptide to dissociate AimR from DNA are well known in the art and include and include, but not limited to, Chromatin Immunoprecipitation (ChIP) Assay, DNA Electrophoretic Mobility Shift Assay (EMSA), DNA Pull-down Assay and Microplate Capture and Detection Assay.

According to specific embodiments binding of the AimP peptide to AimR polypeptide inhibits dimerization of the AimR polypeptide.

As used herein, the terms "inhibit" and "inhibiting" refer to a decrease in activity (e.g. dimerization, binding, lysogeny). According to specific embodiments the decrease is at least 1.5 fold, at least 2 fold, at least 3 fold, at least 5 fold, at least 10 fold, or at least 20 fold as compared to same in the absence of the AimP peptide or AimX.

According to other specific embodiments the decrease is by at least 5%, by at least a 10%, at least 20%, at least 30%, at least 40%, at least 50%, at least 60%, at least 70%, at least 80%, at least 90%, at least 95% or 99% or 100% as compared to same in the absence of the AimP peptide or AimX.

A temperate phage is one capable of entering the lysogenic pathway, in which the phage becomes a dormant, passive part of the cell's genome through prior to completion of its lytic cycle.

According to specific embodiments the phage is capable of infecting a *Bacillus* bacteria.

According to specific embodiments the phage is a prophage.

Table 3 below indicates phages and prophages that can be used according to specific embodiments of the invention. According to a specific embodiment, the phage is a spBeta phage. According to a specific embodiment, the phage is Phi3T.

For the same culture conditions the extent of lysogeny is generally expressed in comparison to the lysogeny in bacteria of the same species but not contacted with the indicated agent (e.g. AimP, AimX) or contacted with a vehicle control, also referred to as control.

Methods of analyzing phage lysogeny are well known in the art and include, but not limited to, DNA sequencing and PCR analysis. As a temperate phage can employ the lysogenic pathway or the lytic pathway, the lysogenic activity of a phage can be assessed indirectly by determining reduction in the lytic activity of a phage by methods well known in the art including, but not limited to, optical density, plaque assay, and living dye indicators.

As used herein, the phrases "leading to lysogeny" and "lead to lysogeny" refers to an increase in lysogeny.

According to specific embodiments the increase is at least 1.5 fold, at least 2 fold, at least 3 fold, at least 5 fold, at least 10 fold, or at least 20 fold as compared to same in the absence of the AimP peptide or AimX downregulating agent.

According to other specific embodiments the increase is by at least 5%, by at least a 10%, at least 20%, at least 30%, at least 40%, at least 50%, at least 60%, at least 70%, at least 80%, at least 90%, at least 95% or 99% or 100% as compared to same in the absence of the AimP peptide or AimX downregulating agent.

According to specific embodiments, the bacteria can be infected with a temperate phage selected from the phages depicted in Table 3 below. According to specific embodiments, the bacteria can be infected with a spBeta phage. According to specific embodiments the bacteria is a *Bacillus* bacteria. According to specific embodiments the bacteria is selected from the group consisting of the bacteria listed in Table 3 below.

The present invention also contemplates isolated polynucleotides encoding the components of the arbitrium system and functional fragments thereof as described herein.

Thus, according to an aspect of the present invention, there is provided an isolated polynucleotide encoding an AimP peptide comprising an amino acid sequence of XXXXGG/A, wherein said peptide is capable of binding an AimR polypeptide comprising a DNA binding domain for binding an AimR responsive element, said AimR comprising a helix-turn-helix (HTH) motif and a tetratricopeptide repeat (TPR) domain; and dissociating said AimR polypeptide from an AimR responsive element.

According to another aspect of the present invention, there is provided an isolated polynucleotide encoding an AimR polypeptide comprising a DNA binding domain for binding an AimR responsive element, said AimR comprising a helix-turn-helix (HTH) motif and a tetratricopeptide repeat (TPR) domain.

According to specific embodiments, the polynucleotide encoding the AimR polypeptide comprises a sequence having at least 80%, at least 85%, at least 90%, at least 95% or 100% identity to a nucleic acid sequence selected from the group consisting of SEQ ID NOs: 1-113.

According to specific embodiments, the polynucleotide encoding the AimR polypeptide comprises a sequence selected from the group consisting of SEQ ID NOs: 1-113.

According to another aspect of the present invention, there is provided an isolated polynucleotide comprising an AimR responsive element, wherein said AimR comprises a DNA binding domain for binding said AimR responsive element, said AimR comprises a helix-turn-helix (HTH) motif and a tetratricopeptide repeat (TPR) domain.

According to specific embodiments, the AimR responsive element comprises a nucleic acid sequence for binding AimR and an AimX polynucleotide, wherein said AimX polynucleotide or an AimX polypeptide encoded by said AimX polynucleotide is capable of inhibiting lysogeny of a temperate phage expressing said AimR in a host bacteria.

According to another aspect of the present invention, there is provided an isolated AimX polynucleotide.

According to another aspect of the present invention, there is provided an isolated polypeptide encoded by the AimX polynucleotide.

As used herein, the term "AimX" refers to the polynucleotide and expression product e.g. polypeptide of the AimX gene. According to specific embodiments, the "AimX" refers to the polynucleotide of the AimX gene. According to specific embodiments, an AimR binding site is operatively linked to the AimX polynucleotide. A functional AimX is capable of inhibiting lysogeny of a temperate phage expressing the respective AimR in a host bacteria. According to specific embodiments, AimX and AimR binding site comprise an AimR responsive element.

According to specific embodiments, AimX comprises a nucleic acid sequence as set forth in SEQ ID NO: 336.

According to specific embodiments, the term "AimX" refers to a full length AimX. According to other specific embodiments, the term "AimX" refers to a fragment of AimX which maintains the activity as described herein.

The term "AimX", also refers to functional AimX homologues which exhibit the desired activity as described herein. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polynucleotide SEQ ID NO:336. The homolog may also refer to an ortholog, a deletion, insertion, or substitution variant, including an amino acid substitution.

AimRs and their cognate AimXs which can be used in accordance with some embodiments are listed in Table 3 hereinbelow.

According to another aspect of the present invention, there is provided an isolated polynucleotide comprising a polynucleotide encoding an AimP peptide, a polynucleotide encoding an AimR polypeptide, a polynucleotide comprising an AimR responsive element and/or an AimX polynucleotide and any combination of same.

According to another aspect of the present invention, there is provided an isolated polynucleotide encoding an arbitrium system comprising a nucleic acid sequence encoding an AimP peptide, a nucleic acid sequence encoding an AimR polypeptide and a nucleic acid sequence for binding AimR operatively linked to an AimX nucleic acid sequence, wherein said arbitrium system is capable of regulating lysogeny of a phage expressing said arbitrium system in a host bacteria.

As used herein "arbitrium system" or a "functional arbitrium", refers to a multi-gene system which comprises AimP, AimR, and AimX as described herein and which activity controls phage lysogeny in its host genome.

The combinations of the arbitrium system components which can be used in accordance with some embodiments are listed in Table 3 hereinbelow.

As used herein, the term "components of the arbitrium system" refers to AimP, AimR, AimR responsive element, AimX and any combination of same or functional fragments thereof such as described hereinabove.

According to specific embodiments, the AimR is encoded by a gene positioned within 1-10 genes of a gene encoding AimP and/or AimR responsive element (e.g. SEQ ID NOs: 287-334, 378) in a genome of a temperate phage.

According to specific embodiments, the AimP is encoded by a gene positioned within 1-10 genes of a gene encoding an AimR responsive element (e.g. SEQ ID NOs: 287-334, 378) in a genome of a temperate phage. According to specific embodiments, the AimR and the AimP and/or the AimR responsive element (e.g. SEQ ID NOs: 287-334, 378) are positioned sequentially 5' to 3' on a nucleic acid molecule of a temperate phage expressing same.

According to specific embodiments, the AimR and the AimP and/or the AimR responsive element (e.g. SEQ ID NOs: 287-334, 378) are positioned sequentially 5' to 3' in a genome of a temperate phage.

According to specific embodiments, the AimR and the AimP and/or the AimR responsive element (e.g. SEQ ID NOs: 287-334, 378) are positioned contiguously 5' to 3' on a nucleic acid molecule of a temperate phage expressing same.

According to specific embodiments, the AimR and the AimP and/or the AimR responsive element (e.g. SEQ ID NOs: 287-334, 378) are positioned contiguously 5' to 3' in a genome of a temperate phage.

According to specific embodiments, the AimP and the AimR responsive element (e.g. SEQ ID NOs: 287-334, 378) are positioned sequentially 5' to 3' on a nucleic acid molecule of a temperate phage expressing same.

According to specific embodiments, the AimP and the AimR responsive element (e.g. SEQ ID NOs: 287-334, 378) are positioned sequentially 5' to 3' in a genome of a temperate phage.

According to specific embodiments, the AimP and the AimR responsive element (e.g. SEQ ID NOs: 287-334, 378) are positioned contiguously 5' to 3' on a nucleic acid molecule of a temperate phage expressing same.

According to specific embodiments, the AimP and the AimR responsive element (e.g. SEQ ID NOs: 287-334, 378) are positioned contiguously 5' to 3' in a genome of a temperate phage.

According to specific embodiments, the AimR is encoded by a gene positioned within 1-10 genes of a gene encoding AimX in a genome of a temperate phage.

According to specific embodiments, the AimP is encoded by a gene positioned within 1-10 genes of a gene encoding AimX in a genome of a temperate phage.

According to specific embodiments, the AimR and the AimP and/or the AimX are positioned sequentially 5' to 3' on a nucleic acid molecule of a temperate phage expressing same.

According to specific embodiments, the AimR and the AimP and/or the AimX are positioned sequentially 5' to 3' in a genome of a temperate phage.

According to specific embodiments, the AimR and the AimP and/or the AimX are positioned contiguously 5' to 3' on a nucleic acid molecule of a temperate phage expressing same.

According to specific embodiments, the AimR and the AimP and/or the AimX are positioned contiguously 5' to 3' in a genome of a temperate phage.

According to specific embodiments, the AimP and the AimX are positioned sequentially 5' to 3' on a nucleic acid molecule of a temperate phage expressing same.

According to specific embodiments, the AimP and the AimX are positioned sequentially 5' to 3' in a genome of a temperate phage.

According to specific embodiments, the AimP and the AimX are positioned contiguously 5' to 3' on a nucleic acid molecule of a temperate phage expressing same.

According to specific embodiments, the AimP and the AimX are positioned contiguously 5' to 3' in a genome of a temperate phage.

Thus, according to specific embodiments, the polynucleotide of the present invention comprises:

(1) a polynucleotide encoding an AimP peptide;

(2) a polynucleotide comprising a nucleic acid sequence encoding an AimR polypeptide;

(3) a polynucleotide comprising an AimR responsive element nucleic acid sequence; (4) an AimX polynucleotide (5) a polynucleotide comprising (2) and (3);

(6) a polynucleotide comprising (2) and (4);

(7) a polynucleotide comprising (1), (2) and (3);

(8) a polynucleotide comprising (1), (2) and (4);

(9) a polynucleotide comprising (1) and (2);

(10) a polynucleotide comprising (1) and (3); or

(11) a polynucleotide comprising (1) and (4)

According to specific embodiments, the AimR polynucleotide is upstream to the AimP polynucleotide.

According to specific embodiments, the AimR polynucleotide is upstream to the AimR responsive element polynucleotide.

According to specific embodiments, the AimR polynucleotide is upstream to the AimX polynucleotide.

According to specific embodiments, the AimR responsive element is upstream to the AimX polynucleotide.

According to specific embodiments, the AimP polynucleotide is upstream to the AimR responsive element polynucleotide.

According to specific embodiments, the AimP polynucleotide is upstream to the Aimx polynucleotide.

As used herein, the terms "peptide" and "polypeptide", which are interchangeably used, encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2), which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethy)glycine | Nasn |
| D-aspartic acid | Dasp | N-(carboxymethyl)glycine | Nasp |
| D-cysteine | Dcys | N-(thiomethyl)glycine | Ncys |

TABLE 2-continued

| Non-conventional amino acid | Code | Non-conventional amino acid | Code |
|---|---|---|---|
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |

TABLE 2-continued

| Non-conventional amino acid | Code | Non-conventional amino acid | Code |
|---|---|---|---|
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclicization does not severely interfere with peptide characteristics, cyclic forms of the peptide can also be utilized.

The peptides of some embodiments of the invention preferably include one or more non-natural or natural polar amino acids, including but not limited to serine and threonine which are capable of increasing peptide solubility due to their hydroxyl-containing side chain.

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH [(—$CH_2$)$_5$—COOH]—CO— for aspartic acid. Those non-conservative substitutions which fall under the scope of the present invention are those which still constitute a peptide having anti-bacterial properties.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

The peptides of the present invention may be attached (either covalently or non-covalently) to a penetrating agent.

As used herein the phrase "penetrating agent" refers to a heterologous agent which enhances translocation of any of the attached peptide across a cell membrane.

According to one embodiment, the penetrating agent is a peptide and is attached to the peptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids. Non-limiting examples of CPPs that can penetrate cells in a non-toxic and efficient manner and may be suitable for use in accordance with some embodiments of the invention include TAT (transcription activator from HIV-1), pAntp (also named penetratin, *Drosophila* antennapedia homeodomain transcription factor) and VP22 (from Herpes Simplex virus). Protocols for producing CPPs-cargos conjugates and for infecting cells with such conjugates can be found, for example L Theodore et al. [The Journal of Neuroscience, (1995) 15(11): 7158-7167], Fawell S, et al. [Proc Natl Acad Sci USA, (1994) 91:664-668], and Jing Bian et al. [Circulation Research. (2007) 100: 1626-1633].

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The peptides of some embodiments of the invention may be synthesized and purified by any techniques known to those skilled in the art of peptide synthesis, such as, but not limited to, solid phase techniques and recombinant techniques such as further described hereinbelow.

As used herein, the term “polynucleotide” refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As the novel “arbitrium” system is involved in controlling integration of DNA into a genome of a host the present teachings suggest that components of the “arbitrium” system described herein can be used for controlling integration of expression product of interest into a target genome.

Thus, according to specific embodiments, the polynucleotides of the present invention comprise a nucleic acid sequence encoding an expression product of interest.

As used herein the term “expression product of interest” refers to a RNA and/or protein of interest.

According to specific embodiments, expression and/or activity of the expression product of interest is dependent on AimX; i.e. expression of AimX controls expression and/or activity of the expression product of interest.

According to specific embodiments, the expression product of interest is a therapeutic expression product such as an antibody, a growth factor, a cytokine etc.

According to specific embodiments, the expression product of interest is a DNA editing agent.

According to specific embodiments, the DNA editing agent expression and/or activity is dependent on AimX; i.e. expression of AimX controls expression and/or activity of the DNA editing agent.

As used herein, the term “DNA editing agent” refers to an agent capable of introducing sequence alterations in the genome of a cell. These targeted sequence alterations may involve loss-of function or gain of function alterations. Non-limiting examples of such alterations include a missense mutation, i.e., a mutation which changes an amino acid residue in the protein with another amino acid residue and thereby modulates the activity of the protein; a nonsense mutation, i.e., a mutation which introduces a stop codon in a protein, e.g., an early stop codon which results in a shorter protein devoid of the activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the activity), or in a longer amino acid sequence (e.g., a readthrough protein) which affects the secondary or tertiary structure of the protein and results in a protein with modulated activity; a readthrough mutation due to a frame-shift mutation or a modified stop codon mutation (i.e., when the stop codon is mutated into an amino acid codon), with a modulated activity; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments DNA sequence alteration of a gene may comprise at least one allele of the gene.

According to other specific embodiments alteration of a gene sequence comprises both alleles of the gene. In such instances gene may be in a homozygous form or in a heterozygous form.

According to specific embodiments the DNA editing agent allows for the integration of exogenous nucleic acid sequences into the genome.

Thus, according to specific embodiments, the polynucleotides of some embodiments of the present invention comprise a nucleic acid sequence to be integrated into a genome of a cell by the DNA editing agent.

Methods of DNA genome editing are well known in the art [see for example Francisco Martin et al. “New Vectors for Stable and Safe Gene Modification” in Gene Therapy-Developments and Future Perspectives (2011) DOI: 10.5772/10622; Menke D. Genesis (2013) 51: —618; Capecchi, Science (1989) 244:1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771, 945, 8,586,526, 6,774,279 and UP Patent Application Publication Nos. 20030232410, 20050026157, US20060014264; the contents of which are incorporated by reference in their entireties] and include, but not limited to integrases and engineered nucleases. Agents for DNA genome editing can be designed publically available sources or obtained commercially from Transposagen, Addgene and Sangamo Biosciences.

According to specific embodiments, the DNA editing agent is an integrase.

As used herein, the term “integrase” refers to a recombinase that is capable of integrating a nucleic acid sequence into another nucleic acid sequence (e.g., a genome of a cell). According to specific embodiments, the integrase is a site-specific recombinase i.e. leads to integration of sequences between two nucleic acids, each nucleic acid comprising at least one recognition site for the recombinase. Such integrases are known in the art [see e.g. in Francisco Martin et al. Gene Therapy—Developments and Future Perspectives (2011) DOI: 10.5772/10622, Recchia A et al. Curr Gene Ther. (2011) 11(5): 399-405, Lim K I, BMB Rep. (2015) 48(1):6-12 and US Patent Application publication No. US20070190601; the contents of which are incorporated by reference in their entireties] and include for example a retroviral integrase (HIV integrase) and phage integrase (e.g. phi C31 integrase, lambda integrase).

According to specific embodiments the DNA editing agent is an engineered endonucleases.

Genome editing using engineered endonucleases such as meganucleases, Zinc finger nucleases (ZFNs), transcription-activator like effector nucleases (TALENs) and CRISPR/Cas system, is well known in the art and described for example in International Patent Application Publication No. WO2015/033343, the contents of which are incorporated herein by reference in their entirety.

According to other specific embodiments, the DNA editing agent is selected from the group consisting of zinc finger nuclease, an effector protein of Class 2 CRISPR/Cas (e.g. Cas9, Cpf1, C2c1, C2c3) and TALEN.

According to specific embodiments, the polynucleotides of the present invention are part of a nucleic acid construct (also referred to herein as an "expression vector").

As used herein, the terms "nucleic acid construct" and "expression vector" refer to a nucleic acid vector designed to introduce specific expression products of interest (i.e. genes) in host cell. The expression can be transient or consistent, episomal or integrated into the chromosome of the host cell. According to specific embodiments, the expression is on a transmissible genetic element such as a plasmid.

Hence, the nucleic acid construct of some embodiments of the invention includes additional sequences which render this vector suitable for replication and integration in prokaryotes, eukaryotes, or preferably both (e.g., shuttle vectors). In addition, a typical cloning vector may contain regulatory elements e.g. promoters, enhancers, transcription and translation initiation sequence, transcription and translation terminator, polyadenylation signal transcription termination signals etc and at least one multiple cloning site (MCS) for cloning of expression products of interest. By way of example, such constructs will typically include a 5' LTR, a tRNA binding site, a packaging signal, an origin of second-strand DNA synthesis, and a 3' LTR or a portion thereof.

Thus, according to an aspect of the present invention, there is provided a nucleic acid construct comprising a polynucleotide encoding an AimP peptide, a polynucleotide encoding an AimR polypeptide, a polynucleotide comprising an AimR responsive element and/or an AimX polynucleotide and any combination of same; and a MCS.

According to another aspect of the present invention, there is provided a nucleic acid construct comprising a polynucleotide encoding an AimP peptide, a polynucleotide encoding an AimR polypeptide, a polynucleotide comprising an AimR responsive element and/or an AimX polynucleotide and any combination of same; and a cis-acting regulatory element heterologous to AimP, AimR, AimR responsive element and/or AimX for directing expression of the polynucleotide.

Thus, according to specific embodiments, the nucleic acid construct may comprise any of the polynucleotides (1)-(11) described hereinabove.

Teachings of the invention further contemplate that the polynucleotides are part of a nucleic acid construct system whereby the components of the arbitrium system are expressed from different constructs.

Thus, according to specific embodiments, the present invention provides for a nucleic acid construct system comprising at least two nucleic acid constructs each expressing at least one of the polynucleotides of the present invention.

Thus according to specific embodiments, the nucleic acid construct system comprises an individual nucleic acid construct for each polynucleotide of the present invention (i.e. AimP, AimR, AimR responsive element and AimX).

According to other specific embodiments a single construct comprises a number of polynucleotide of the present invention, as described hereinabove.

According to specific embodiments, the nucleic acid construct system comprises at least one construct allowing integration of the polynucleotide into the chromosome of the cell and at least one construct allowing episomal expression of the polynucleotide.

As used herein, the term "multiple cloning site (MCS)" refers to a nucleic acid sequence comprising at least one restriction site, and more typically a number of restriction sites, for the purpose of cloning nucleic acid sequences into an expression vector. The MCS is recognized and digested by a specific restriction enzyme, such that a target expression product of interest can be inserted into the digested MCS site. Any MCS known in the art can be used in the nucleic acid constructs of the present invention. It can be obtained from various commercially available vectors known in the art having MCS (e.g., pUC18, pUC19, etc.).

Cis acting regulatory sequences include those that direct constitutive expression of a nucleotide sequence as well as those that direct inducible expression of the nucleotide sequence only under certain conditions.

The cis regulatory sequences of the present invention are heterologous to the polynucleotides of the present invention (i.e. AimP, AimR, AimR responsive element and AimX).

As used herein, the term "heterologous" means derived from a different genetic location. For example, a polynucleotide may be placed by genetic engineering techniques into a vector derived from a different source, and is a heterologous polynucleotide; a promoter removed from its native coding sequence and operatively linked to a coding sequence other than the native sequence is a heterologous promoter.

According to specific embodiments, the nucleic acid construct includes a promoter sequence for directing transcription of the polynucleotide sequence in the cell in a constitutive or inducible manner.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

According to specific embodiments, the promoter is a viral (e.g. phage) promoter.

According to specific embodiments the promoter is a bacterial promoter.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA and sequences for genomic integration of the promoter-chimeric polypeptide, as described in details herein above and below.

According to specific embodiments, the construct encodes a polycistronic mRNA comprising the polynucleotides of the present invention.

Various construct schemes can be utilized to express few genes from a single nucleic acid construct. According to specific embodiments, the construct encodes a polycistronic mRNA comprising the polynucleotides of the present invention; that is the polynucleotides can be co-transcribed as a polycistronic message from a single promoter sequence of the nucleic acid construct. To enable co-translation of all the genes from a single polycistronic message, the different polynucleotide segments can be transcriptionally fused via a linker sequence including an internal ribosome entry site (IRES) sequence which enables the translation of the polynucleotide segment downstream of the IRES sequence. In this case, a transcribed polycistronic RNA molecule including the coding sequences of different combinations of the polynucleotides of the present invention will be translated from both the capped 5' end and the internal IRES sequence of the polycistronic RNA molecule.

Alternatively, each two polynucleotide segments can be translationally fused via a protease recognition site cleavable by a protease expressed by the cell to be transformed with the nucleic acid construct. In this case, a chimeric polypeptide translated will be cleaved by the cell expressed protease.

Still alternatively, the nucleic acid construct of some embodiments of the invention can include at least two promoter sequences each being for separately expressing a distinct polynucleotide. These at least two promoters which can be identical or distinct can be constitutive, tissue specific or regulatable (e.g. inducible) promoters functional in one or more cell types.

When secretion of the polypeptides is desired the polynucleotides of the invention can be expressed as fusion polypeptides comprising the nucleic acid sequence encoding e.g. the components of the “arbitrium” system (e.g. AimP) ligated in frame to a nucleic acid sequence encoding a signal peptide that provides for secretion. According to specific embodiments, the signal sequence is an N-terminal signal sequence. According to specific embodiments, the signal peptide is cleaved upon peptide secretion.

DNA encoding suitable signal sequences can be derived from genes for secreted bacterial proteins, such as the *E. coli* outer membrane protein gene (ompA) (Masui et al. (1983) FEBS Lett. 151(1):159-164; Ghrayeb et al. (1984) EMBO J. 3:2437-2442) and the *E. coli* alkaline phosphatase signal sequence (phoA) (Oka et al. (1985) Proc. Natl. Acad. Sci. 82:7212). Other prokaryotic signals include, for example, the signal sequence from penicillinase, Ipp, or heat stable enterotoxin II leaders and signal sequences of the Phr family of quorum sensing systems [described e.g. in Pottathil, M. & Lazazzera, B. A. *Front. Biosci.* 8, d32-45 (2003)].

According to specific embodiments, the signal sequence is as set forth in SEQ ID NO: 342.

Selectable marker genes that ensure maintenance of the vector in the cell can also be included in the expression vector. Preferred selectable markers include those which confer resistance to drugs such as ampicillin, chloramphenicol, erythromycin, kanamycin (neomycin), and tetracycline (Davies et al. (1978) Annu. Rev. Microbiol. 32:469). Selectable markers can also allow a cell to grow on minimal medium or in the presence of toxic metabolite and can include biosynthetic genes, such as those in the histidine, tryptophan, and leucine biosynthetic pathways.

Other than containing the necessary elements for the transcription and translation of the inserted coding sequence, the expression construct of some embodiments of the invention can also include sequences engineered to enhance stability, production, purification, yield or toxicity of the expressed polypeptide. Thus, for example, the peptide of some embodiments of the invention (e.g. AimP) may be a pro-peptide containing a sequence processed by extracellular proteases to produce the mature peptide. According to specific embodiments the signal for extracellular processing is as set forth in SEQ ID NO: 348.

Or, for example, the expression of a fusion protein or a cleavable fusion protein comprising the protein of some embodiments of the invention (e.g. AimP) and a heterologous protein can be engineered. Such a fusion protein can be designed so that the fusion protein can be readily isolated by affinity chromatography; e.g., by immobilization on a column specific for the heterologous protein. Where a cleavage site is engineered between the protein of some embodiments of the invention and the heterologous protein, the protein of some embodiments of the invention can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

When needed, recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Where appropriate, the polynucleotides may be optimized for increased expression in the transformed organism. For example, the polynucleotides can be synthesized using preferred codons for improved expression.

It will be appreciated that the individual elements comprised in the expression vector can be arranged in a variety of configurations. For example, enhancer elements, promoters and the like, and even the polynucleotide sequence(s) encoding components of the "arbitrium" system can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Examples of bacterial constructs include the pET series of *E. coli* expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art can also be used by some embodiments of the invention.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/$A^+$, pMTO10/$A^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. Recombinant viral vectors are useful for in vivo expression of the polynucleotides and polypeptides of some embodiments of the present invention since they offer advantages such as lateral infection and targeting specificity.

Various methods can be used to introduce the polynucleotides, expression vectors and polypeptides of some embodiments of the invention into cells. The polynucleotides and nucleic acid construct described herein can be introduced into cells by any method known in the art, as further described in details hereinbelow. Alternatively or additionally, the polypeptides described herein can be contacted with the cell per se.

It will be appreciated that the cell may be comprised inside a particular organism, for example inside a mammalian body or inside a plant.

Thus, according to a specific embodiment introducing and/or contacting is effected in-Vivo.

According to another specific embodiment introducing and/or contacting is effected ex-vivo or in-vitro.

Various methods can be used to introduce the polynucleotides and expression vectors of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. Other vectors can be used that are non-viral, such as cationic lipids, polylysine, and dendrimers.

Regardless of the method of introduction, the present teachings provide for an isolated cell which comprises the polynucleotides, the nucleic acid constructs and/or the polypeptides, as described herein.

As used herein, the term "cell" refers to a prokaryotic or a eukaryotic cell. Non-limiting examples of cells that can be used in some embodiments of the present invention include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence.

According to specific embodiments the cell is a bacteria.

According to specific embodiments the cell is a mammalian cell.

According to specific embodiments, the mammalian cell is selected from the group consisting of a Chinese Hamster Ovary (CHO), HEK293, PER.C6, HT1080, NS0, Sp2/0, BHK, Namalwa, COS, HeLa and Vero cell.

According to another specific embodiment, the cell is a primary cell.

According to a specific embodiment, the cell is a cell line.

The cell may be derived from a suitable tissue including but not limited to blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids.

According to specific embodiment the cell does not express the polynucleotides and/or the polypeptides of the present invention endogenously.

According to specific embodiments, the cell expresses AimR endogenously.

The term "endogenous" as used herein, refers to the expression of the native gene in its natural location and expression level in the genome of an organism.

As shown in the Examples section which follows the arbitrium system is a genetic system that uses peptides to control the integration of specific DNA into a specific target site. Thus, the present teachings suggest the use of the polynucleotides, the nucleic acid construct and/or the polypeptides described hereinabove for inducible gene expression in general and to control genome editing in particular.

Thus, according to an aspect of the present invention, there is provided a method of expressing an expression product of interest, the method comprising:

(i) introducing into a cell a polynucleotide comprising an AimR responsive element operatively linked to a nucleic acid sequence encoding the expression product of interest, wherein said AimR comprises a DNA binding domain for binding said AimR responsive element, said AimR comprising a helix-turn-helix (HTH) motif and a tetratricopeptide repeat (TPR) domain; and (ii) contacting said cell with an AimP peptide comprising an amino acid sequence of XXXXGG/A, wherein said AimP peptide is capable of binding said AimR polypeptide and dissociating said AimR polypeptide from an AimR responsive element, thereby expressing the expression product of interest.

According to another aspect of the present invention, there is provided a method of expressing an expression product of interest, the method comprising introducing into a cell a polynucleotide comprising an AimR responsive element operatively linked to a heterologous nucleic acid sequence encoding the expression product of interest, wherein said AimR comprises a DNA binding domain for binding said AimR responsive element, said AimR comprising a helix-turn-helix (HTH) motif and a tetratricopeptide repeat (TPR) domain, thereby expressing the expression product of interest.

According to specific embodiments, the method comprising introducing into the cell a polynucleotide encoding AimR.

According to another aspect of the present invention, there is provided a method of expressing an expression product of interest, the method comprising introducing into a cell a polynucleotide comprising an AimR responsive element operatively linked to a nucleic acid sequence encoding the expression product of interest; and a nucleic acid construct comprising an AimR polynucleotide and a cis-acting regulatory element heterologous to said AimR for directing expression of said AimR polynucleotide, wherein said AimR comprises a DNA binding domain for binding said AimR responsive element, said AimR comprising a helix-turn-helix (HTH) motif and a tetratricopeptide repeat (TPR) domain, thereby expressing the expression product of interest.

According to specific embodiments, the method comprising contacting the cell with an AimP peptide or a nucleic acid sequence encoding same.

According to specific embodiments, the method comprising contacting the cell with an agent capable of downregulating expression and/or activity of said AimR responsive element.

As used herein the phrase "dowregulating expression" refers to dowregulating the expression at the genomic (e.g. homologous recombination and site specific endonucleases) and/or the transcript level using a variety of molecules which interfere with transcription and/or translation (e.g., RNA silencing agents e.g. RNA interference (RNAi), transcriptional gene silencing (TGS), post-transcriptional gene silencing (PTGS), quelling, co-suppression, and translational repression) or on the protein level (e.g., aptamers, small molecules and inhibitory peptides, antagonists, enzymes that cleave the polypeptide, antibodies and the like).

According to specific embodiments, the downregulating agent is a nucleic acid agent.

According to specific embodiments, the downregulating agent is an effector protein of Class 2 CRISPR/Cas (e.g. Cas9, Cpf1, C2c1, C2c3).

According to specific embodiments, the downregulating agent is a crRNA or a sgRNA of a CRISPR/Cas system.

According to specific embodiments, the downregulating agent is an RNAi.

According to specific embodiments, down regulating expression refers to the absence of mRNA and/or protein, as detected by RT-PCR or Western blot, respectively.

According to other specific embodiments down regulating expression refers to a decrease in the level of mRNA and/or protein, as detected by RT-PCR or Western blot, respectively as compared to same in the absence of the downregulating agent. The reduction may be by at least a 10%, at least 20%, at least 30%, at least 40%, at least 50%, at least 60%, at least 70%, at least 80%, at least 90%, at least 95% or at least 99% reduction.

As the CRISPR/Cas system used by the present inventors for downregulating expression and/or activity of AimX disclosed in the Examples section which follows is novel; according to an aspect of the present invention there is provided an isolated nucleic acid agent capable of downregulating expression and/or activity of an AimR responsive element.

According to specific embodiments, the downregulating agent is capable of downregulating expression and/or activity of an AimX.

As used herein, "expressing" or "expression" refers to gene expression at the nucleic acid and/or protein level. Expression can be determined using methods known in the art e.g. but not limited to selectable marker gene, Northern blot analysis, PCR analysis, DNA sequencing, RNA sequencing, Western blot analysis, and Immunohistochemistry.

When expression of the expression product of interest results in modulated activity, qualifying efficacy of DNA integration can also be determined by determining activity.

In addition, one ordinarily skilled in the art can readily design a knock-in/knock-out construct including positive and/or negative selection markers for efficiently selecting transformed cells that underwent DNA integration event with the polynucleotide or construct. Positive selection provides a means to enrich the population of clones that have taken up foreign DNA. Non-limiting examples of such positive markers include Human influenza hemagglutinin (HA) tag, glutamine synthetase, dihydrofolate reductase (DHFR), His-tag, FLAG peptide, and markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosytransferase (ARPT).

According to specific embodiments, the expression product of interest is endogenous to the cell.

According to other specific embodiments, the expression product of interest is exogenous to the cell.

As mentioned above the expression product of interest may be a DNA editing agent. Thus, according to specific embodiments the method comprising introducing into the cell a nucleic acid sequence to be integrated into a genome of the cell by the DNA editing agent.

Methods for qualifying efficacy and detecting integration of a nucleic acid sequence into the genome of the cell are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

According to another aspect there is provided an article of manufacture identified for expressing an expression product of interest comprising a packaging material packaging at least two of:

(i) a polynucleotide comprising an AimR responsive element;

(ii) a polynucleotide encoding said AimR;

(iii) an AimP peptide; and/or (iv) an agent capable of downregulating expression and/or activity of said AimR responsive element.

The article of manufacture may comprise two, three or all; i.e. (i)+(ii), (i)+(iii), (i)+(iv), (ii)+(iii), (ii)+(iv), (i)+(ii)+(iii), (ii)+(iii)+(iv), (i)+(ii)+(iv), (i)+(iii)+(iv) or (i)+(ii)+(iii)+(iv).

According to another aspect there is provided an article of manufacture identified for expressing an expression product of interest comprising a packaging material packaging:

(a) at least one of the (2)-(6) polynucleotides of the present invention or functional fragments thereof or a nucleic acid construct comprising same as described hereinabove; and (b) at least one of an AimP peptide, AimP polynucleotide, functional fragments thereof, a nucleic acid construct comprising same or an AimR responsive element downregulating agent as described hereinabove.

According to specific embodiments, the polynucleotide encoding the AimR is comprised in a nucleic acid construct comprising a cis-acting regulatory element heterologous to the AimR for directing expression of the AimR polynucleotide.

According to specific embodiment, the article of manufacture comprises a multiple cloning site (MCS).

According to specific embodiment, the article of manufacture comprises a polynucleotide encoding the expression product of interest.

According to specific embodiments of these aspects of the present invention the (i), (ii) (iii) and/or (iv) or the (a) and (b) are packaged in separate containers.

According to yet other specific embodiments of these aspects of the present invention the (i), (ii) (iii) and/or (iv) or the (a) and (b) are in c-formulation.

It is expected that during the life of a patent maturing from this application many relevant DNA editing agents will be developed and the scope of the term DNA editing agent is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

TABLE 3

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| | | 114 | | Phage Phi3T | KY030782 | 68883 | 70019 | + | 378 | 0 | MKKVFFGLVILTA LAISFVAGQQSVST ASASDEVTVASAIR GA | 227 | SAIRGA | 269 | Phage | SpBeta-like | 287 |
| Ga0069201_120285 | 2 | 115 | 2635513586 | *Bacillus amyloliquefaciens plantarum* GR4-5 | Ga0069201_120 | 208226 | 209371 | - | 381 | 0 | LKKTILGVAIIAAL ALSFVAGQKSVSTA APNDEISVASIIRGA | 228 | SIIRGA | 270 | Pro - | SpBeta-like | 288 |
| C379DRAFT_03616 | 3 | 116 | 2552910987 | *Bacillus subtilis* S1-4 | C379DRAFT_ANIP01000036_1.36 | 266 | 1426 | - | 386 | 1.00E-86 | MKKLIMALVILGA LGTSFISADSSIRQA SGDYEVAGMPRGA | 229 | GMPRGA | 271 | uncertain | SpBeta-like | 289 |
| SPBc2p081 | 4 | 117 | 638282206 | *Bacillus* phage SPbeta | NC_001884 | 76295 | 77455 | + | 386 | 5.00E-88 | MKKLIMAILVILGA LGTSYISADSSIQQA SGDYEVAGMPRGA | 230 | GMPRGA | 271 | Phage SpBeta | SpBeta-like | 290 |
| BsubsJ_010100011343 | 5 | 118 | 643902925 | *Bacillus subtilis subtilis* JH642 | NZ_ABQM01000008 | 230462 | 231622 | - | 386 | 5.00E-88 | MKKLIMALVILGA LGTSYISADSSIQQA SGDYEVAGMPRGA | 230 | GMPRGA | 271 | Prophage | SpBeta-like | 290 |
| BacJ22_0011.00000140 | 6 | 119 | 2505840589 | *Bacillus subtilis* J22 | BacJ22_scaffold_10 | 6956 | 8116 | + | 386 | 5.00E-87 | MKKLIMALVILGA LGTSYISADSSIQQA SGDYEVAGMPRGA | 230 | GMPRGA | 271 | Prophage | SpBeta-like | 290 |
| BacJ26_0006.00000860 | 7 | 120 | 2505863705 | *Bacillus subtilis* J22 | BacJ22_scaffold_5 | 49692 | 50852 | - | 386 | 3.00E-86 | MKKLIMALVILGA LGTSYISADSSIQQA SGDYEVAGMPRGA | 230 | GMPRGA | 271 | Prophage | SpBeta-like | 290 |
| B657_20860 | 8 | 121 | 2518770117 | *Bacillus subtilis* QB928 | CP003783 | 2188487 | 2189647 | - | 386 | 5.00E-88 | MKKLIMALVILGA LGTSYISADSSIQQA SGDYEVAGMPRGA | 230 | GMPRGA | 271 | Prophage | SpBeta-like | 290 |
| BSU6051_20860 | 9 | 122 | 2540550687 | *Bacillus subtilis* | CP003329 | 2208993 | 2210153 | - | 386 | 5.00E-88 | MKKLIMALVILGA LGTSYISADSSIQQA | 230 | GMPRGA | 271 | Prophage | SpBeta-like | 290 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Str-and | Amino Acid Length (aa) | E-value of Homology to phi3T AimR | Associated AimP Sequence | Associated AimP SEQ ID NO | Mature peptide sequence Se-quence | Mature peptide sequence SEQ ID NO | Genomic context | Phage type | DNA binding region SEQ ID NO |
|---|---|---|---|---|---|---|---|---|---|---|---|---|---|---|---|---|---|
| | | | | *subtilis* 6051-HGW | | | | | | | SGDYEVAGMPRGA | | | | | | |
| A154DRAFT_ 00465 | 10 | 123 | 2551879023 | *Bacillus amyloli-quefaciens amyloli-quefaciens* DC-12 | A154DRAFT_ AMQ101000006_ 1.6 | 91519 | 92481 | + | 320 | 6.00E-57 | MKKVFIGLTIVAS LAVGFVAGQQTTIH SASGEGTFHVAGFG RGA | 231 | GFGRGA | 272 | Pro-phage | un-certain | 290 |
| Ga0054580_ 1011017 | 11 | 124 | 2612412751 | *Bacillus subtilis* GXA-28 | Ga0054580_ 101 | 10029 | 1004108 | + | 386 | 5.00E-87 | MKKLIMALVILGA LGTSYISADSSIQQA SGDYEVAGMPRGA | 230 | GMPRGA | 271 | Pro-phage | SpBeta-like | 290 |
| Ga0098749_ 1011083 | 12 | 125 | 2642060655 | *Bacillus murimartini* LMG21005 | Ga0098749_ 101 | 963601 | 964761 | + | 386 | 5.00E-88 | MKKLIMALVVILGA LGTSYISADSSIQQA SGDYEVAGMPRGA | 230 | GMPRGA | 271 | Pro-phage | SpBeta-like | 290 |
| Ga0098284_ 112311 | 13 | 126 | 2648115039 | *Bacillus subtilis* BS49 | Ga0098284_ 11 | 2227091 | 2228251 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0111823_ 112291 | 14 | 127 | 2661428278 | *Bacillus subtilis subtilis* 168 | Ga0111823_ 11 | 2209094 | 2210254 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| BSUA_ 02243 | 15 | 128 | 2585935209 | *Bacillus subtilis subtilis* JH642 subAG174 | CP007800 | 2181762 | 2182922 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0098717_ 105270 | 16 | 129 | 2649478018 | *Bacillus subtilis* MS1577 | Ga0098717_ 105 | 213507 | 214667 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Bsubs1_010 100011496 | 17 | 130 | 643894000 | *Bacillus subtilis* | NZ_ ABQK01000005 | 1189758 | 1190897 | - | 379 | 5.00E-88 | MKKLIMALVILGA LGTSYISADSSIQQA | 230 | GMPRGA | 271 | Pro-phage | SpBeta-like | 290 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| | | | | *subtilis* 168 | | | | | | | SGDYEVAGMPRGA | | | | | | |
| BSUB_ 02243 | 18 | 131 | 2585930860 | *Bacillus subtilis subtilis* AG1839 | CP008698 | 2181762 | 2182922 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0060198_ 10884 | 19 | 132 | 2624474520 | *Bacillus subtilis inaquosorum* BGSC3A28 | Ga0060198_ 108 | 72834 | 73994 | + | 386 | 5.00E-87 | MKKLIMALVILGA LGTSYISADSSIQQA SGDYEVAGMPRGA | 230 | GMPRGA | 271 | Pro-phage | SpBeta-like | 290 |
| Ga0077871_ 112265 | 20 | 133 | 2633570397 | *Bacillus subtilis subtilis* 3NA | Ga0077871_ 11 | 2188573 | 2189733 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0112192_ 12634 | 21 | 134 | 2662146470 | *Bacillus subtilis* B4146 | Ga0112192_ 126 | 18734 | 19894 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0112188_ 17017 | 22 | 135 | 2663822497 | *Bacillus subtilis* B4071 | Ga0112188_ 170 | 8284 | 9444 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0111750_ 112291 | 23 | 136 | 2668370401 | *Bacillus subtilis subtilis* 168 | Gs0111750_ 11 | 2208841 | 2210001 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0112185_ 101037 | 24 | 137 | 2665375350 | *Bacillus subtilis* B4068 | Ga0112185_ 1010 | 18751 | 19911 | - | 386 | 2.00E-87 | MKKLIMALVILGA LGTSFISADSSIRQA SGDYEVAGMPRGA | 229 | GMPRGA | 271 | Pro-phage | SpBeta-like | 290 |
| Ga0112983_ 104062 | 25 | 138 | 2670038339 | *Bacillus subtilis subtilis* B4067 | Ga0112983_ 1040 | 53996 | 55156 | + | 386 | 1.00E-86 | MKKLIMALVILGA LGTSFISADSSIRQA SGDYEVAGMPRGA | 229 | GMPRGA | 271 | Pro-phage | SpBeta-like | 290 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| BsubsN3_ 010100011417 | 26 | 139 | 643898395 | *Bacillus subtilis* NCIB 3610 | NZ_ ABQL01000005 | 1189759 | 1190919 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| Ga0072477_ 112290 | 27 | 140 | 2637211300 | *Bacillus subtilis* KCTC 1028 | Ga0072477_ 11 | 2209087 | 2210247 | - | 386 | 5.00E-88 | MKKLIMALVILGA LGTSYISADSSIQQA SGDYEVAGMPRGA | 230 | GMPRGA | 271 | Pro-phage | SpBeta-like | 290 |
| AUSI98 DRAFT_ 00510 | 28 | 141 | 2547773423 | *Bacillus subtilis subtilis* AUSI98 | AUSI98DRAFT_ AFSF0100 | 27978 | 29138 | + | 386 | 5.00E-88 | MKKLIMALVILGA LGTSYISADSSIQQA SGDYEVAGMPRGA | 230 | GMPRGA | 271 | Pro-phage | SpBeta-like | 291 |
| Ga0112186_ 158126 | 29 | 142 | 2662791384 | *Bacillus subtilis* B4069 | Ga0112186_ 158 | 72619 | 73779 | - | 386 | 1.00E-85 | MKKLIMALVILGA LGTSYISADSSIQQA SGDYEVAGMPRGA | 230 | GMPRGA | 271 | Pro-phage | SpBeta-like | 292 |
| BsubsS_ 0100011472 | 30 | 143 | 643907317 | *Bacillus subtilis subtilis* SMY | NZ_ ABQN01000008 | 1024361 | 1025500 | - | 379 | 5.00E-88 | MKKLIMALVILGA LGTSYISADSSIQQA SGDYEVAGMPRGA | 230 | GMPRGA | 271 | Pro-phage | SpBeta-like | 293 |
| Ga0077513_ 1097185 | 31 | 144 | 2640459274 | *Bacillus glycini-fermentans* TH008 | Ga0077513_ 1097 | 120393 | 121595 | - | 400 | 9.00E-90 | MKKLLIGIFVSATL LAVGYVASQVNNS GYSIAGFTVGA | 232 | GFTVGA | 273 | Pro-phage | SpBeta-like | 294 |
| Ga0100863_ 10136 | 32 | 145 | 2651529367 | *Bacillus amyloli-quefaciens* | Ga0100863_ 101 | 37279 | 38310 | + | 343 | 2.00E-53 | MKKITMSVIVLA AIVTVVLGSVQHQE AKSHTVNQLADPG RGG | 233 | DPGRGG | 274 | Pro-phage | phage group D | 295 |
| BMSB_ 03973 | 33 | 146 | 2525735558 | *Bacillus pumilus* CCMA-560 (Bio-suractant) | BMSB_NODE_ 203_3_len_ 235571_cov_ 807_850708. 114 | 193495 | 194652 | + | 385 | 8.00E-117 | MKKLVMALVLLA AVAGVFSGTQQSIA LDDEKVSTSSASRG A | 234 | SASRGA | 275 | Pro-phage | SpBeta-like | 296 |
| V529_20920 | 34 | 147 | 2578426885 | *Bacillus amyloli-* | CP006890 | 2191528 | 2192682 | - | 384 | 2.00E-154 | MKKFNCAIVILLA LTVGFVSGQQSVQ | 235 | SASRGA | 275 | Pro-phage | SpBeta-like | 297 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| | | | | *quefaciens* SQR9 | | | | | | | TANGDITVASASRG A | | | | | | |
| Ga0077150_ 10184 | 35 | 148 | 2630228571 | *Bacillus amyloli-quefaciens* JJC33M | Ga0077150_ 101 | 64995 | 66149 | + | 384 | 1.00E-154 | MKKFNCAIVILLA LAVGFVSGQQSVQ TANGDITVASASRG A | 236 | SASRGA | 275 | Pro-phage | SpBeta-like | 297 |
| Ga0100863_ 12531 | 36 | 149 | 2651532210 | *Bacillus amyloli-quefaciens* RHNK22 | Ga0100863_ 125 | 17241 | 18395 | + | 384 | 1.00E-154 | MKKFNCAIVILLA LTVGFVSGQQSVQ TANGDITVASASRG A | 235 | SASRGA | 275 | Pro-phage | SpBeta-like | 297 |
| K667DRAFT_ 03728 | 37 | 150 | 554710456 | *Bacillus subtilis* SPZ1 | K667DRAFT_ AQGM010000023_ 1.23 | 43047 | 44201 | - | 384 | 2.00E-155 | MKKFNCAIVILLA LTVGFVSGQQSVQ TANGDITVASASRG A | 235 | SASRGA | 275 | Pro-phage | SpBeta-like | 298 |
| L145DRAFT_ 03550 | 38 | 151 | 2554737155 | *Paeni-bacillus polymyxa* ATCC 12321 | L145DRAFT_ ARYD01000023_ 1.23 | 2478 | 6632 | + | 384 | 2.00E-155 | MKKFNCAIVILLA LTVGFVSGQQSVQ TANGDITVASASRG A | 235 | SASRGA | 275 | Pro-phage | SpBeta-like | 298 |
| BATRDET 2DRAFT_ 00678 | 39 | 152 | 2547896382 | *Bacillus atrophaeus* Detrick-2 | BATRD ET2DRAFT_ AEFQ01000007_ 1.7 | 96814 | 97707 | - | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| BAC51E DRAFT_ 03601 | 40 | 153 | 2548050036 | *Bacillus atrophaeus* BACI051-E | BAC51EDRAFT_ AEFX01000024_ 1.24 | 108728 | 109621 | - | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| BATR8221 DRAFT_ 04209 | 41 | 154 | 2547925085 | *Bacillus atrophaeus globigii* ATCC 49822-1 | BATR82 21DRAFT_ ARFV01000030_ 1.30 | 105859 | 109482 | - | 297 | 1.00E-61 | MKKIFMGITIAAV LMFSYASVKLASN EQTLGDYEVAGVV RGA | 237 | GVVRGA | 276 | Pro-phage | SpBeta-like | 299 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| BATR8222 DRAFT_ 04125 | 42 | 155 | 2547920785 | *Bacillus atrophaeus globigii* ATCC 49822-2 | BATR82 22DRAFT_ AEFW01000028_ 1.28 | 107377 | 108270 | - | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| Ga0057413_ 02088 | 43 | 156 | 2598460075 | *Bacillus atrophaeus globigii* BSS | Ga0057413_ gi673978761.1 | 2140405 | 2141298 | - | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| BATR132 DRAFT_ 04097 | 44 | 157 | 2547912402 | *Bacillus atrophaeus* 1013-2 | BATR132 DRAFT_ AEFT01000028_ 1.28 | 47035 | 47928 | + | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| BAC51ND RAFT_ 02086 | 45 | 158 | 2548024839 | *Bacillus atrophaeus* BACI051-N | BAC51N DRAFT_ AEFY01000036_ 1.36 | 55449 | 56342 | + | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| BATR DRAFT_ 04181 | 46 | 159 | 2547985264 | *Bacillus atrophaeus globigii* Dugway | BATR DRAFT_ AEFO01000042_ 1.42 | 47819 | 48712 | + | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| RBAU_ 2086 | 47 | 160 | 2541780767 | *Bacillus amyloli-quefaciens plantarum* UCMB5033 | HG328253 | 2209877 | 2211025 | - | 382 | 1.00E-155 | MKNILGIVILLAM AVGFVAGQQSIETA SVDHVDQPVKVAS PSRGA | 238 | SPSRGA | 277 | Pro-phage | SpBeta-like | 300 |
| BAMTA208_ 15460 | 48 | 161 | 651181381 | *Bacillus amyloli-quefaciens* TA208 | CP002627 | 2938440 | 2939402 | - | 320 | 2.00E-57 | MKKVFIGLTIVAS LAVGFVAGQQTTIH TASGEETFHVAGFG RGA | 239 | GFGRGA | 272 | Pro-phage | phi105-like | 301 |
| Ga0069498_ 113134 | 49 | 162 | 2628601775 | *Bacillus subtilis* | Ga0069498_11 | 2941301 | 2942263 | - | 320 | 2.00E-57 | MKKVFIGLTIVAS LAVGFVAGQQTTIH | 239 | GFGRGA | 272 | Pro-phage | phi105-like | 301 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| | | | | ATCC 13952 | | | | | | | TASGEETFHVAGFG RGA | | | | | | |
| BAXH7_03158 | 50 | 163 | 2511913376 | *Bacillus amyloliquefaciens* XH7 | CP002927 | 2940486 | 2941448 | - | 320 | 2.00E-57 | MKKVFIGLTIVAS LAVGFVAGQQTTIH TASGEETFHVAGFG RGA | 239 | GFGRGA | 272 | Prophage | phi105-like | 301 |
| BAMF_2913 | 51 | 164 | 649669044 | *Bacillus amyloliquefaciens* Campbell F, DSM 7 | NC_014551 | 2971658 | 2972620 | - | 320 | 2.00E-57 | MKKVFIGLTIVAS LAVGFVAGQQTTIH TASGEETFHVAGFG RGA | 239 | GFGRGA | 272 | Prophage | phi105-like | 301 |
| Ga0100815_114334 | 52 | 165 | 2646412539 | *Bacillus amyloliquefaciens* XK-4-1 | Ga0100815_114 | 292702 | 293664 | + | 320 | 2.00E-56 | MKKVFIGLTIVAS LAVGFVAGQQTTIH SASGEETFHVAGFG RGA | 240 | GFGRGA | 272 | Prophage | phi105-like | 302 |
| H008DRAFT_01224 | 53 | 166 | 2586341037 | *Bacillus methylotrophicus* SK19.001 | H008DRAFT_AOFO01000003_1.3 | 256225 | 257187 | + | 320 | 6.00E-57 | MKKVFIGLTIVAS LAVGFVAGQQTTIH SASGEGTFHVAGFG RGA | 231 | GFGRGA | 272 | Prophage | Mu-like (virfam) | 303 |
| EGDHOCAQ14_02563 | 54 | 167 | 2545558323 | *Bacillus amyloliquefaciens* EGD-AQ14 | EGDHPCAQ14_contig00004.4 | 293215 | 294177 | + | 320 | 4.00E-56 | MKKVFIGLTIVAS LAVGFVAGQQTTIH SASGEETFHVAGFG RGA | 240 | GFGRGA | 272 | uncertain | uncertain | 304 |
| O205_13015 | 55 | 168 | 2578932748 | *Bacillus amyloliquefaciens* EGD-AQ14 | AVQH010000344 | 293215 | 294177 | + | 320 | 4.00E-56 | MKKVFIGLTIVAS LAVGFVAGQQTTIH SASGEETFHVAGFG RGA | 240 | GFGRGA | 272 | uncertain | uncertain | 304 |
| Ga0077150_109123 | 56 | 169 | 2630231491 | *Bacillus amyloliquefaciens* JJC33M | GA0077150_109 | 118370 | 119332 | + | 320 | 7.00E-58 | MKKVFIGLTIVAS LAVGFVAGQQTTIH NAASGEETFHVAG FGRGA | 241 | GFGRGA | 272 | Prophage | phi105-like | 305 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| ba1_12134 | 57 | 170 | 2535064176 | Bacillus sp. HYC-10 | AMSH01000035 | 31377 | 32540 | - | 387 | 7.00E-78 | MKKTALFLIVAVTIFSVGFASGQTSEQAIEFIKTAAMGNGGFGRGA | 242 | AMGNGG | 278 | Prophage | Mu-like (virfam) | 306 |
| Ga0111348_123252 | 58 | 171 | 2656454588 | *Bacillus amyloliquefaciens plantarum* NAU-B3 null replaces 81671 | Ga0111348_12 | 3159949 | 3160911 | - | 320 | 3.00E-46 | MSMKIKLGLAADAVALFVAGYATNQAVKDVAAGQDTVFKVATIGRG | 243 | TIGRG | 279 | Prophage | phi105-like | 307 |
| Ga0081671_113251 | 59 | 172 | 2638063346 | *Bacillus amyloliquefaciens plantarum* NAU-B3 | Ga0081671_11 | 3159949 | 3160911 | - | 320 | 3.00E-46 | MSMKIKLGLAADAVALFVAGYATNQAVKDVAAGQDTVFKVATIGRG | 243 | TIGRG | 279 | Prophage | phi105-like | 307 |
| C379DRAFT_01654 | 60 | 173 | 2552909043 | *Bacillus subtilis* S1-4 | C379DRAFT_ANIP01000010_1.10 | 93495 | 94667 | + | 390 | 2.00E-121 | MKKVFIGLTIVAALAVAFVAGQHSQVDTASGSVSVASASRGA | 244 | SASRGA | 275 | Prophage | Mu-like (virfam) | 308 |
| BSSC8_21910 | 61 | 175 | 2521025224 | *Bacillus subtilis subtilis* SC-8 | AGFW01000004 | 67653 | 68813 | + | 386 | 4.00E-86 | MKKLIMALVILGALGTSYISADSSIQQASGDYEVAGMPRGA | 230 | GMPRGA | 271 | Prophage | SpBeta-like | 309 |
| Ga0077901_112256 | 62 | 175 | 2645892320 | *Bacillus methylotrophicus* JJ-D34 | Ga0077901_11 | 2230615 | 2231754 | - | 379 | 0 | MKKIIFGTAILAALAISFIAGQHSVNTASVSDEISVASAIRGA | 245 | SAIRGA | 269 | Prophage | SpBeta-like | 310 |
| Ga0071349_112240 | 63 | 176 | 2616415682 | *Bacillus methylotrophicus* JJ-D34 | Ga0071349_11 | 2230136 | 2231275 | - | 379 | 0 | MKKIIFGTAILAALAISFIAGQHSVNTASVSDEISVASAIRGA | 245 | SAIRGA | 269 | Prophage | SpBeta-like | 310 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| BACAU_2847 | 64 | 177 | 2511700821 | *Bacillus amyloliquefaciens* CAU-B946 | NC_016784 | 3053043 | 3054005 | - | 320 | 2.00E-56 | MKKVFIGLTIVASLAVGFVAGQQTTIHSASGEETFHVAGFGRGA | 240 | GFGRGA | 272 | Prophage | phi105-like | 311 |
| Ga0111348_121799 | 65 | 178 | 2656453156 | *Bacillus amyloliquefaciens plantarum* NAU-B3 null replaces 81671 | Ga0111348_12 | 1723410 | 1724549 | + | 379 | 0 | MKKIIFGTAILASLAISFIAGQSVNTASASDEISVASAIRGA | 246 | SAIRGA | 269 | Prophage | SpBeta-like | 312 |
| O205_01290 | 66 | 179 | 2578929474 | *Bacillus amyloliquefaciens* EGD-AQ14 | AVQH01000001 | 220604 | 221743 | - | 379 | 0 | MKKIIFGTAILASLAISFIAGQSVNTASASDEISVASAIRGA | 246 | SAIRGA | 269 | Prophage | SpBeta-like | 312 |
| Ga0081671_111799 | 67 | 180 | 2638061915 | *Bacillus amyloliquefaciens plantarum* NAU-B3 | Ga0081671_11 | 1723410 | 1724549 | + | 379 | 0 | MKKIIFGTAILASLAISFIAGQSVNTASASDEISVASAIRGA | 246 | SAIRGA | 269 | Prophage | SpBeta-like | 312 |
| LL3_01627 | 68 | 181 | 651184090 | *Bacillus amyloliquefaciens* LL3 | CP002634 | 1507610 | 1508575 | + | 321 | 4.00E-58 | MKNKLKIGLAVAVLSVSVIGFVANKAMNAAADAKEPQFKVATIGRGG | 247 | TIGRGG | 280 | Prophage | phage group D | 312 |
| EGDHPCAQ14_00251 | 69 | 182 | 2545556050 | *Bacillus amyloliquefaciens* EGD-AQ14 | EGDHPCAQ14_contig0000.1. | 220604 | 221743 | - | 379 | 0 | MKKIIFGTAILASLAISFIAGQSVNTASASDEISVASAIRGA | 246 | SAIRGA | 269 | Prophage | SpBeta-like | 312 |
| M769_0124555 | 70 | 183 | 2571030593 | *Bacillus licheniformis* S 16 | AZYP01000118 | 269 | 1435 | - | 388 | 9.00E-93 | MKKLFVGIVVSVSLLAVGIAAAQINSGFSVAGFTVGA | 248 | GFTVGA | 23 | uncertain | uncertain | 313 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| Ga0102445_ 1200198 | 71 | 184 | 2645666845 | *Bacillus* sp. Leaf49 | Ga0102445_ 120 | 161090 | 162247 | - | 385 | 2.00E-109 | MKKLVMALVLVA AVAGVFSGTQQSIA MDAEKSVTSSASR GA | 249 | GASRGA | 275 | Pro-phage | SpBeta-like | 314 |
| BSONL12_ 23325 | 72 | 185 | 2546447199 | *Bacillus sonorensis* L12 | AOFM01000019 | 77077 | 78243 | - | 388 | 1.00E-94 | MKKWLFSIAVVA ALLITGVAVAESTH QAEGGYYIAGRPRG A | 250 | GFPRGA | 281 | Pro-phage | SpBeta-like | 315 |
| Ga0077185_ 1131171 | 73 | 186 | 2655559738 | *Bacillus licheniformis* GB2 | Ga0077185_ 113 | 1026770 | 1027939 | + | 389 | 6.00E-90 | MKKLFVGIVVSVS LLAVGIAAAQVNS GFSVAGFTVGA | 251 | GFTVGA | 273 | Pro-phage | SpBeta-like | 316 |
| C650DRAFT_ 02718 | 74 | 187 | 2553299155 | *Bacillus licheniformis* CGMCC 3963 | C650DRAFT_ AMWQ01000046_ 1.46 | 13723 | 14892 | - | 389 | 6.00E-90 | MKKLFVGIVVSVS LLAVGIAAAQVNS GFSVAGFTVGA | 251 | GFTVGA | 273 | Pro-phage | SpBeta-like | 316 |
| M661DRAFT_ 01208 | 75 | 188 | 2555268673 | *Bacillus* sp. SB47 | M661DRAFT_ ATNR01000004_ 1.4 | 78786 | 79955 | + | 389 | 2.00E-91 | MKKLFVGIVVSVS LLAVGIAAAQVNS GFSVAGFTVGA | 251 | GFTVGA | 273 | Pro-phage | SpBeta-like | 316 |
| Ga0098704_ 11068 | 76 | 189 | 2647076482 | *Bacillus licheniformis* S127 | Ga0098704_ 110 | 40519 | 41574 | - | 351 | 1.00E-77 | MKKLFVGIVVSVS LLAVGIAAAQVNS GFSVAGFTVGA | 251 | GFTVGA | 273 | Pro-phage | SpBeta-like | 316 |
| HMPREF1012_ 01017 | 77 | 190 | 650030994 | *Bacillus* sp. BT1B_CT2 | NZ_ ACWC01000004 | 25867 | 27036 | - | 389 | 3.00E-90 | MKKLFVGIVVSVS LLAVGIAAAQVNS GFSVAGFTVGA | 251 | GFTVGA | 273 | un-certain | SpBeta-like | 316 |
| N399_ 24140 | 78 | 191 | 2576359374 | *Bacillus licheniformis* CG-B52 | AVEZ01000043 | 78729 | 79886 | + | 385 | 5.00E-92 | MKKLFVGIVVSVT LLAVGIAAAKINSG FSVAGFTVGA | 252 | GFTVGA | 273 | Pro-phage | SpBeta-like | 317 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| W9SDRAFT_ 00383 | 79 | 192 | 2550811423 | *Bacillus lichen- iformis* 10-1-A | W9SDRAFT_ AJL V01000017_ 1.17 | 15375 | 16532 | + | 385 | 2.00E-91 | MKKLFVGIVVSVS LLAVGIAASQINSG FSVAGFTVGA | 253 | GFTVGA | 273 | Pro- phage | SpBeta- like | 318 |
| Ga0057513_ 02496 | 80 | 193 | 2598368491 | *Bacillus subtilis* var *niger* PCI246 | Ga0057513_ gi674581281.3 | 2066016 | 2066909 | + | 297 | 1.00E-61 | MKKIFMGITIAAV LMFSYASVKLASN EQTLGDYEVAGVV RGA | 237 | GVVRGA | 276 | Pro- phage | SpBeta- like | 319 |
| BATR1942_ 07720 | 81 | 194 | 649707910 | *Bacillus atrophaeus* 1942 | NC_014639 | 1594016 | 1594909 | - | 297 | 1.00E-61 | MKKIFMGITIAAV LMFSYASVKLASN EQTLGDYEVAGVV RGA | 237 | GVVRGA | 276 | Pro- phage | SpBeta- like | 319 |
| C379DRAFT_ 03789 | 82 | 195 | 2552911160 | *Bacillus subtilis* S1-4 | C379DRAFT_ ANIP01000036_ 1.36 | 145417 | 146379 | - | 320 | 2.00E-51 | MAKKMKLGLATA AVALFLAGYATNL VVSDVAAGKGDVF KVATIGRG | 254 | TIGRG | 279 | Pro- phage | phi105- like | 320 |
| BAMTA208_ 06415 | 83 | 196 | 651179561 | *Bacillus amyloli- quefaciens* TA208 | CP002627 | 1257136 | 1258296 | + | 386 | 5.00E-95 | MKKLFMGITIAAV LMFSYASVKLVSN EQASGDYEVAGVV RGA | 255 | GVVRGA | 276 | Pro- phage | SpBeta- like | 321 |
| Ga0069498_ 112187 | 84 | 197 | 2628600848 | *Bacillus subtilis* ATCC 13952 | Ga0069498_ 11 | 2117404 | 2118564 | - | 386 | 5.00E-95 | MKKLFMGITIAAV LMFSYASVKLVSN EQASGDYEVAGVV RGA | 255 | GVVRGA | 276 | Pro- phage | SpBeta- like | 321 |
| BSI_ 39170 | 85 | 198 | 2536647131 | *Bacillus subtilis inaquosorum* KCTC 13429 | AMXN01000009 | 83188 | 83904 | + | 238 | 3.00E-37 | MKKVTIGLTIVAA LAIGFVAGQQSGLH SASGNETFHVAGFG RGA | 256 | GFGRGA | 272 | un- certain | un- certain | 322 |
| Ga0055124_ 109116 | 86 | 199 | 2612266796 | *Bacillus subtilis* E1 | Ga0055124_ 109 | 106622 | 107584 | - | 320 | 6.00E-50 | MKKVTIGLVTIVAA LTIGFVAGQQSGLH SASGNKTFHVAGF GRGA | 257 | GFGRGA | 272 | un- certain | un- certain | 323 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| BAME_ 14140 | 87 | 200 | 2540180739 | *Bacillus* sp. M 2-6 (**Bacillus aerophilus* KACC 16563 Gil) | AJWW01000017 | 45331 | 46491 | - | 386 | 7.00E-79 | MKKVFALTIVAAAIFFGGVVTGTQINSASDFNTAGFGHGA | 258 | GFGHGA | 282 | Pro-phage | Mu-like (virfam) | 324 |
| Ga0102445_ 121323 | 88 | 201 | 2645667694 | *Bacillus* sp. Leaf49 | Ga0102445_ 121 | 280606 | 281766 | - | 386 | 1.00E-87 | MKKVFALTIVVAAIFFGGVATGTQIDTASDYSTAGFGRGA | 259 | GFGRGA | 272 | Pro-phage | phi105-like | 325 |
| EGDHPCAQ14_ 03492 | 89 | 202 | 2545559244 | *Bacillus amyloliquefaciens* EGD-AQ14 | EGDHPCAQ14_ contig00011. 11 | 2398 | 3576 | - | 392 | 8.00E-67 | MKKVLIGLTIVAALTVGFVGGQYSVNNASGDVQVASIGHGA | 260 | SIGHGA | 283 | un-certain | un-certain | 326 |
| O205_ 97690 | 90 | 203 | 2578930197 | *Bacillus amyloliquefaciens* EGD-AQ14 | AVQH01000003 | 2398 | 3576 | - | 392 | 8.00E-67 | MKKVLIGLTIVAALTVGFVGGQYSVNNASGDVQVASIGHGA | 260 | SIGHGA | 283 | un-certain | un-certain | 326 |
| Ga0112190_ 1037117 | 91 | 24 | 2668626179 | *Bacillus subtilis* B4073 | Ga0112190_ 1037 | 69813 | 70967 | - | 384 | 8.00E-1.72 | MKKVLYSLIIVIALAVGFVGGQKSMETASVDQPIKVASPSRGA | 261 | SPSRGA | 277 | Pro-phage | SpBeta-like | 327 |
| Bcell_ 2296 | 92 | 205 | 649826024 | *Bacillus cellulosilyticus* N-4, DSM 2522 | NC_014829 | 2492123 | 2493163 | + | 346 | 5.00E-39 | MKKFIKGLIIAVTLVAASTSIPTSSVAYDVDFRVRSIEVVDVQPLYDVDFRVRSVEQFDVQPLYDVDFRVR | 262 | ? | 284 | not pro-phage | | 328 |
| BSU20860 | 93 | 206 | 646318642 | *Bacillus subtilis subtilis* 168 | NC_000964 | 2208994 | 2210154 | - | 386 | 5.00E-88 | MKKLIMALVILGALGTSYISADSSIQQASGDYEVAGMPRGA | 230 | GMPRGA | 271 | Pro-phage | SpBeta-like | 290 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Str-and | Amino Acid Length (aa) | E-value of Homology to phi3T AimR | Associated AimP Sequence | Associated AimP SEQ ID NO | Mature peptide sequence Se-quence | Mature peptide sequence SEQ ID NO | Genomic context | Phage type | DNA binding region SEQ ID NO |
|---|---|---|---|---|---|---|---|---|---|---|---|---|---|---|---|---|---|
| LL3_02315 | 94 | 207 | 651184775 | *Bacillus amyloli-quefaciens* LL3 | CP002634 | 2201471 | 2202610 | - | 379 | 0 | MKKIIFGTAILAAL AISFIAGQHSVNTA SASDEISVASAIRGA | 263 | SAIRGA | 269 | Pro-phage | SpBeta-like | 329 |
| BacJ24_ 0008. 00001040 | 95 | 208 | 2505852091 | *Bacillus subtilis* J24 | BacJ24_ scaffold_7 | 83769 | 84929 | + | 386 | 3.00E-86 | MKKLIMALVILGA LGTSYISADSSIQQA SGDYEVAGMPRGA | 230 | GMPRGA | 271 | Pro-phage | SpBeta-like | 290 |
| BAXH7_ 01322 | 96 | 209 | 2511911529 | *Bacillus amyloli-quefaciens* XH7 | CP002927 | 1258713 | 1259873 | + | 386 | 5.00E-95 | MKKLFMGITIAAV LMFSYASVKLVSN EQASGDYEVAGVV RGA | 255 | GVVRGA | 276 | Pro-phage | SpBeta-like | 321 |
| BANAU_ 1103 | 97 | 210 | 2514130679 | *Bacillus amyloli-quefaciens planatarum* YAU B9601-Y2 | NC_017061 | 1159971 | 1160933 | + | 320 | 2.00E-57 | MKKVFICLTIVAS LAVGFIAGQQTTIH SASGEETFHVAGFG RGA | 264 | GRGRGA | 272 | Pro-phage | Mu-like (virfam) | 330 |
| BANAU_ 1431 | 98 | 211 | 2514131006 | *Bacillus amyloli-quefaciens planatarum* YAU B9601-Y2 | NC_017061 | 1528667 | 1529629 | + | 320 | 5.00E-56 | MKKVLIGLAIVAA LAVGFVGGQHFKT ASGDIQMANPGRG A | 265 | NRGRGA | 285 | Pro-phage | phage group D | 331 |
| BANAU_ 1775 | 99 | 212 | 2514131350 | *Bacillus amyloli-quefaciens planatarum* YAU B9601-Y2 | NC_017061 | 1939108 | 1940262 | + | 384 | 6.00E-155 | MKKFNCAIVILLA LTVGFVSGQQSVQ TANGDITVASASRG A | 235 | SASRGA | 275 | Pro-phage | SpBeta-like | 297 |
| BS732_ 3741 | 100 | 213 | 2531250071 | *Bacillus subtilis* MB732 | AOTY01000004 | 37378 | 38517 | + | 379 | 5.00E-88 | MKKLIMALVILGA LGTSYISADSSIQQA SGDYEVAGMPRGA | 230 | GMPRGA | 271 | Pro-phage | SpBeta-like | 290 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Strand | Amino Acid Length (aa) | E-value of Homology to phi3T AimR | Associated AimP Sequence | Associated AimP SEQ ID NO | Mature peptide sequence Sequence | Mature peptide sequence SEQ ID NO | Genomic context | Phage type | DNA binding region SEQ ID NO |
|---|---|---|---|---|---|---|---|---|---|---|---|---|---|---|---|---|---|
| MUS_1241 | 101 | 214 | 2540720195 | *Bacillus amyloliquefaciens* Y2 | CP003332 | 1158120 | 1159082 | + | 320 | 2.00E-57 | MKKVFICLTIVASLAVGFIAGQQTTIHSASGEETFHVAGFGRGA | 264 | GRGRGA | 272 | Prophage | Mu-like (virfam) | 330 |
| MUS_1619 | 102 | 215 | 2540720547 | *Bacillus amyloliquefaciens* Y2 | CP003332 | 1524792 | 1525754 | + | 320 | 5.00E-56 | MKKVLIGLAIVAALAVGFVGGQHFKTASGDIQMANPGRGA | 265 | NRGRGA | 285 | Prophage | phage group D | 331 |
| MUS_1994 | 103 | 216 | 2540720888 | *Bacillus amyloliquefaciens* Y2 | CP003332 | 1935234 | 1936334 | + | 384 | 6.00E-155 | MKKFNCAIVILLALTVGFVSGQQSVQTANGDITVASASRGA | 235 | SASRGA | 275 | Prophage | SpBeta-like | 297 |
| GYSDRAFT_03015 | 104 | 217 | 2547506781 | *Bacillus vallismortis* DV1-F-131_.71 | GYSDRAFT_AFSH0100007 | 106 | 1116 | + | 336 | 6.00E-63 | MKKLIMALVILGALGTSYISADSSNQQASGDYEVAGMPRGA | 266 | GMPRGA | 271 | Prophage | SpBeta-like | 332 |
| BATRMS DRAFT_04055 | 105 | 218 | 2547798787 | *Bacillus atrophaeus* ATCC 9372 | BATRMDRAFT_AEFM01000025_1.25 | 108435 | 109328 | - | 297 | 1.00E-61 | MKKIFMGITIAAVLMFSYASVKLASNEQTLGDYEVAGVVRGA | 237 | GVVRGA | 276 | Prophage | SpBeta-like | 299 |
| BATRDET3 DRAFT_04168 | 106 | 219 | 2547887380 | *Bacillus atrophaeus* Detrick-3 | BATRDET3 DRAFT_AEFR01000030_1.30 | 47822 | 48715 | + | 297 | 1.00E-61 | MKKIFMGITIAAVLMFSYASVKLASNEQTLGDYEVAGVVRGA | 237 | GVVRGA | 276 | Prophage | SpBeta-like | 299 |
| BATRDET1 DRAFT_02926 | 107 | 220 | 2547902834 | *Bacillus atrophaeus* Detrick-1 | BATRDET1 DRAFT_AEFP01000015_1.15 | 123791 | 124684 | - | 297 | 1.00E-61 | MKKIFMGITIAAVLMFSYASVKLASNEQTLGDYEVAGVVRGA | 237 | GVVRGA | 276 | Prophage | SpBeta-like | 299 |
| BATR722 DRAFT_03603 | 108 | 221 | 2547907714 | *Bacillus atrophaeus* ATCC 9372-2 | BATR272 DRAFT_AEFU01000031_1.31 | 123820 | 124713 | - | 297 | 1.00E-61 | MKKIFMGITIAAVLMFSYASVKLASNEQTLGDYEVAGVVRGA | 237 | GVVRGA | 276 | Prophage | SpBeta-like | 299 |

TABLE 3-continued

Homologs of AimR-AimP in sequenced genomes

| Locus Tag of Aim R | NA SEQ ID NO | AA SEQ ID NO | IMG_oid AimR | Genome Name | Scaffold Accession | Start Coord | End Coord | Str-and | Amino Acid Length (aa) | E-value of Homology to phi3T AimR | Associated AimP Sequence | Associated AimP SEQ ID NO | Mature peptide sequence Se-quence | Mature peptide sequence SEQ ID NO | Genomic context | Phage type | DNA binding region SEQ ID NO |
|---|---|---|---|---|---|---|---|---|---|---|---|---|---|---|---|---|---|
| BATR131 DRAFT_ 03725 | 109 | 222 | 2547916178 | *Bacillus atrophaeus* 1013-1 | BATR131 DRAFT_ AEFS01000022_ 1.22 | 173190 | 174083 | + | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| EF83_ 22295 | 110 | 223 | 2579676294 | *Bacillus subtilis* KATMIRA 1933 | JMEF01000083 | 1896 | 3056 | - | 386 | 5.00E-92 | MKGGDKMKKFIM AITIAAVLSISFVGA KASSNEQASGDYQ VAGIVRGA | 267 | GIVRGA | 286 | Pro-phage | un-certain | 333 |
| EF83_ 22800 | 111 | 224 | 2579676381 | *Bacillus subtilis* KATMIRA 1933 | JMEF01000107 | 1005 | 1721 | - | 238 | 8.00E-78 | MKKVFIGLAIVAA LAVAFVAGQHSQT DNASGNVSVASAS RGA | 268 | SASRGA | 275 | un-certain | un-certain | 334 |
| Ga0077944_ 112105 | 112 | 225 | 2635815553 | *Bacillus atrophaeus* NRS 1221A | Ga0077944_ 11 | 2140380 | 2141273 | - | 297 | 1.00E-61 | MKKIFMGITIAAV LMFSYASVKLASN EQTLGDYEVAGVV RGA | 237 | GVVRGA | 276 | Pro-phage | SpBeta-like | 299 |
| Ga0098211_ 112309 | 113 | 226 | 2652254345 | *Bacillus* sp. BS34A | Ga0098211_ 11 | 2227093 | 2228253 | - | 386 | 5.00E-88 | MKKLIMALVILGA LGTSYISADSSIQQA SGDYEVAGMPRGA | 230 | GMPRGA | 271 | Pro-phage | SpBeta-like | 290 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells— A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Oligos and Reagents—

All oligos were purchased from Sigma (St. Louis, Mo.) or Integrated DNA Technologies (IDT, San Jose, Calif.). Synthetic peptides were purchased from Peptide 2.0 Inc. (Chantilly, Va.), at 98% purity, desalted.

Preparation of Conditioned Media—

A schematic representation of the procedure is shown in FIG. 1A. Specifically, overnight cultures of *B. subtilis* strain 168 were diluted 1:50 in LB media supplemented with 0.1 mM $MnCl_2$ and 5 mM $MgCl_2$, and incubated at 37° C. with shaking until reaching optical density (O.D) 600 nm=0.5. Phages (phi29, phi105, rho14 or phi3T) were added to the bacterial culture at MOI=1 and incubated for 3 hours. The media were centrifuged at 4000 rpm for 10 minutes at 4° C. and the supernatant was filtered with 0.2 μm filer (GE Healthcare Life Sciences, Whatman, CAT #10462200). Phages and large molecules were further filtered out from the media by using Amicon Ultra centrifugal filters at a cutoff of 3,000 NMWL (3 kDa) (Milipore, CAT #UFC900324). A plaque assay was performed in order to verify that no phages were left in the medium.

Proteinase K Treatment—

7.5 mg (per reaction) of Proteinase K-Agarose from *Tritirachium album* (Sigma, CAT #P9290) were washed twice with 750 μl of sterile water and then resuspended with 750 μl of LB supplemented with 0.1 mM $MnCl_2$ and 5 mM $MgCl_2$. Following, the tubes were centrifuged again and the supernatant was discarded. 1.5 ml of phi3T-derived conditioned medium or control medium was added to a tube containing the washed proteinase K. The media were incubated for 2 hours at 37° C. with the proteinase K. The media were centrifuged and the supernatants were collected for the infection assay.

Growth Dynamics of Phage-Infected Cultures—

Overnight cultures of bacteria were diluted 1:100 in LB media and incubated at 37° C. with shaking until reaching O.D 600 nm=0.1. The bacterial culture was centrifuged at 4000 rpm for 10 minutes at room temperature. The supernatant was discarded and the pellet was resuspended in LB medium supplemented with 0.1 mM $MnCl_2$ and 5 mM $MgCl_2$ at 10% of the initial volume. The concentrated bacterial culture was added to conditioned medium or medium supplemented with synthesized arbitrium peptide in a ratio of 1:9 (bacteria to medium) and incubated for 1 hour at room temperature. Following, the culture was infected with phages at MOI=0.1. Optical density measurements at a wavelength of 600 nm were taken using a TECAN Infinite 200 μlate reader in a 96-wells plate. For infection experiments that did not include conditioned medium or addition of a synthesized peptide, the diluted overnight culture was grown to early-logarithmic phase and then infected as described above.

Semi Quantitative PCR Assay for Lysogeny—

An overnight culture of bacteria was diluted 1:100 until reaching O.D 600 nm=0.1. Medium was replaced (with conditioned medium or control medium) as described above, and the culture was incubated for 1 hour at room temperature. Bacteria were infected by phi3T at MOI=5. Cell pellets were collected at 0, 15, 30, 40 and 60 minutes post infection in the presence of conditioned or control medium. DNA was extracted using DNeasy blood and tissue kit (CAT #69504). Multiplex PCR assays to detect phage phi3T DNA, *B.*

*subtilis* DNA, and the junction between integrated phage and bacterial genome were performed as previously described at Goldfarb et al[29].

Mass Spec—

Conditioned media was filtered using 3 kDa MW cutoff filters (Millipore) and the low molecular weight fraction was desalted using the Oasis HLB uElution plates (Waters Corp.). Samples were dried and stored at −80° C. until analysis. ULC/MS grade solvents were used for all chromatographic steps. Each sample was loaded using split-less nano-Ultra Performance Liquid Chromatography (10 kpsi nanoAcquity; Waters, Milford, Mass., USA). The mobile phase was: A) $H_2O$+0.1% formic acid and B) acetonitrile+0.1% formic acid. Samples' desalting was performed online using a reversed-phase C18 trapping column (180 μm internal diameter, 20 mm length, 5 μm particle size; Waters). Following, the peptides were separated using a T3 HSS nano-column (75 μm internal diameter, 250 mm length, 1.8 μm particle size; Waters) at 0.35 μL/min. The peptides were eluted from the column into the mass spectrometer using the following gradient: 4% to 35% B in 65 min, 35% to 90% B in 5 min, maintained at 90% for 5 min and then back to initial conditions. The nanoUPLC was coupled online through a nanoESI emitter (10 μm tip; New Objective; Woburn, Mass., USA) to a quadrupole orbitrap mass spectrometer (Q Exactive Plus, Thermo Scientific) using a Flexlon nanospray apparatus (Proxeon). Data was acquired in parallel reaction monitoring (PRM) mode, targeting precursor masses 574.33 and 287.67, the singly and doubly charged forms of peptide SAIRGA (SEQ ID NO: 269). MS2 resolution was set to 35,000 and the maximum injection time set to 200 msec, automatic gain control was set to 2e5. Raw data was imported to Skyline software[30] version 3.5. Product ion intensities were extracted and the total area under the curve was calculated.

AimR Purification—

AimR (SEQ ID NO: 1) was cloned into the expression vector pET28a (Novagen) using Transfer-PCR (TPCR)[31], using the following primers:

| | | |
|---|---|---|
| SEQ ID NO: 356 | TP28_aimR_F | TTTGTTTAACTTTAAGAAGGAGATATACCATGATT AAGAATGA ATGCGAAAAGG |
| SEQ ID NO: 357 | TP28_aimR_ cHis_R | CTTTGTTAGCAGCCGGATCTTAGTGGTG GTGGTGGTGGTGAATGAGAGATAAGGTTTAATAAG TCAAG |

Following, AimR was expressed in *E. coli* BL21(DE3) cells with a C-terminal 6× His-tag. Expression was performed at 15° C. for about ~18 hours using 200 μM IPTG (Isopropyl β-D-1-thiogalactopyranoside) as an inducer. The cells pellet was resuspended in lysis buffer [50 mM Tris pH 8, 0.3M NaCl, 20 mM Imidazole, 2 mM DTT, 0.2 mg/ml Lysozyme, 1 μg/ml DNAse, protease inhibitor cocktail (Calbiochem)], disrupted by a cell disrupter at 4° C. and clarified at 15,000 g for 30 minutes. The clarified lysate was loaded onto a HisTrap_FF_5 ml column (GE Healthcare) and washed with buffer containing 50 mM Tris pH 8, 0.3 M NaCl, 20 mM imidazole and 2 mM DTT. AimR was eluted from the column in one step with the same buffer containing 0.5 M imidazole. Fractions containing AimR were pooled and injected to a size exclusion column (HiLoad_16/60_Superdex_200_prepgrade,GE_Healthcare) equilibrated with 20 mM Tris pH 8, 0.3 M NaCl, 2 mM TCEP. Fractions containing pure AimR were pooled and flash frozen in aliquots using liquid nitrogen.

Pure AimR was injected to an analytical gel filtration column (Superdex_200_Increase_10/30 GL, GE Healthcare) equilibrated with buffer containing 20 mM Tris pH 8, 0.3 M NaCl, 2 mM TCEP. The migration position of pure AimR was compared to that of AimR-peptide mixtures at the following molar ratios: AimR and SAIRGA (SEQ ID NO: 269) peptide (1:2), AimR and GMPRGA (SEQ ID NO: 271) peptide (1:1). The column was calibrated (inset of FIG. 4C) by monitoring the migration positions of the following known proteins/polymers: blue dextran (2000 kDa), Thyroglobulin (669 kDa), Apoferritin (443 kDa), beta-amylase (200 kDa), alcohol dehydrogenase (150 kDa), Albumin (66 kDA) and Carbonic anhydrase (29 kDa).

Microscale Thermophoresis (MST)—

Two-step purified 6×His-tagged AimR stored in Tris/NaCl buffer (50 mM Tris pH 8.0, 150 mM NaCl, 2 mM TCEP) at −80° C. was thawed on ice and centrifuged at 21,000 g for 10 minutes at 4° C. prior to analysis. Peptides [SAIRGA (SEQ ID NO: 269) and GMPRGA (SEQ ID NO: 271)] were solubilized in 50 mM Tris-HCl pH 8.0, 150 mM NaCl to a final concentration of 100 μM. AimR was diluted to 200 nM and was incubated with 16 different peptide concentrations varying between 9-4000 nM, which were prepared in Tris/NaCl buffer containing 0.1% [v/v] Pluronic acid (NanoTemper). Roughly 3 μl were loaded into NT.LabelFree Zero-Background Premium Coated Capillaries (NanoTemper) and inserted into a Monolith NT.LabelFree device (NanoTemper). MST experiments were performed at 60% MST power (infra-red laser) and 20% LED power at 23° C. using the Monolith NT.LabelFree instrument (Nanotemper). Ratios between normalized initial fluorescence and post-temperature-jump and thermophoresis were calculated and averaged from 3 independent runs (runs were incubated for 20 minutes at room temperature before the measurement). A plot of fluorescence ratios versus peptide concentration was used to assess the binding capacity of the phage protein and its cognate peptide ligand.

ChIP-Seq—

For the ChIP-seq experiments, *B. subtilis* cell cultures were grown in 100 ml to O.D of 0.1 in LB at 37° C. Following, 50 ml of culture was centrifuged at 4000 rpm for 10 minutes at room temperature. The pellets were then suspended with 25 ml LB either containing or lacking the peptide (SAIRGA, SEQ ID NO: 269) at a final concentration of 1 μM. The cultures were placed for an additional incubation hour at room temperature with shaking. The cultures were then infected with phage (MOI=0.5) having a final plaque forming units (PFU) of $5\times10^7$ PFU/ml phages. 15 minutes post phage infection the cultures were centrifuged at 3000 g for 5 minutes at 4° C. The supernatant was discarded and the pellets were resuspended with 1 ml of ice-cold 1×PBS (10 mM Phosphate, 137 mM NaCl, 2.7 mM KCl, pH of 7.4).

For the formaldehyde fixation of protein to DNA, the 1 ml PBS resuspended pellets were mixed with 62.5 μl formaldehyde (Thermoscientific 16% formaldehyde solution (w/v) methanol-free ampule) yielding a final formaldehyde concentration of 1% (w/v) within the solution. The formaldehyde-containing cell suspension was incubated at room temperature for 10 minutes with mild agitation. Following, 75 μl 2M Glycine (f.c. 150 mM) was added to quench residual formaldehyde. Glycine-containing samples were kept on ice for an additional 10 minutes followed by centrifugation at 5500 g for 1 minute at 4° C. The supernatants were discarded and the pellets were washed with a 1 ml of ice-cold 1×PBS. Centrifugation and wash were repeated 3 times for each sample.

The cell pellets were suspended with 600 μl lysis buffer containing 50 mM Tris-HCl pH 7.5, 150 mM NaCl and a protease inhibitor mix (cOmplete ULTRA Tablets Roche). The lysis-buffer-containing cells were applied on a lysing matrix B (MP Biomedicals) 0.1 mm silica beads. The mixture and beads were placed in a FastPrep-24 (MP Biomedicals) apparatus and shaken aggressively for 20 seconds 6 m/sec at 4° C. The beads were then separated from lysed cells by centrifugation at 10,000 g for 1 minutes at 4° C. according to manufacturer's instructions. Following, 300 μl of the supernatant, containing the lysed cell mixture, were transferred into a 1.5 ml Bioruptor® Plus TPX microtubes (diagenode) and kept on ice for 10 minute (according to manufacturer's instructions). The samples were sonicated at 4° C. with full power for 15 minutes (30 seconds off/on cycles) using the BioRuptor plus (Diagenode) apparatus. Sonication sheared the DNA to an average size of ~500 bp. Following sonication, samples were centrifuge at 20,000 g for 10 minutes at 4° C.

For the IP experiments, supernatant containing the lysis buffer and cellular content was mixed with Triton X-100 and deoxycholate yielding a final IP-buffer composition containing 50 mM Tris-HCl, pH 7.5, 150 mM NaCl, 1% [vol/vol] Triton X-100, 0.1% [wt/vol] sodium deoxycholate supplemented with proteases inhibitors (cOmplete ULTRA Tablets Roche). Anti-6×His Tag® ChIP-grade antibody (abcam (ab9108)) was then added to the sonicated samples and gently mixed over night at 4° C. In parallel, Protein G Dynabeads (100.04 D; Invitrogen) were washed three times with IP buffer.

DNA-protein-antibody complexes (300 μl) were captured with a 100 μl Dynabeads protein G by mixing them for 1 hour at room temperature with rotation. 0.72 μl of 0.5M EDTA (f.c. 1 mM) was added to that mixture to prevent DNase activity at room temperature. Beads were applied to a magnetic stand (Qiagen) and washed three times with IP buffer (200 μl) at room temperature. Two elution steps were applied with 100 μl and 50 μl of elution buffer (50 mM Tris-HCl, pH 7.5, 10 mM EDTA, 1% [wt/vol] SDS) for 15 minutes at 65° C. on a rocking platform. The eluate (100 μl) was incubated with 5 μl of proteinase K (20 mg $ml^{-1}$) for 1 hour at 50° C. followed by 6 hours at 65° C. Immunoprecipitated DNA was recovered using a QIAquick PCR Purification kit (Qiagen). Immunoprecipitated DNA was then converted into NGS libraries using an existing protocol[32] and was sequenced on a NextSeq500 Illumina machine generating 75nt-long reads.

Sequencing-Based Assay for Lysogeny—

An overnight culture of bacteria was diluted 1/100 until reaching O.D 600 nm=0.1. Medium was replaced as described above [LB supplemented with 0.1 mM $MnCl_2$ and 5 mM $MgCl_2$ with or without SAIRGA (SEQ ID NO: 269)], and incubated for 1 hour at room temperature. Bacteria were infected by phi3T at multiplicity of infection (MOI)=2. Cell pellets were collected at 5, 10, 20 and 60 minutes post infection in the presence or absence of SAIRGA (SEQ ID NO: 269) peptide at 1 μM final concentration in the medium. DNA was extracted using QIAGEN DNeasy blood and tissue kit (CAT #69504) and subjected to Illumina-based whole genome sequencing on NextSeq500. The relative abundance of lysogens in each sample was estimated using the number of reads mapped to the uninterrupted integration site versus reads mapped to the integration junction spanning the prophage DNA on one end and the bacterial DNA on the other end.

CRISPRI Experiments—

Construction of strains silencing phage genes was done by inserting a dCas9 construct controlled by a xylose promoter[22], into the lacA region in *B. subtilis* 168 genome, and sgRNA with spacers targeting the gene of choice under constitutive promoter to thrC region [Spacer targeting aimR: ACCATTACTTTTCATAAC (SEQ ID NO: 358), spacer targeting aimX: TTTCCGCTTCATCTCAAGA (SEQ ID NO: 359)]. Infection assays in CRISPRi strains were performed in LB supplemented with 0.1 mM $MnCl_2$, 5 mM $MgCl_2$ and 0.2% xylose.

For complementation assays of aimR on the background of aimR-silenced CRISPRi strain, aimR was amplified from the phi3T genome using the following primers:

| | | |
|---|---|---|
| SEQ ID NO: 360 | fwd primer | AAGAATTCCTCATTGTGTTTAGGTAAAATAA GAATTC |
| SEQ ID NO: 361 | rev primer | AACTGCAGTTAGTGGTGGTGGTGGTGGTGAA TTAGAGATAAGGTTAATAATTCAAG* |

*includes a 6xHis tag

These primers amplify aimR together with 158 bases from it upstream region, with a 6×His at its C-terminus. The amplified fragment was cloned into the pBS1C plasmid (received from BGSC). Following, the native protospacer adjacent motif in the complemented aimR gene was changed by a synonymous point mutation (C→A at codon #20 of the aimR gene) using a primer set containing the point mutation and Gibson assembly. The modified gene was then integrated into the amyE locus in the *B. subtilis* genome. The aimX complementation was constructed on the background of aimR-silenced CRISPRi strain. For this, aimX was amplified from the phi3T genome using the following primers:

| | | |
|---|---|---|
| SEQ ID NO: 362 | fwd primer | AAACTAGTTTTAAGGGAAAGTTCCAGAAATT C |
| SEQ ID NO: 363 | rev primer | AACTGCAGTCCGTTGCCAATAGATTATGC |

These primers amplify aimX together with 60 bases from its upstream region and 107 bases from its downstream region (containing the gene terminator). The amplified aimX was cloned into a pBS1C plasmid modified to contain a xylose promoter, and was then integrated into the amyE locus in the *B. subtilis* genome.

RNA-Seq—

To determine the difference in gene expression with and without the peptide, bacteria were incubated for 1 hour in LB medium supplemented with 0.1 mM $MnCl_2$ and 5 mM $MgCl_2$ in the presence or absence of 1 μM synthesized SAIRGA (SEQ ID NO: 269) peptide. Following, the bacteria were infected with phi3T (MOI=0.1); and cell pellets were collected at 0, 5, 10 and 20 minutes post infection.

RNA extraction and RNA-seq was performed as described in Dar et al.[33]. Briefly, pellets were lysed using the Fastprep homogenizer (MP Biomedicals, Santa Ana, Calif.)

and RNA was extracted with the FastRNA PRO blue kit (MP Biomedicals, 116025050) according to manufacturer's instructions. RNA samples were treated with TURBO deoxyribonuclease (DNase) (Life technologies, AM2238) and fragmented with fragmentation buffer (Ambion) in 72° C. for 1:45 minutes. The reactions were cleaned by adding× 2.5 SPRI beads. The beads were washed twice with 80% EtOH, and air dried for 5 minutes. The RNA was eluted using $H_2O$. rRNA was depleted by using the Ribo-Zero rRNA Removal Kit (epicenter, MRZB12424). Strand-specific RNA-seq was performed using the NEBNext Ultra Directional RNA Library Prep Kit (NEB, E7420) with the following adjustments: all cleanup stages were performed using×1.8 SPRI beads, and only one cleanup step was performed after the end repair step.

To determine the effect of CRISPRi silencing of the aimR gene, bacteria at early logarithmic stage were infected with phi3T (MOI=0.1) and cell pellets were collected 20 minutes post infection. RNA-seq libraries were prepped as described above.

RNA-seq libraries were sequenced using the Illumina NextSeq500 platform. Sequenced reads were demultiplexed and adapters were trimmed using fastx_clipper with default parameters. Reads were mapped to the reference genomes (gene annotation and sequences were downloaded from Genbank: NC_000964 for *Bacillus subtilis* str. 168, AP012496 for *Bacillus subtilis* BEST7003) using NovoAlign (Novocraft) V3.02.02 with default parameters. All downstream analyses and normalized genome-wide RNA-seq coverage maps were generated as described in Dar et al[33].

Differential Expression Analysis—

Reads per gene were calculated for each biological replicate at 20 minutes post infection with and without the synthetic peptide and normalized relative to the total mapped reads hitting the phage genome in each replicate. Log 10 transformation of the average of 3 replicates per gene in each condition was used to plot FIG. 4I and calculate the fold change of gene AimX.

Identification of AimR Homologs and the Arbitrium Peptide Code—

Homologs for the phi3T AimR receptor were searched for using the BLAST option in the Integrated Microbial Genomes (IMG) web server (img(dot)jgi(dot)doe(dot)gov/cgi-bin/mer/main(dot)cgi). The phi3T AimR (SEQ ID NO: 114) was provided as a query sequence and was searched against all isolated genomes with an e-value threshold of 1e-35. The gene neighborhood for each AimR homolog was visually inspected via the IMG "gene neighborhood" representation, and genes found located next to proteins annotated as phage proteins were considered as found in a prophage. The immediate downstream gene for each AimR homolog was considered the respective AimP gene if it contained a signal peptide as predicted by the IMG web server. If no immediate downstream gene was annotated, the intergenic region immediately downstream to the AimR homolog was translated using the Expasy Translate Tool (web(dot)expasy(dot)org/translate/), and short translated ORFs were inspected for the AimP signature. Results of this analysis are presented in Table 3 above.

Plasmid Construction—

The vectors were constructed using the following primers and oligonucleotides:

| SEQ ID NO: | primer | sequence 5'-3' |
|---|---|---|
| 364 | A | AATCGCCATTCGCCAGGGCTGCAGGAATTCCCCTCATTGTGTTTAGGTAAAATAAGAA |
| 365 | B | GTGTTTAAAATGTCTATTTTATTTAGTTTCAATATGCTCATG |
| 366 | C | GAAACTAAATAAAATAGACATTTTTACACTGATTAACTAATAAGGAGGACAAACATGTC |
| 367 | D | GGTAATGGTAGCGACCGGCGCTCAGGATCCTAAATACGCTTCACAGTTTCTTCTTCATT |
| 368 | E | TATTCTCACCTCCTTTCAAATTTGTCAAACC |
| 369 | F | GTTTGACAAATTTGAAAGGAGGTGAGAATATTAAATAATTGAATAGGTAATACATAATACTATCATAGACG |
| 370 | G | TCTAATAACCCCCATGTTCTTATTTTTTGATTTTTG |
| 371 | H | TCAAAAAATAAGAACATGGGGGTTATTAGAGCATATTGAAACTAAATAAAATAGACATTTTAAACAC |

Construct #1 comprises 2 components: the Bacteriophage Phi3T virus aimR-aimP-aimX locus and a Fluorescent reporter gene (Superfolder Green Fluorescent Protein (sfGFP(sp)), denoted herein as GFP. Both components were inserted into a target shuttle plasmid (pDR111) that enabled propagation of the plasmid in *E. coli* followed by transformation into the *Bacillus subtilis* BEST7003 genome. pDR111 contains two sequences, each matching either the 5'-end or the 3'-end of the target gene (amyE) which through homologous recombination allows insertion of Construct #1. In addition, pDR111 also includes a Spectinomycin antibiotic resistance (spec) gene that allows for selection of the desired insertion, namely Construct #1.

Specifically, the aimR-aimP-aimX locus (SEQ ID NO: 372) was directly amplified from bacteriophage Phi3T genome, using primers A+B, which contains the aimR, aimP and aimX coding genes, including their intergenic spaces (Erez Z, et al., Nature. 2017; 541(7638):488-493).

The reporter GFP gene (SEQ ID NO: 373) was amplified, using primers C+D, from plasmid pDR111-sfGFP(sp) which contains a *Bacillus subtilis*-optimized superfolder-GFP (Overkamp W, et al., Appl Environ Microbiol. 2013 October; 79(20):6481-90).

The reporter gene GFP was genetically fused to the Phi3T aimR-aimP-aimX locus by inserting 3 STOP codons followed by a ribosome-binding-site (denoted herein as rbs) immediately downstream of the 37 bp long 3'UTR of aimX (see FIG. 6). A transcription-terminator element (rrnB) was placed downstream to the GFP gene. The genetic fusion of the aimR-aimP-aimX locus together with the GFP reporter gene yielded Construct #1 (FIG. 6, SEQ ID NO: 374).

The construct was inserted into the shuttle plasmid pDR111 between the restriction sites EcoRI and BamHI using the NEB builder HIFI DNA assembly reaction kit (NEB, MA, USA), resulting in the plasmid pDR111-Construct #1 (FIG. 6, SEQ ID NO: 375).

The pDR111-Construct #1 plasmid was propagated in *Escherichia coli* and then used as a shuttle vector to insert the Construct #1 operon into the *Bacillus subtilis* genome within the amyE gene together with a spec gene on the opposite strand upstream of the RPX operon (FIG. 7). Whole genome sequencing, using a High-throughput Illumina NextSeq sequencer, was applied to verify the sequence of the Construct #1 operon and its precise position within the bacterial genome.

In order to create a minimized expression system the pDR111-Construct #1 plasmid was amplified using primers E+F followed by DNA assembly using the NEB builder HIFI DNA assembly reaction kit (NEB, MA, USA), resulting in the plasmid pDR111-Construct #1 with a deleted aimP gene. This construct was further amplified using primers G+H followed by DNA assembly leading to deletion of the aimX gene as well. The end product, pDR111-Construct #2 (SEQ ID NO: 377), contained the double gene deletion Δ aimP/Δ aimX variant of Construct #1 [i.e. Construct #2 (SEQ ID NO: 376)]. pDR111-Construct #2 was used as a shuttle plasmid in a similar manner to pDR111-Construct #1. This led to insertion of Construct #2 into the bacterial genome as described above for Construct #1 (FIG. 8).

Growth Dynamics of Plasmid-Containing Cultures—

Starter growths of wild type (WT) *Bacillus subtilis* BEST7003 strain and of *Bacillus subtilis* BEST7003 strains containing Construct #1 or Construct #2 were cultured in 3 ml Luria-Bertani (LB) broth until the growth curve indicated stationary phase. Following, the bacterial cells were diluted in a ratio of 1/100 in LB broth or LB broth supplemented with a SAIRGA (SEQ ID NO: 269) peptide at a concentration range of 62.5 nM-1000 nM. Optical density (O.D. at 600 nm) and GFP fluorescence levels (488 nm excitation/518 nm emission) were measured over time in a 96 wells plate using a TECAN Infinite 200 μlate reader.

Example 1

A Short Peptide is Released to the Medium Following phi3T Phage Infection Affecting the Lysis/Lysogeny Decision Cultures of *Bacillus subtilis* str. 168 were infected by 1 of the four different phages: phi29 (Podoviridae, obligatory lytic), phi105 (Siphoviridae, temperate, lambda-like), rho14 (Siphoviridae, temperate, lambda-like) or phi3T (Siphoviridae, temperate, spBeta-like) in control and in phage-derived conditioned media (see FIG. 1A). Surprisingly, for one of the tested phages, phi3T, the infection dynamics in the conditioned medium, as inferred from the bacterial growth curve, was dramatically different than the dynamics in the control medium. As shown in FIG. 1B, whereas a substantial fraction of the phi3T infected bacterial culture had lysed in the control medium two hours post infection, the culture grown in the conditioned medium appeared to be largely protected from lysis. This effect was not detected for any of the other three phages tested, for which no difference in infection dynamics between the control and conditioned media was observed. Moreover, the conditioned medium prepared from phi3T infection did not affect the infection dynamics of other phages, and vice versa, conditioned media prepared from other phages did not affect the infection dynamics of phi3T.

Taken together, these results imply that a small molecule is released to the medium during infection of *B. subtilis* by phi3T and this molecule can affect infection dynamics of downstream infections of this phage.

It is known that quorum sensing (QS) in Bacilli and other Firmicutes is typically based on short peptides that are secreted to the medium and sensed by intra-cellular or membrane bound receptors[1-3]. Thus, to test whether the active substance in the medium is proteinaceous the conditioned medium was treated with proteinase K. As shown in FIG. 1E, infection dynamics in the proteinase-treated conditioned medium were similar to the dynamics in the control medium, suggesting that the active component in the medium is indeed proteinaceous. Since communication peptides in *Bacillus* quorum sensing systems are frequently imported into the cell by the oligopeptide permease transporter (OPP), phage infection dynamics was tested in bacteria in which an essential subunit of the OPP transporter, oppD, was deleted (FIG. 1C). The phage-derived conditioned medium lost its effect when the bacteria lacking the functional OPP were infected by phi3T, suggesting that the active substance in the conditioned medium is a 3aa-aa long peptide, which is the size range of peptides that can be imported by the OPP transporter of Gram positive bacteria[4].

A close examination of the phage infection dynamics in the oppD mutant showed increased culture lysis in both control and conditioned media as compared to infection of wild type bacteria (FIGS. 1B-C). Phage phi3T is a temperate phage that may choose to infect either through the lytic or the lysogenic cycles[6,7]. Whereas the lytic cycle leads to lysis of the bacterial cell, in the lysogenic cycle the phage genome integrates into the bacterial genome, and the lysogenized bacterium becomes protected from further infection by the same phage[7]. In accordance, the growth curve of bacteria infected by phi3T in the control medium presents partial, but not full, lysis of the culture, followed by culture recovery due to growth of lysogenized bacteria. The observation that the infection dynamics curve of the oppD mutant presents a complete lysis of the culture suggests that the active peptide released to the medium may promote lysogeny of the phage. Hence, to test whether the reduced bacterial lysis observed during infection in the phage-derived conditioned medium is due to increased lysogeny phage phi3T integration into the *B. subtilis* genome during infection was examined using a semi-quantitative PCR assay. Indeed, as shown in FIG. 1D, increased lysogeny was observed when the bacterial culture was infected in the conditioned medium.

Taken together, these results suggest that during phi3T infection a short peptide is released to the medium and, as this peptide accumulates, it acts as a communication agent affecting the lysis/lysogeny decision of later generations of the phage progeny. This newly discovered putative communication molecule is denoted herein as arbitrium (the Latin word for "decision").

Example 2

The Peptide Affecting the Lysis/Lysogeny Decision is Encoded by the aimP Gene Phi3T was isolated 4 decades ago and was characterized as belonging to the spBeta family of phages, although to date its genome was not sequenced[6]. To search for the possible genetic system encoding the arbitrium peptide, the genome of phi3T was sequenced and analyzed. This genome assembled into a single 128 kbps contig containing 185 predicted genes. To search for proteins likely to be secreted into the medium all of the open reading frames (ORFs) in phi3T were screened for the presence of an N-terminal signal peptide using the signalP software[8]. Three ORFs were predicted to have a signal peptide, suggesting that they are secreted or membrane-localized. While two of these genes seemed irrelevant (one was an integral membrane protein and the other was a large nuclease), the third gene exhibited features reminiscent of *Bacillus* quorum sensing peptides (FIGS. 2A-B). Peptides belonging to the Phr family of quorum sensing systems in *B. subtilis* are typically processed from a pre-pro-peptide that contains an N-terminal signal sequence, which is recognized by the Sec system and cleaved upon secretion[1]. Once outside the cell, the propeptide is further processed by *B. subtilis* extracellular proteases to produce the mature short (5-6 amino acids) peptide that is typically found on the C-terminal end of the pro-peptide[1]. The selected candidate gene encoded a short ORF (43 amino acids, SEQ ID NO: 227), and displayed both an N-terminal signal sequence and the consensus cleavage site for peptide maturation at its C-terminus (FIGS. 2A-B). If this phi3T-encoded protein is secreted and matured extracellularly, then the predicted mature communication peptide after pro-peptide cleavage would be Ser-Ala-Ile-Arg-Gly-Ala (SAIRGA, SEQ ID NO: 269). Indeed, mass spectrometry analysis confirmed the presence of the SAIRGA peptide in the conditioned medium but not in the control medium (FIG. 2C).

To test whether the predicted mature peptide is indeed the arbitrium molecule that influences the phage lysogeny decision, bacteria were infected with phi3T in LB medium supplemented with increasing amounts of synthesized SAIRGA (SEQ ID NO: 269) peptide. A clear concentration-dependent effect on the phage infection dynamics was observed, such that reduced culture lysis was apparent when the medium contained higher concentrations of the synthesized peptide (FIG. 2D). These effects were specific to that peptide, and were neither observed for shorter, 5 amino acids versions of the peptide (SAIRG or AIRGA, SEQ ID NOs: 355 and 354, respectively), nor for PhrC (SEQ ID NO: 350), a known quorum sensing peptide of *B. subtilis* (FIGS. 2D-E). The maximal effect on the culture growth curve was observed at SAIRGA (SEQ ID NO: 269) peptide concentration of 500 nM, above which the effect seemed saturated (FIG. 2D).

To verify that the observed effect of the SAIRGA peptide on the dynamics of the infected culture was the result of increased lysogeny, total DNA of bacteria collected from a time course experiment during infection by phi3T with and without the peptide was directly sequenced. By comparing the fraction of sequencing reads passing through the intact phage integration site in the bacterial genome to reads demonstrating phage integration at that site, the fraction of lysogenized bacteria at each time point was directly quantified. Remarkably, a consistently elevated lysogeny in the presence of the SAIRGA (SEQ ID NO: 269) peptide was observed, such that 48% (±7.9%) of the bacteria were lysogenized at 60 minutes post infection, as compared to 18% (±3.3%) of bacteria grown without the peptide (FIG. 2F). These results suggest that the phage-encoded gene identified is secreted and processed into the mature arbitrium communication peptide that further affects the phage lysis/lysogeny decision. This gene was denoted herein as aimP.

The aimP gene is located immediately downstream of a gene (SEQ ID NO: 1) encoding a 378 amino acids long open reading frame (SEQ ID NO: 114), suggesting that these two genes may be co-transcribed from the phage genome as a polycistron. This upstream gene encodes a predicted tetratricopeptide repeat (TPR) domain, typical of intracellular peptide receptors of the RRNPP family in QS systems of Gram positive bacteria[9-11] (FIG. 2A). It was therefore hypothesized that this upstream gene, which was denoted aimR, is the receptor of the AimP-derived arbitrium peptide. To test this hypothesis a C-terminal His-tagged AimR was purified, and microscale thermophoresis (MST) was used to measure the binding between the purified receptor and the synthesized arbitrium peptide. This analysis showed high-affinity binding, at an effective peptide concentration of $EC_{50}$=138 nM (118-162 nM at confidence interval of 95%), between the phi3T AimR receptor and the cognate SAIRGA (SEQ ID NO: 269) peptide (FIG. 2G), confirming that AimR most probably functions as the intracellular receptor of the arbitrium SAIRGA peptide.

Example 3

A Conserved Peptide Communication Code Guiding Lysogeny in *Bacillus* Phages To appreciate the abundance of this system in nature, a homology search was conducted to find homologs of the aimR gene in available sequenced genomes. Using this search 112 instances of AimR homologs were detected, virtually all of them in *Bacillus* phages or in prophages found integrated within Bacilli genomes, suggesting that this gene primarily fulfills a phage-related function (FIG. 3A and Table 3 above). In all cases, aimR homologs were found upstream of aimP candidate genes, i.e., short polypeptides encoding an N-terminal signal peptide, followed by a pro-peptide conforming with the processing maturation signal of the *Bacillus* extracellular proteases (Table 3 above; FIG. 2B). Although the sequences of the predicted mature peptides were diverse, all of them maintained strict rules for their sequence composition, with an obligatory glycine residue at the $5^{th}$ position, glycine or alanine at the $6^{th}$ position, and a preference for positively charged residue at the $4^{th}$ position (FIGS. 3B-C).

To test the hypothesis that the phage-encoded communication peptides guide phage lysogeny in a sequence-specific manner, the infection dynamics of the spBeta phage, in which a homolog of the AimR-AimP system was identified, was evaluated. The predicted mature AimP-derived arbitrium peptide of spBeta was GMPRGA (SEQ ID NO: 271), a sequence that differs by the 3 N-terminal amino acids from the SAIRGA (SEQ ID NO: 269) peptide of phi3T. As shown in FIGS. 3D-F, whereas the GMPRGA (SEQ ID NO: 271) peptide promoted lysogeny of spBeta, it did not affect the lysogeny profile of phi3T; and similarly, the phi3T-derived SAIRGA (SEQ ID NO: 269) peptide had no effect on the infection dynamics of spBeta. In accordance, the spBeta-derived GMPRGA (SEQ ID NO: 271) peptide did not show specific binding to the phi3T AimR receptor (FIG. 2G).

Taken together, these results demonstrate a sequence-specific peptide code that guides phage lysogeny in a phage species-specific manner.

Example 4

The AimP Peptide Alters the Oligomeric State of its AimR and Arters the Expression of AimX In communication systems of Gram positive bacteria, the binding of the communication peptide to its receptor usually leads to reprogramming of the transcriptional response. This can occur either directly, when the receptor is a transcription regulator such as in the cases of the PrgX[12,13] in Enterococci, the PlcR[14-16] of the *Bacillus cereus* group, and in other systems[17,18]; or indirectly, as in the case of Rap/Phr systems of Bacilli, in which the receptor is a phosphatase that regulates downstream transcriptional regulators by dephosphorylation[19,20], or steric interference[21]. The presence of a predicted helix-turn-helix (HTH) motif in the N-terminus of AimR suggested that the receptor of the arbitrium system directly binds DNA. To test whether AimR binds the phage DNA in vivo, a His-tagged aimR gene was engineered into a *B. subtilis* 168 strain in which a dCas9 (CRISPRi) technology[22] was used to silence the expression of the phage AimR gene, but not the cloned His-tagged AimR (see Materials and Methods hereinabove). Following, a ChIP-seq assay was performed 15 minutes after phage infection with and without the presence of the arbitrium peptide. Sequencing of the DNA bound to AimR clearly showed that AimR binds a single site in the phage genome, directly downstream of the aimP gene (FIGS. 4A-B). Moreover, this binding only occurred when the arbitrium peptide was absent in the medium, suggesting that binding of the arbitrium peptide to its AimR receptor leads to dissociation of the receptor from its binding site on the phage DNA.

During the process of AimR purification it was noticed that the protein migrates as homodimer in a gel filtration column. Upon addition of the phi3T-derived SAIRGA (SEQ ID NO: 269) peptide, however, the protein strictly migrated as a monomer (FIG. 4C). These results suggest that the arbitrium peptide transfers the signal via alteration of the oligomeric state of its AimR receptor from a DNA binding dimer to a peptide-bound, dissociated monomer. Addition of the spBeta GMPRGA (SEQ ID NO: 271) peptide did not lead to a change in the AimR oligomeric state, pointing, again, to the high specificity between the peptide and its receptor in the arbitrium system (FIG. 4C).

To examine whether binding of the arbitrium peptide to its AimR receptor leads to a transcriptional response in the phage genome RNA-seq was applied to RNA extracted from bacteria during a time course of infection with and without the peptide. As shown in FIGS. 4D-I, the most dramatic change in the expression was observed for a single gene, which was denoted herein as aimX, that was immediately downstream to the AimR DNA binding site. This gene showed substantial expression in the absence of the arbitrium peptide starting 10 minutes following infection, but its expression was reduced more than 20 fold when the medium was supplemented by 1 μM of the SAIRGA (SEQ ID NO: 269) peptide (FIGS. 4D-G).

These results suggest that AimR, when bound to the phage DNA as a dimer in the absence of the arbitrium peptide, is a transcriptional activator of AimX. Indeed, when AimR was silenced using dCas9, the expression of AimX was dramatically reduced (FIG. 4D). Moreover, silencing of AimR resulted in increased lysogeny, suggesting that binding of AimR to the phage DNA inhibits lysogeny (or promotes lysis), possibly by activating the expression of AimX (FIG. 4H).

Since the AimR knockdown did not lead a dramatic transcriptional effect for any gene except AimX at 20 minutes post infection (FIG. 4I), it was hypothesized that the main function of AimR is to control the expression of the aimX gene, and that the AimX gene product works downstream to the AimR-AimP communication system to execute the lysis-lysogeny decision. Consistent with this hypothesis, knockdown of AimX using dCas9 resulted in increased lysogeny (FIG. 4H). Moreover, complementing with an ectopic AimX on the background of AimR knockdown (in which AimX expression is naturally silenced, FIG. 4D) resulted in culture lysis, demonstrating that AimX functions downstream to AimR, and works as the inhibitor of the lysogenic or the promoter of the lytic cycle (FIG. 4H).

Taken together, the present inventors have shown that a large family of phages uses communication peptides in order to decide whether to enter a lytic cycle or lysogenize the infected bacterium. In a sense, the communication mechanism described allows an offspring phage particle to communicate with its ancestors, i.e., measure the amount of the predecessor phages that completed successful infections in prior cycles. The biological logic behind this strategy is clear: when a single phage encounters a bacterial colony, there is ample prey for the progeny phages that are produced from the first cycles of infection, and hence a lytic cycle is preferred. In later stages of the infection dynamics the number of bacterial cells is reduced to a point that progeny phages are at risk of no longer having a new host to infect. Then, it is logical for the phage to switch into lysogeny to preserve chances for viable reproduction.

The arbitrium system provides an elegant mechanism for a phage particle to estimate the amount of recent prior infections and hence decide whether to employ the lytic or lysogenic cycle. Without being bound by theory, the results point to the following model (FIGS. 5A-C): upon initial infection of a bacterial culture, phi3T expresses the early operon AimR-AimP. AimR, as a dimer, activates the expression of AimX, which, in turn, blocks the pathway to lysogeny and promotes the lytic cycle. At the same time, AimP is secreted into the medium and processed into the mature arbitrium peptide. Following several cycles of infection, arbitrium peptides will accumulate in the medium. At this stage, when a phage particle infects a yet-uninfected bacterium, the concentration of the arbitrium peptide, which is internalized into the bacteria by the OPP transporter, will be high enough to bind the AimR receptor. Upon binding, the AimR receptor changes its oligomeric state from the active dimer to the inactive monomer, silencing the AimX lysogeny-inhibitor and leading to lysogeny.

Example 5

The Arbitrium System as a System for Expressing an Expression Product of Interest To demonstrate that the AimR-AimP system can function as a heterologous expression system in a phage-independent context, it was utilized to control the expression of a GFP reporter gene in *Bacillus subtilis* BEST7003.

To this end, the arbitrium locus (AimR-AimP-AimR binding site-AimX) was engineered such that the AimX gene was fused to a GFP reporter gene (Construct #1, FIG. 6). This construct was integrated into the genome of *Bacillus subtilis* BEST7003 at the AmyE locus (FIG. 7). As shown in FIG. 9A, integration of Construct #1 resulted in significant expression of GFP in liquid cultures of the bacteria, reaching a plateau following about 6 hours of culture probably due to expression of the AimP peptide encoded by the construct. Moreover, when the bacteria was grown in liquid culture in the presence of various concentrations of the arbitrium peptide (SAIRGA, SEQ ID NO: 269), a concentration-dependent expression of the GFP fluorescence was observed, such that maximal fluorescence was detected in the absence of the peptide; and fluorescence gradually repressed in a manner proportional to the concentration of the peptide in the growth media.

Following, a minimized expression system containing only the AimR gene, AimR binding site and a GFP downstream to the AimR binding site was engineered (Construct #2, FIG. 8) and integrated into the genome of *Bacillus subtilis* BEST7003 at the AmyE locus (i.e. this system did not contain the AimP and AimX genes). Similarly to a bacteria containing Construct #1, integration of the minimized Construct #2 resulted in significant expression of GFP in liquid cultures of the bacteria; and when the bacteria was grown in the presence of various concentrations of the arbitrium peptide (SAIRGA, SEQ ID NO: 269), a differential expression of GFP dependent on the concentration of the peptide in the medium was observed (FIG. 9B).

Importantly, SAIRGA (SEQ ID NO: 269) peptide concentration or GFP expression did not affect the growth rate of the bacteria (FIGS. 9A-B).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES (Additional References are Cited in Text)

1. Pottathil, M. & Lazazzera, B. A. The extracellular Phr peptide-Rap phosphatase signaling circuit of *Bacillus subtilis*. *Front. Biosci.* 8, d32-45 (2003).
2. Perego, M. Forty years in the making: understanding the molecular mechanism of peptide regulation in bacterial development. *PLoS Biol.* 11, e1001516 (2013).
3. Waters, C. M. & Bassler, B. L. Quorum sensing: cell-to-cell communication in bacteria. *Annu. Rev. Cell Dev. Biol.* 21, 319-46 (2005).
4. Lanfermeijer, F. C., Detmers, F. J., Konings, W. N. & Poolman, B. On the binding mechanism of the peptide receptor of the oligopeptide transport system of *Lactococcus lactis*. *EMBO J.* 19, 3649-56 (2000).
5. Patrick, J. E. & Kearns, D. B. Laboratory Strains of *Bacillus subtilis* Do Not Exhibit Swarming Motility. *J. Bacteriol.* 191, 7129-7133 (2009).
6. Tucker, R. G. Acquisition of Thymidylate Synthetase Activity by a Thymine-requiring Mutant of *Bacillus subtilis* following Infection by the Temperate Phage 3. *J. Gen. Virol.* 4, 489-504 (1969).
7. Rutberg, L. in *The Molecular Biology of Bacilli* Vol. 1 *Bacillus subtilis* (ed Dubnau, D. A.) Ch. Temperate Bacteriophages of *Bacillus Subtilis,* 247-268 (Academic press, 1982).
8. Emanuelsson, O., Brunak, S., von Heijne, G. & Nielsen, H. Locating proteins in the cell using TargetP, SignalP and related tools. *Nat. Protoc.* 2, 953-971 (2007).
9. Rocha-Estrada, J., Aceves-Diez, A. E., Guarneros, G. & de la Torre, M. The RNPP family of quorum-sensing proteins in Gram-positive bacteria. *Appl. Microbiol. Biotechnol.* 87, 913-23 (2010).
10. Do, H. & Kumaraswami, M. Structural Mechanisms of Peptide Recognition and Allosteric Modulation of Gene Regulation by the RRNPP Family of Quorum-Sensing Regulators. *J. Mol. Biol.* 428, 2793-2804 (2016).
11. Perez-Pascual, D., Monnet, V. & Gardan, R. Bacterial Cell-Cell Communication in the Host via RRNPP Peptide-Binding Regulators. *Front. Microbiol.* 7, 706 (2016).
12. Dunny, G. M. & Bemtsson, R. P.-A. Enterococcal Sex Pheromones: Evolutionary Pathways to Complex, Two-Signal Systems. *J. Bacteriol.* 198, 1556-1562 (2016).
13. Shi, K. et al. Structure of peptide sex pheromone receptor PrgX and PrgX/pheromone complexes and regulation of conjugation in *Enterococcus faecalis*. *Proc. Natl. Acad. Sci. U.S.A* 102, 18596-601 (2005).
14. Lereclus, D., Agaisse, H., Gominet, M., Salamitou, S. & Sanchis, V. Identification of a *Bacillus thuringiensis* gene that positively regulates transcription of the phosphatidylinositol-specific phospholipase C gene at the onset of the stationary phase. *J. Bacteriol.* 178, 2749-56 (1996).
15. Slamti, L. & Lereclus, D. A cell-cell signaling peptide activates the PlcR virulence regulon in bacteria of the *Bacillus cereus* group. *EMBO J.* 21, 4550-9 (2002).
16. Declerck, N. et al. Structure of PlcR: Insights into virulence regulation and evolution of quorum sensing in Gram-positive bacteria. *Proc. Natl. Acad. Sci. U.S.A* 104, 18490-5 (2007).
17. Dubois, T. et al. Activity of the *Bacillus thuringiensis* NprR-NprX cell-cell communication system is co-ordinated to the physiological stage through a complex transcriptional regulation. *Mol. Microbiol.* 88, 48-63 (2013).
18. Fleuchot, B. et al. Rgg proteins associated with internalized small hydrophobic peptides: a new quorum-sensing mechanism in streptococci. *Mol. Microbiol.* 80, 1102-1119 (2011).
19. Parashar, V., Mirouze, N., Dubnau, D. A. & Neiditch, M. B. Structural Basis of Response Regulator Dephosphorylation by Rap Phosphatases. *PLoS Biol.* 9, e1000589 (2011).
20. Ishikawa, S., Core, L. & Perego, M. Biochemical characterization of aspartyl phosphate phosphatase interaction with a phosphorylated response regulator and its inhibition by a pentapeptide. *J. Biol. Chem.* 277, 20483-20489 (2002).
21. Baker, M. D. & Neiditch, M. B. Structural Basis of Response Regulator Inhibition by a Bacterial Anti-Activator Protein. *PLoS Biol.* 9, e1001226 (2011).
22. Peters, J. M. et al. A Comprehensive, CRISPR-based Functional Analysis of Essential Genes in Bacteria. *Cell* 165, 1493-1506 (2016).
23. Johnson, C. M. & Grossman, A. D. Integrative and Conjugative Elements (ICEs): What They Do and How They Work. *Annu. Rev. Genet.* 49, 577-601 (2015).
24. Auchtung, J. M., Lee, C. A., Monson, R. E., Lehman, A. P. & Grossman, A. D. Regulation of a *Bacillus subtilis* mobile genetic element by intercellular signaling and the global DNA damage response. *Proc. Natl. Acad. Sci. U.S.A* 102, 12554-9 (2005).
25. Hargreaves, K. R. et al. What Does the Talking?: Quorum Sensing Signalling Genes Discovered in a Bacteriophage Genome. *PLoS One* 9, e85131 (2014).
26. Jiang, M., Grau, R. & Perego, M. Differential Processing of Propeptide Inhibitors of Rap Phosphatases in *Bacillus subtilis*. *J. Bacteriol.* 182, 303-310 (2000).
27. Dodd, I. B., Shearwin, K. E. & Egan, J. B. Revisited gene regulation in bacteriophage lambda. *Curr. Opin. Genet. Dev.* 15, 145-52 (2005).
28. Oppenheim, A. B., Kobiler, O., Stavans, J., Court, D. L. & Adhya, S. Switches in bacteriophage lambda development. *Annu. Rev. Genet.* 39, 409-29 (2005).
29. Goldfarb, T. et al. BREX is a novel phage resistance system widespread in microbial genomes. *EMBO J.* 34, 169-83 (2015).
30. MacLean, B. et al. Skyline: an open source document editor for creating and analyzing targeted proteomics experiments. *Bioinformatics* 26, 966-8 (2010).
31. Erijman, A., Dantes, A., Bernheim, R., Shifman, J. M. & Peleg, Y. Transfer-PCR (TPCR): a highway for DNA cloning and protein engineering. *J. Struct. Biol.* 175, 171-177 (2011).
32. Garber, M. et al. A High-Throughput Chromatin Immunoprecipitation Approach Reveals Principles of Dynamic Gene Regulation in Mammals. *Mol. Cell* 47, 810-822 (2012).
33. Dar, D. et al. Term-seq reveals abundant ribo-regulation of antibiotics resistance in bacteria. *Science,* 352, 187 (2016).

What is claimed is:

1. A method of expressing an expression product of interest, the method comprising:

(i) introducing into a cell a polynucleotide comprising an AimR responsive element operatively linked to a nucleic acid sequence encoding the expression product of interest, wherein said cell expresses an AimR polypeptide, wherein said AimR polypeptide comprises a DNA binding domain for binding said AimR responsive element such that binding of said AimR polypeptide to said AimR responsive element leads to activation of transcription of said expression product of interest, wherein said AimR polypeptide comprises an amino acid sequence having at least 80% identity to a sequence selected from the group consisting of SEQ ID NOs: 114-226 or a fragment thereof, said AimR polypeptide comprising a helix-turn-helix (HTH) motif and a tetratricopeptide repeat (TPR) domain and wherein said AimR responsive element comprises a nucleic acid sequence having at least 80% identity to a sequence selected from the group consisting of SEQ ID NOs: 287-334 and 378 or a fragment thereof; and (ii) contacting said cell following said introducing with an AimP peptide capable of binding said AimR polypeptide and dissociating said AimR polypeptide from said AimR responsive element, wherein said AimP peptide comprises an amino acid sequence having at least 80% identity to a sequence selected from the group consisting of SEQ ID NOs: 269-283 and 285-286 or a fragment thereof, said AimP peptide comprising an amino acid sequence of XXXXGG/A, thereby expressing the expression product of interest.

2. A method of expressing an expression product of interest, the method comprising introducing into a cell a polynucleotide comprising an AimR responsive element operatively linked to a heterologous nucleic acid sequence encoding the expression product of interest, wherein said cell expresses an AimR polypeptide, wherein said AimR polypeptide comprises a DNA binding domain for binding said AimR responsive element such that binding of said AimR polypeptide to said AimR responsive element leads to activation of transcription of said expression product of interest, wherein said AimR polypeptide comprises an amino acid sequence having at least 80% identity to a sequence selected from the group consisting of SEQ ID NOs: 114-226 or a fragment thereof, said AimR polypeptide comprising a helix-turn-helix (HTH) motif and a tetratricopeptide repeat (TPR) domain and wherein said AimR responsive element comprises a nucleic acid sequence having at least 80% identity to a sequence selected from the group consisting of SEQ ID NOs: 287-334 and 378 or a fragment thereof, thereby expressing the expression product of interest.

3. A method of expressing an expression product of interest, the method comprising introducing into a cell a polynucleotide comprising an AimR responsive element operatively linked to a nucleic acid sequence encoding the expression product of interest; and a nucleic acid construct encoding an AimR polypeptide comprising an AimR polynucleotide and a cis-acting regulatory element heterologous to said AimR for directing expression of said AimR polynucleotide, wherein said AimR polypeptide comprises a DNA binding domain for binding said AimR responsive element such that binding of said AimR polypeptide to said AimR responsive element leads to activation of transcription of said expression product of interest, wherein said AimR polypeptide comprises an amino acid sequence having at least 80% identity to a sequence selected from the group consisting of SEQ ID NOs:

114-226 or a fragment thereof, said AimR polypeptide comprising a helix-turn-helix (HTH) motif and a tetratricopeptide repeat (TPR) domain and wherein said AimR responsive element comprises a nucleic acid sequence having at least 80% identity to a sequence selected from the group consisting of SEQ ID NOs: 287-334 and 378 or a fragment thereof, thereby expressing the expression product of interest.

4. The method of claim 2, comprising contacting said cell following said introducing with an AimP peptide or a nucleic acid sequence encoding same, wherein said AimP peptide is capable of binding said AimR polypeptide and dissociating said AimR polypeptide from said AimR responsive element, wherein said AimP peptide comprises an amino acid sequence having at least 80% identity to a sequence selected from the group consisting of SEQ ID NOs: 269-283 and 285-286 or a fragment thereof, said AimP peptide comprising an amino acid sequence of XXXXGG/A.

5. The method of claim 2, comprising contacting said cell with an agent capable of downregulating expression and/or activity of said AimR responsive element.

6. The method of claim 2, wherein said expression product of interest is endogenous to said cell.

7. The method of claim 2, wherein said expression product of interest is exogenous to said cell.

8. The method of claim 2, wherein said expression product of interest is a DNA editing agent.

9. The method of claim 2, wherein said AimR responsive element comprises a nucleic acid sequence for binding said AimR and an AimX polynucleotide, wherein said AimX polynucleotide comprises a nucleic acid sequence having at least 80% identity to SEQ ID NO: 336 or a fragment thereof, said AimX polynucleotide or an AimX polypeptide encoded by said AimX polynucleotide is capable of inhibiting lysogeny of a temperate phage expressing said AimR in a host bacteria.

10. The method of claim 9, wherein said expression product of interest is an AimX dependent DNA editing agent.

11. The method of claim 10, comprising introducing into said cell a nucleic acid sequence to be integrated into a genome of said cell by said DNA editing agent.

12. The method of claim 8, wherein said DNA editing agent is an integrase.

13. The method of claim 8, wherein said DNA editing agent is selected from the group consisting of zinc finger nuclease, an effector protein of Class 2 CRISPR/Cas and TALEN.

14. The method of claim 4, wherein said AimP peptide is capable of leading to lysogeny of a temperate phage expressing said AimR in a host bacteria.

15. The method of claim 4, wherein said AimP peptide comprises said amino acid sequence selected from the group consisting of SEQ ID NOs: 269-283 and 285-286.

16. The method of claim 3, wherein said AimR polynucleotide comprises a nucleic acid sequence having at least 80% identity to a sequence selected from the group consisting of SEQ ID NO: 1-113.

17. The method of claim 9, wherein said AimX comprises said nucleic acid sequence as set forth in SEQ ID NO: 336.

18. The method of claim 2, wherein said AimR and said AimR responsive element are positioned sequentially 5' to 3' in a genome of a temperate phage.

19. The method of claim 1, wherein said cell expresses said AimR polypeptide endogenously.

20. The method of claim 1, wherein said cell expresses said AimR polypeptide exogenously.

21. The method of claim 1, wherein said at least 80% identity to a sequence selected from the group consisting of SEQ ID NOs: 114-226 or a fragment thereof is at least 90% identity to a sequence selected from the group consisting of SEQ ID NOs: 114-226 or a fragment thereof, said at least 80% identity to a sequence selected from the group consisting of SEQ ID NOs: 287-334 and 378 or a fragment thereof is at least 90% identity to a sequence selected from the group consisting of SEQ ID NOs: 287-334 and 378 or a fragment thereof, and said at least 80% identity to a sequence selected from the group consisting of SEQ ID NOs: 269-283 and 285-286 or a fragment thereof is at least 90% identity to a sequence selected from the group consisting of SEQ ID NOs: 269-283 and 285-286 or a fragment thereof.

22. The method of claim 1, wherein said at least 80% identity to a sequence selected from the group consisting of SEQ ID NOs: 114-226 or a fragment thereof is at least 95% identity to a sequence selected from the group consisting of SEQ ID NOs: 114-226 or a fragment thereof, said at least 80% identity to a sequence selected from the group consisting of SEQ ID NOs: 287-334 and 378 or a fragment thereof is at least 95% identity to a sequence selected from the group consisting of SEQ ID NOs: 287-334 and 378 or a fragment thereof, and said at least 80% identity to a sequence selected from the group consisting of SEQ ID NOs: 269-283 and 285-286 or a fragment thereof is at least 95% identity to a sequence selected from the group consisting of SEQ ID NOs: 269-283 and 285-286 or a fragment thereof.

23. The method of claim 1, wherein said AimR polypeptide comprises said amino acid sequence selected from the group consisting of SEQ ID NOs: 114-226, said AimR responsive element comprises said nucleic acid sequence selected from the group consisting of SEQ ID NOs: 287-334 and 378, and said AimP peptide comprises said amino acid sequence selected from the group consisting of SEQ ID NOs: 269-283 and 285-286.

24. The method of claim 2, wherein said at least 80% identity to a sequence selected from the group consisting of SEQ ID NOs: 114-226 or a fragment thereof is at least 90% identity to a sequence selected from the group consisting of SEQ ID NOs: 114-226 or a fragment thereof, and said at least 80% identity to a sequence selected from the group consisting of SEQ ID NOs: 287-334 and 378 or a fragment thereof is at least 90% identity to a sequence selected from the group consisting of SEQ ID NOs: 287-334 and 378 or a fragment thereof.

25. The method of claim 2, wherein said at least 80% identity to a sequence selected from the group consisting of SEQ ID NOs: 114-226 or a fragment thereof is at least 95% identity to a sequence selected from the group consisting of SEQ ID NOs: 114-226 or a fragment thereof, and said at least 80% identity to a sequence selected from the group consisting of SEQ ID NOs: 287-334 and 378 or a fragment thereof is at least 95% identity to a sequence selected from the group consisting of SEQ ID NOs: 287-334 and 378 or a fragment thereof.

26. The method of claim 2, wherein said AimR polypeptide comprises said amino acid sequence selected from the group consisting of SEQ ID NOs: 114-226, and said AimR responsive element comprises said nucleic acid sequence selected from the group consisting of SEQ ID NOs: 287-334 and 378.

27. The method of claim 3, wherein said at least 80% identity to a sequence selected from the group consisting of SEQ ID NOs: 114-226 or a fragment thereof is at least 90% identity to a sequence selected from the group consisting of SEQ ID NOs: 114-226 or a fragment thereof, and said at least 80% identity to a sequence selected from the group consisting of SEQ ID NOs: 287-334 and 378 or a fragment thereof is at least 90% identity to a sequence selected from the group consisting of SEQ ID NOs: 287-334 and 378 or a fragment thereof.

28. The method of claim 3, wherein said at least 80% identity to a sequence selected from the group consisting of SEQ ID NOs: 114-226 or a fragment thereof is at least 95% identity to a sequence selected from the group consisting of SEQ ID NOs: 114-226 or a fragment thereof, and said at least 80% identity to a sequence selected from the group consisting of SEQ ID NOs: 287-334 and 378 or a fragment thereof is at least 95% identity to a sequence selected from the group consisting of SEQ ID NOs: 287-334 and 378 or a fragment thereof.

29. The method of claim 3, wherein said AimR polypeptide comprises said amino acid sequence selected from the group consisting of SEQ ID NOs: 114-226, and said AimR responsive element comprises said nucleic acid sequence selected from the group consisting of SEQ ID NOs: 287-334 and 378.

30. The method of claim 13, wherein the Class 2 CRISPR/Cas is selected from the group consisting of Cas9, Cpf1, C2c1 and C2c3.

* * * * *